United States Patent
Liu et al.

(10) Patent No.: US 12,371,431 B2
(45) Date of Patent: Jul. 29, 2025

(54) TRIFLUOROMETHYL-SUBSTITUTED SULFONAMIDE AS BCL-2-SELECTIVE INHIBITOR

(71) Applicant: Chia Tai Tianqing Pharmaceutical Group Co., Ltd., Lianyungang (CN)

(72) Inventors: Fei Liu, Lianyungang (CN); Weiwei Feng, Lianyungang (CN); Bin Wang, Lianyungang (CN); Hongjiang Xu, Lianyungang (CN); Jinan Wang, Lianyungang (CN); Xiquan Zhang, Lianyungang (CN); Shanchun Wang, Lianyungang (CN); Yanlong Liu, Lianyungang (CN); Jianqing Zhang, Lianyungang (CN); Yiyan Yao, Lianyungang (CN); Xujing Tang, Lianyungang (CN); Wei Shi, Lianyungang (CN); Hongying Zhang, Lianyungang (CN); Yang Li, Lianyungang (CN); Song Tang, Lianyungang (CN); Yizhong Zhu, Lianyungang (CN); Limin Liu, Lianyungang (CN); Hongmei Gu, Lianyungang (CN); Ling Yang, Lianyungang (CN)

(73) Assignee: Chia Tai Tianqing Pharmaceutical Group Co., Ltd., Lianyunggang (CN)

( * ) Notice: Subject to any disclaimer, the term of this patent is extended or adjusted under 35 U.S.C. 154(b) by 931 days.

(21) Appl. No.: 17/289,406

(22) PCT Filed: Oct. 29, 2019

(86) PCT No.: PCT/CN2019/113963
§ 371 (c)(1),
(2) Date: Apr. 28, 2021

(87) PCT Pub. No.: WO2020/088442
PCT Pub. Date: May 7, 2020

(65) Prior Publication Data
US 2022/0002290 A1  Jan. 6, 2022

(30) Foreign Application Priority Data

Oct. 29, 2018  (CN) .......................... 201811268572.2
Mar. 29, 2019  (CN) .......................... 201910249783.X
Sep. 29, 2019  (CN) .......................... 201910933513.0

(51) Int. Cl.
C07D 471/04 (2006.01)
A61P 35/00 (2006.01)

(52) U.S. Cl.
CPC ............ C07D 471/04 (2013.01); A61P 35/00 (2018.01)

(58) Field of Classification Search
CPC ..................... C07D 471/04; A61P 35/00
See application file for complete search history.

(56) References Cited

FOREIGN PATENT DOCUMENTS

| CN | 102307872 A | 1/2012 | |
|----|---|---|---|
| CN | 104876927 A | 9/2015 | |
| CN | 103167867 B | 12/2016 | |
| WO | WO 2010/065824 A2 | 6/2010 | |
| WO | WO-2010138588 A2 * | 12/2010 | ........... A61K 31/437 |
| WO | WO 2012/058392 A1 | 5/2012 | |
| WO | WO 2019/185025 A1 | 10/2019 | |

OTHER PUBLICATIONS

Patani. Chem. Rev. 1996, 96, 3147-3176 (Year: 1996).*
Shah et al. Journal of Enzyme Inhibition and Medicinal Chemistry, 2007; 22(5): 527-540 (Year: 2007).*
International Search Report for PCT/CN2019/113963 dated Jan. 23, 2020.

* cited by examiner

*Primary Examiner* — Clinton A Brooks
*Assistant Examiner* — Jerica Katlynn Wilson
(74) *Attorney, Agent, or Firm* — Knobbe Martens Olson & Bear LLP

(57) ABSTRACT

Disclosed is a trifluoromethyl-substituted sulfonamide BCL-2-selective inhibitor, in particular disclosed are a compound of formula I, a stereoisomer or a pharmaceutically acceptable salt thereof, a preparation method therefor, and a pharmaceutical composition thereof. Also disclosed are the uses of said compound and of a pharmaceutical composition comprising same for treating anti-apoptotic BCL-2-related diseases, such as cancer.

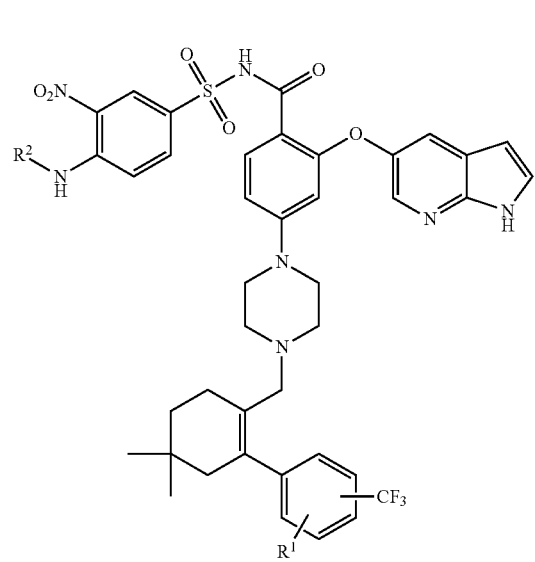

20 Claims, No Drawings

TRIFLUOROMETHYL-SUBSTITUTED SULFONAMIDE AS BCL-2-SELECTIVE INHIBITOR

CROSS-REFERENCE TO RELATED APPLICATIONS

This application is a U.S. National Phase Application of PCT International Application Number PCT/CN2019/113963, filed on Oct. 29, 2019, designating the United States of America and published in the Chinese language, which is an International Application of and claims the benefit of priority to Chinese Patent Application No. 201811268572.2, filed on Oct. 29, 2018, Chinese Patent Application No. 201910249783.X, filed on Mar. 29, 2019 and Chinese Patent Application No. 201910933513.0, filed on Sep. 29, 2019. The disclosures of the above-referenced applications are hereby expressly incorporated by reference in their entireties.

TECHNICAL FIELD

The present application relates to compounds that selectively inhibit anti-apoptotic protein BCL-2, a method for preparing the same, a pharmaceutical composition containing the same and use of the same in treating an anti-apoptotic protein BCL-2-related disease, e.g., cancer.

BACKGROUND

BCL-2 proteins are classified into three families: BCL-2 family (including members such as BCL-2 and BCL-XL), BAX family and BH3-only family. Among them, the BCL-2 family plays an anti-apoptotic role, while members of the other two families play a pro-apoptotic role.

Anti-apoptotic proteins of the BCL-2 family are associated with many diseases and are being investigated as potential targets of therapeutic drugs. These targets for interventional therapy include, for example, proteins BCL-2 and BCL-XL of the BCL-2 family, etc. Recently, inhibitors for proteins of BCL-2 family have been reported in WO2012071374, WO2010138588 and WO2010065865. Although inhibitors that bind to a target protein with high affinity are introduced therein, binding affinity of compounds is only one of many parameters to be considered. One objective is to produce a compound that preferentially binds to, i.e., has selectivity for, one protein over another. To show this selectivity, it is well known that the compound exhibits high binding affinity for a specific protein and lower binding affinity for another.

Disclosed BCL-2 inhibitors are less selective for anti-apoptotic BCL-XL and BCL-2 proteins, and thus have a greater probability of causing side effects. They are characterized by inhibiting anti-apoptotic BCL-XL protein and causing side effects such as thrombocytopenia.

The present application includes a series of compounds that exhibit higher selectivity for anti-apoptotic BCL-2 and BCL-XL proteins, and also have better performance in inhibiting the activity of anti-apoptotic BCL-2 protein. Meanwhile, these compounds have better stability of liver microsomes and optimized pharmacokinetic parameters, showing a better druggability prospect.

SUMMARY

In one aspect, the prevent application relates to a compound of formula I, a stereoisomer thereof or a pharmaceutically acceptable salt thereof,

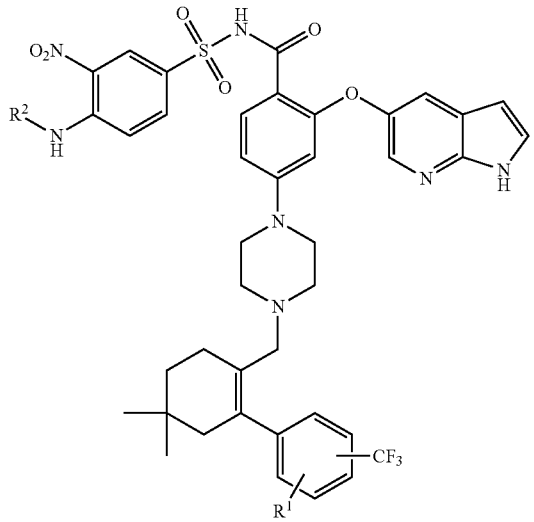

I wherein, $R^1$ is selected from halogen; $R^2$ is selected from —$C_{0-6}$ alkylene-$R^3$; $R^3$ is selected from 5-6 membered heterocycloalkyl, wherein the 5-6 membered heterocycloalkyl is optionally substituted with one or two groups selected from the group consisting of 3-6 membered heterocycloalkyl, $C_{3-6}$ cycloalkyl, —$COR^a$, —$SO_2R^b$, —$COOC_{1-6}$ alkyl, and $C_{1-6}$ alkyl optionally substituted with halogen; and $R^a$ or $R^b$ is each independently selected from the group consisting of H, 3-6 membered heterocycloalkyl, $C_{3-6}$ cycloalkyl and $C_{1-6}$ alkyl, wherein the $C_{1-6}$ alkyl is optionally substituted with halogen, —CN, —N($C_{1-6}$ alkyl)$_2$, —NH$C_{1-6}$ alkyl or —O$C_{1-6}$ alkyl.

In some embodiments, the structural fragment

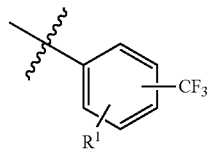

is selected from

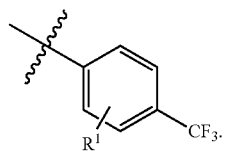

In some embodiments, the structural fragment

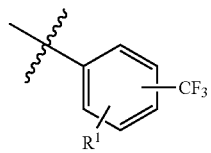

is selected from the group consisting of

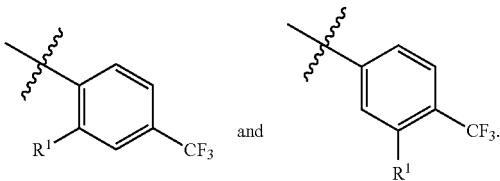

In some embodiments, the structural fragment

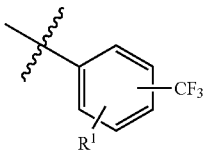

is selected from

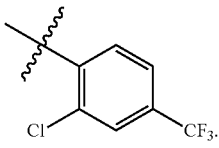

In some embodiments, the structural fragment

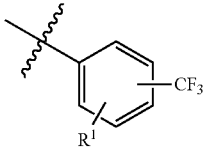

is selected from

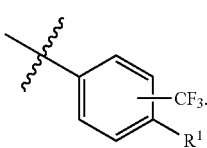

In some embodiments, the structural fragment

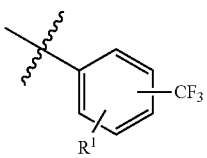

is selected from the group consisting of

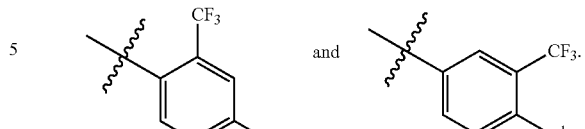

In some embodiments, $R^1$ is selected from the group consisting of fluorine and chlorine. In some embodiments, $R^1$ is selected from chlorine.

In some embodiments, $R^2$ is selected from the group consisting of —$R^3$ and —$C_{1-6}$ alkylene-$R^3$. In some embodiments, $R^2$ is selected from —$C_{1-4}$ alkylene-$R^3$.

In some embodiments, $R^2$ is selected from —$(CH_2)_n$—$R^3$, wherein n is 0, 1, 2, 3 or 4; or n is 1, 2 or 3; or n is 1 or 2.

In some embodiments, $R^3$ is selected from 5-6 membered heterocycloalkyl, wherein the 5-6 membered heterocycloalkyl is optionally substituted with one or two groups at ring N atom.

In some embodiments, $R^3$ is selected from 5-6 membered heterocycloalkyl, wherein the 5-6 membered heterocycloalkyl is optionally substituted with one or two groups selected from the group consisting of 3-6 membered heterocycloalkyl, $C_{3-6}$ cycloalkyl, —$COR^a$, —$SO_2R^b$, and $C_{1-6}$ alkyl optionally substituted with halogen.

In some embodiments, $R^3$ is selected from 5-6 membered heterocycloalkyl, wherein the 5-6 membered heterocycloalkyl is optionally substituted with one or two groups selected from the group consisting of 3-6 membered heterocycloalkyl, —$COR^a$, —$SO_2R^b$, —$COOC_{1-6}$ alkyl, and $C_{1-6}$ alkyl optionally substituted with halogen.

In some embodiments, $R^3$ is selected from 5-6 membered heterocycloalkyl, wherein the 5-6 membered heterocycloalkyl is optionally substituted with one or two groups selected from the group consisting of 3-6 membered heterocycloalkyl, —$COR^a$, —$SO_2R^b$, and $C_{1-6}$ alkyl optionally substituted with halogen.

In some embodiments, $R^3$ is selected from 5-6 membered heterocycloalkyl, wherein the 5-6 membered heterocycloalkyl is optionally substituted with one or two groups selected from the group consisting of —$COR^a$, —$SO_2R^b$, —$COOC_{1-6}$ alkyl, and $C_{1-6}$ alkyl optionally substituted with halogen.

In some embodiments, $R^3$ is selected from 5-6 membered heterocycloalkyl, wherein the 5-6 membered heterocycloalkyl is optionally substituted with one or two groups selected from the group consisting of —$COR^a$, —$SO_2R^b$, and $C_{1-6}$ alkyl optionally substituted with halogen.

In some embodiments, $R^3$ is selected from 5-6 membered heterocycloalkyl, wherein the 5-6 membered heterocycloalkyl is optionally substituted with 3-6 membered heterocycloalkyl.

In some embodiments, $R^3$ is selected from 5-6 membered heterocycloalkyl, wherein the 5-6 membered heterocycloalkyl is optionally substituted with —$COR^a$.

In some embodiments, $R^3$ is selected from 5-6 membered heterocycloalkyl, wherein the 5-6 membered heterocycloalkyl is optionally substituted with —$SO_2R^b$.

In some embodiments, $R^3$ is selected from 5-6 membered heterocycloalkyl, wherein the 5-6 membered heterocycloalkyl is optionally substituted with —$COOC_{1-6}$ alkyl. In some embodiments, $R^3$ is selected from 5-6 membered heterocycloalkyl, wherein the 5-6 membered heterocycloalkyl is optionally substituted with —$COOC_{1-4}$ alkyl.

In some embodiments, $R^3$ is selected from 5-6 membered heterocycloalkyl, wherein the 5-6 membered heterocycloalkyl is optionally substituted with $C_{1-6}$ alkyl, wherein the $C_{1-6}$ alkyl is optionally substituted with halogen; in some embodiments, the $C_{1-6}$ alkyl is optionally substituted with fluorine. In some embodiments, the 5-6 membered heterocycloalkyl is optionally substituted with methyl, ethyl, methyl substituted with fluorine, or ethyl substituted with fluorine.

In some embodiments, $R^a$ or $R^b$ is each independently selected from the group consisting of H, 3-6 membered heterocycloalkyl, $C_{3-6}$ cycloalkyl and $C_{1-4}$ alkyl, wherein the $C_{1-4}$ alkyl is optionally substituted with halogen, —CN, —N($C_{1-4}$ alkyl)$_2$, —NHC$_{1-4}$ alkyl or —OC$_{1-4}$ alkyl. In some embodiments, $R^a$ is selected from the group consisting of H, 3-6 membered heterocycloalkyl, $C_{3-6}$ cycloalkyl and $C_{1-4}$ alkyl, wherein the $C_{1-4}$ alkyl is optionally substituted with halogen, —CN, —N($C_{1-4}$ alkyl)$_2$ or —OC$_{1-4}$ alkyl. In some embodiments, $R^b$ is selected from the group consisting of 3-6 membered heterocycloalkyl, $C_{3-6}$ cycloalkyl and $C_{1-4}$ alkyl, wherein the $C_{1-4}$ alkyl is optionally substituted with halogen or —CN.

In some embodiments, $R^a$ or $R^b$ is each independently selected from the group consisting of H, methyl, ethyl, isopropyl, tert-butyl, cyclopropyl, cyclobutyl and monooxacyclobutyl, wherein the methyl or ethyl is optionally substituted with fluorine, —CN, —OCH$_3$ or —N(CH$_3$)$_2$. In some embodiments, $R^a$ is selected from the group consisting of H, methyl, isopropyl, tert-butyl, cyclopropyl and monooxacyclobutyl, wherein the methyl is optionally substituted with fluorine, —CN, —OCH$_3$ or —N(CH$_3$)$_2$. In some embodiments, $R^b$ is selected from the group consisting of methyl, ethyl, cyclopropyl, cyclobutyl and monooxacyclobutyl, wherein the methyl or ethyl is optionally substituted with fluorine.

In some embodiments, $R^a$ or $R^b$ is each independently selected from the group consisting of H, methyl, ethyl, isopropyl, tert-butyl, trifluoromethyl, pentafluoroethyl, —CH$_2$OCH$_3$, —CH$_2$CN, —CH$_2$N(CH$_3$)$_2$, cyclopropyl, cyclobutyl and monooxacyclobutyl. In some embodiments, $R^a$ is selected from the group consisting of H, methyl, isopropyl, tert-butyl, trifluoromethyl, —CH$_2$OCH$_3$, —CH$_2$CN, —CH$_2$N(CH$_3$)$_2$, cyclopropyl and monooxacyclobutyl. In some embodiments, $R^b$ is selected from the group consisting of methyl, ethyl, trifluoromethyl, pentafluoroethyl, cyclopropyl, cyclobutyl and monooxacyclobutyl.

In some embodiments, $R^a$ or $R^b$ is each independently selected from the group consisting of H, $C_{3-6}$ cycloalkyl and $C_{1-4}$ alkyl, wherein the $C_{1-4}$ alkyl is optionally substituted with halogen, —CN, —N($C_{1-4}$ alkyl)$_2$, —NHC$_{1-4}$ alkyl or —OC$_{1-4}$ alkyl. In some embodiments, $R^a$ is selected from the group consisting of H, $C_{3-6}$ cycloalkyl and $C_{1-4}$ alkyl, wherein the $C_{1-4}$ alkyl is optionally substituted with halogen, —CN, —N($C_{1-4}$ alkyl)$_2$ or —OC$_{1-4}$ alkyl. In some embodiments, $R^b$ is selected from the group consisting of $C_{3-6}$ cycloalkyl and $C_{1-4}$ alkyl, wherein the $C_{1-4}$ alkyl is optionally substituted with halogen or —CN.

In some embodiments, $R^a$ or $R^b$ is each independently selected from the group consisting of H, methyl, ethyl, isopropyl, tert-butyl, cyclopropyl and cyclobutyl, wherein the methyl or ethyl is optionally substituted with fluorine, —CN, —OCH$_3$ or —N(CH$_3$)$_2$. In some embodiments, $R^a$ is selected from the group consisting of H, methyl, isopropyl, tert-butyl and cyclopropyl, wherein the methyl is optionally substituted with fluorine, —CN, —OCH$_3$ or —N(CH$_3$)$_2$. In some embodiments, $R^b$ is selected from the group consisting of methyl, ethyl, cyclopropyl and cyclobutyl, wherein the methyl is optionally substituted with fluorine.

In some embodiments, $R^a$ or $R^b$ is each independently selected from the group consisting of H, methyl, ethyl, isopropyl, tert-butyl, trifluoromethyl, —CH$_2$OCH$_3$, —CH$_2$CN, —CH$_2$N(CH$_3$)$_2$, cyclopropyl and cyclobutyl. In some embodiments, $R^a$ is selected from the group consisting of H, methyl, isopropyl, tert-butyl, trifluoromethyl, —CH$_2$OCH$_3$, —CH$_2$CN, —CH$_2$N(CH$_3$)$_2$ and cyclopropyl. In some embodiments, $R^b$ is selected from the group consisting of methyl, ethyl, trifluoromethyl, cyclopropyl and cyclobutyl.

In some embodiments, $R^a$ or $R^b$ is each independently selected from $C_{1-4}$ alkyl optionally substituted with —OC$_{1-4}$ alkyl.

In some embodiments, $R^a$ or $R^b$ is each independently selected from the group consisting of methyl, isopropyl and —CH$_2$OCH$_3$.

In some embodiments, $R^a$ is selected from $C_{1-4}$ alkyl optionally substituted with —OC$_{1-4}$ alkyl.

In some embodiments, $R^a$ is selected from the group consisting of methyl, isopropyl and —CH$_2$OCH$_3$.

In some embodiments, $R^b$ is selected from $C_{1-4}$ alkyl.

In some embodiments, $R^b$ is selected from methyl.

In some embodiments, $R^3$ is selected from 5-6 membered heterocycloalkyl, wherein the 5-6 membered heterocycloalkyl is optionally substituted with —C(O)H, —COCH$_3$, —COCH(CH$_3$)$_2$, —COC(CH$_3$)$_3$, —COCF$_3$, —COCH$_2$CN, —COCH$_2$OCH$_3$, —COCH$_2$N(CH$_3$)$_2$, —SO$_2$CH$_3$, —SO$_2$CH$_2$CH$_3$, —SO$_2$CF$_3$, —SO$_2$C$_2$F$_5$, methyl, ethyl, —CF$_3$, —CH$_2$CH$_2$F, —C$_2$F$_5$, tetrahydropyran, monooxacyclobutane, —SO$_2$-cyclopropane, —CO-cyclopropane, —CO-monooxacyclobutane, —SO$_2$-monooxacyclobutane, —SO$_2$-cyclobutane, —COOCH$_2$CH$_3$ or —COOCH$_3$. In some embodiments, $R^3$ is selected from 5-6 membered heterocycloalkyl, wherein the 5-6 membered heterocycloalkyl is optionally substituted with —COCH$_3$, —COCH(CH$_3$)$_2$, —COCH$_2$OCH$_3$, —SO$_2$CH$_3$, methyl, ethyl or —CH$_2$CH$_2$F.

In some embodiments, $R^3$ is selected from 5-6 membered heterocycloalkyl, wherein the 5-6 membered heterocycloalkyl is optionally substituted with —C(O)H, —COC(CH$_3$)$_3$, —COCF$_3$, —COCH$_2$CN, —COCH$_2$N(CH$_3$)$_2$, —SO$_2$CH$_2$CH$_3$, —SO$_2$CF$_3$, —SO$_2$C$_2$F$_5$, —CF$_3$, —C$_2$F$_5$, tetrahydropyran, monooxacyclobutane, —SO$_2$-cyclopropane, —CO-cyclopropane, —CO-monooxacyclobutane, —SO$_2$-monooxacyclobutane or —SO$_2$-cyclobutane.

In some embodiments, $R^3$ is selected from 5-6 membered heterocycloalkyl, wherein the 5-6 membered heterocycloalkyl is optionally substituted with —COOCH$_2$CH$_3$ or —COOCH$_3$.

In some embodiments, $R^3$ is selected from 5-6 membered heterocycloalkyl, wherein the 5-6 membered heterocycloalkyl is optionally substituted with —C(O)H, —COCH$_3$, —COCH(CH$_3$)$_2$, —COC(CH$_3$)$_3$, —COCF$_3$, —COCH$_2$CN, —COCH$_2$OCH$_3$, —COCH$_2$N(CH$_3$)$_2$, —SO$_2$CH$_3$, —SO$_2$CH$_2$CH$_3$, —SO$_2$CF$_3$, methyl, ethyl, —CH$_2$CH$_2$F, tetrahydropyran, —SO$_2$-cyclopropane, —CO-cyclopropane or —SO$_2$-cyclobutane.

In some embodiments, $R^3$ is selected from 5-6 membered heterocycloalkyl, wherein the 5-6 membered heterocycloalkyl is optionally substituted with —C(O)H, —COC(CH$_3$)$_3$, —COCF$_3$, —COCH$_2$CN, —COCH$_2$N(CH$_3$)$_2$, —SO$_2$CH$_2$CH$_3$, —SO$_2$CF$_3$, —SO$_2$C$_2$F$_5$, —CF$_3$, —C$_2$F$_5$, tetrahydropyran, —SO$_2$-cyclopropane, —CO-cyclopropane or —SO$_2$-cyclobutane.

In some embodiments, $R^3$ is selected from the group consisting of tetrahydropyran, piperidine, morpholine and dioxane, wherein the tetrahydropyran, piperidine, morpholine or dioxane is optionally substituted with —C(O)H, —COCH₃, —COCH₂OCH₃, —SO₂CH₃, —SO₂CH₂CH₃, —CO-cyclopropane, —COCH₂CN, —COCF₃, —COCH₂N(CH₃)₂ or methyl.

In some embodiments, R³ is selected from the group consisting of tetrahydropyran, piperidine, morpholine and dioxane, wherein the tetrahydropyran, piperidine, morpholine or dioxane is optionally substituted with —COCH₃, —COCH(CH₃)₂, —COCH₂OCH₃, —SO₂CH₃, methyl, ethyl or —CH₂CH₂F.

In some embodiments, R³ is selected from the group consisting of tetrahydropyran, piperidine, morpholine and dioxane, wherein the tetrahydropyran, piperidine, morpholine or dioxane is optionally substituted with —COOCH₂CH₃ or —COOCH₃.

In some embodiments, R³ is selected from the group consisting of tetrahydropyran and dioxane.

In some embodiments, R³ is selected from dioxane.

In some embodiments, R³ is selected from the group consisting of piperidine and morpholine, wherein the piperidine or morpholine is optionally substituted with —C(O)H, —COCH₃, —COCH₂OCH₃, —SO₂CH₃, —SO₂CH₂CH₃, —CO-cyclopropane, —COCH₂CN, —COCF₃, —COCH₂N(CH₃)₂ or methyl. In some embodiments, R³ is selected from the group consisting of piperidine and morpholine, wherein the piperidine or morpholine is optionally substituted with —COCH₃, —COCH(CH₃)₂, —COCH₂OCH₃, —SO₂CH₃, methyl, ethyl or —CH₂CH₂F.

In some embodiments, R³ is selected from the group consisting of piperidine and morpholine, wherein the piperidine or morpholine is optionally substituted with —COOCH₂CH₃ or —COOCH₃.

In some embodiments, R³ is selected from the group consisting of

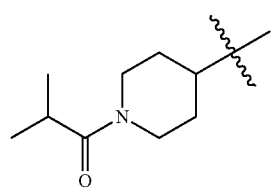

,


,

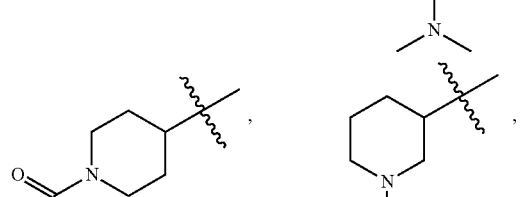

-continued

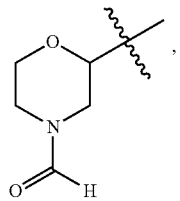 , 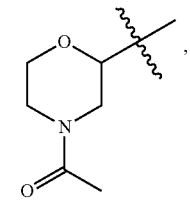 ,

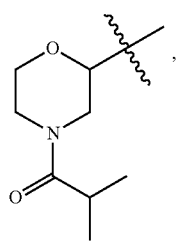 , 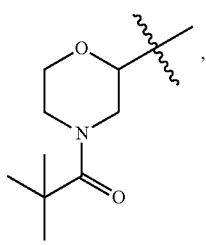 ,

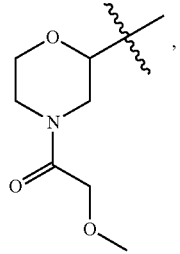 , 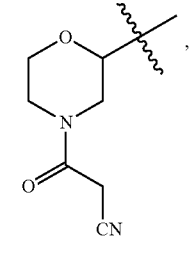 ,

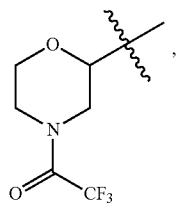 , 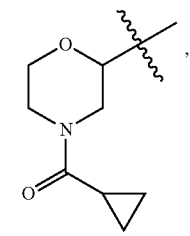 ,

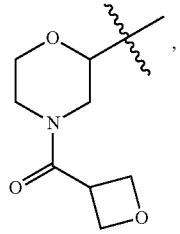 , 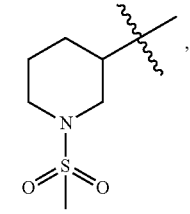 ,

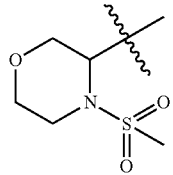 , 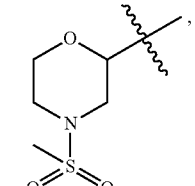 ,

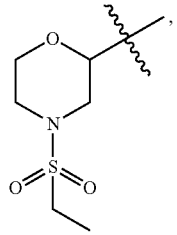 , 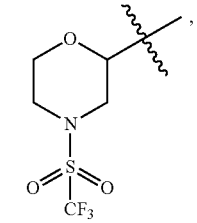 ,

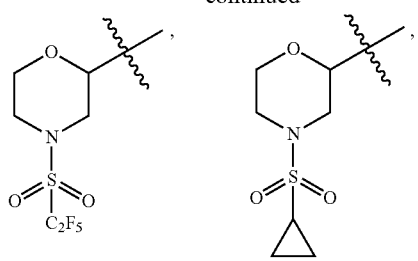
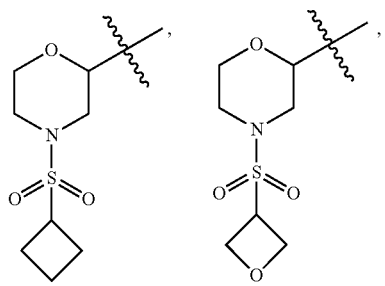
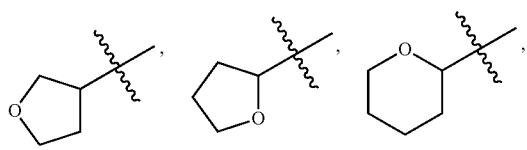
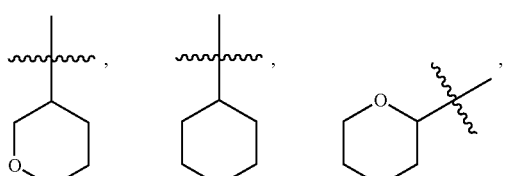
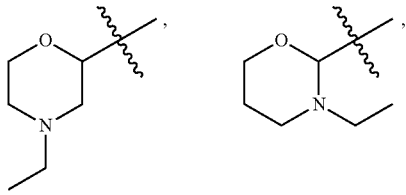
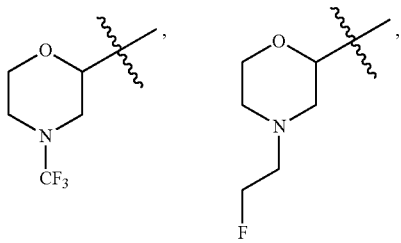
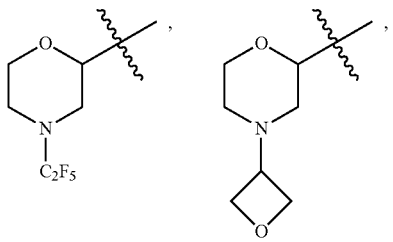
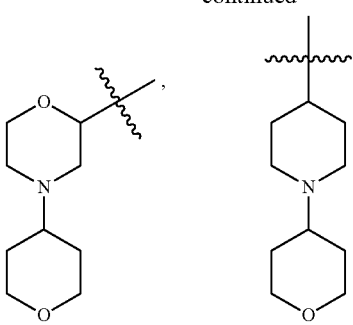
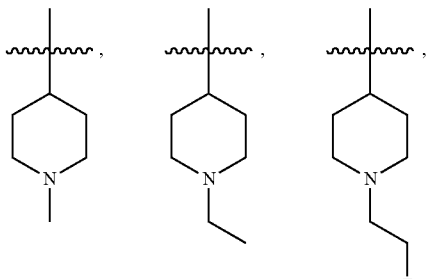
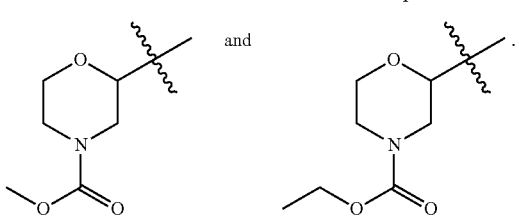
In some embodiments, R³ is selected from the group consisting of
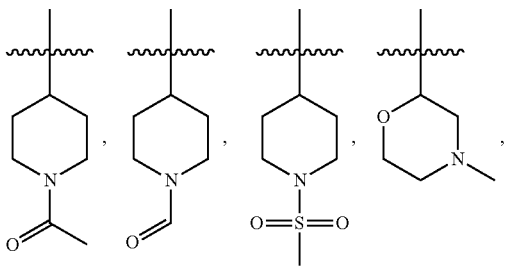
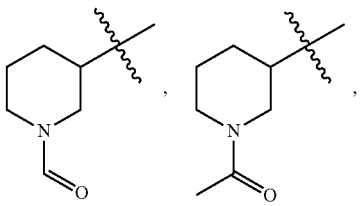
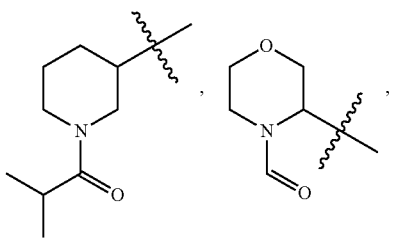

-continued
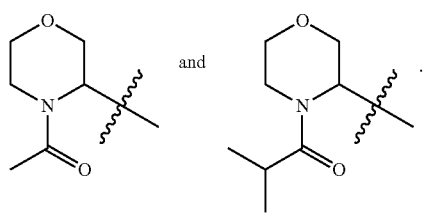
In some embodiments, $R^3$ is selected from the group consisting of
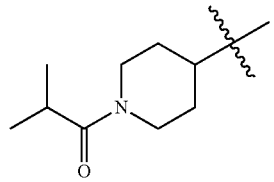,
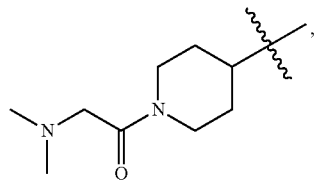,
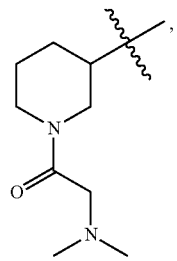,
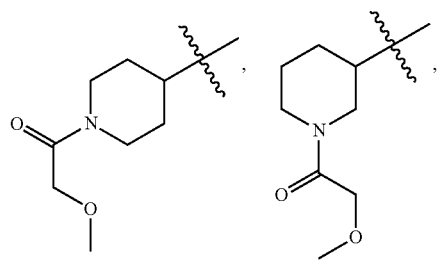,
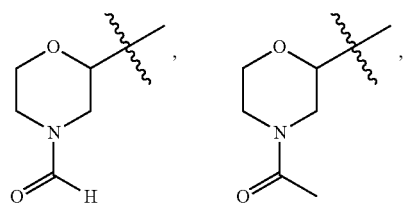,
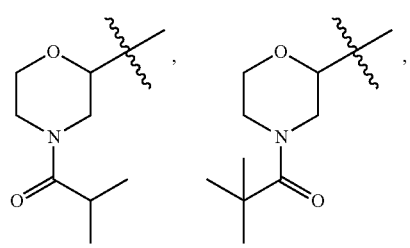,
-continued
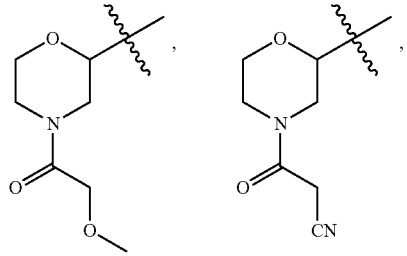,
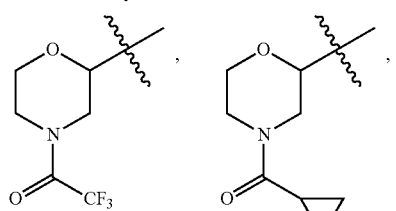,
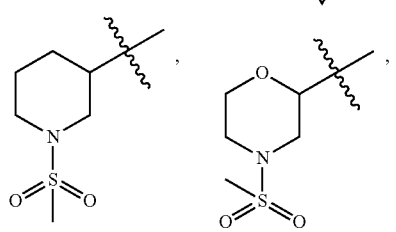,
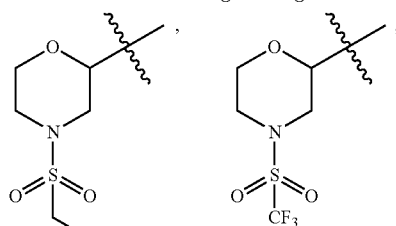,
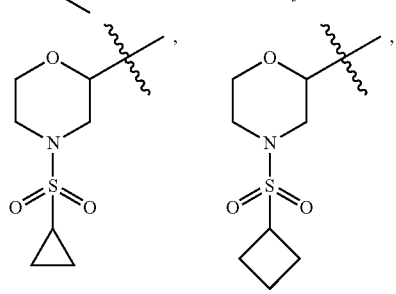,
,
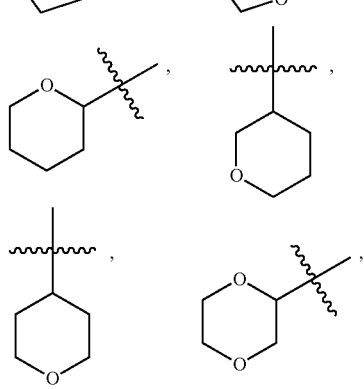

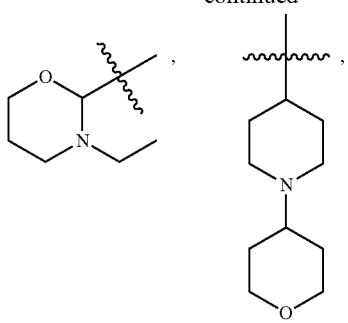
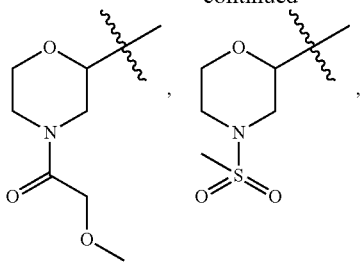
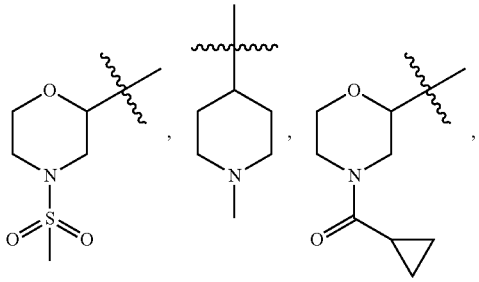
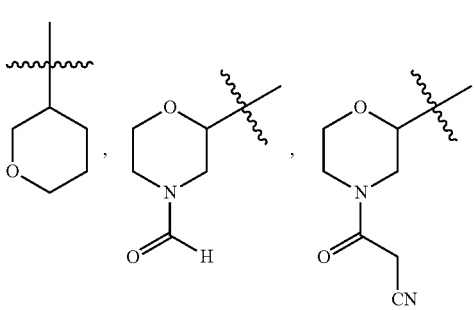
In some embodiments, R³ is selected from the group consisting of
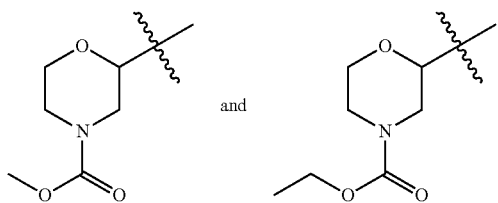
In some embodiments, R³ is selected from the group consisting of
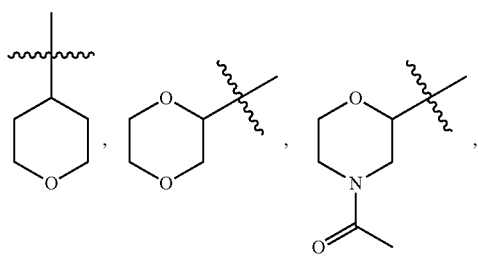

In some embodiments, R³ is selected from the group consisting of
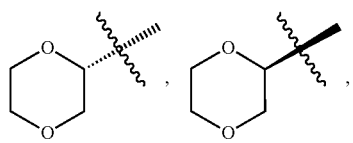
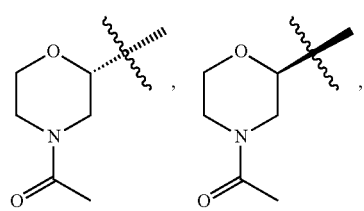
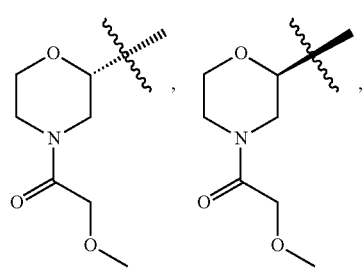
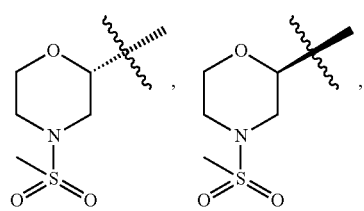
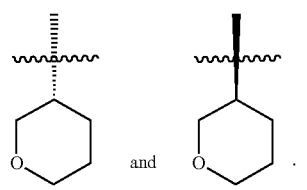 and
In some embodiments, R³ is selected from the group consisting of
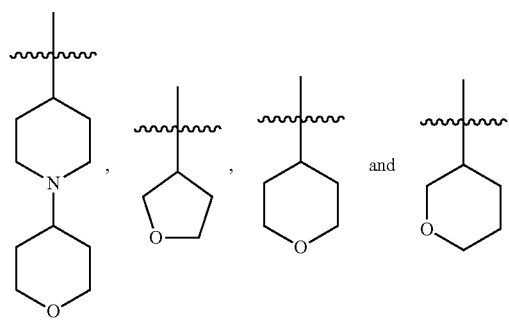
In some embodiments, R³ is selected from the group consisting of
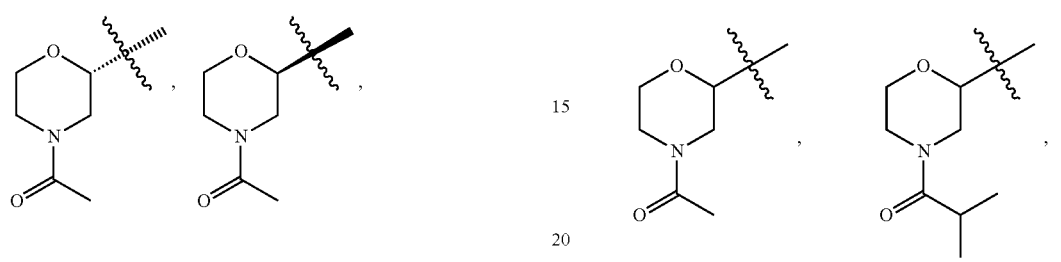
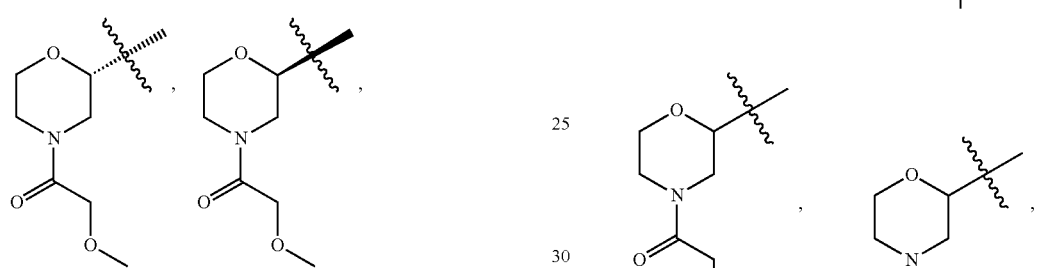
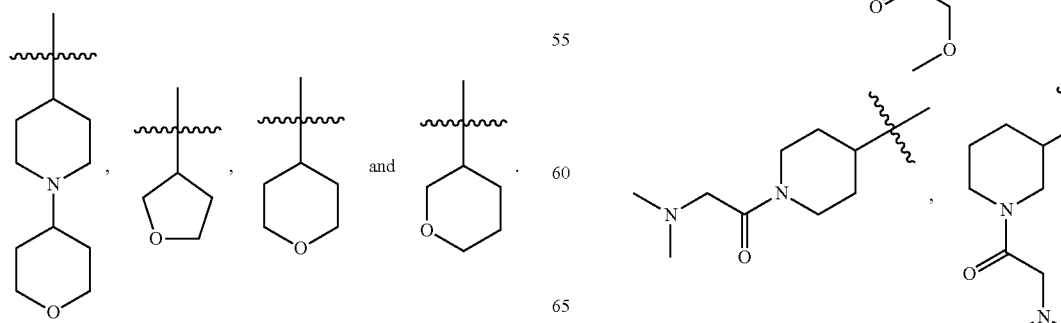

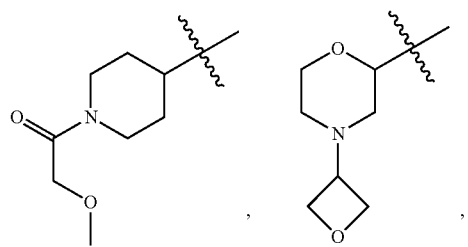
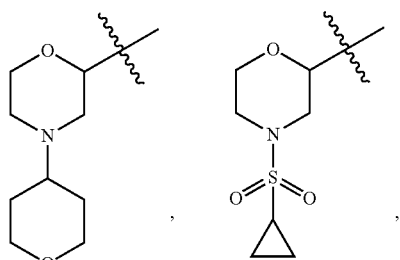
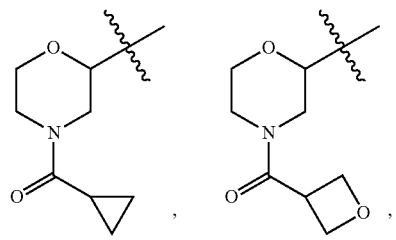
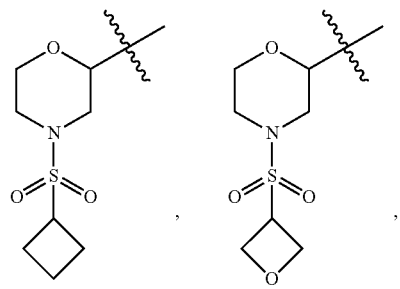
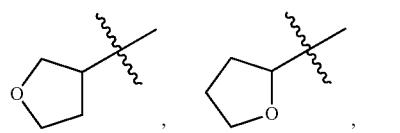
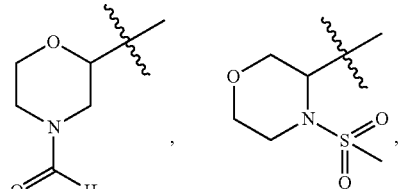
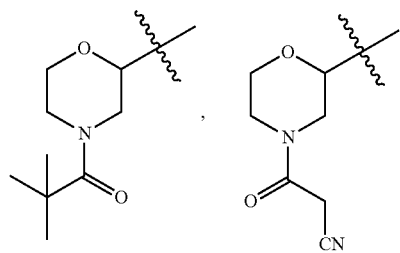
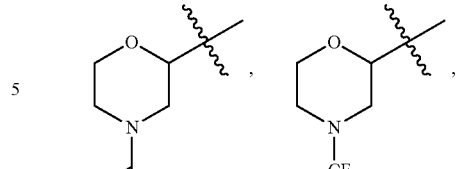
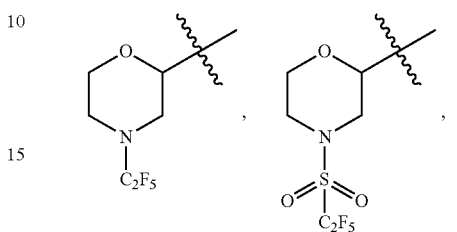
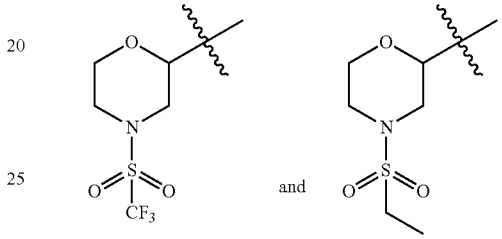
In some embodiments, $R^3$ is selected from the group consisting of
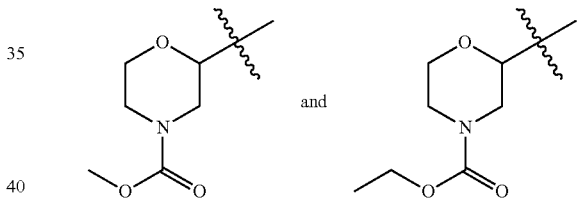
In some embodiments, $R^3$ is selected from the group consisting of
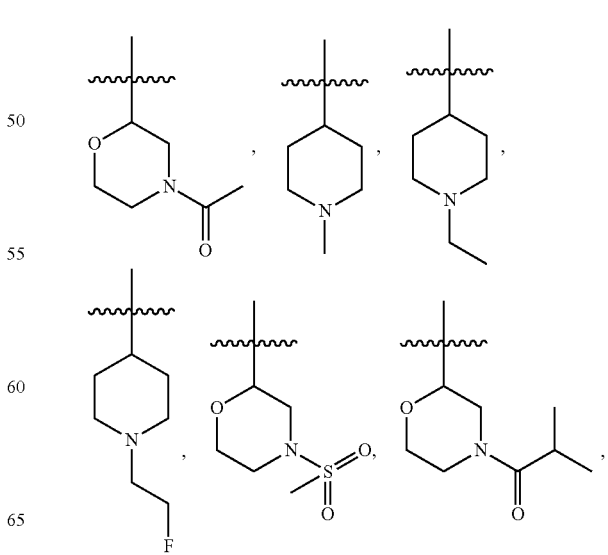

-continued

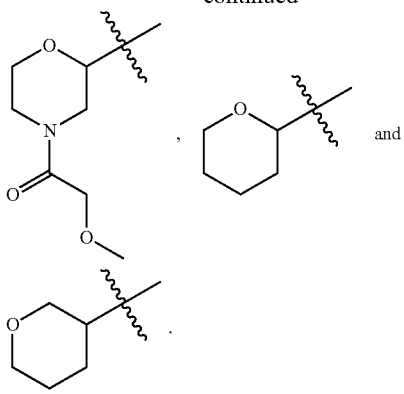

In some embodiments, R³ is selected from the group consisting of

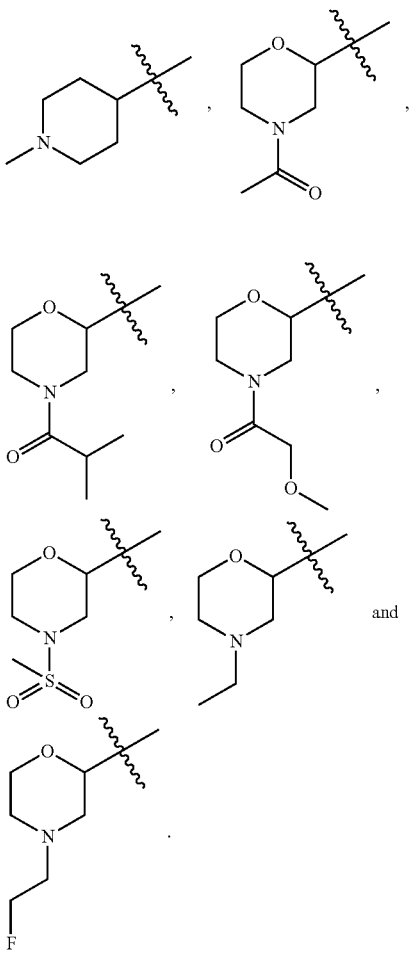

In some embodiments, the heteroatom in the 5-6 membered heterocycloalkyl is selected from the group consisting of N and O, and the number of the heteroatom is 1 or 2.

In some embodiments, the 5-6 membered heterocycloalkyl is selected from the group consisting of dioxanyl, morpholinyl, tetrahydropyranyl, piperidinyl and tetrahydrofuranyl.

In some embodiments, the 5-6 membered heterocycloalkyl is selected from 6 membered heterocycloalkyl.

In some embodiments, the 5-6 membered heterocycloalkyl is selected from the group consisting of dioxanyl, morpholinyl, tetrahydropyranyl and piperidinyl.

In some embodiments, the 5-6 membered heterocycloalkyl is selected from dioxanyl.

In some embodiments, the 5-6 membered heterocycloalkyl is selected from morpholinyl.

In some embodiments, the 5-6 membered heterocycloalkyl is selected from tetrahydropyranyl.

In some embodiments, the heteroatom in the 3-6 membered heterocycloalkyl is selected from the group consisting of N and O, and the number of the heteroatom is 1 or 2. In some embodiments, the heteroatom in the 3-6 membered heterocycloalkyl is selected from O, and the number of the heteroatom is 1 or 2. In some embodiments, the 3-6 membered heterocycloalkyl is selected from 4-6 membered heterocycloalkyl. In some embodiments, the 3-6 membered heterocycloalkyl is selected from the group consisting of 4-membered heterocycloalkyl and 6-membered heterocycloalkyl.

In some embodiments, the 3-6 membered heterocycloalkyl is selected from the group consisting of monooxacyclobutyl, tetrahydrofuranyl and tetrahydropyranyl.

In some embodiments, the $C_{3-6}$ cycloalkyl is selected from the group consisting of cyclopropyl, cyclobutyl and cyclopentyl. In some embodiments, the $C_{3-6}$ cycloalkyl is selected from $C_{3-4}$ cycloalkyl.

In another aspect, the present application relates to a compound of formula II, a stereoisomer thereof or a pharmaceutically acceptable salt thereof:

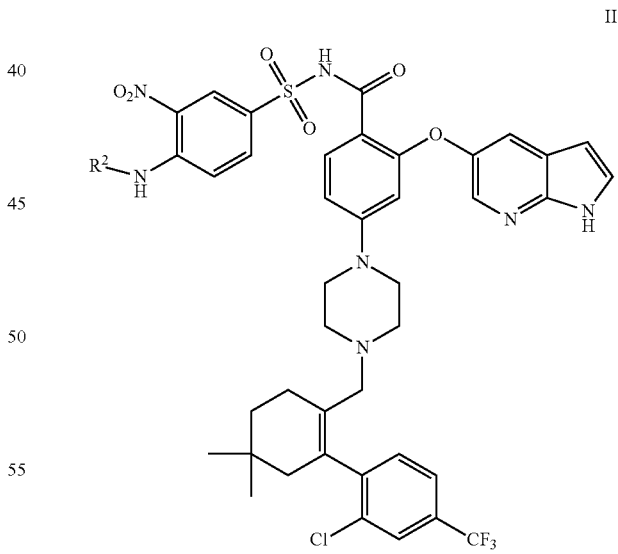

II wherein R² is defined the same as in the compound of formula I.

The present application relates to a compound of a formula selected from the group consisting of the following formulas, a stereoisomer thereof or a pharmaceutically acceptable salt thereof:

21
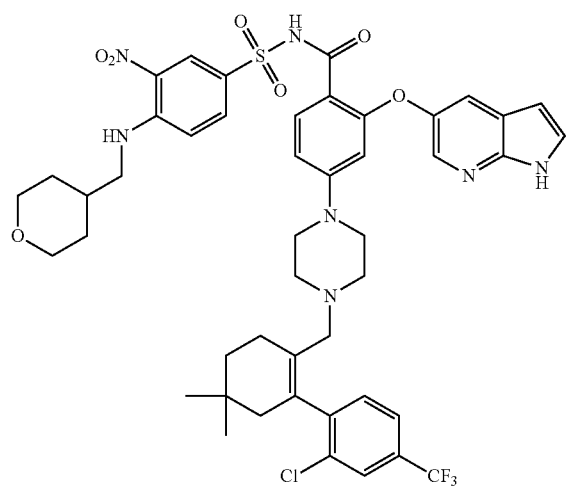
22
-continued
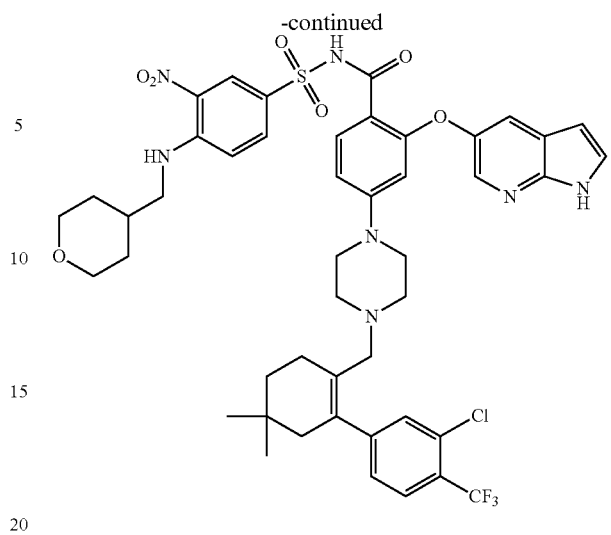
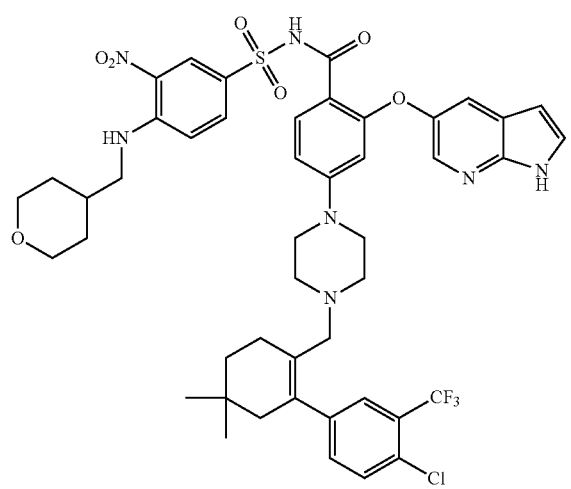
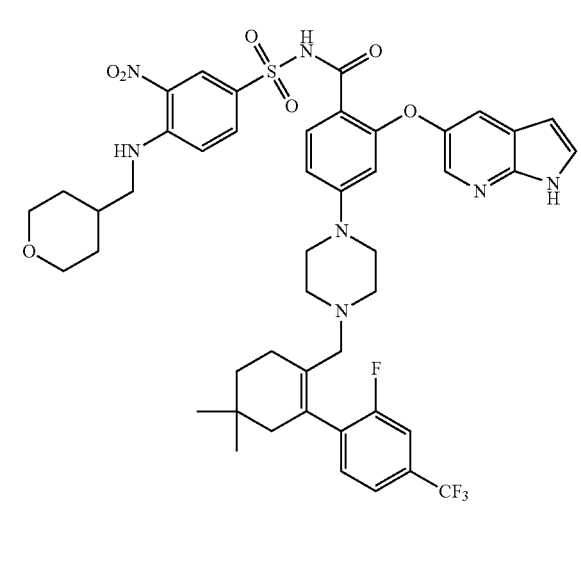
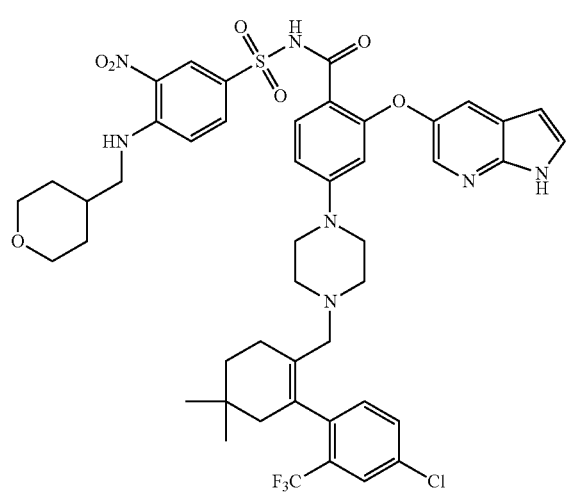
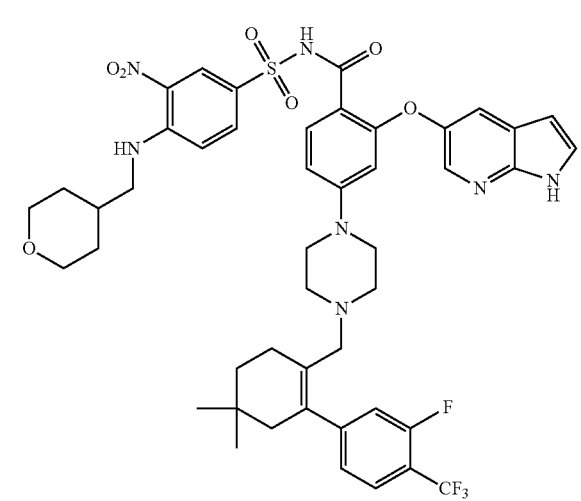

23
-continued
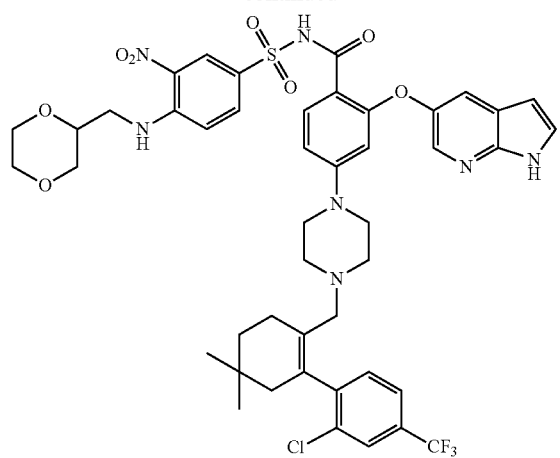
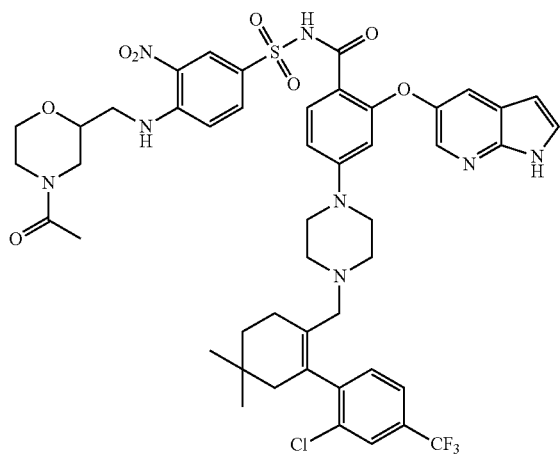
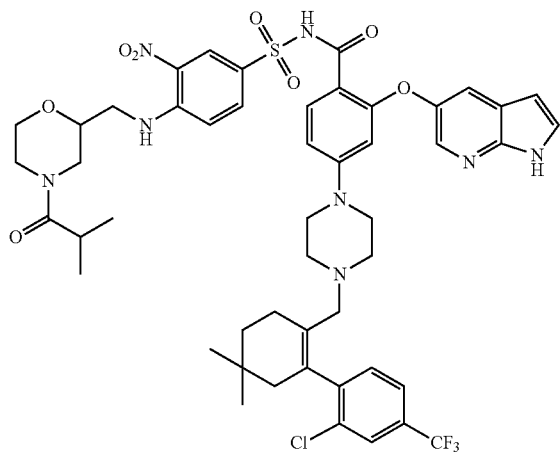
24
-continued
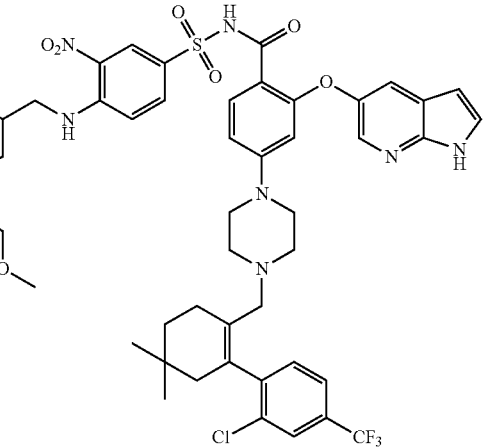
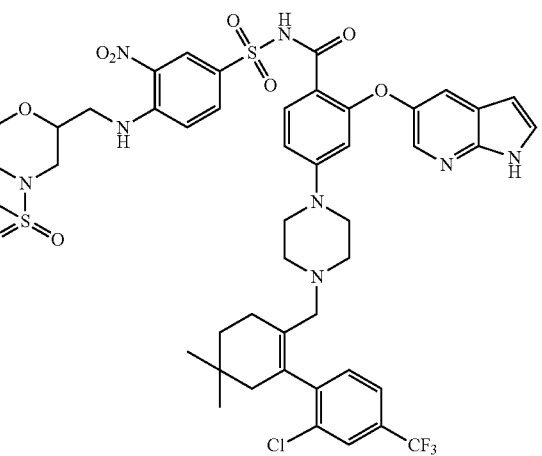
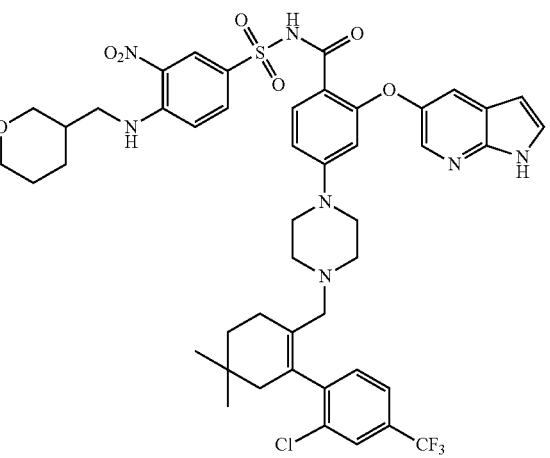

25
-continued
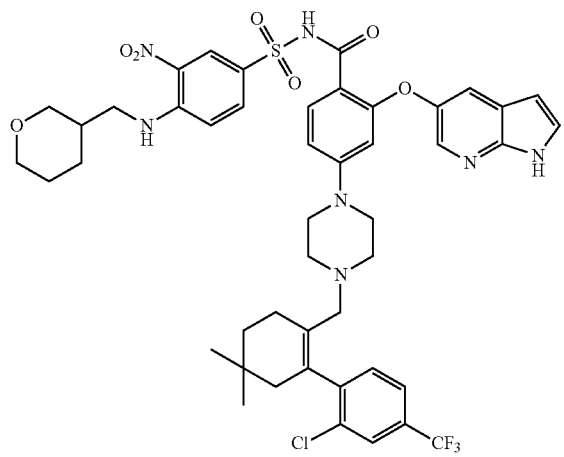
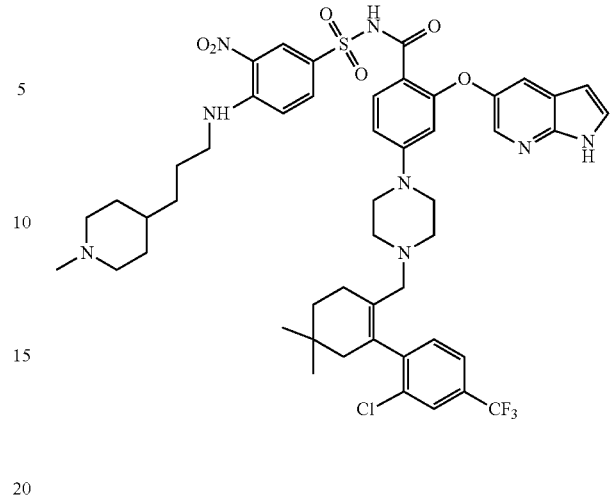
26
-continued
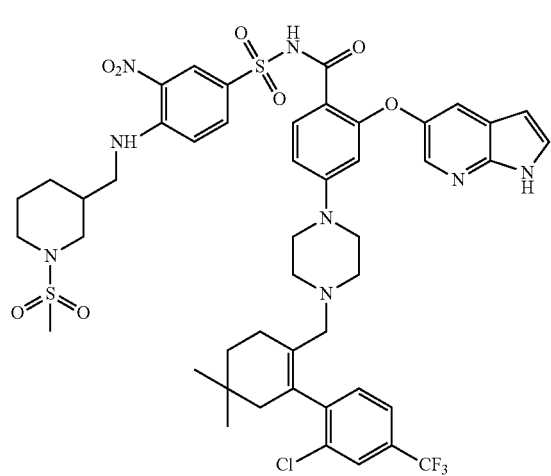
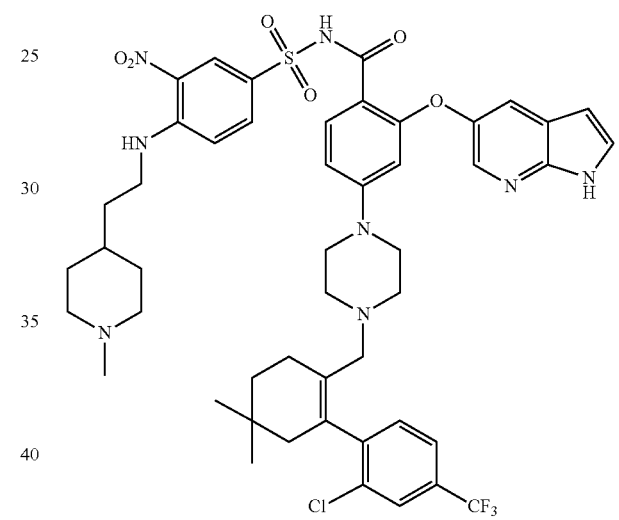
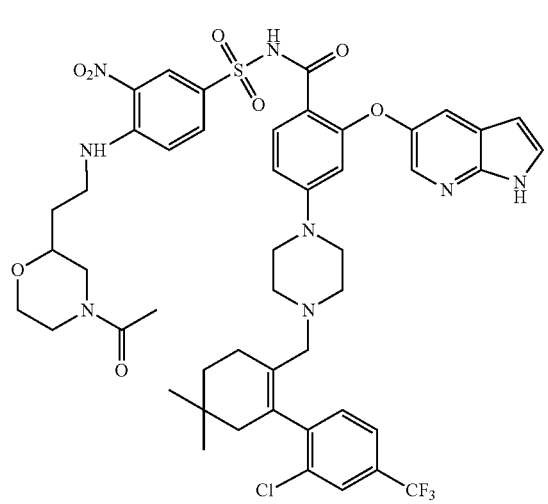
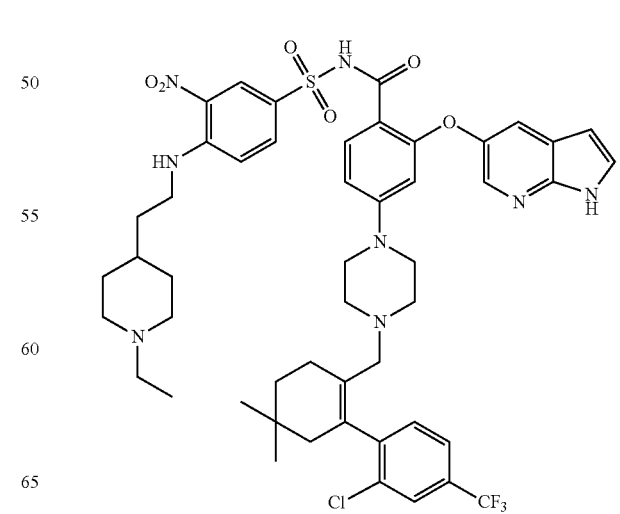

27
-continued
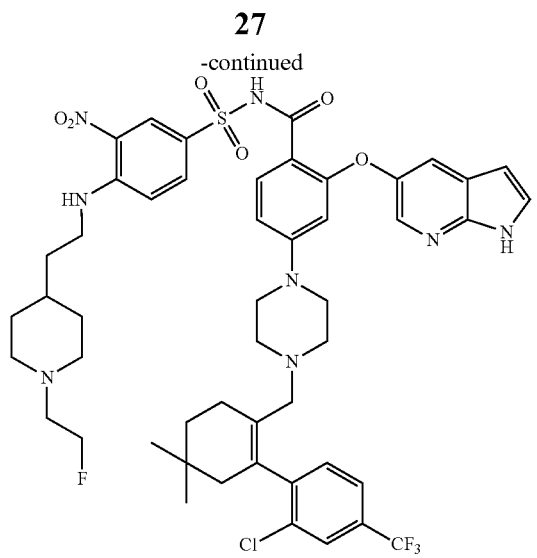
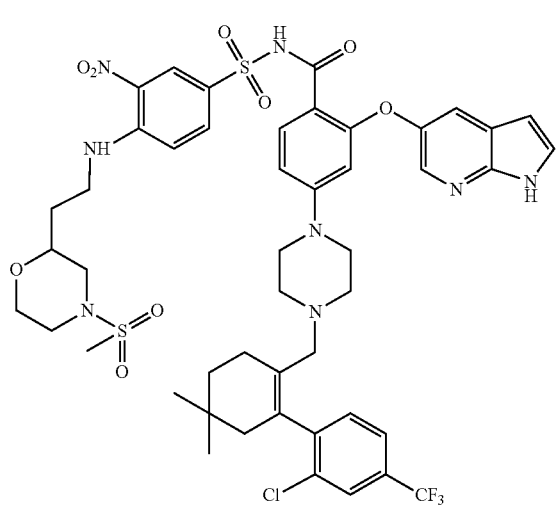
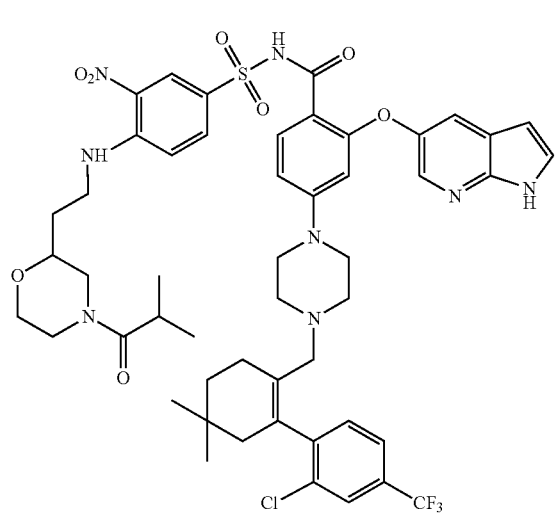
28
-continued
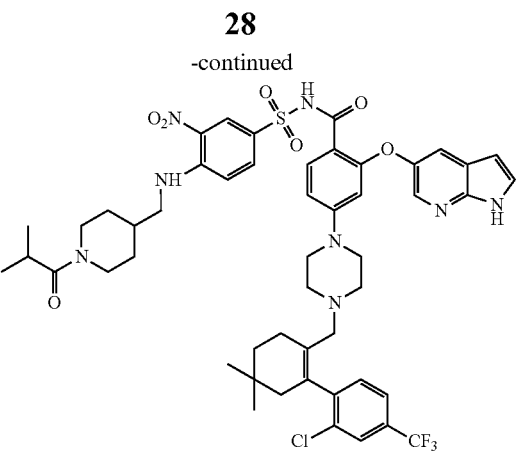
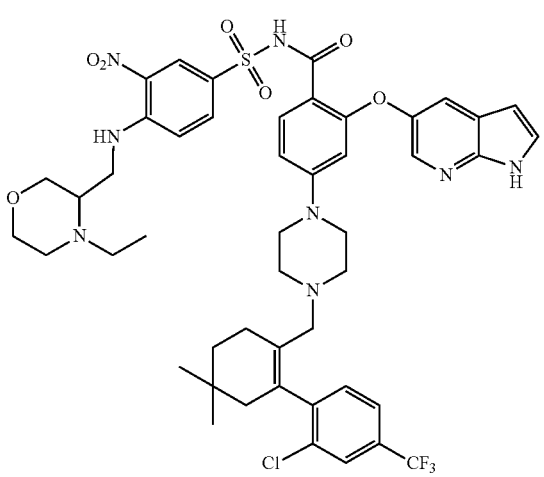
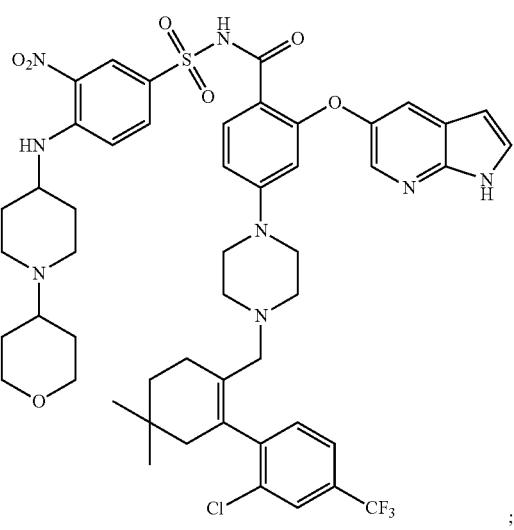
;

or a compound of the following formula, a stereoisomer thereof or a pharmaceutically acceptable salt thereof:
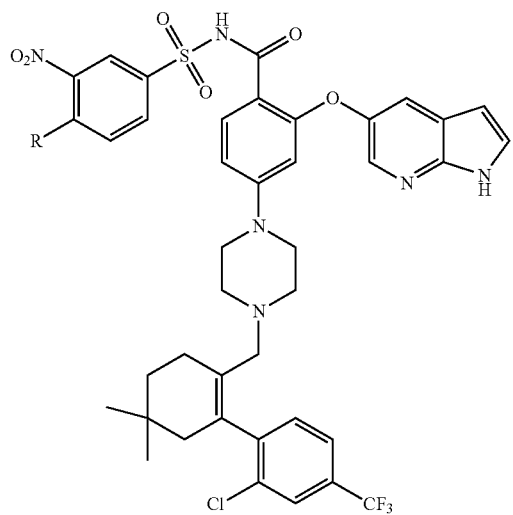
wherein R is independently selected from the group consisting of:
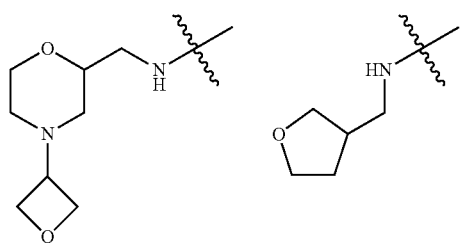
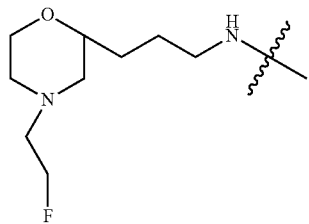
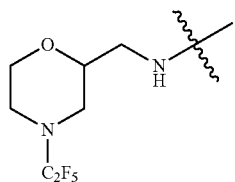
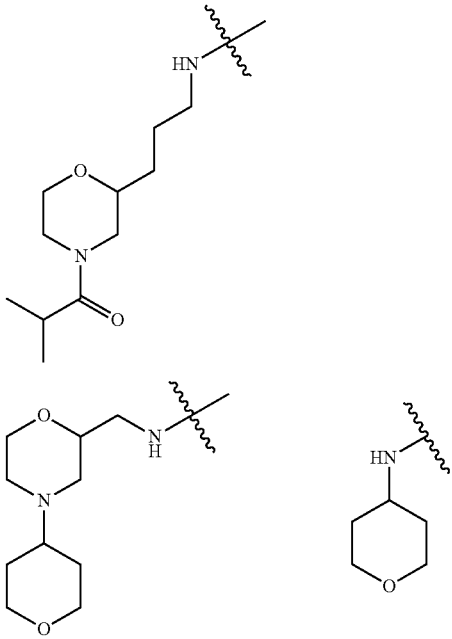
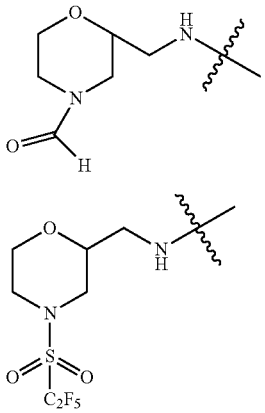
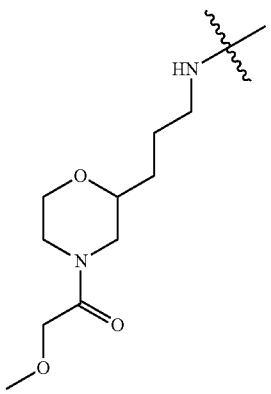
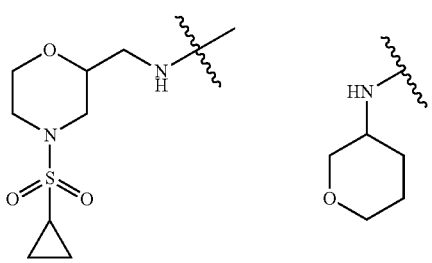

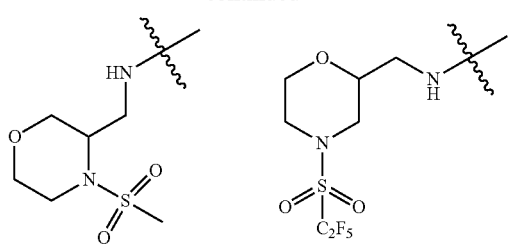
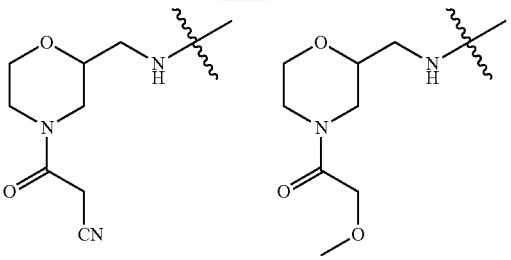
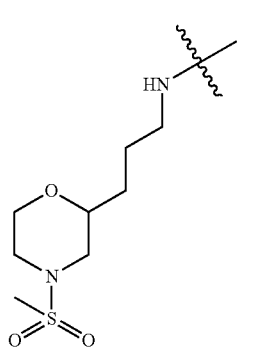
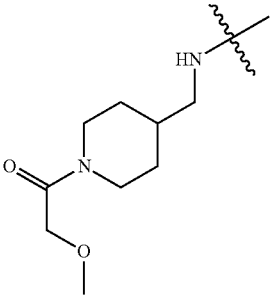
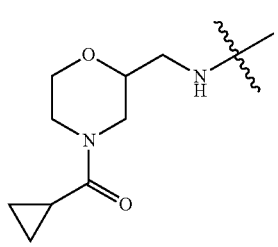
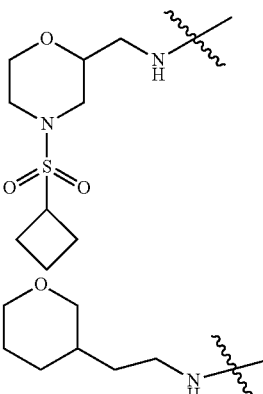
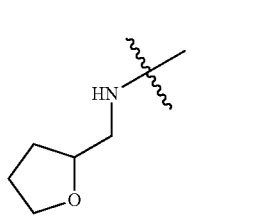
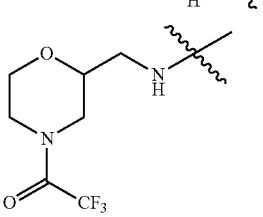
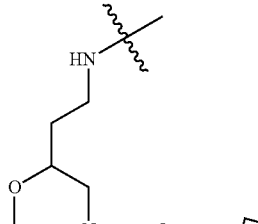
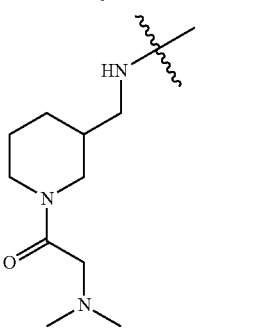
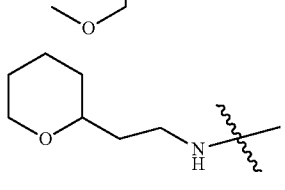
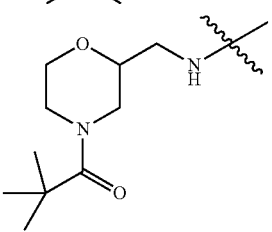

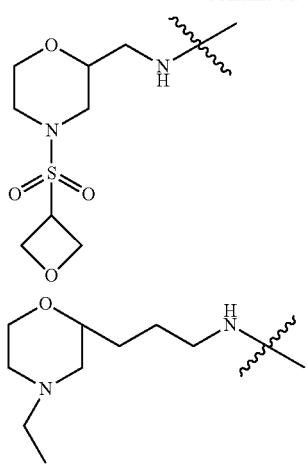
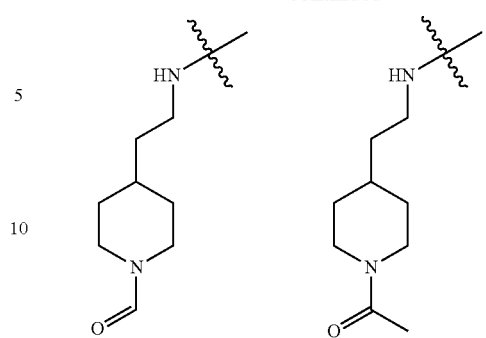
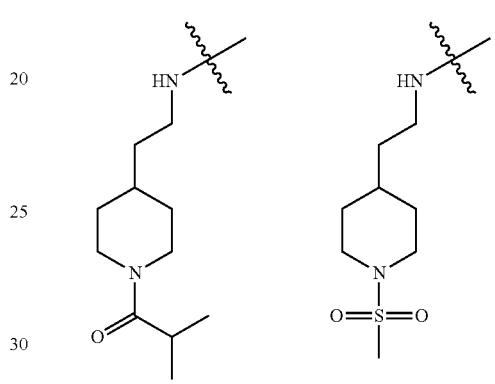
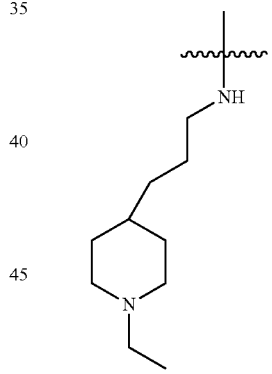
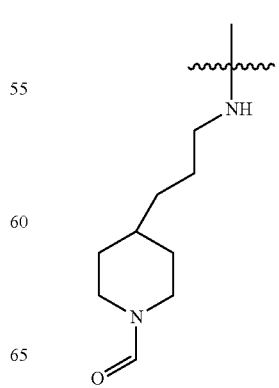
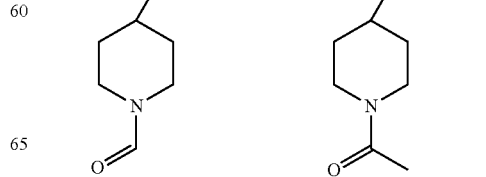

-continued
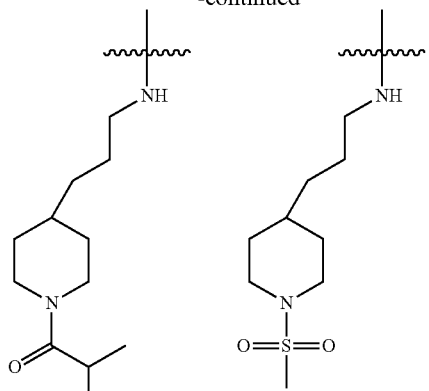
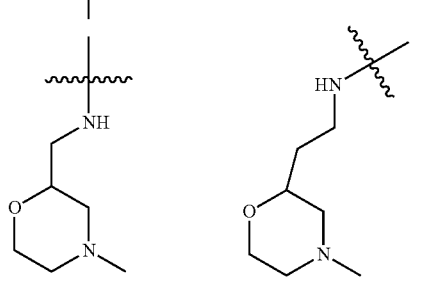
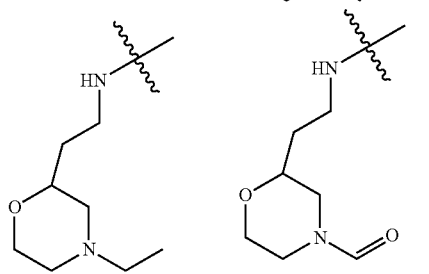
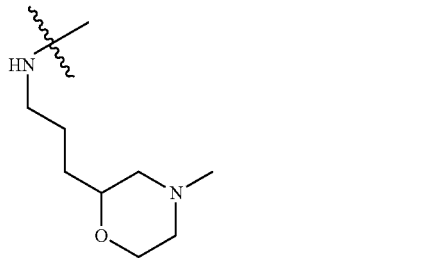
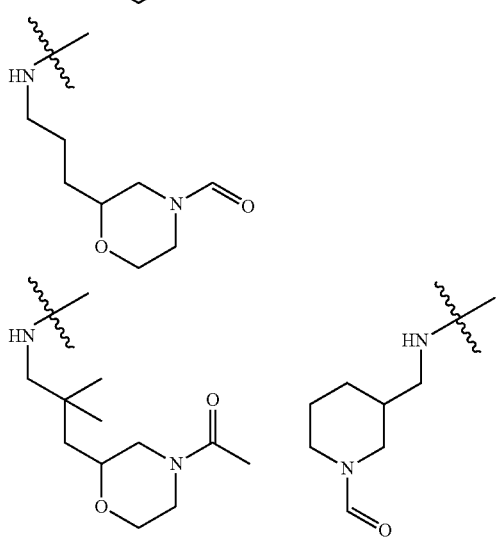
-continued
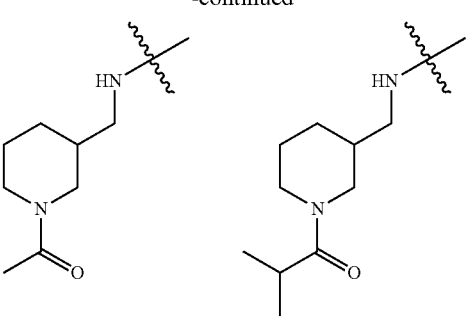
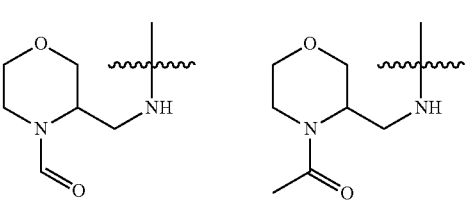
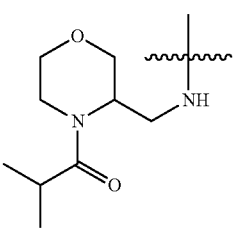
The present application relates to a compound of a formula selected from the group consisting of the following formulas or a pharmaceutically acceptable salt thereof:
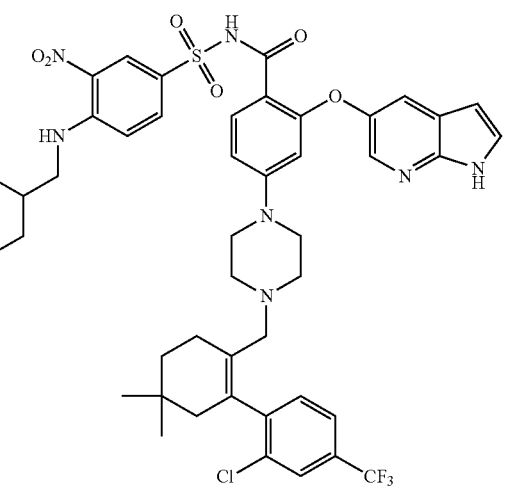

37
-continued
38
-continued
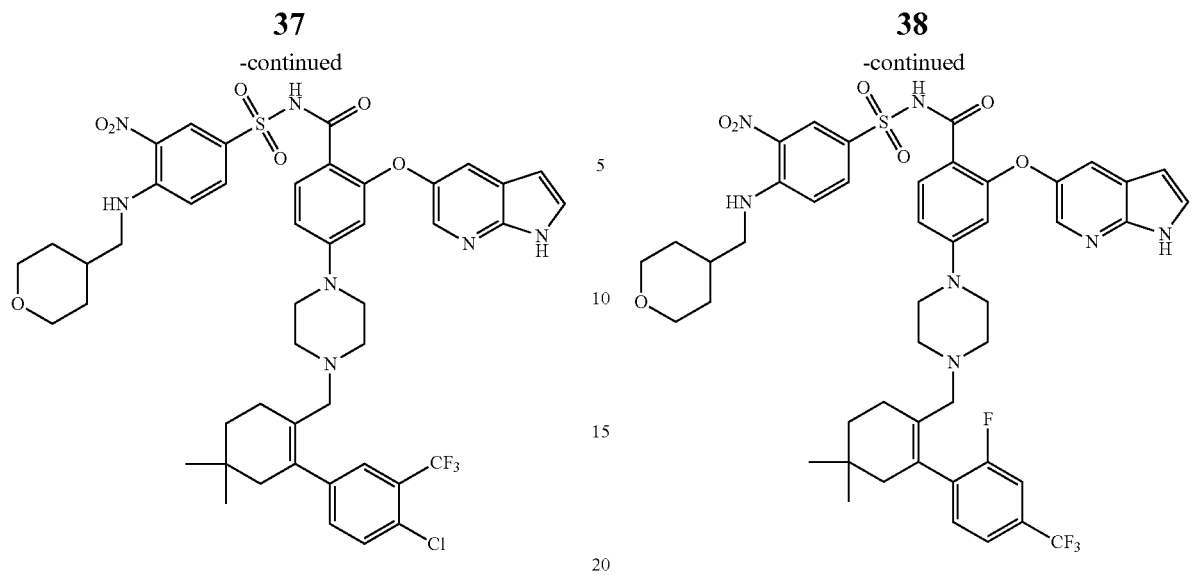
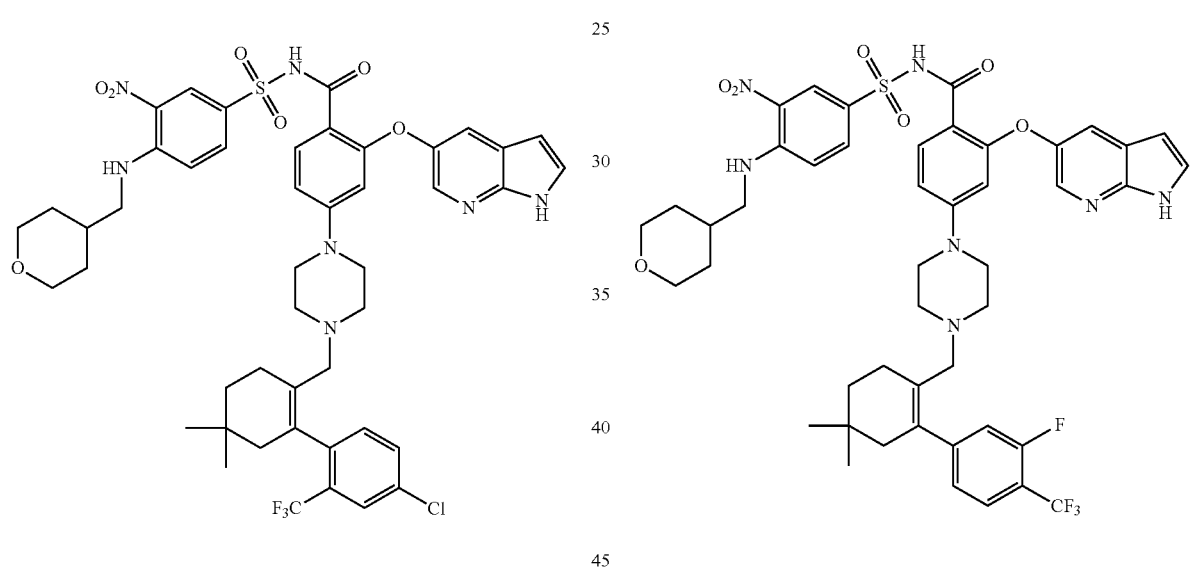
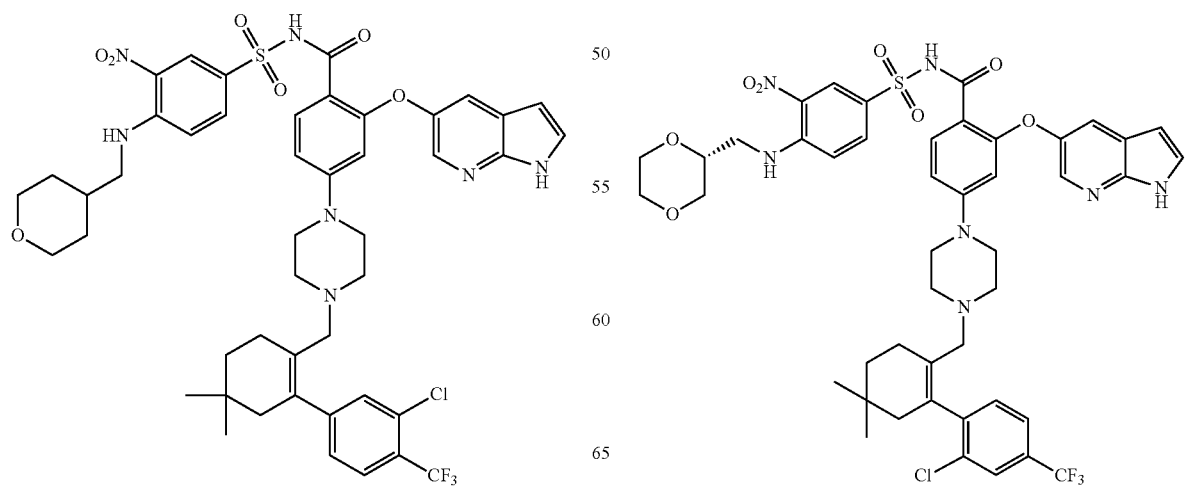

39
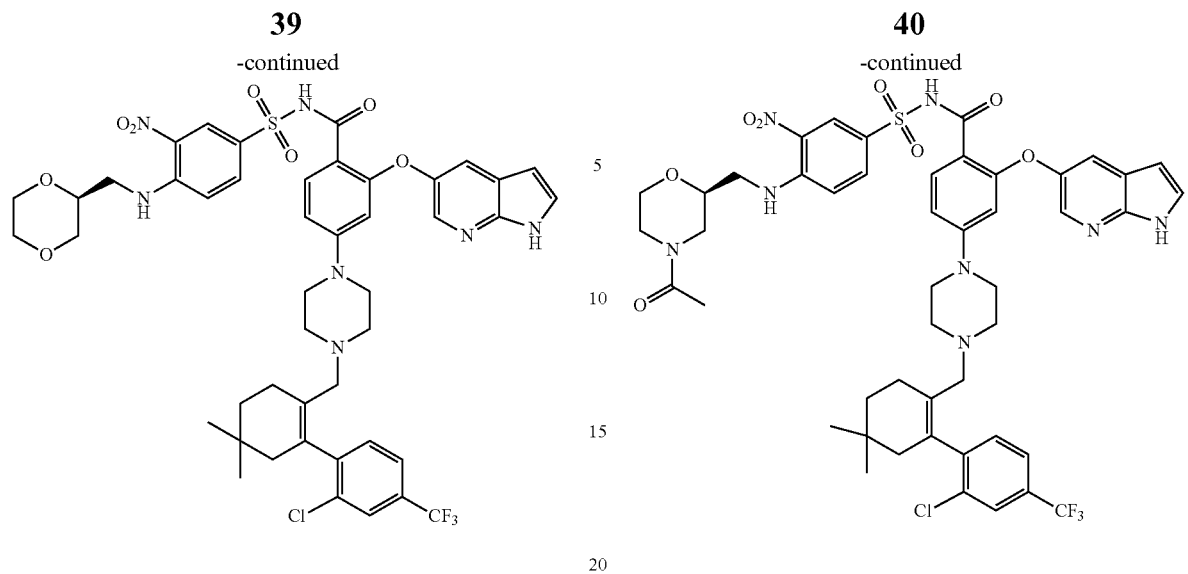
40
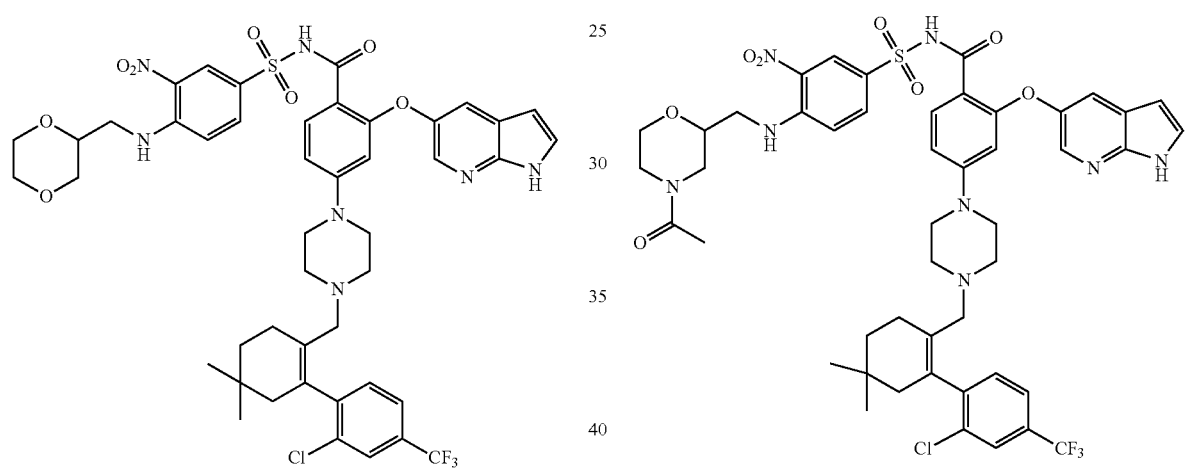
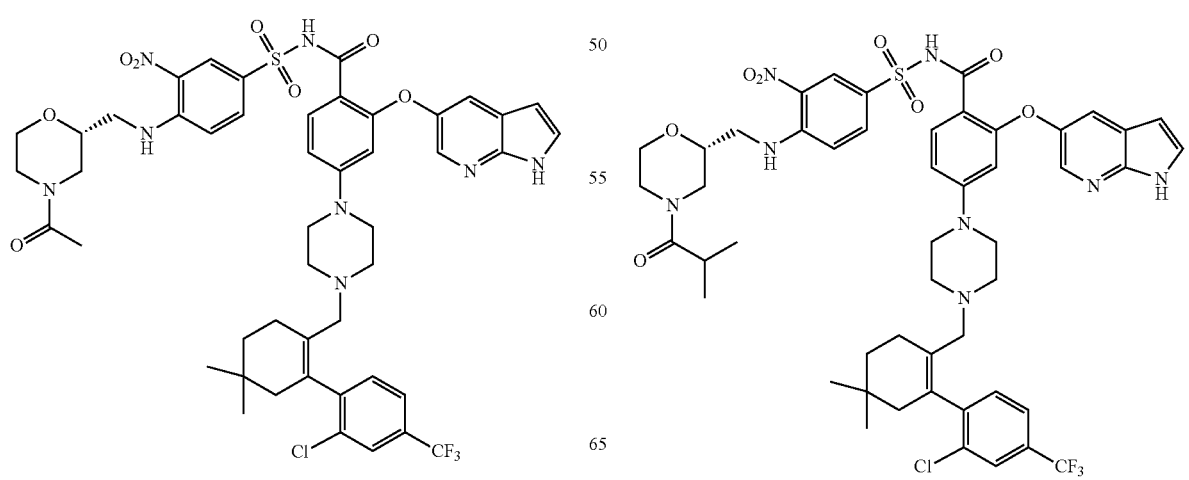

41
-continued
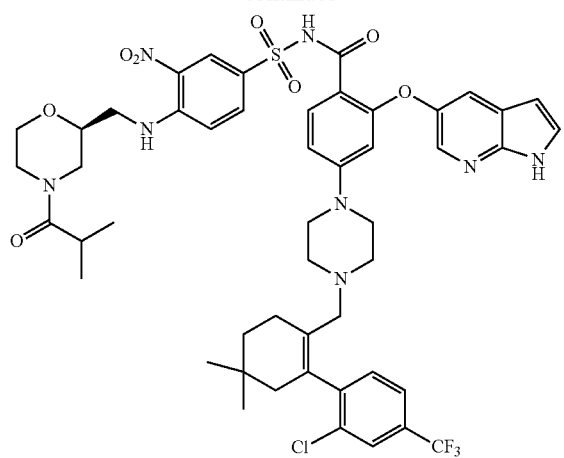
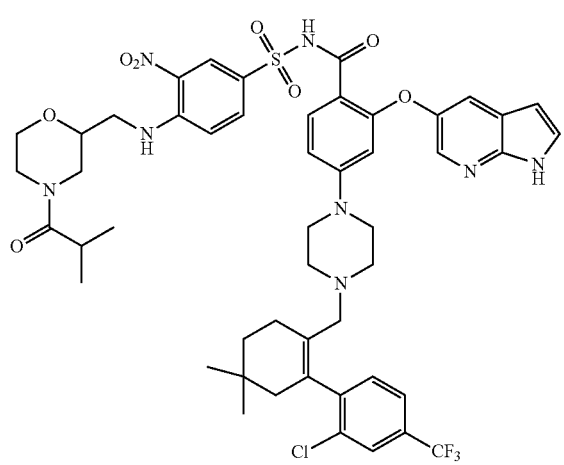
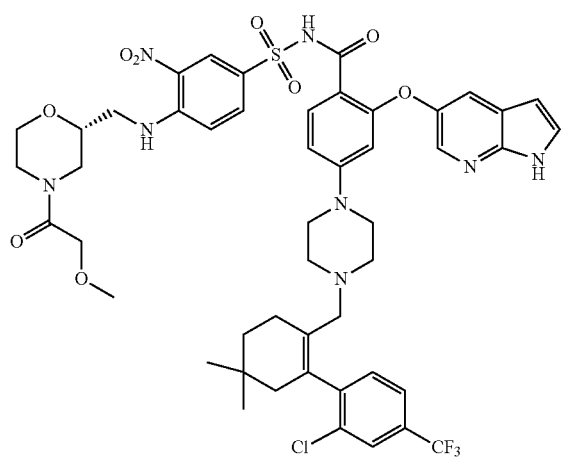
42
-continued
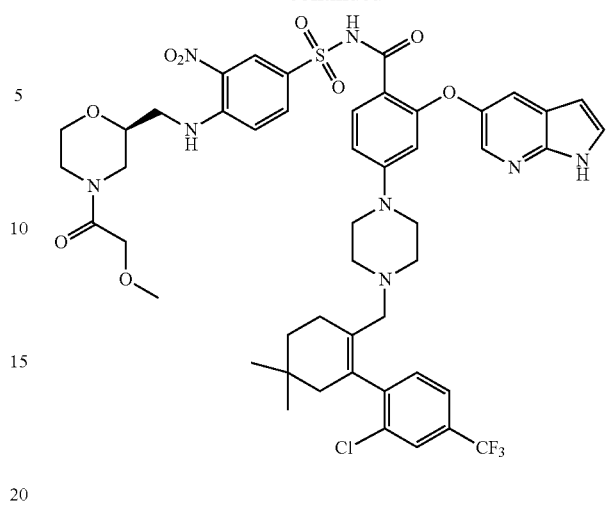
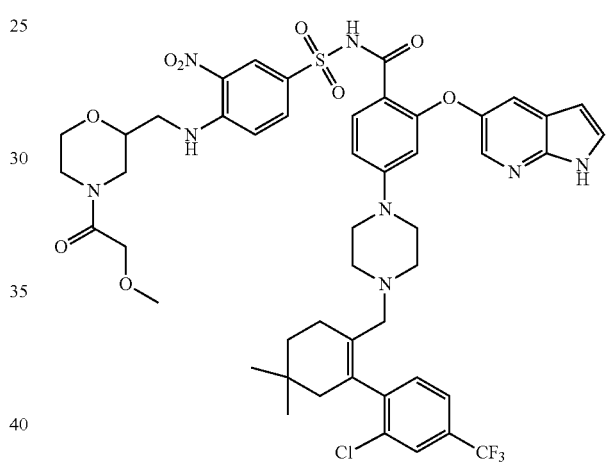
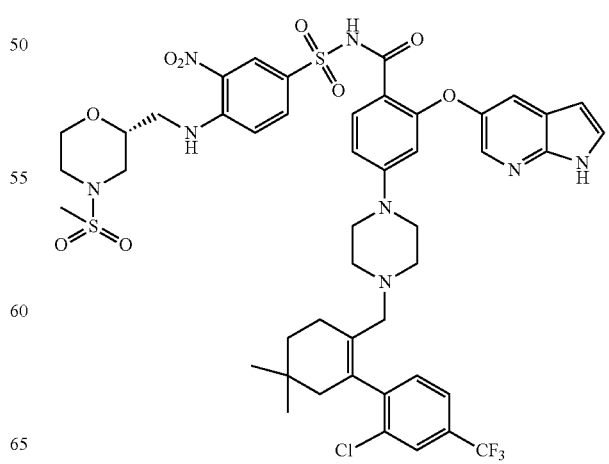

43
-continued
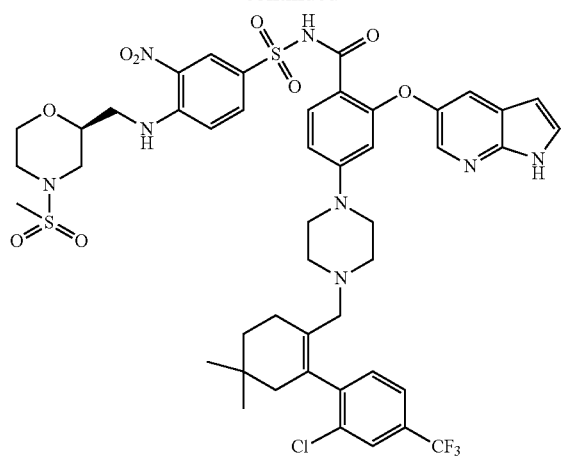
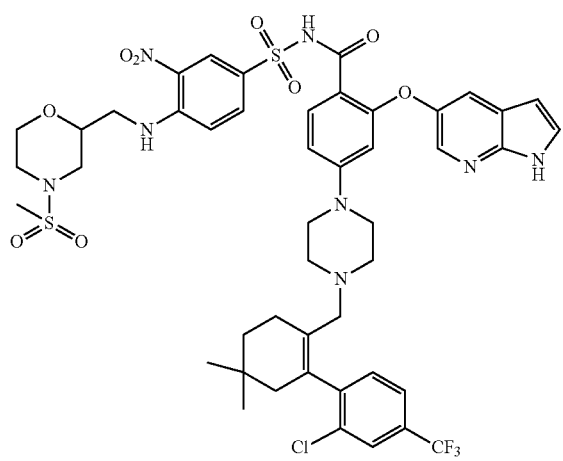
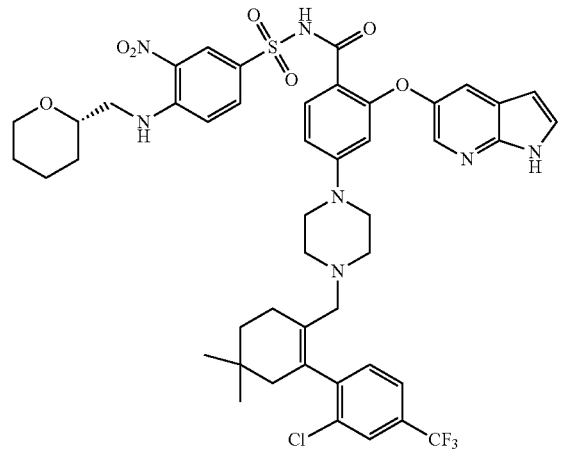
44
-continued
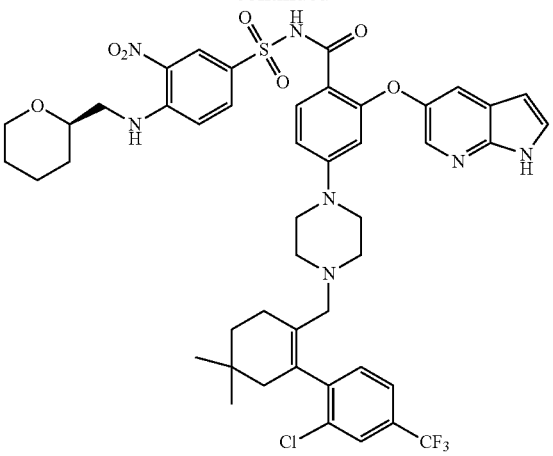
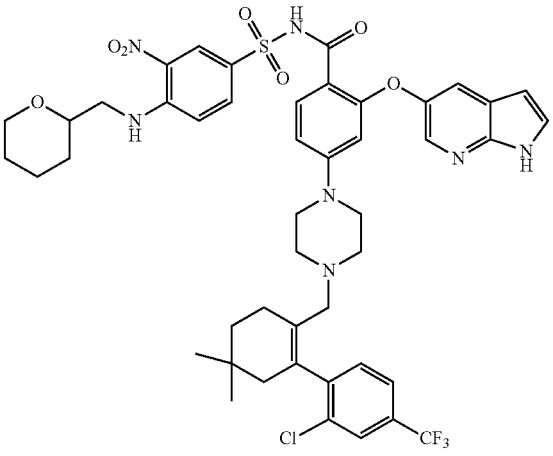

45
-continued
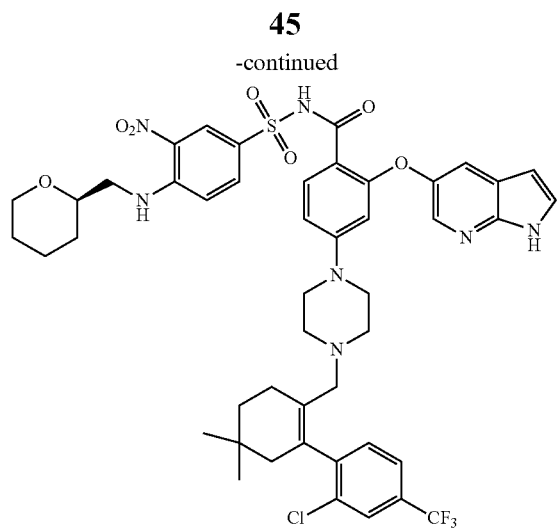
46
-continued
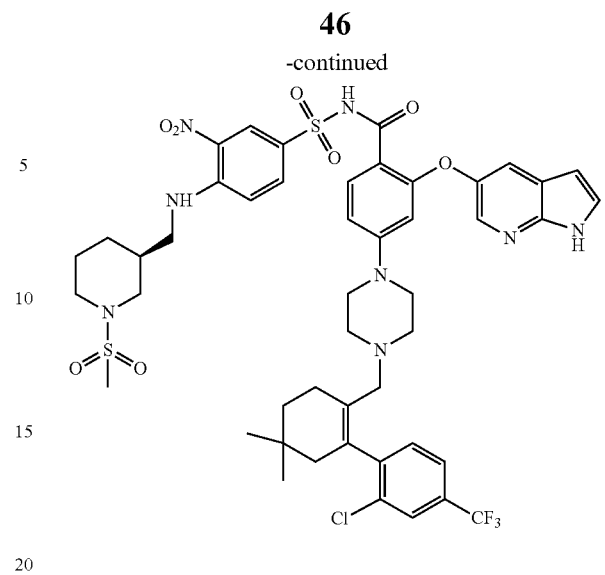
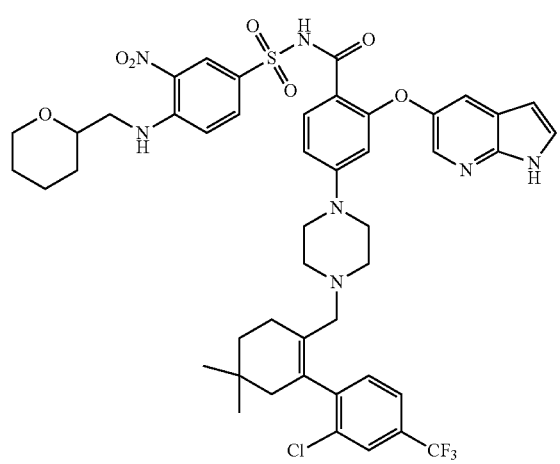
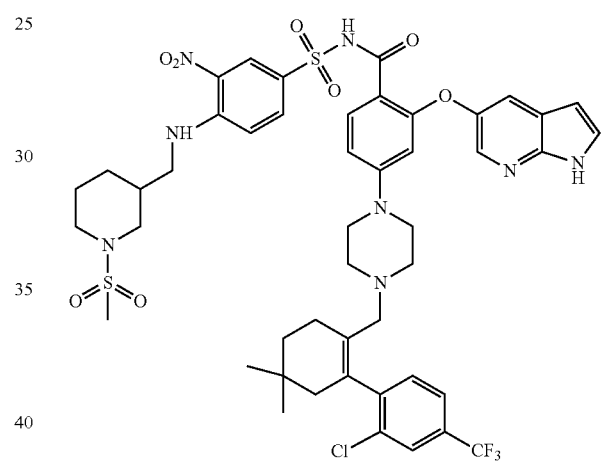
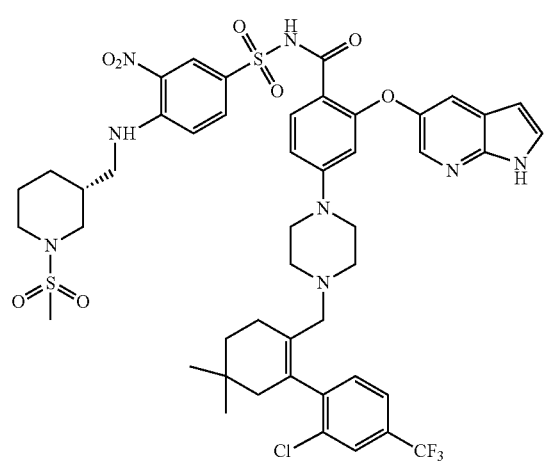
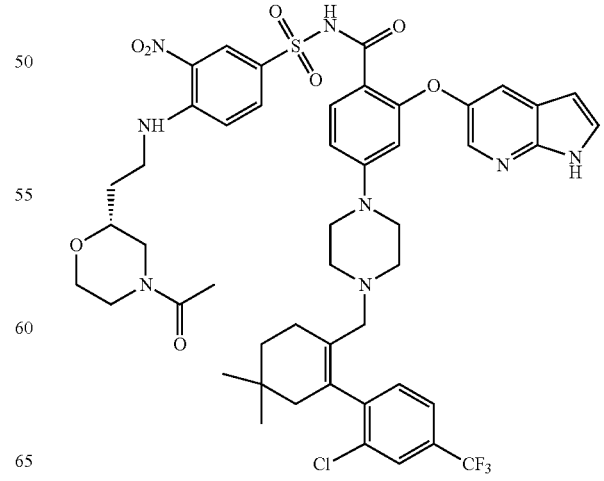

47
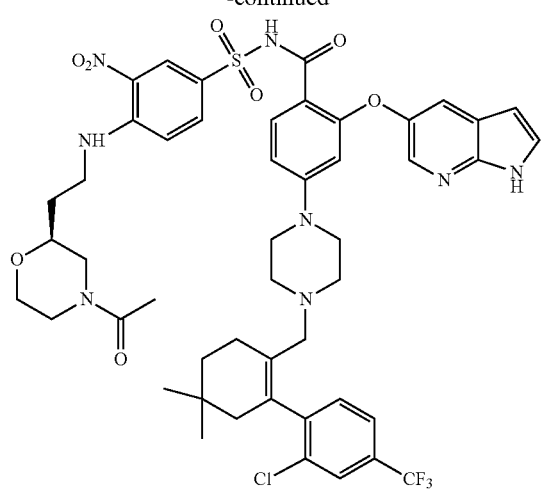
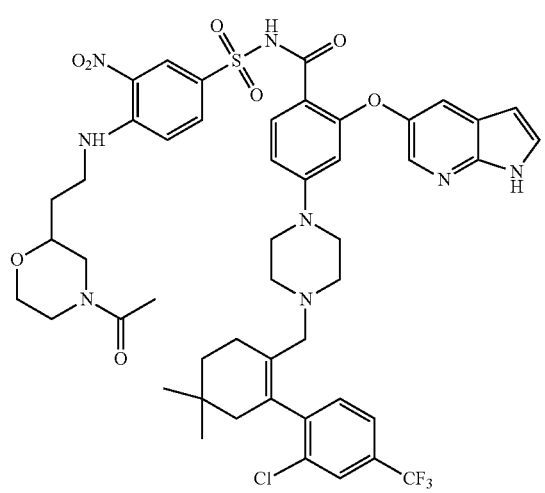
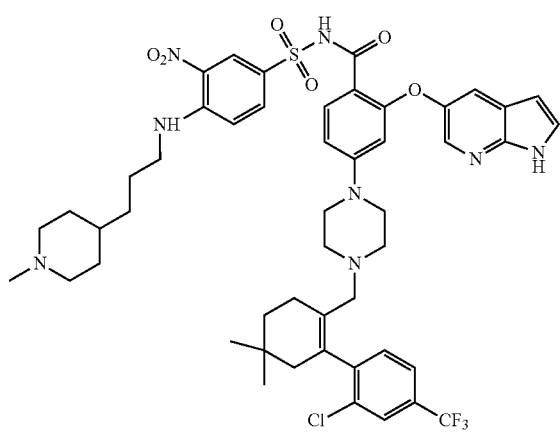
48
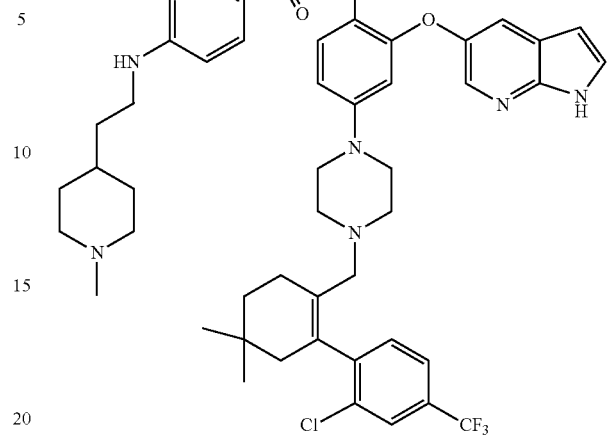
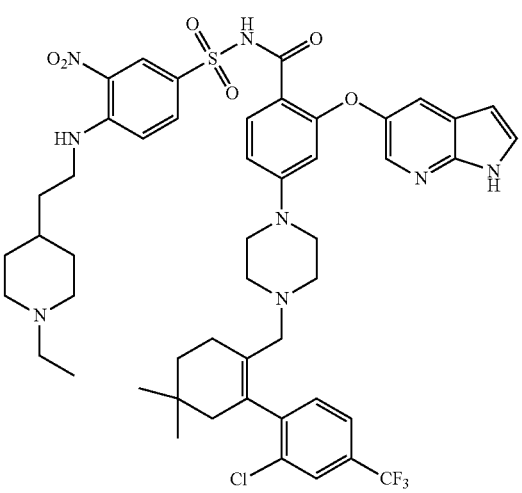
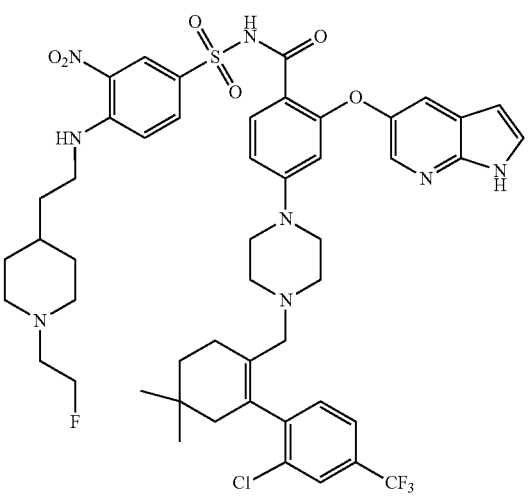

49
-continued
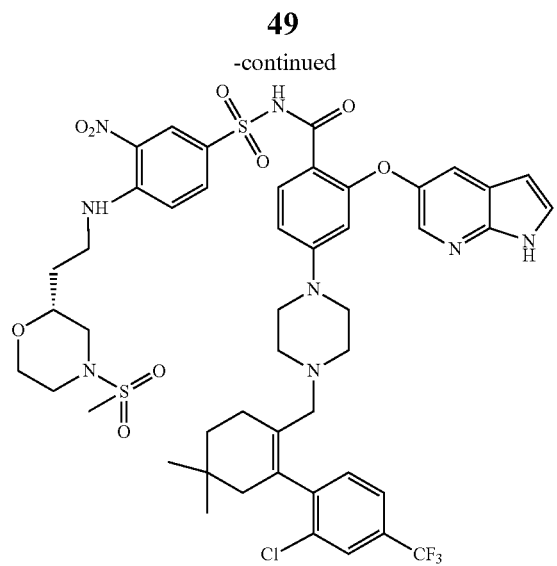
50
-continued
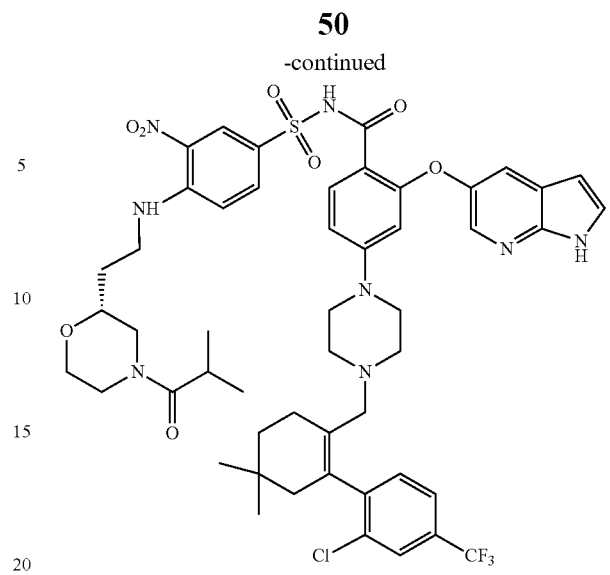
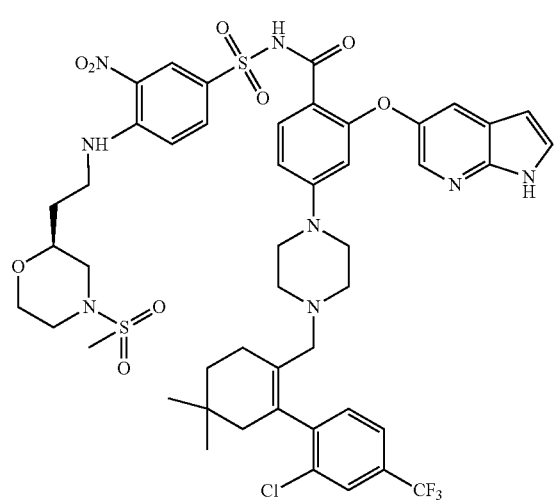
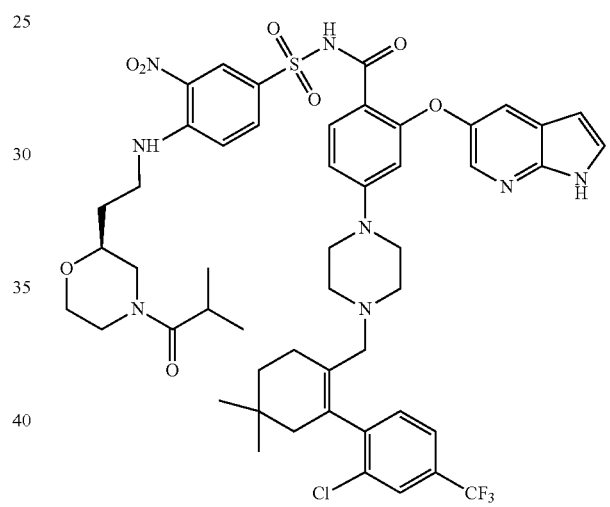
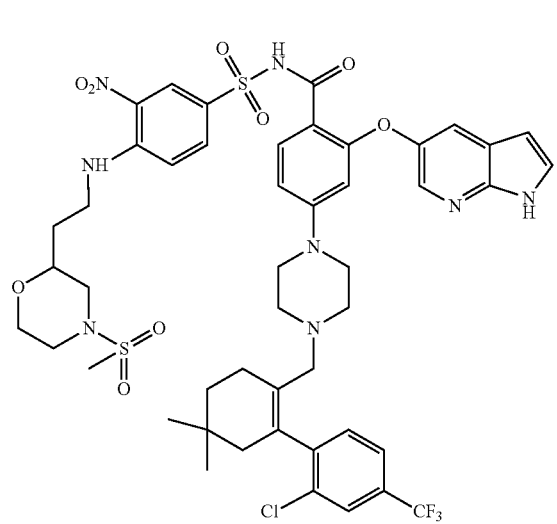
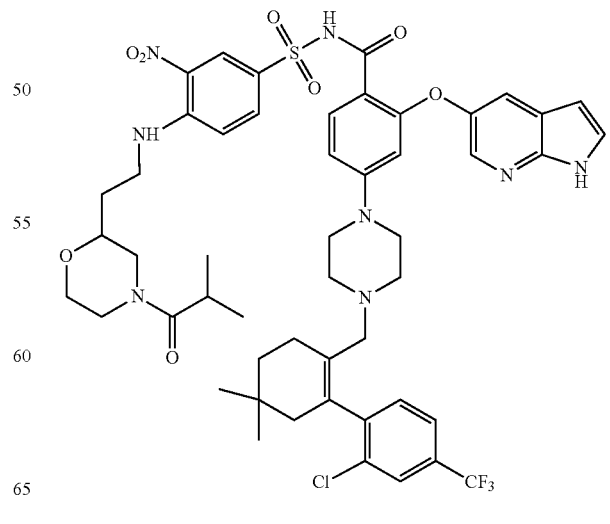

51
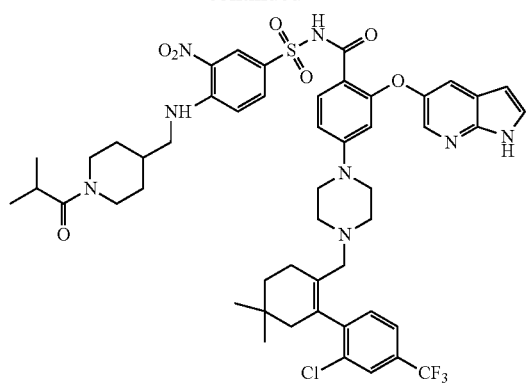
52
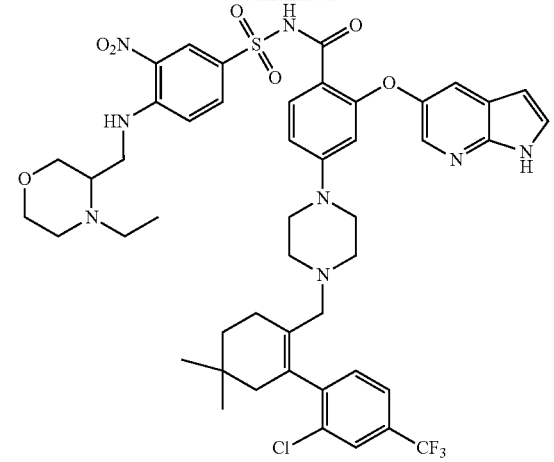
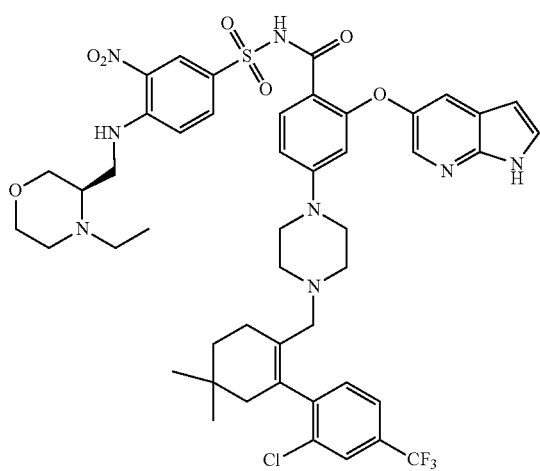
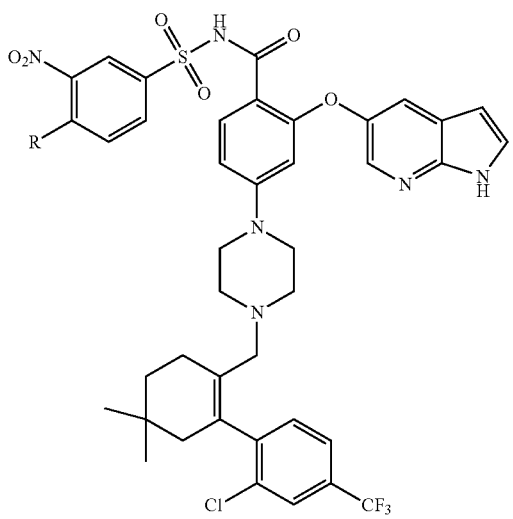
or a compound of the following formula or a pharmaceutically acceptable salt thereof:

wherein R is independently selected from the group consisting of:
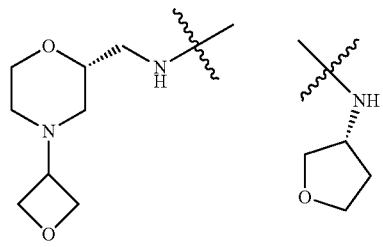
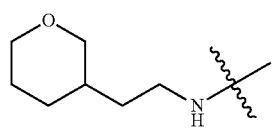
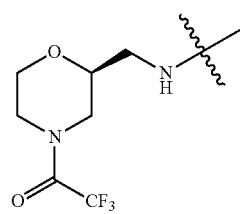
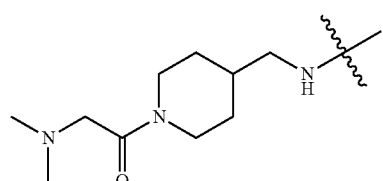
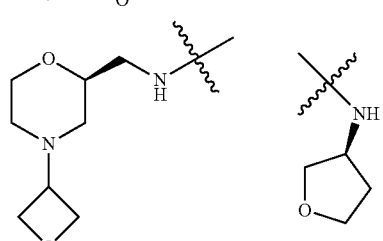
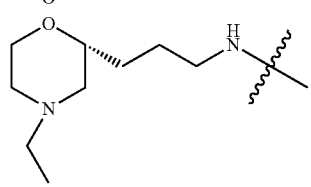
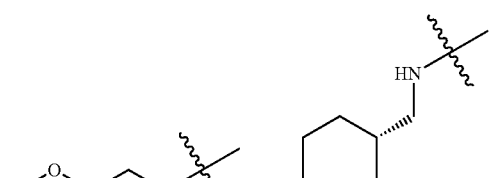
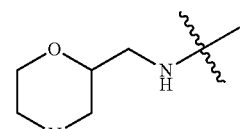
-continued
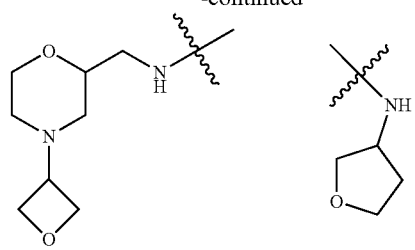
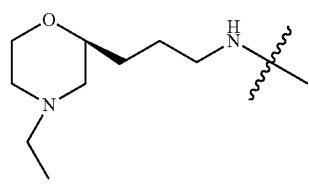
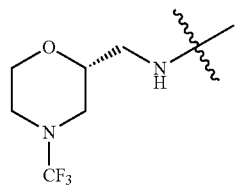
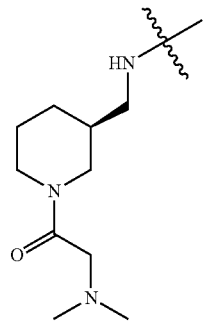
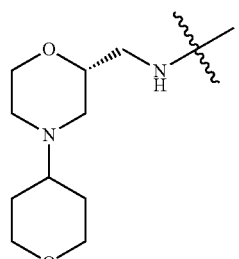
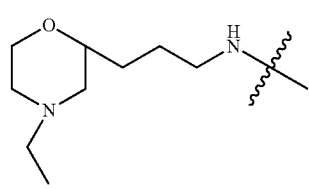
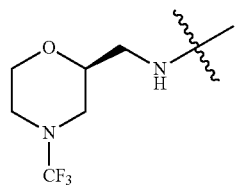
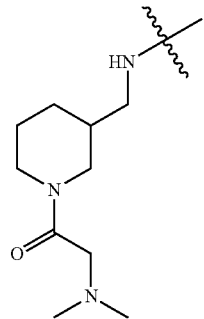

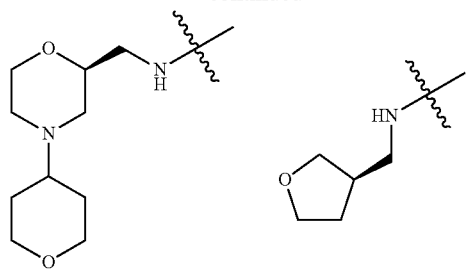
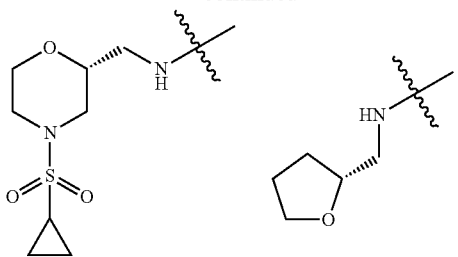
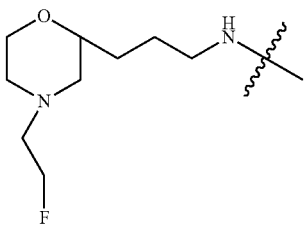
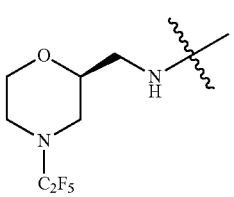
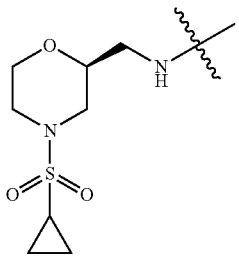
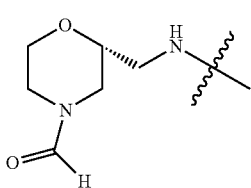
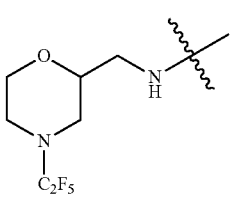

-continued
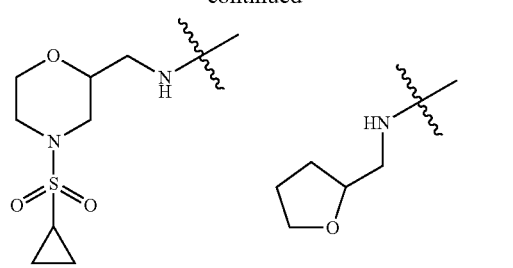 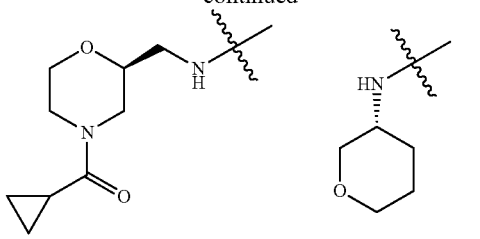
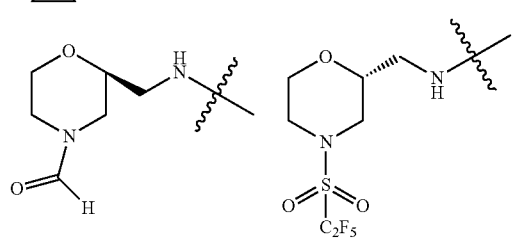 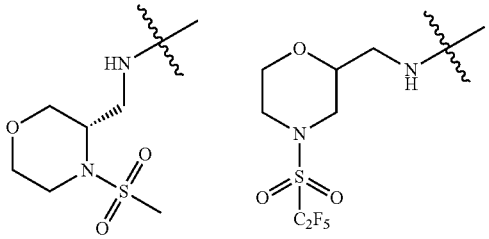
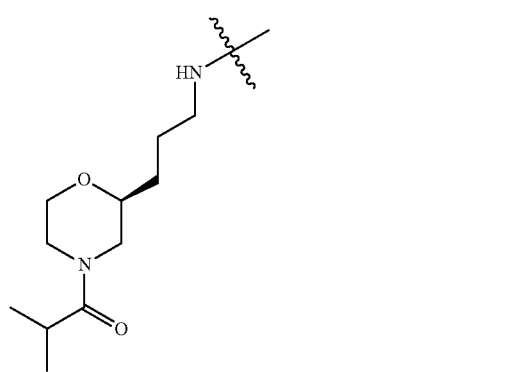 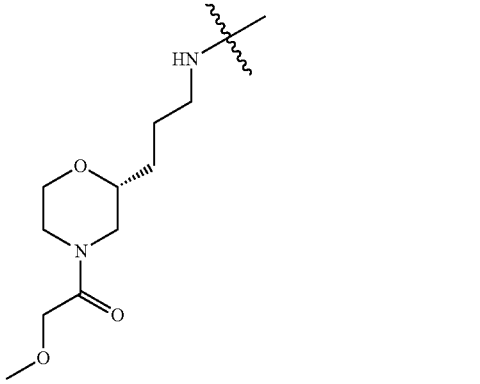
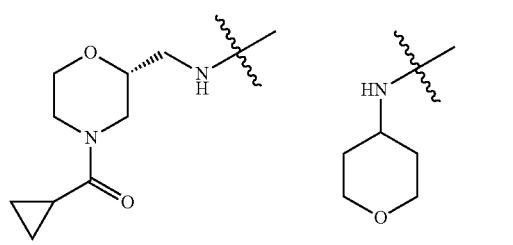 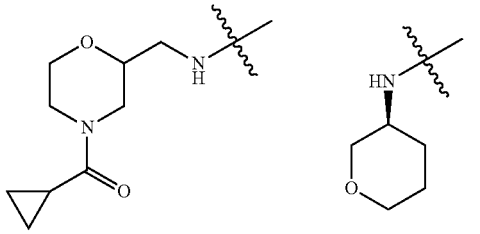
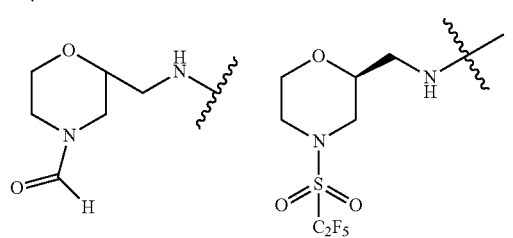 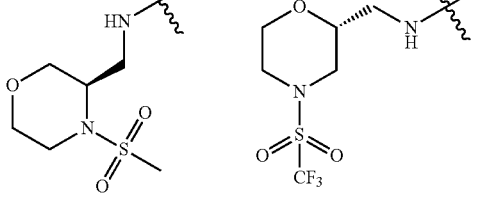
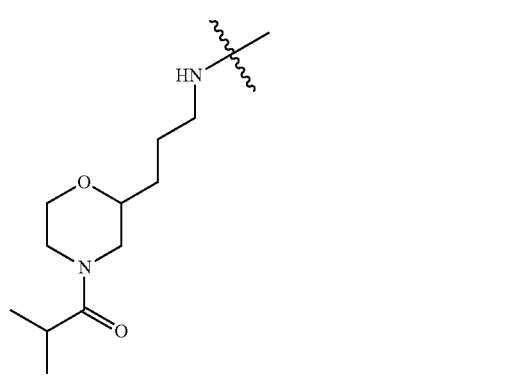 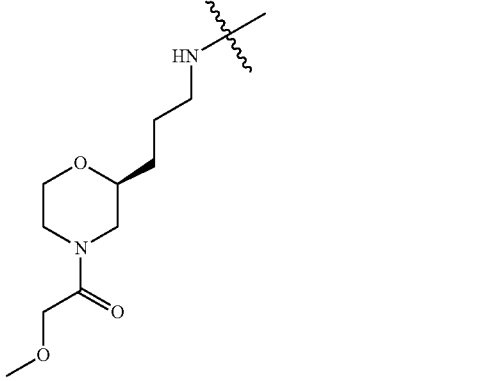

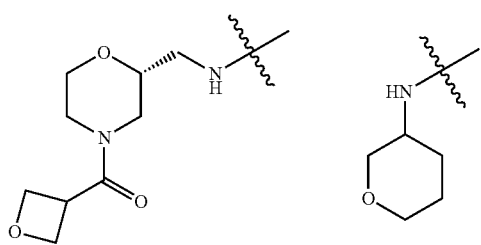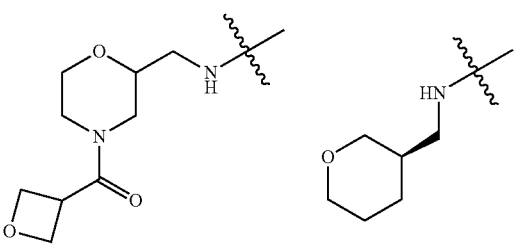

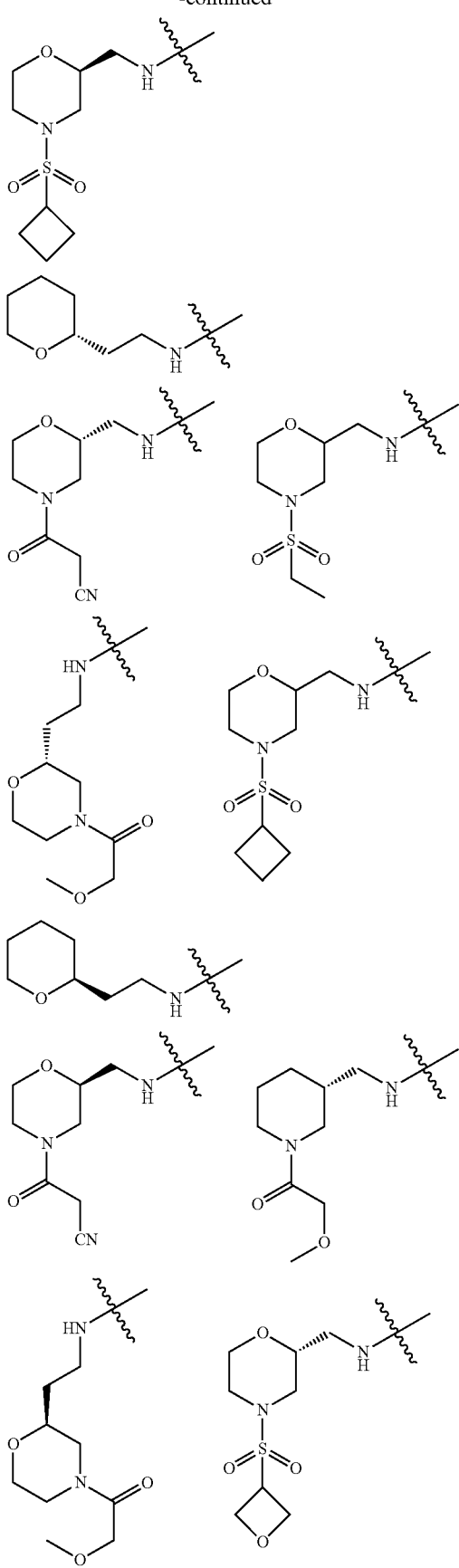
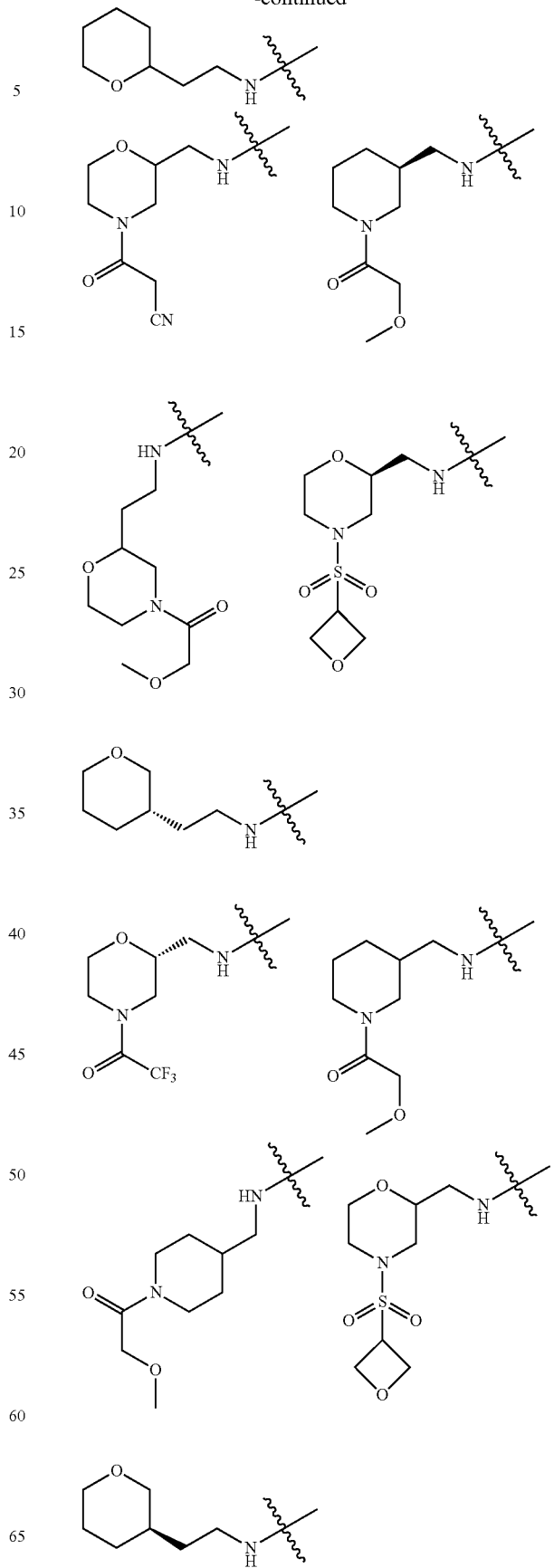

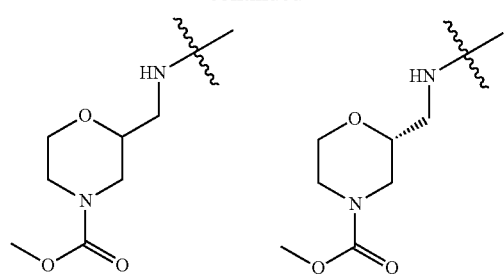
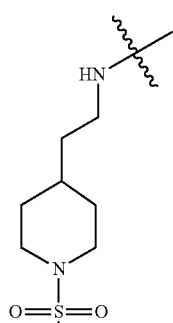
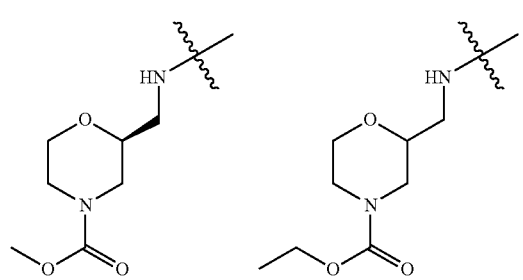
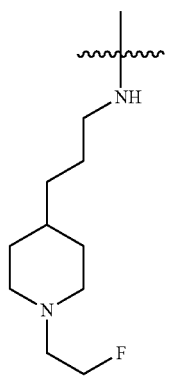
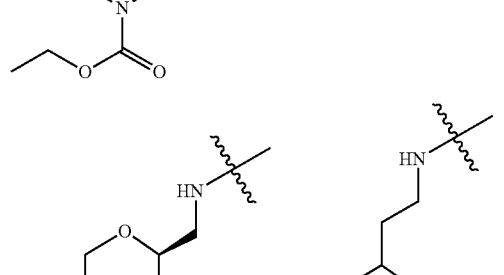
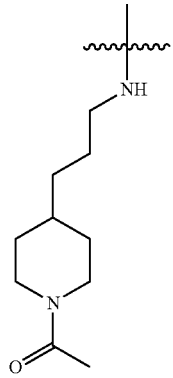
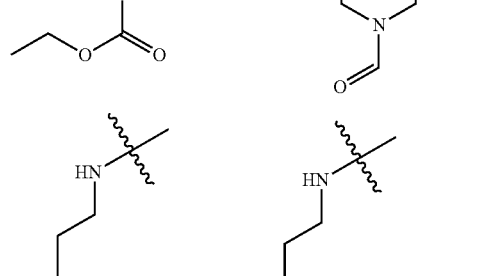
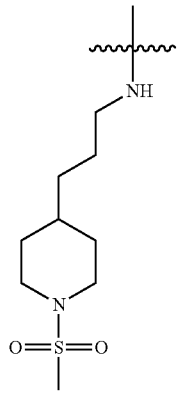
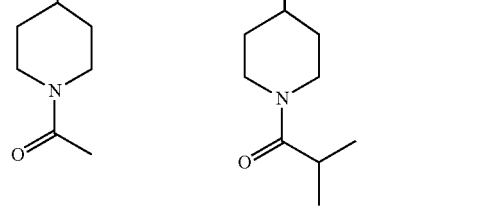

65
-continued
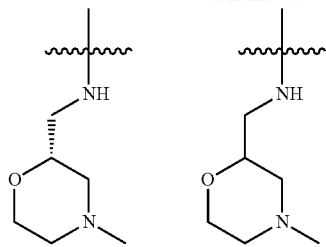
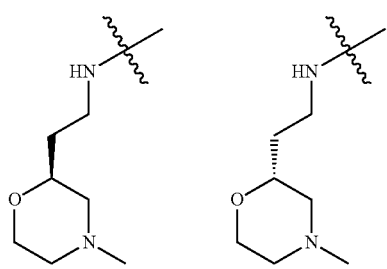
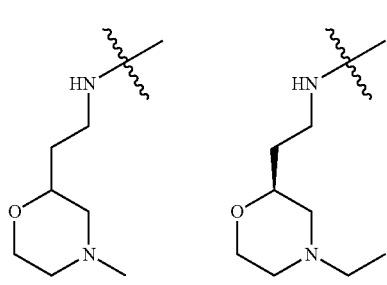
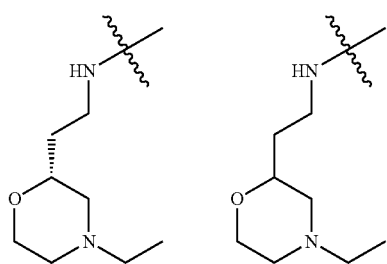
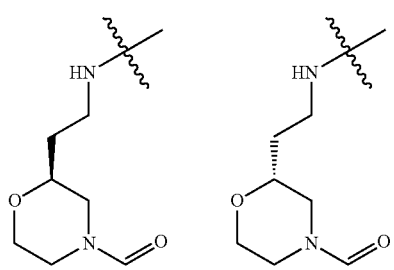
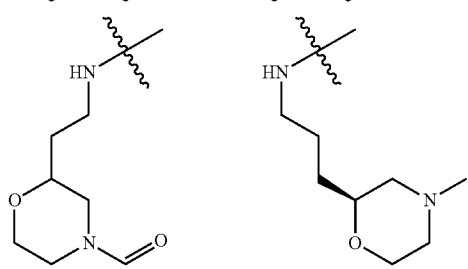
66
-continued
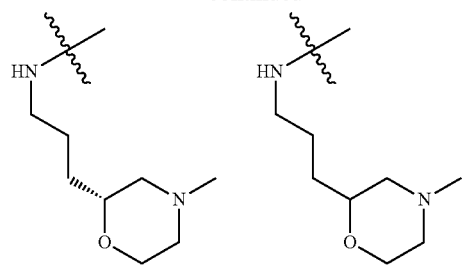
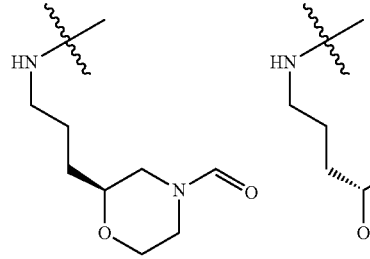
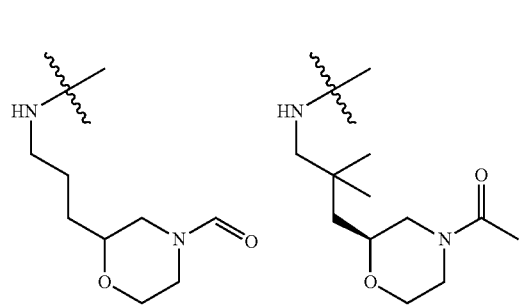
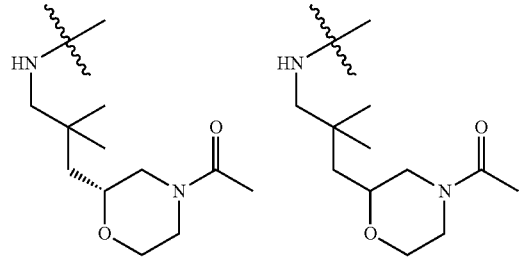
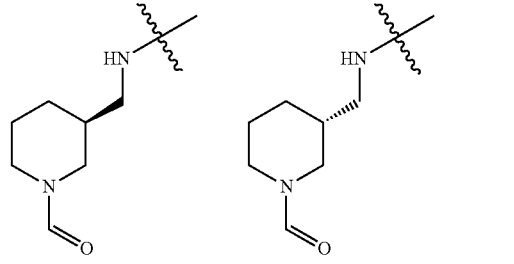
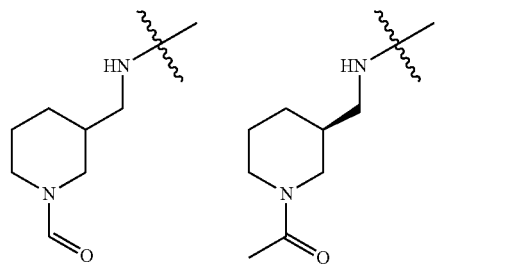

-continued

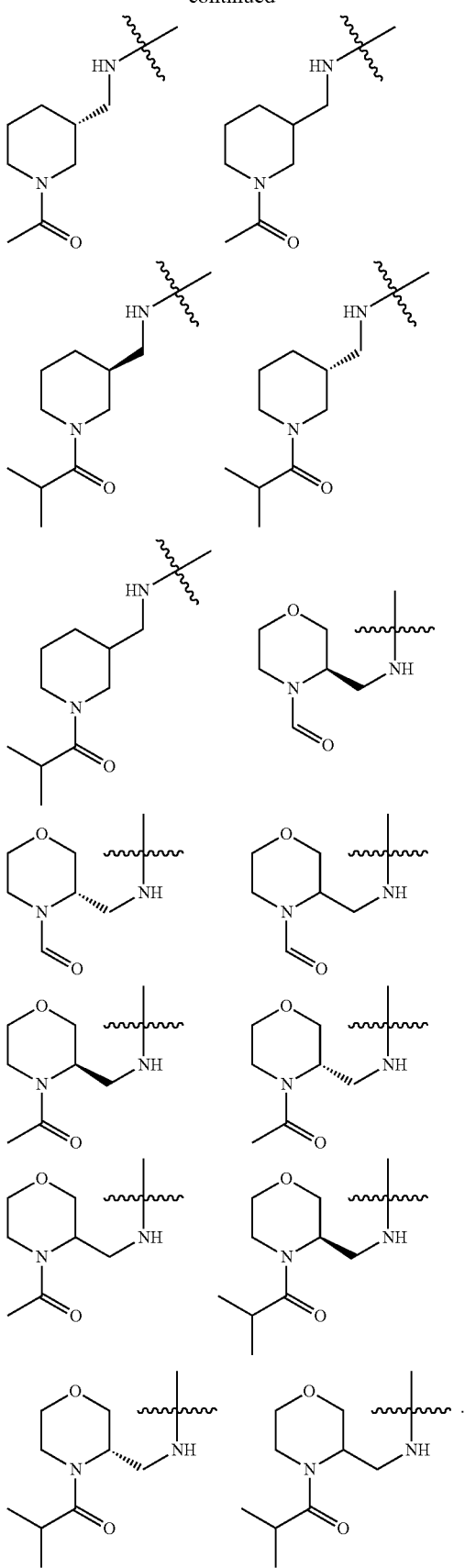

In another aspect, the present application relates to a pharmaceutical composition comprising the compound of formula I, the compound of formula II or a specific compound, the stereoisomer thereof or the pharmaceutically acceptable salt thereof disclosed herein. In some embodiments, the pharmaceutical composition disclosed herein further comprises a pharmaceutically acceptable excipient.

In another aspect, the present application describes a method for treating an anti-apoptotic protein BCL-2-related disease in a mammal, comprising administering to a mammal (preferably a human) in need of such treatment a therapeutically effective amount of the compound of formula I, the compound of formula II or a specific compound, the stereoisomer thereof or the pharmaceutically acceptable salt thereof, or the pharmaceutical composition thereof.

In another aspect, the present application describes use of the compound of formula I, the compound of formula II or a specific compound, the stereoisomer thereof or the pharmaceutically acceptable salt thereof, or the pharmaceutical composition thereof in preparing a medicament for preventing or treating an anti-apoptotic protein BCL-2-related disease.

In another aspect, the present application describes use of the compound of formula I, the compound of formula II or a specific compound, the stereoisomer thereof or the pharmaceutically acceptable salt thereof, or the pharmaceutical composition thereof in preventing or treating an anti-apoptotic protein BCL-2-related disease.

In another aspect, the present application describes the compound of formula I, the compound of formula II or a specific compound, the stereoisomer thereof or the pharmaceutically acceptable salt thereof, or the pharmaceutical composition thereof for use in preventing or treating an anti-apoptotic protein BCL-2-related disease.

The anti-apoptotic protein BCL-2-related disease is selected from cancer. The cancer is selected from acute lymphocytic leukemia.

Definitions

Unless otherwise stated, the following terms used in the present application shall have the following meanings. A specific term, unless otherwise specifically defined, should not be considered uncertain or unclear, but construed according to its common meaning in the field. When referring to a trade name, it is intended to refer to its corresponding commercial product or its active ingredient.

The term "substituted" means that any one or more hydrogen atoms on a specific atom are substituted with substituents, as long as the valence of the specific atom is normal and the resulting compound is stable. When the substituent is oxo (namely =O), it means that two hydrogen atoms are substituted, and oxo is not available on an aromatic group.

The terms "optional" or "optionally" means that the subsequently described event or circumstance may, but not necessarily, occur. The description includes instances where the event or circumstance occurs and instances where the event or circumstance does not. For example, an ethyl being "optionally" substituted with halogen means that the ethyl may be unsubstituted (—CH$_2$CH$_3$), monosubstituted (for example, —CH$_2$CH$_2$F), polysubstituted (for example, —CHFCH$_2$F, —CH$_2$CHF$_2$ and the like) or fully substituted (—CF$_2$CF$_3$). It will be understood by those skilled in the art that for any group comprising one or more substituents, no substitution or substituting pattern that is spatially impossible to exist or cannot be synthesized will be introduced.

C$_{m-n}$ used herein means that the moiety has an integer number of carbon atoms in the given range. For example, "$C_{1-6}$" means that the group may have 1 carbon atom, 2 carbon atoms, 3 carbon atoms, 4 carbon atoms, 5 carbon atoms or 6 carbon atoms.

The term "halo" or "halogen" refers to fluorine, chlorine, bromine and iodine.

The term "alkyl" refers to hydrocarbyl with a general formula of $C_nH_{2n+1}$. The alkyl may be linear or branched. For example, the term "$C_{1-6}$ alkyl" refers to alkyl containing 1-6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). The alkyl moieties (namely alkyl) of alkoxy, alkylamino, dialkylamino, alkylsulfonyl and alkylthio are similarly defined as above. For another example, the term "$C_{1-4}$ alkyl" refers to alkyl containing 1-4 carbon atoms (for example, methyl, ethyl, n-propyl, isopropyl, n-butyl, isobutyl, sec-butyl, tert-butyl, etc.).

The term "alkylene" refers to a divalent group formed by the removal of 1 hydrogen at any position of alkyl. For example, non-limiting examples of the term "$C_{0-6}$ alkylene" include, but are not limited to, methylene, ethylidene, methylmethylene, dimethylmethylene, 1,3-propylidene and the like. $C_0$ represents a bond.

The term "cycloalkyl" refers to a carbon ring that is fully saturated and may exist as a monocyclic, bridged cyclic or spiro structure. Unless otherwise specified, the carbon ring is generally a 3-10 membered ring. Non-limiting examples of cycloalkyl include, but are not limited to, cyclopropyl, cyclobutyl, cyclopentyl, cyclohexyl, norbornyl(bicyclo[2.2.1]heptyl), bicyclo[2.2.2]octyl, adamantyl and the like.

The term "heterocycloalkyl" refers to a cyclic group that is fully saturated and may exist as a monocyclic, bridged cyclic or spiro structure. Unless otherwise specified, the heterocyclyl is generally a 3-7 membered ring containing 1-3 heteroatoms (preferably 1 or 2 heteroatoms) independently selected from the group consisting of sulfur, oxygen and/or nitrogen. Examples of 3 membered heterocycloalkyl include, but are not limited to, oxiranyl, thiiranyl, and aziranyl. Non-limiting examples of 4 membered heterocycloalkyl include, but are not limited to, azetidinyl, oxetanyl, and thietanyl. Examples of 5 membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl. Examples of 6 membered heterocycloalkyl include, but are not limited to, piperidinyl, tetrahydropyranyl, tetrahydrothiopyranyl, morpholinyl, piperazinyl, 1,4-oxathianyl, 1,4-dioxanyl, thiomorpholinyl, 1,3-dithianyl, and 1,4-dithianyl. Examples of 7 membered heterocycloalkyl include, but are not limited to, azacycloheptanyl, oxacycloheptanyl and thiocycloheptanyl. Preferably, the heterocycloalkyl is a monocyclic heterocycloalkyl having 5 or 6 ring atoms.

The term "treat" or "treatment" means administering the compound or formulation disclosed herein to prevent, ameliorate or eliminate a disease or one or more symptoms associated with the disease, and includes: (i) preventing the occurrence of a disease or disease state in a mammal, particularly when such a mammal is predisposed to the disease state but has not yet been diagnosed as having it; (ii) inhibiting a disease or disease state, i.e., arresting its development; and (iii) alleviating a disease or disease state, i.e., causing its regression.

The term "therapeutically effective amount" refers to an amount of the compound disclosed herein for (i) treating or preventing a specific disease, condition or disorder; (ii) alleviating, ameliorating or eliminating one or more symptoms of a specific disease, condition or disorder, or (iii) preventing or delaying onset of one or more symptoms of a specific disease, condition or disorder described herein. The amount of the compound disclosed herein that is considered as the "therapeutically effective amount" varies dependently on the compound, the disease state and its severity, the administration regimen, and the age of the mammal to be treated, but can be determined routinely by those skilled in the art in accordance with their knowledge and the present disclosure.

The term "pharmaceutically acceptable" means that those compounds, materials, compositions, and/or dosage forms are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or pharmaceutically acceptable salts thereof disclosed herein and a pharmaceutically acceptable excipient. The pharmaceutical composition is intended to facilitate the administration of the compound to an organic entity.

The term "pharmaceutically acceptable excipient" refers to those excipients which do not have a significant irritating effect on an organic entity and do not impair the biological activity and properties of the active compound. Suitable excipients are well known to those skilled in the art, for example carbohydrate, wax, water-soluble and/or water-swellable polymers, hydrophilic or hydrophobic material, gelatin, oil, solvent, or water.

The word "comprise" and variations thereof such as "comprises" or "comprising" will be understood in an open, non-exclusive sense, i.e., "including but not limited to".

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerization and imine-enamine isomerization. A specific example of a proton tautomer is an imidazole moiety where a proton can transfer between two ring nitrogens. A valence tautomer includes the interconversion via recombination of some bonding electrons.

The present application also comprises isotopically-labeled compounds which are identical to those recited herein but have one or more atoms replaced by an atom having an atomic mass or mass number different from the atomic mass or mass number usually found in nature. Examples of isotopes that can be incorporated into the compounds disclosed herein include isotopes of hydrogen, carbon, nitrogen, oxygen, phosphorus, sulfur, fluorine, iodine, and chlorine, such as $^2H$, $^3H$, $^{11}C$, $^{13}C$, $^{14}C$, $^{13}N$, $^{15}N$, $^{15}O$, $^{17}O$, $^{31}P$, $^{32}P$, $^{35}S$, $^{18}F$, $^{123}I$, $^{125}I$ and $^{36}Cl$.

Certain isotopically-labeled compounds disclosed herein (e.g., those labeled with $^3H$ and $^{14}C$) can be used to analyze compounds and/or substrate tissue distribution. Tritiated (i.e., $^3H$) and carbon-14 (i.e., $^{14}C$) isotopes are particularly preferred for their ease of preparation and detectability. Positron emitting isotopes, such as $^{15}O$, $^{13}N$, $^{11}C$, and $^{18}F$ can be used in positron emission tomography (PET) studies to determine substrate occupancy. Isotopically-labeled compounds disclosed herein can generally be prepared by following procedures analogous to those disclosed in the schemes and/or examples below while substituting a non-isotopically labeled reagent with an isotopically-labeled reagent.

Furthermore, substitution with heavier isotopes such as deuterium (i.e., $^2$H) may provide certain therapeutic advantages (e.g., increased in vivo half-life or reduced dosage requirement) resulting from greater metabolic stability and hence may be preferred in some circumstances in which deuterium substitution may be partial or complete, wherein partial deuterium substitution refers to substitution of at least one hydrogen with at least one deuterium.

The compound disclosed herein can be asymmetrical, for example, has one or more stereoisomers. Unless otherwise stated, all stereoisomers are included in the present application, such as enantiomers and diastereoisomers. The compound containing asymmetrical carbon atoms disclosed herein can be separated in an optically pure form or in a racemic form. The optically pure form can be separated from a racemic mixture or can be synthesized using a chiral raw material or a chiral reagent.

The pharmaceutical composition disclosed herein can be prepared by combining the compound disclosed herein with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, aerosol, and the like.

Typical routes of administration of the compound or the pharmaceutically acceptable salt thereof or the pharmaceutical composition thereof disclosed herein include, but are not limited to, oral, rectal, local, inhalation, parenteral, sublingual, intravaginal, intranasal, intraocular, intraperitoneal, intramuscular, subcutaneous and intravenous administration.

The pharmaceutical composition disclosed herein can be manufactured by methods well known in the art, such as by conventional mixing, dissolving, granulating, dragee-making, levigating, emulsifying, lyophilizing, and the like.

In some embodiments, the pharmaceutical composition is in an oral form. For oral administration, the pharmaceutical composition can be formulated by mixing the active compounds with pharmaceutically acceptable excipients well known in the art. These excipients enable the compounds disclosed herein to be formulated into tablets, pills, pastilles, dragees, capsules, liquids, gels, slurries, suspensions and the like for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

The pharmaceutical compositions may also be suitable for parenteral administration, such as sterile solutions, suspensions or lyophilized products in suitable unit dosage forms.

In all of the administration methods of the compound of formula I described herein, the daily dosage administered is from 0.01 mg/kg to 200 mg/kg body weight, given in individual or separated dosages.

The compounds disclosed herein can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples disclosed herein. The chemical reactions of the embodiments disclosed herein are carried out in a suitable solvent that must be suitable for the chemical changes in the present application and the reagents and materials required therefor. In order to acquire the compounds disclosed herein, it is sometimes necessary for one skilled in the art to modify or select a synthesis procedure or a reaction scheme based on the existing embodiments.

An important consideration in synthesis route planning in the art is the selection of suitable protecting groups for reactive functional groups (e.g., hydroxyl in the present application). For example, reference may be made to Greene's Protective Groups in Organic Synthesis (4th Ed.) Hoboken, New Jersey: John Wiley & Sons, Inc.

In some embodiments, the compound of formula I disclosed herein can be prepared by one skilled in the art of organic synthesis through the following routes:

Route 1

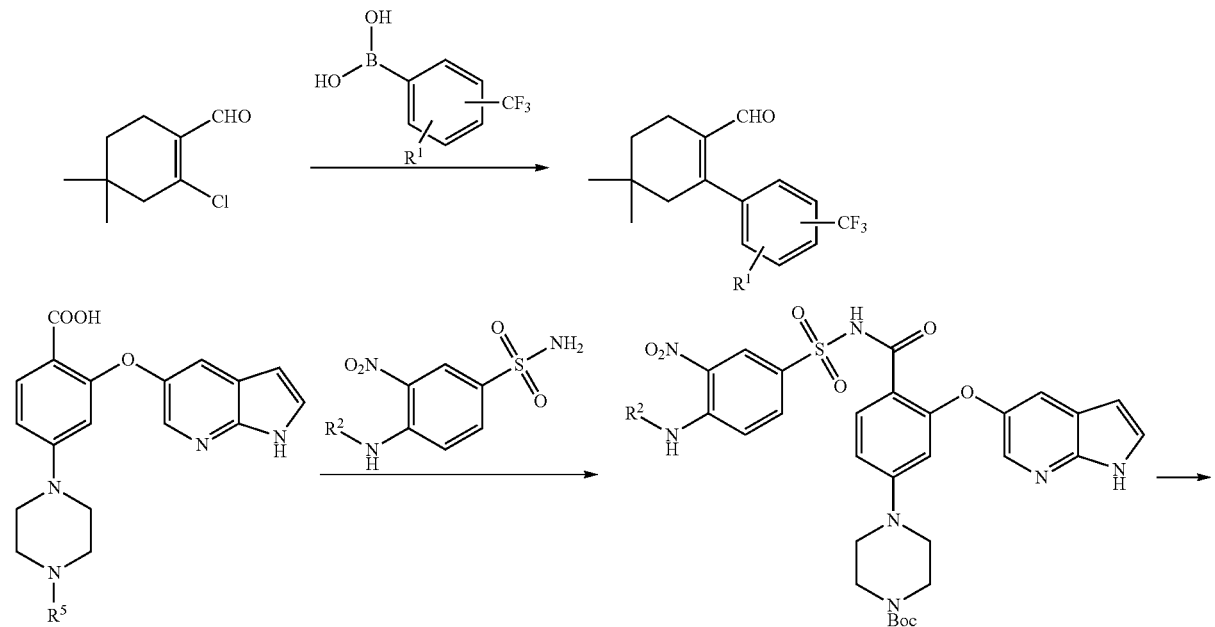

73
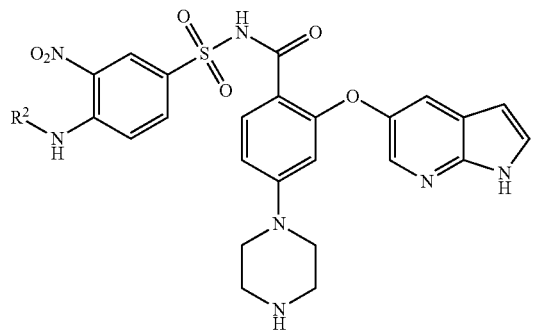
74
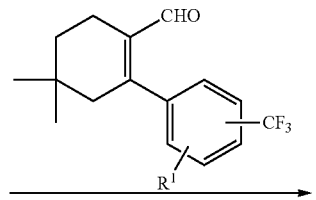
-continued
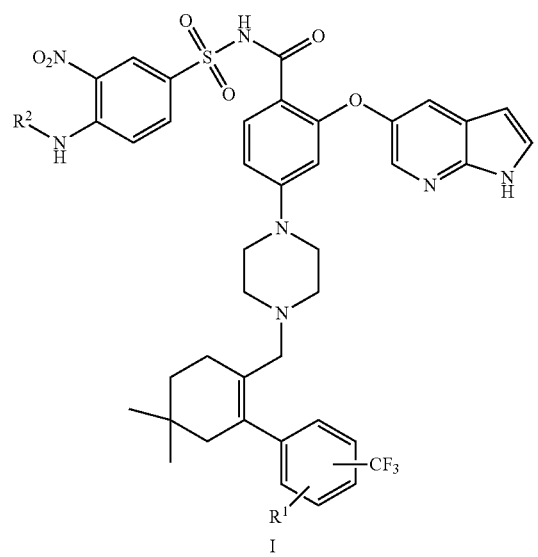
I
Route 2
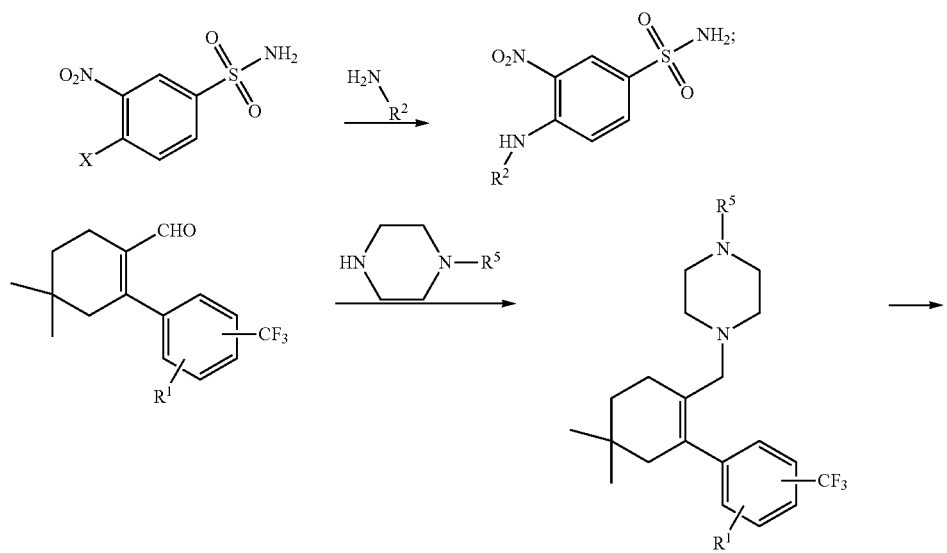

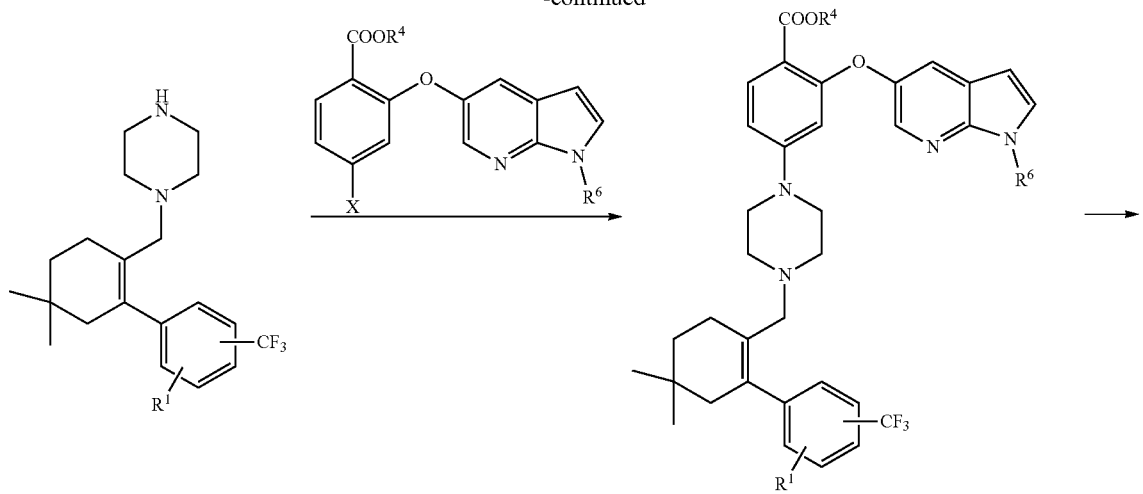

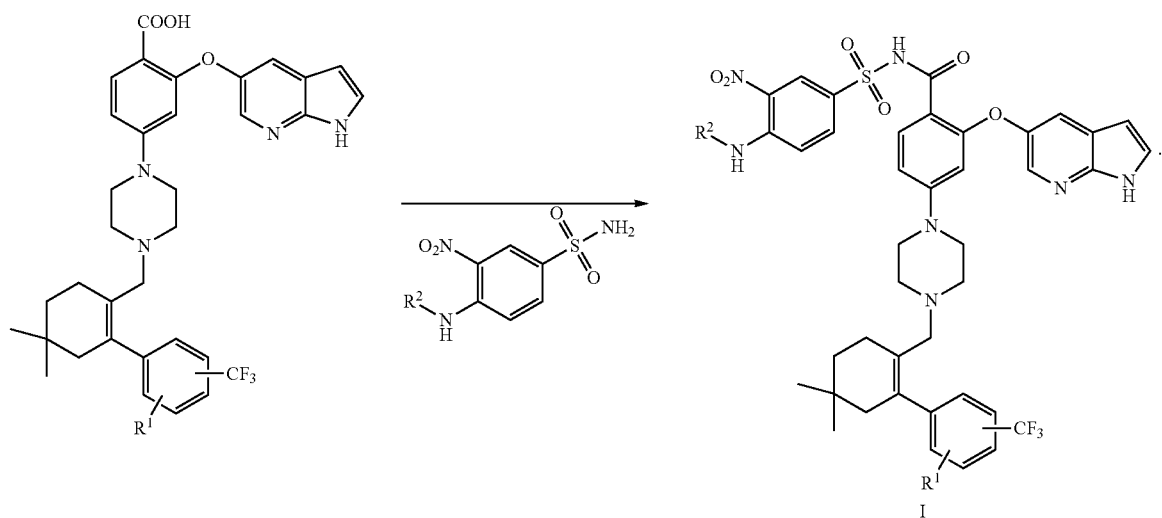

In above routes, R¹, R² or

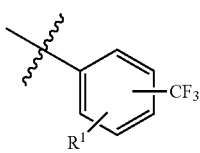

is defined as above; X is selected from the group consisting of leaving groups, preferably fluorine, chlorine, bromine and iodine; R⁴ is selected from the group consisting of $C_{1-6}$ alkyl and $C_{1-4}$ alkyl, preferably tert-butyl, methyl and ethyl; R⁵ is selected from the group consisting of amino protecting groups, preferably Boc and benzyloxycarbonyl (Cbz); and R⁶ is selected from the group consisting of amino protecting groups, preferably silane protecting groups, and more preferably tert-butyldimethylsilyl (TBS) and tert-butyldiphenyl- silyl (TBDPS), or trimethylsilyl (TMS), triethylsilyl (TES) and triisopropylsilyl (TIPS) protecting groups.

The present application also provides a method for preparing a compound of formula A-4, comprising:

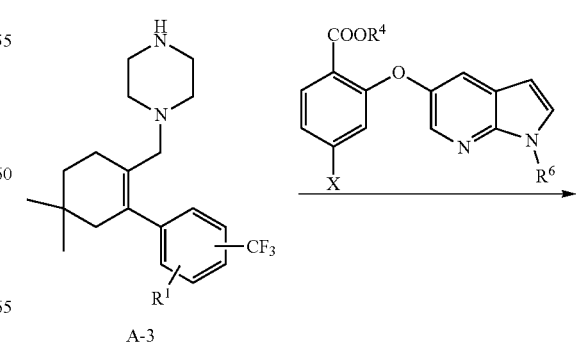

77

-continued

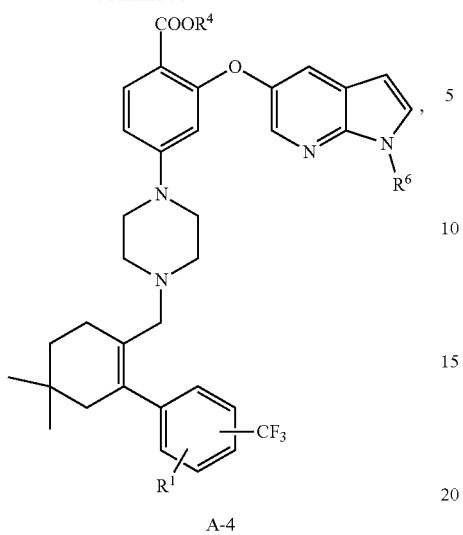

A-4 wherein R¹ or

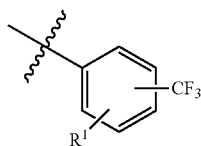

is defined as above; X is selected from the group consisting of leaving groups, preferably fluorine, chlorine, bromine and iodine; R⁴ is selected from the group consisting of $C_{1-6}$ alkyl and $C_{1-4}$ alkyl, preferably tert-butyl, methyl and ethyl; and R⁶ is selected from the group consisting of amino protecting groups, preferably silane protecting groups, and more preferably tert-butyldimethylsilyl (TBS) and tert-butyldiphenylsilyl (TBDPS), or trimethylsilyl (TMS), triethylsilyl (TES) and triisopropylsilyl (TIPS) protecting groups.

The present application also provides a method for preparing a compound of formula A-3, comprising:

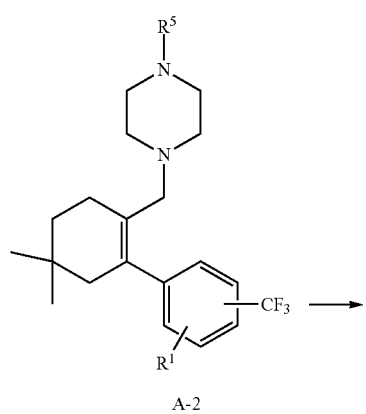

78

-continued

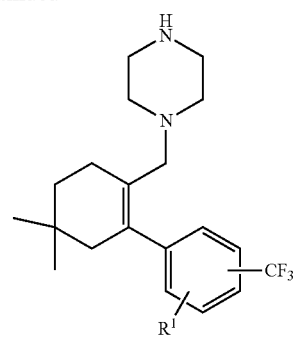

A-3 wherein R¹ or

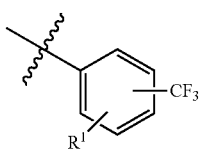

is defined as above, and R⁵ is selected from the group consisting of amino protecting groups, preferably Boc and benzyloxycarbonyl (Cbz). The present application also provides a method for preparing a compound of formula A-2, comprising:

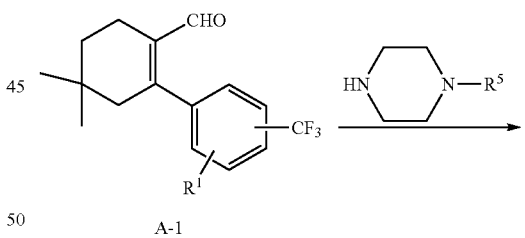

A-2 wherein $R^1$ or

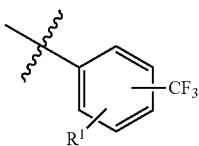

is defined as above, and $R^5$ is selected from the group consisting of amino protecting groups, preferably Boc and benzyloxycarbonyl (Cbz). The present application also provides a method for preparing a compound of formula A-5, comprising:

wherein $R^1$ or

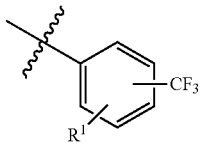

is defined as above; $R^4$ is selected from the group consisting of $C_{1-6}$ alkyl and $C_{1-4}$ alkyl, preferably tert-butyl, methyl and ethyl; and $R^6$ is selected from the group consisting of amino protecting groups, preferably silane protecting groups, and more preferably tert-butyldimethylsilyl (TBS) and tert-butyldiphenylsilyl (TBDPS), or trimethylsilyl (TMS), triethylsilyl (TES) and triisopropylsilyl (TIPS) protecting groups. The present application also provides a method for preparing a compound of formula I, comprising:

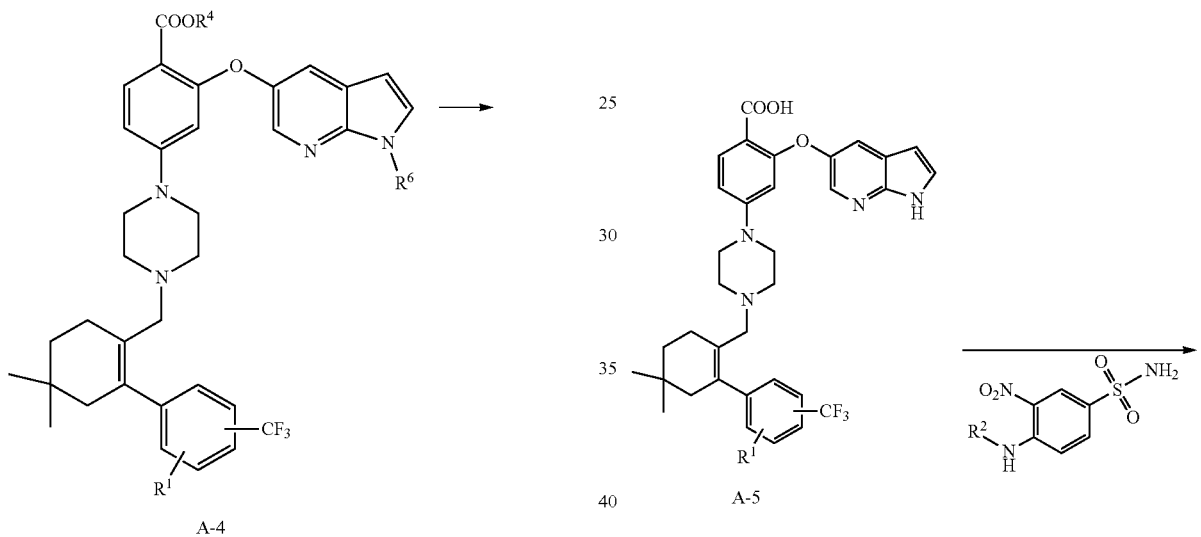

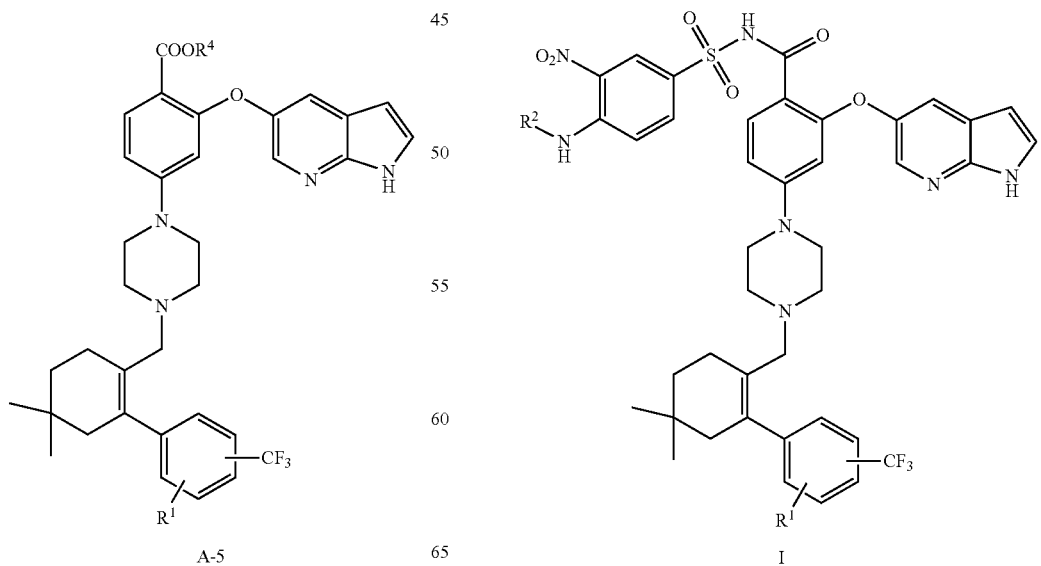

wherein $R^1$, $R^2$ or

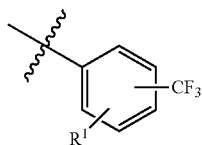

is defined as above.

The present application also provides intermediate compounds of the following formulas or salts thereof:

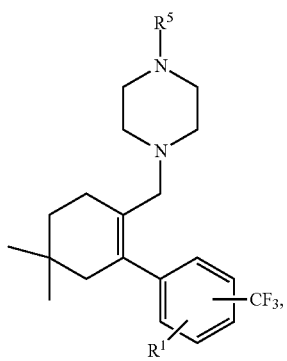

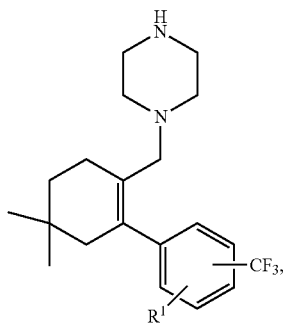

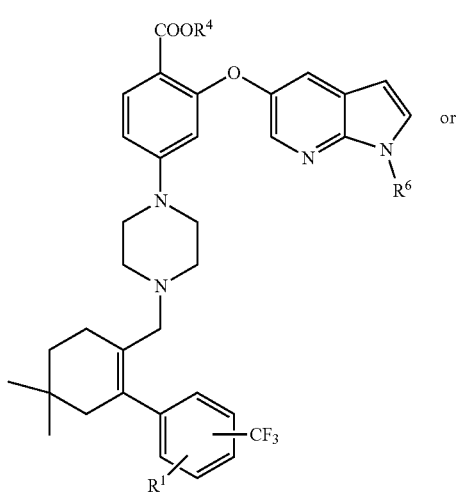

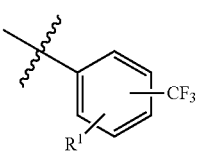

wherein $R^1$ or

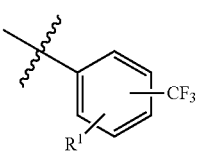

is defined as above; $R^4$ is selected from the group consisting of $C_{1-6}$ alkyl and $C_{1-4}$ alkyl, preferably tert-butyl, methyl and ethyl; $R^5$ is selected from the group consisting of amino protecting groups, preferably Boc and benzyloxycarbonyl (Cbz); and $R^6$ is selected from the group consisting of amino protecting groups, preferably silane protecting groups, and more preferably tert-butyldimethylsilyl (TBS) and tert-butyldiphenylsilyl (TBDPS) or trimethylsilyl (TMS), triethylsilyl (TES) and triisopropylsilyl (TIPS) protecting groups. The salt may be selected from the group consisting of hydrochloride salts and the like.

In more specific embodiments, the compounds are each selected from the group consisting of the compounds of the following formulas or salts thereof:

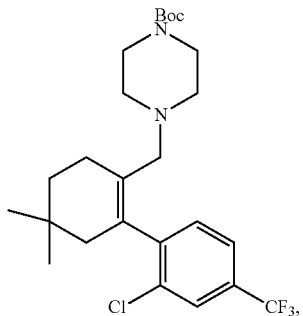

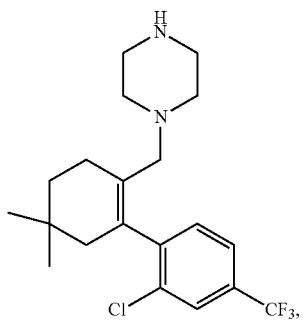

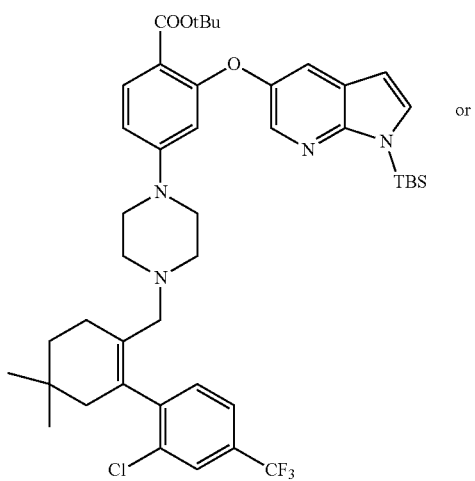

or

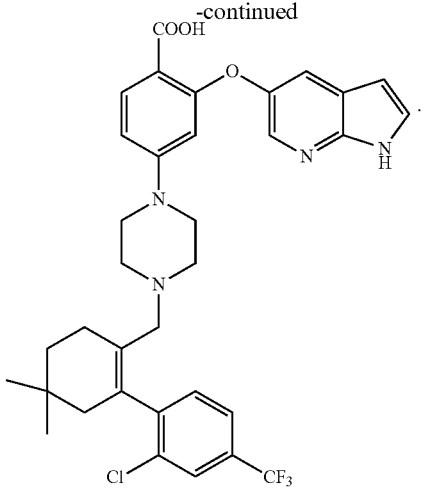

The salt may be selected from the group consisting of hydrochloride salts and the like.

DETAILED DESCRIPTION

Abbreviation: DMF represents N,N-dimethylformamide; Boc represents tert-butyloxycarbonyl; NaOAc represents sodium acetate; tBu represents tert-butyl; TBS represents tert-butyldimethylsilyl; THF represents tetrahydrofuran; and DMSO represents dimethyl sulfoxide.

For clarity, the present application is further described with the following examples, which are, however, not intended to limit the scope of the present application. All reagents used are commercially available and can be used without further purification.

Example 1

4-(4-{[2-(2-chloro-4-trifluoromethylphenyl)-4,4-dimethylcyclohex-1-enyl]methyl}-piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)-benzamide

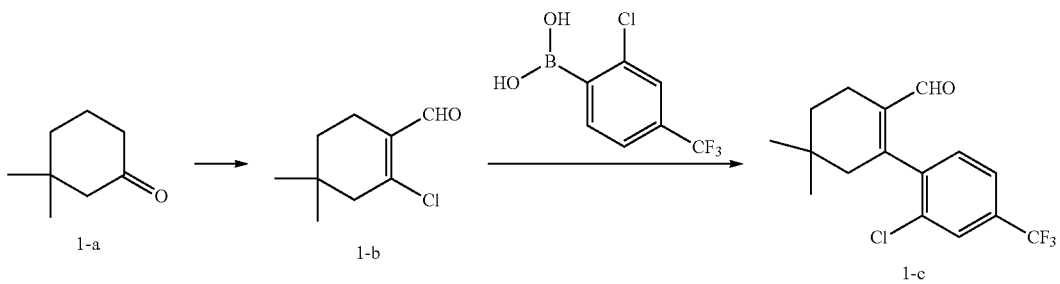

-continued
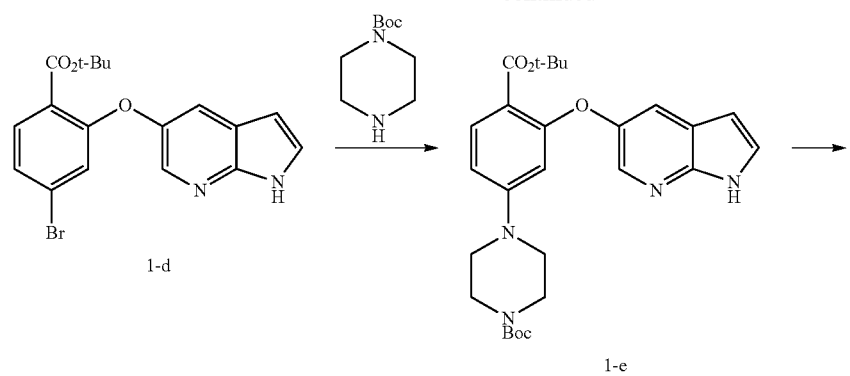
1-d → 1-e
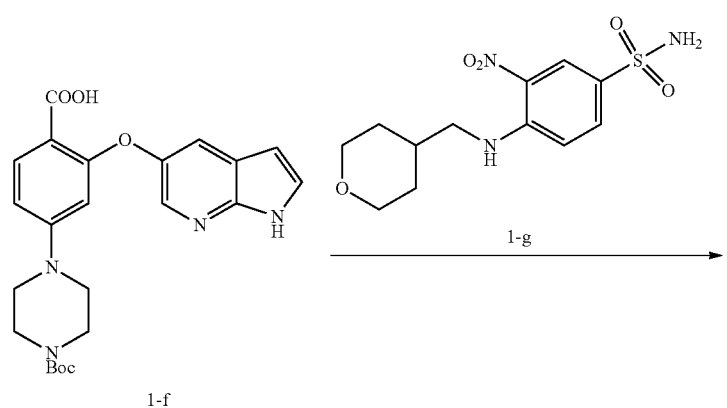
1-f
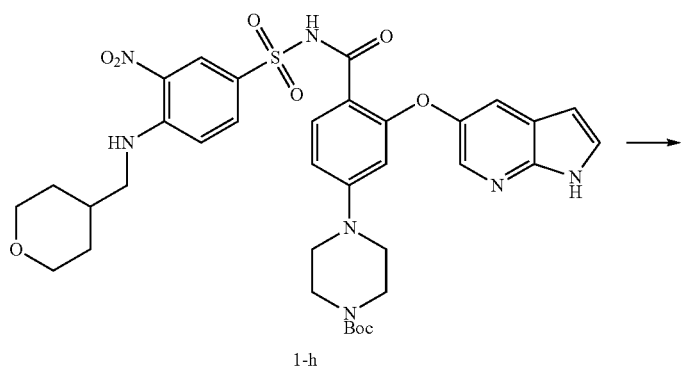
1-h
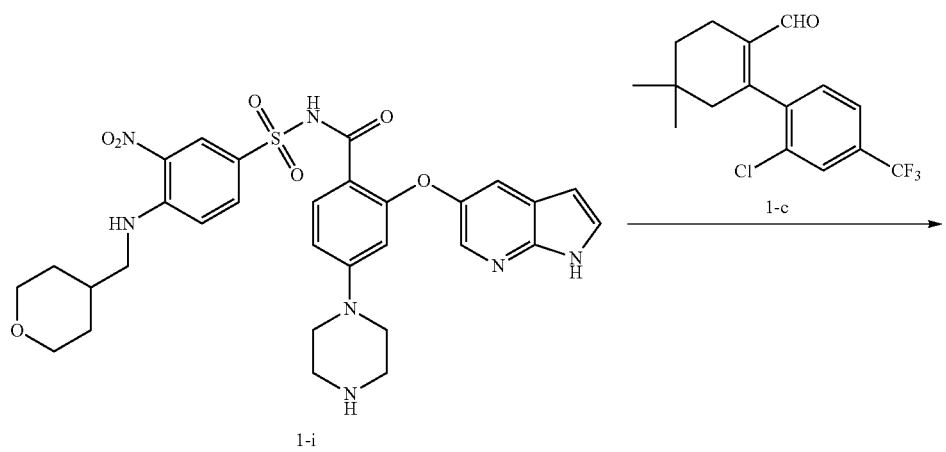
1-i

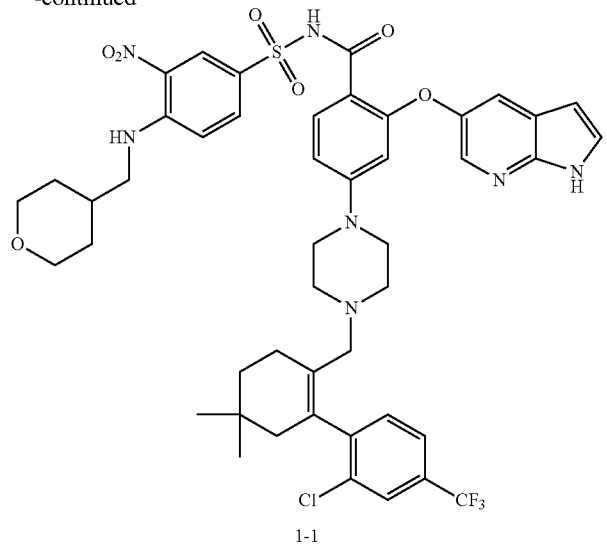

1-1

1) Preparation of Compound 1-b

To a solution of DMF (173.7 g) in dichloromethane (460 mL) was added phosphorus oxychloride dropwise at 0° C. After the addition, the mixture was heated to 20° C. and stirred for 1 h, then cooled to 0° C. and added with 3,3-dimethylcyclohexanone (1-a) (200 g) dropwise. After the addition, the mixture was heated to reflux overnight. The reaction solution was added to a solution containing NaOAc (86.7 g), NaCl (80 g), water (1.2 L) and dichloromethane (600 mL) dropwise while stirring. The resulting mixture was stirred at room temperature for 20 min, followed by liquid separation. The aqueous phase was extracted with dichloromethane (500 mL). The organic phases were combined, washed once with a solution of $K_3PO_4$ (40 g) and NaCl (90 g) in water (1 L), dried over anhydrous sodium sulfate, filtered and concentrated to give compound 1-b (249 g).

2) Preparation of Compound 1-c

Compound 1-b (5.36 g), tetrakis(triphenylphosphine)palladium (0.18 g), $K_3PO_4$ (16.5 g), DMF (60 mL) and water (60 mL) were mixed, and the mixture was stirred for 10 min. Then 2-chloro-4-trifluoromethylphenylboronic acid (6.96 g) was added and the mixture was reacted at 100° C. for 6 h under $N_2$ atmosphere until the reaction was completed. The reaction solution was added with a solution of 5 wt % $NaHCO_3$ and 2 wt % L-cysteine in water (30 mL) and ethyl acetate (50 mL), stirred for 0.5 h and filtered, followed by liquid separation. The aqueous phase was extracted with ethyl acetate (60 mL×2). The organic phases were combined, washed with saturated aqueous NaCl solution, dried over anhydrous $Na_2SO_4$, filtered, concentrated, and subjected to column chromatography to give compound 1-c (2 g).

3) Preparation of Compound 1-e

Tert-butyl 2-[(1H-pyrrolo[2,3-b]pyridin-5-yl)oxy]-4-bromobenzoate (compound 1-d) (77.8 g), Boc-piperazine (55.8 g), tris(dibenzylideneacetone)dipalladium (9 g), [(4-(N,N-dimethylamino)phenyl]di-tert-butylphosphine (5.2 g), sodium tert-butoxide (96.1 g), toluene (800 mL) and tetrahydrofuran (300 mL) were mixed and the mixture was stirred, heated to 60° C. and reacted for 24 h under nitrogen atmosphere. The reaction solution was washed successively with a solution of L-cysteine (100 g) and $NaHCO_3$ (150 g) in water (1.5 L) (750 mL×2), and then washed with saturated aqueous NaCl solution, dried over anhydrous $Na_2SO_4$, filtered and concentrated to give compound 1-e (40 g). ESI-MS: m/z=495.4 [M+H]+.

4) Preparation of Compound 1-f

Compound 1-e (40 g), tetrahydrofuran (800 mL), ethanol (270 mL) and water (15 mL) were mixed, and the mixture was stirred. Then KOH (45.3 g) was added, and the mixture was heated to 80° C. and stirred under reflux for 8 h until the reaction was completed. The reaction solution was added with water (500 mL), stirred, adjusted to pH 5-6 with diluted hydrochloric acid, filtered, slurried with water (1 L) (500 mL×2) and dried to give compound 1-f (35 g).

5) Preparation of Compound 1-h

Compound 1-f (35 g) and dichloromethane (100 mL) were mixed and the mixture was stirred at room temperature. Then 4-dimethylaminopyridine (38.5 g) and 1-ethyl-(3-dimethylaminopropyl) carbodiimide hydrochloride (65.8 g) were added and dissolved by stirring, and the solution was added with 3-nitro-4-[[(tetrahydropyran-4-yl)methyl]amino]benzenesulfonamide (compound 1-g) (25.2 g) and reacted at room temperature for 3 h. The reaction solution was washed successively with 5 wt % hydrochloric acid, saturated aqueous sodium bicarbonate solution and saturated aqueous sodium chloride solution, dried over anhydrous $Na_2SO_4$, filtered and concentrated. The concentrate was added with dichloromethane (200 mL), stirred at room temperature for 2 h, filtered and dried to give compound 1-h (40 g).

6) Preparation of Compound 1-i

Compound 1-h was added to isopropanol (500 mL), and the mixture was stirred. Then concentrated HCl (50 mL) was added, and the mixture was heated to 65° C. and stirred for 8 h until the reaction was completed. The reaction mixture was filtered, and the filter cake was dissolved in water (300 mL), added dropwise with saturated sodium bicarbonate to adjust the pH to 6-7, filtered and dried. The resulting solid was slurried with ethyl acetate (200 mL), filtered and dried to give compound 1-i (27 g).

7) Preparation of Compound 1-1

Compound 1-c (1 g) and compound 1-i (2 g) were dissolved in methanol (20 mL), and the solution was stirred. Then sodium borohydride (0.24 g) was added, and the mixture was stirred for 6 h until the reaction was completed.

The reaction solution was added with saturated aqueous ammonium chloride solution (10 mL) to quench the reaction, extracted with ethyl acetate (20 mL×2), washed with saturated aqueous sodium chloride solution, dried over anhydrous Na$_2$SO$_4$ and filtered. The filtrate was concentrated and subjected to column chromatography to give compound 1-1 (200 mg).

Compound 1-1: $^1$H NMR (500 MHz, DMSO-d6), δ: 11.72 (s, 1H), 11.68 (s, 1H), 8.62 (m, 1H), 8.58 (d, 1H), 8.04 (d, 1H), 7.83 (s, 1H), 7.81 (dd, 1H), 7.70 (d, 1H), 7.54 (m, 3H), 7.40 (d, 1H), 7.12 (d, 1H), 6.74 (d, 1H), 6.40 (s, 1H), 6.29 (s, 1H), 3.87 (m, 4H), 3.55 (d, 2H), 3.37 (d, 2H), 3.32 (m, 4H), 2.27 (d, 1H), 2.19 (m, 1H), 2.09 (s, 1H), 1.96 (s, 2H), 1.89 (m, 1H), 1.63 (d, 2H), 1.50 (m, 2H), 1.28 (m, 4H), 0.98 (d, 6H).

$^{13}$C NMR (125 MHz, DMSO-d6), δ: 163.9, 158.8, 153.9, 147.9, 142.9, 132.5, 130.1, 128.3, 125.6, 124.7, 120.3, 118.4, 115.5, 114.1, 109.6, 103.4, 100.4, 67.0, 58.3, 50.9, 48.4, 46.9, 44.1, 34.6, 30.6, 29.1, 25.2. ESI-MS: m/z=936.5 [M+H]+.

Example 2

4-(4-{[2-(3-trifluoromethyl-4-chlorophenyl)-4,4-dimethylcyclohex-1-enyl]methyl}-piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)-benzamide

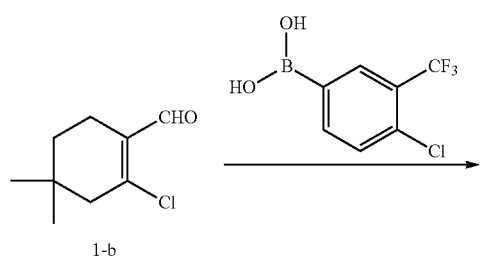

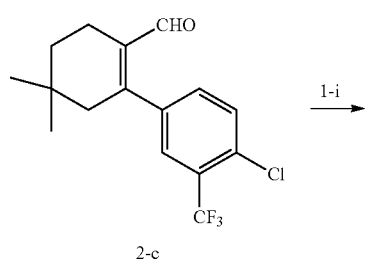

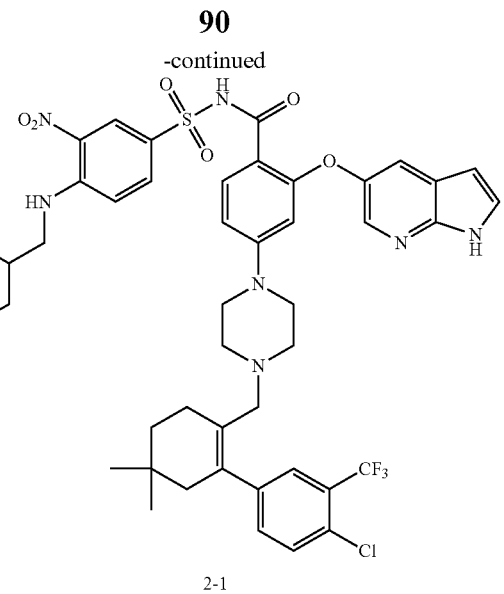

1) Preparation of Compound 2-c

Compound 1-b (5.16 g), tetrakis(triphenylphosphine)palladium (0.17 g), K$_3$PO$_4$ (12.74 g), DMF (60 mL), and water (60 mL) were mixed, and the mixture was stirred for 10 min. Then 3-trifluoromethyl-4-chlorobenzeneboronic acid (6.72 g) was added, and the mixture was reacted at 100° C. for 6 h under N$_2$ atmosphere until the reaction was completed. The reaction solution was added with a solution of 5 wt % NaHCO$_3$ and 2 wt % L-cysteine in water (30 mL) and ethyl acetate (50 mL), stirred for 0.5 h and filtered, followed by liquid separation. The aqueous phase was extracted with ethyl acetate (60 mL×2). The organic phases were combined, washed with saturated aqueous NaCl solution, dried over anhydrous Na$_2$SO$_4$, filtered, concentrated, and subjected to column chromatography to give compound 2-c (1.2 g).

2) Preparation of Compound 2-1

Compound 2-c (1 g) and compound 1-i (2.01 g) were dissolved in methanol (20 mL), and the solution was stirred. Then sodium borohydride (0.27 g) was added, and the mixture was stirred for 6 h until the reaction was completed. The reaction solution was added with saturated aqueous ammonium chloride solution (10 mL) to quench the reaction, extracted with ethyl acetate (20 mL×2), washed with saturated aqueous sodium chloride solution, dried over anhydrous Na$_2$SO$_4$ and filtered. The filtrate was concentrated and subjected to column chromatography to give compound 2-1 (80 mg).

Compound 2-1: $^1$H NMR (500 MHz, DMSO-d6), δ: 11.72 (s, 1H), 11.66 (s, 1H), 8.61 (m, 1H), 8.57 (d, 1H), 8.04 (d, 1H), 7.81 (dd, 1H), 7.67 (d, 1H), 7.54 (m, 4H), 7.40 (d, 1H), 7.12 (d, 1H), 6.74 (d, 1H), 6.40 (s, 1H), 6.29 (s, 1H), 3.87 (m, 4H), 3.55 (d, 2H), 3.32 (m, 6H), 3.01 (s, 2H) 2.21 (d, 2H), 1.98 (m, 2H), 1.87 (m, 1H), 1.60 (d, 2H), 1.45 (m, 2H), 1.28 (m, 4H), 0.98 (d, 6H). $^{13}$C NMR (125 MHz, DMSO-d6), δ: 163.9, 158.7, 158.4, 158.2, 153.9, 147.9, 146.8, 145.9, 141.5, 135.6, 134.3, 134.2, 132.5, 132.4, 130.1, 130.0, 129.8, 128.3, 127.6, 127.4, 124.7, 122.1, 120.2, 118.4, 115.5, 114.0, 109.5, 103.4, 100.4, 67.0, 58.3, 50.8, 48.4, 46.7, 44.3, 34.6, 34.3, 30.6, 29.2, 28.3, 25.2, 14.4. ESI-MS: m/z=936.5 [M+H]$^+$.

Example 3

4-(4-{[2-(4-chloro-2-trifluoromethylphenyl)-4,4-dimethylcyclohex-1-enyl]methyl}-piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)-benzamide

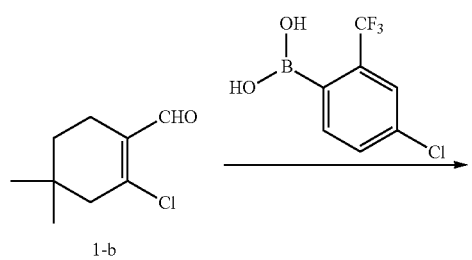

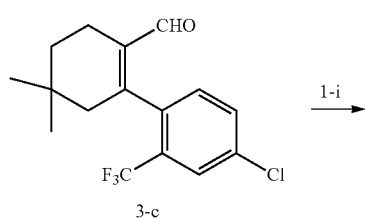

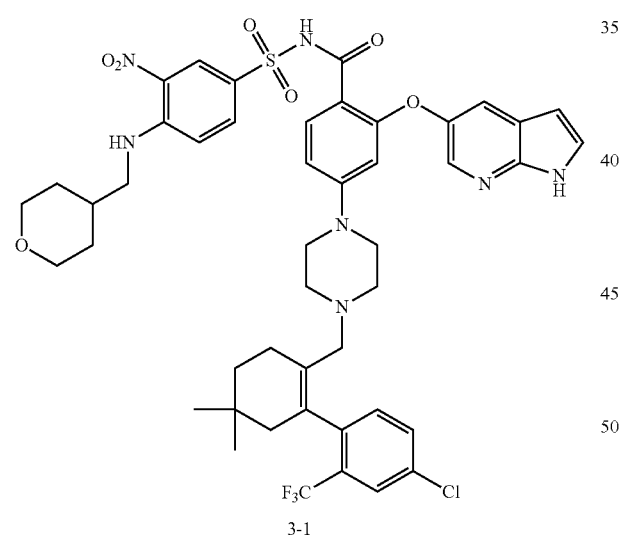

1) Preparation of Compound 3-c

Compound 1-b (5.16 g), tetrakis(triphenylphosphine)palladium (0.17 g), $K_3PO_4$ (12.74 g), DMF (60 mL), and water (60 mL) were mixed, and the mixture was stirred for 10 min. Then 2-trifluoromethyl-4-chlorobenzeneboronic acid (6.72 g) was added, and the mixture was reacted at 100° C. for 6 h under $N_2$ atmosphere until the reaction was completed. The reaction solution was added with a solution of 5 wt % $NaHCO_3$ and 2 wt % L-cysteine in water (30 mL) and ethyl acetate (50 mL), stirred for 0.5 h and filtered, followed by liquid separation. The aqueous phase was extracted with ethyl acetate (60 mL×2). The organic phases were combined, washed with saturated aqueous NaCl solution, dried over anhydrous $Na_2SO_4$, filtered, concentrated, and subjected to column chromatography to give compound 3-c (1.6 g).

2) Preparation of Compound 3-1

Compound 3-c (1 g) and compound 1-i (2.01 g) were dissolved in methanol (20 mL), and the solution was stirred. Then sodium borohydride (0.27 g) was added, and the mixture was stirred for 6 h until the reaction was completed. The reaction solution was added with saturated aqueous ammonium chloride solution (10 mL) to quench the reaction, extracted with ethyl acetate (20 mL×2), washed with saturated aqueous sodium chloride solution, dried over anhydrous $Na_2SO_4$ and filtered. The filtrate was concentrated and subjected to column chromatography to give compound 3-1 (110 mg).

Compound 3-1: $^1$H NMR (500 MHz, DMSO-d6), δ: 11.73 (s, 1H), 11.67 (s, 1H), 8.61 (m, 1H), 8.58 (d, 1H), 8.05 (d, 1H), 7.79 (m, 2H), 7.71 (d, 1H), 7.52 (m, 3H), 7.29 (d, 1H), 7.13 (d, 1H), 6.74 (d, 1H), 6.41 (s, 1H), 6.26 (s, 1H), 3.84 (d, 2H), 3.61 (d, 2H), 3.18 (m, 4H), 3.05 (s, 3H), 2.31 (d, 1H), 1.89 (m, 5H), 1.61 (d, 2H), 1.51 (m, 1H), 1.41 (m, 1H), 1.24 (d, 6H), 0.91 (m, 6H). $^{13}$C NMR (125 MHz, DMSO-d6), δ: 163.9, 158.8, 158.5, 158.2, 153.9, 147.9, 146.7, 145.9, 139.1, 135.6, 134.3, 133.4, 133.1, 133.0, 132.6, 130.0, 128.3, 126.7, 124.7, 120.3, 118.5, 115.5, 114.1, 109.6, 103.3, 100.4, 67.0, 58.7, 48.4, 46.8, 44.3, 34.5, 34.3, 30.6, 29.4, 29.0, 28.9, 27.5, 27.0, 24.6, 22.5. ESI-MS: m/z=936.5 [M+H]$^+$.

Example 4

4-(4-{[2-(3-chloro-4-trifluoromethylphenyl)-4,4-dimethylcyclohex-1-enyl]methyl}-piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)-benzamide

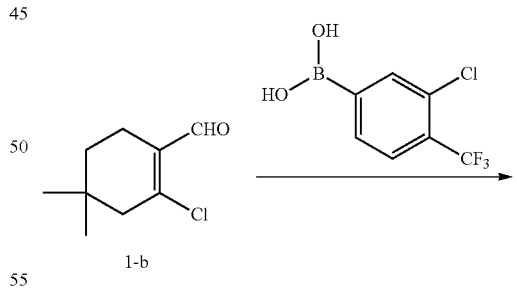

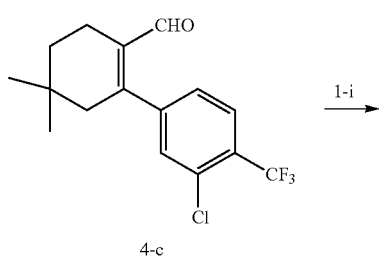

-continued

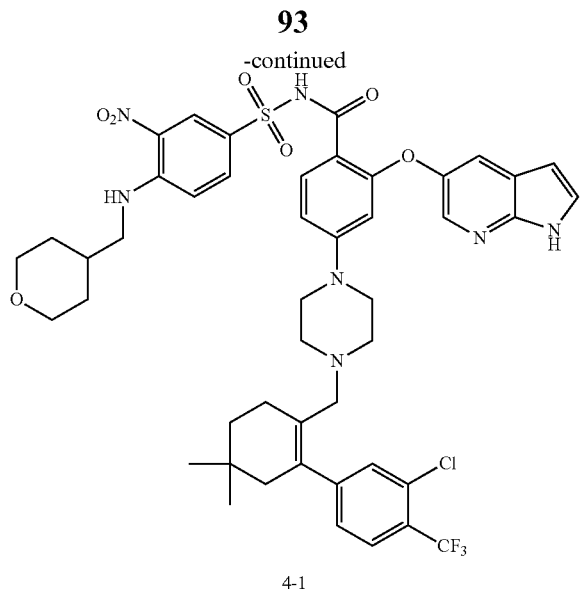

4-1

1) Preparation of Compound 4-c

Compound 1-b (5.16 g), tetrakis(triphenylphosphine)palladium (0.17 g), $K_3PO_4$ (12.74 g), DMF (60 mL) and water (60 mL) were mixed, and the mixture was stirred for 10 min. Then 3-chloro-4-trifluoromethylphenylboronic acid (6.72 g) was added and the mixture was reacted at 100° C. for 6 h under $N_2$ atmosphere until the reaction was completed. The reaction solution was added with a solution of 5 wt % $NaHCO_3$ and 2 wt % L-cysteine in water (30 mL) and ethyl acetate (50 mL), stirred for 0.5 h and filtered, followed by liquid separation. The aqueous phase was extracted with ethyl acetate (60 mL×2). The organic phases were combined, washed with saturated aqueous NaCl solution, dried over anhydrous $Na_2SO_4$, filtered, concentrated, and subjected to column chromatography to give compound 4-c (1.5 g).

2) Preparation of Compound 4-1

Compound 4-c (1 g) and compound 1-i (2.01 g) were dissolved in methanol (20 mL), and the solution was stirred. Then sodium borohydride (0.27 g) was added, and the mixture was stirred for 6 h until the reaction was completed. The reaction solution was added with saturated aqueous ammonium chloride solution (10 mL) to quench the reaction, extracted with ethyl acetate (20 mL×2), washed with saturated aqueous sodium chloride solution, dried over anhydrous $Na_2SO_4$ and filtered. The filtrate was concentrated and subjected to column chromatography to give compound 4-1 (120 mg).

Compound 4-1: $^1H$ NMR (500 MHz, DMSO-d6), δ: 11.71 (s, 1H), 11.62 (s, 1H), 8.61 (m, 1H), 8.57 (d, 1H), 8.04 (d, 1H), 7.79 (m, 2H), 7.50 (m, 3H), 7.43 (s, 1H), 7.23 (d, 1H), 7.12 (d, 1H), 6.71 (dd, 1H), 6.39 (m, 1H), 6.25 (d, 1H), 3.84 (dd, 2H), 3.29 (m, 4H), 3.24 (m, 2H), 2.21 (d, 3H), 2.03 (d, 3H), 1.88 (m, 1H), 1.60 (m, 2H), 1.43 (m, 3H), 1.22 (m, 4H), 0.94 (d, 9H). $^{13}C$ NMR (125 MHz, DMSO-d6), δ: 163.9, 158.8, 158.6, 158.3, 154.1, 147.9, 146.8, 145.9, 135.7, 134.7, 134.3, 132.5, 131.4, 130.0, 128.3, 127.8, 125.7, 124.7, 124.5, 120.2, 118.4, 115.5, 114.0, 109.5, 103.3, 100.4, 67.0, 64.6, 51.0, 48.4, 46.4, 45.2, 44.6, 34.6, 34.3, 30.6, 29.3, 29.1, 28.2, 28.1, 25.2, 24.8. ESI-MS: m/z=936.5 $[M+H]^+$.

Example 5

4-(4-{[2-(2-fluoro-4-trifluoromethylphenyl)-4,4-dimethylcyclohex-1-enyl]methyl}-piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)-benzamide

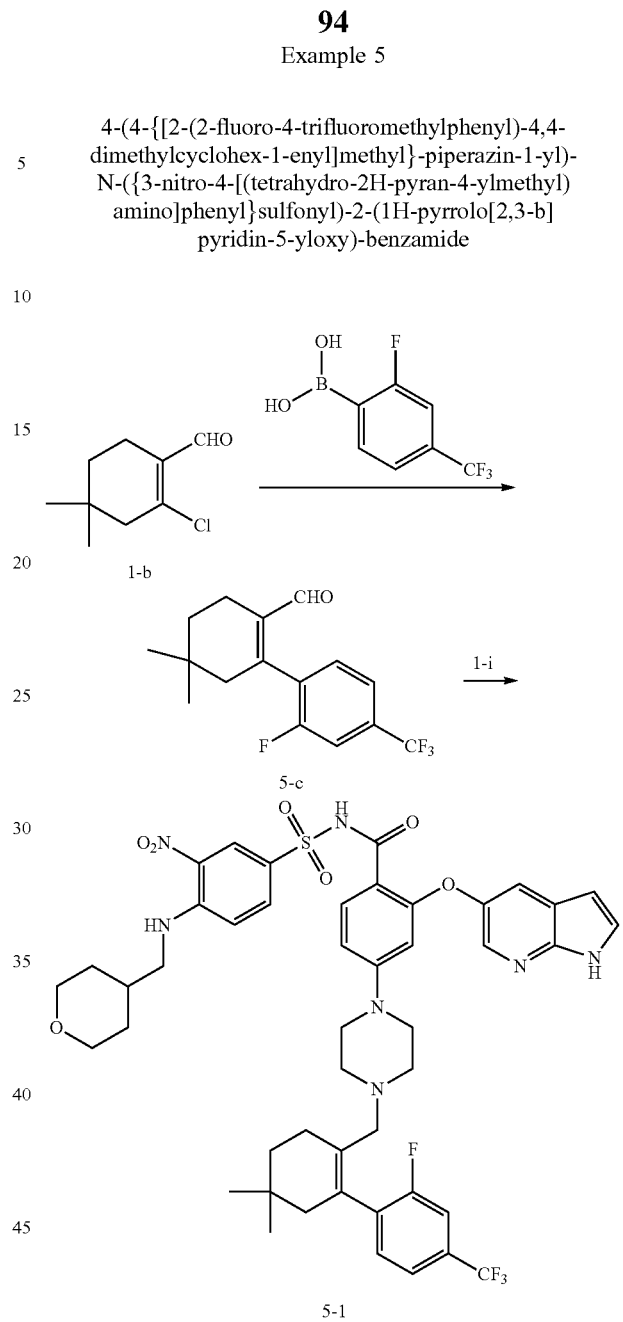

1) Preparation of Compound 5-c

Compound 1-b (5.16 g), tetrakis(triphenylphosphine)palladium (0.17 g), $K_3PO_4$ (12.74 g), DMF (60 mL) and water (60 mL) were mixed and the mixture was stirred for 10 min. Then 2-fluoro-4-trifluoromethylphenylboronic acid (6.24 g) was added, and the mixture was reacted at 100° C. for 6 h under $N_2$ atmosphere until the reaction was completed. The reaction solution was added with a solution of 5 wt % $NaHCO_3$ and 2 wt % L-cysteine in water (30 mL) and ethyl acetate (50 mL), stirred for 0.5 h and filtered, followed by liquid separation. The aqueous phase was extracted with ethyl acetate (60 mL×2). The organic phases were combined, washed with saturated aqueous NaCl solution, dried over anhydrous $Na_2SO_4$, filtered, concentrated, and subjected to column chromatography to give compound 5-c (1.8 g).

2) Preparation of Compound 5-1

Compound 5-c (1 g) and compound 1-i (2.12 g) were dissolved in methanol (20 mL), and the solution was stirred. Then sodium borohydride (0.27 g) was added, and the mixture was stirred for 6 h until the reaction was completed. The reaction solution was added with saturated aqueous ammonium chloride solution (10 mL) to quench the reaction, extracted with ethyl acetate (20 mL×2), washed with saturated aqueous sodium chloride solution, dried over anhydrous Na$_2$SO$_4$ and filtered. The filtrate was concentrated and subjected to column chromatography to give compound 5-1 (90 mg).

Compound 5-1: $^1$H NMR (500 MHz, DMSO-d6), δ:11.71 (s, 2H), 8.61 (m, 1H), 8.57 (d, 1H), 8.03 (d, 1H), 7.80 (dd, 1H), 7.66 (d, 1H), 7.56 (d, 1H), 7.51 (dd, 3H), 7.35 (m, 1H), 7.12 (d, 1H), 6.73 (dd, 1H), 6.39 (m, 1H), 6.29 (d, 1H), 3.84 (m, 3H), 3.55 (d, 5H), 3.24 (d, 6H), 2.25 (s, 2H), 1.98 (m, 2H), 1.88 (m, 1H), 1.60 (d, 2H), 1.47 (m, 2H), 1.24 (m, 4H), 0.95 (d, 6H). $^{13}$C NMR (125 MHz, DMSO-d6), δ: 163.9, 159.6, 158.7, 158.5, 158.1, 157.7, 154.0, 147.9, 146.9, 145.9, 135.6, 134.3, 133.2, 132.5, 132.1, 130.0, 128.3, 124.9, 124.7, 122.7, 122.1, 120.2, 118.2, 115.5, 114.1, 109.6, 103.5, 100.4, 67.0, 58.6, 50.8, 48.4, 45.7, 44.3, 34.5, 34.3, 30.6, 29.1, 28.6, 27.6, 25.1. ESI-MS: m/z=920.6 [M+H]$^+$.

Example 6

4-(4-{[2-(3-fluoro-4-trifluoromethylphenyl)-4,4-dimethylcyclohex-1-enyl]methyl}-piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)-benzamide

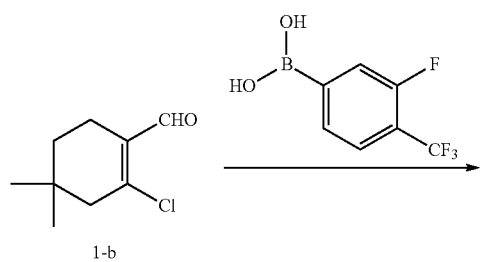

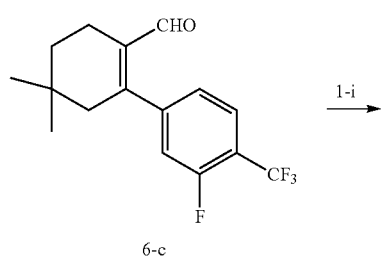

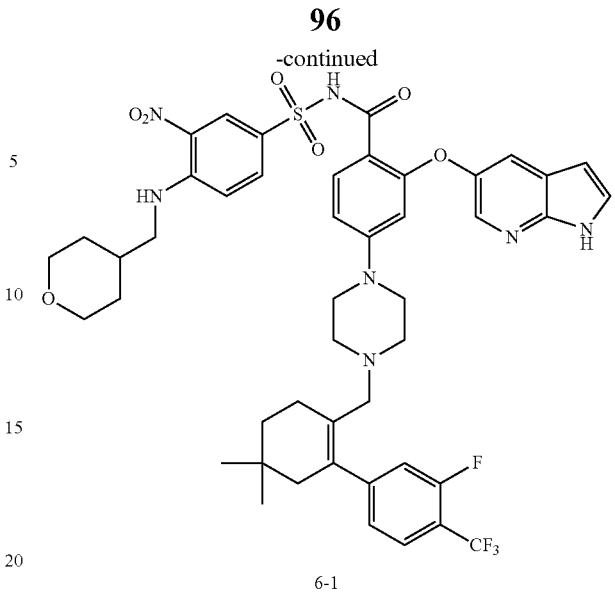

1) Preparation of Compound 6-c

Compound 1-b (5.16 g), tetrakis(triphenylphosphine)palladium (0.17 g), K$_3$PO$_4$ (12.74 g), DMF (60 mL) and water (60 mL) were mixed and the mixture was stirred for 10 min. Then 3-fluoro-4-trifluoromethylphenylboronic acid (6.24 g) was added, and the mixture was reacted at 100° C. for 6 h under N$_2$ atmosphere until the reaction was completed. The reaction solution was added with a solution of 5 wt % NaHCO$_3$ and 2 wt % L-cysteine in water (30 mL) and ethyl acetate (50 mL), stirred for 0.5 h and filtered, followed by liquid separation. The aqueous phase was extracted with ethyl acetate (60 mL×2). The organic phases were combined, washed with saturated aqueous NaCl solution, dried over anhydrous Na$_2$SO$_4$, filtered, concentrated, and subjected to column chromatography to give compound 6-c (1.6 g).

2) Preparation of Compound 6-1

Compound 6-c (1 g) and compound 1-i (2.12 g) were dissolved in methanol (20 mL), and the solution was stirred. Then sodium borohydride (0.27 g) was added, and the mixture was stirred for 6 h until the reaction was completed. The reaction solution was added with saturated aqueous ammonium chloride solution (10 mL) to quench the reaction, extracted with ethyl acetate (20 mL×2), washed with saturated aqueous sodium chloride solution, dried over anhydrous Na$_2$SO$_4$ and filtered. The filtrate was concentrated and subjected to column chromatography to give compound 6-1 (150 mg).

Compound 6-1: $^1$H NMR (500 MHz, DMSO-d6), δ: 11.72 (s, 1H), 11.67 (s, 1H), 8.61 (m, 1H), 8.57 (d, 1H), 8.04 (d, 1H), 7.81 (dd, 1H), 7.72 (m, 1H), 7.52 (dd, 3H), 7.24 (d, 1H), 7.09 (m, 2H), 6.72 (dd, 1H), 6.39 (m, 1H), 6.27 (d, 1H), 3.87 (m, 4H), 3.55 (d, 2H), 3.37 (d, 2H), 3.32 (m, 4H), 2.27 (d, 1H), 2.19 (m, 2H), 2.09 (s, 1H), 1.96 (s, 2H), 1.89 (m, 1H), 1.63 (d, 2H), 1.50 (m, 2H), 1.28 (m, 4H), 0.98 (d, 6H). $^{13}$C NMR (125 MHz, DMSO-d6), δ: 163.9, 158.8, 158.5, 158.2, 154.0, 149.2, 147.9, 146.8, 145.9, 135.6, 134.3, 132.5, 132.4, 130.1, 130.0, 128.3, 128.1, 125.1, 120.3, 118.4, 117.6, 117.2, 117.1, 115.5, 115.3, 109.6, 103.4, 100.4, 67.0, 58.3, 50.9, 48.4, 46.4, 44.3, 34.5, 34.3, 31.7, 30.6, 29.0, 28.2, 25.5, 25.1. ESI-MS: m/z=920.6 [M+H]$^+$.

Example 7
(R)-4-(4-{[2-(2-chloro-4-trifluoromethylphenyl)-4,4-dimethylcyclohex-1-enyl]methyl}-piperazin-1-yl)-N-({3-nitro-4-[(1,4-dioxan-2-yl)methyl)amino]phenyl}sulfonyl)-2-(1H-pyrrolo[2,3-b]pyridin-5-yloxy)-benzamide
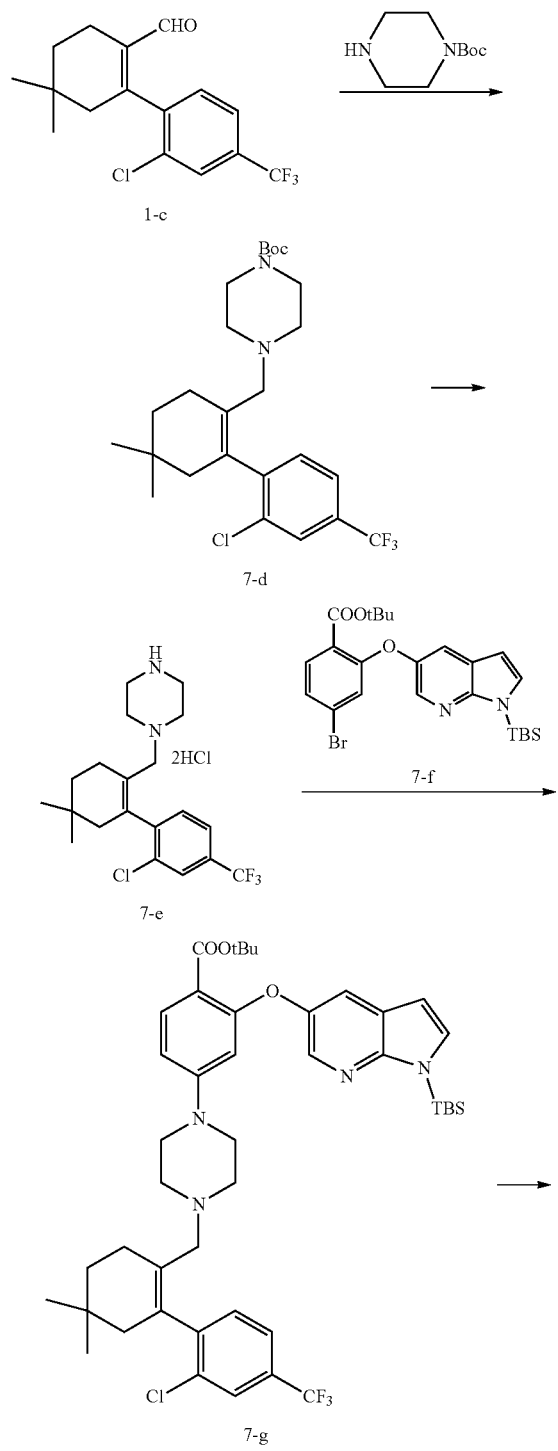
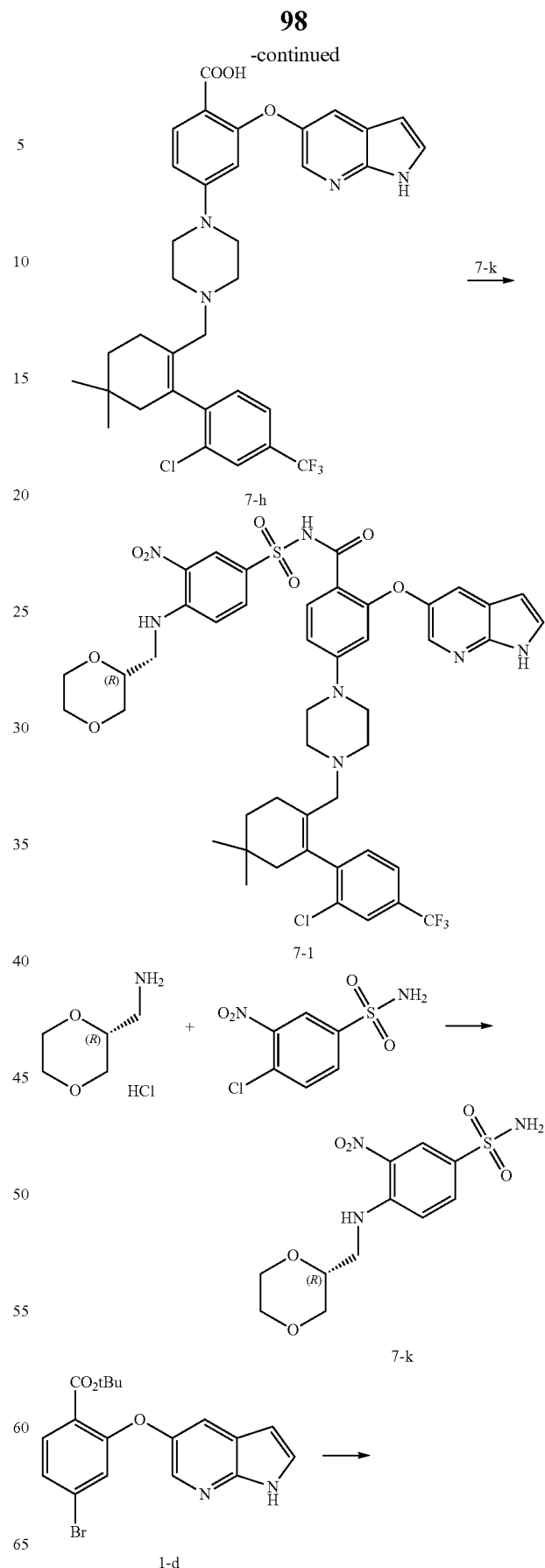

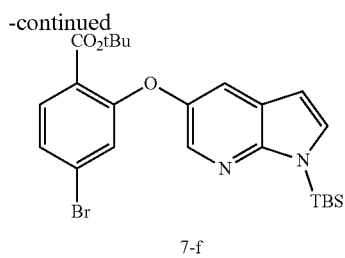

7-f

1) Preparation of Compound 7-d

Compound 1-c (198.6 g) and 1-Boc-piperazine (175.5 g) were dissolved in acetonitrile (800 mL), and the solution was stirred and cooled to 0° C. Then sodium triacetoxyborohydride (532.6 g) was slowly added, and the mixture was stirred at room temperature for 5 h. After the reaction was completed, the reaction solution was extracted with water (1 L) and ethyl acetate (300 mL). The organic phase was collected, dried over anhydrous $Na_2SO_4$, filtered and concentrated to give compound 7-d (269.8 g).

2) Preparation of Compound 7-e

Compound 7-d (269.8 g), isopropanol (800 mL) and hydrochloric acid (36-38 wt %, 169 mL) were mixed, and the mixture was heated to 65° C. and reacted for 3 h. The reaction solution was cooled to precipitate a solid, filtered and dried to give compound 7-e (151.2 g).

Compound 7-e: $^1$H NMR (500 MHz, DMSO-d6), δ: 7.82 (s, 1H), 7.68 (d, 1H), 7.36 (d, 1H), 7.10 (dd, 1H), 2.98 (s, 4H), 2.63 (d, 2H), 2.23 (m, 6H), 1.89 (m, 2H), 1.43 (s, 2H), 0.94 (s, 6H). $^{13}$C NMR (125 MHz, DMSO-d6), δ: 133.1, 132.6, 131.9, 130.9, 129.3, 128.6, 126.5, 125.7, 124.9, 124.6, 122.7, 60.2, 49.4, 44.7, 35.2, 29.4, 28.4, 27.1, 25.2, 21.4. ESI-MS: m/z=387.1 [M+H]$^+$.

3) Preparation of Compound 7-g

NaH (21.1 g) was dissolved in THF (100 mL), and the solution was cooled to –20° C. and stirred for 10 min. Tert-butyl 2-[(1H-pyrrolo[2,3-b]pyridin-5-yl)oxy]-4-bromobenzoate (compound 1-d, 128.3 g) was dissolved in THF (200 mL), and then was slowly added dropwise to the reaction solution, with the internal temperature maintained below 0° C. After the addition, the mixture was stirred for 30 min. The reaction solution was added dropwise with a solution of TBSCl (64.7 g) in THF (200 mL), with the internal temperature maintained at about –10° C., and reacted for 30 min after the addition. After the reaction was completed, the reaction solution was extracted with 500 mL of saturated sodium bicarbonate and ethyl acetate. The organic phase was collected, dried over anhydrous $Na_2SO_4$, filtered, concentrated and purified by column chromatography to give compound 7-f (150 g). ESI-MS: m/z=503.1 [M+H]$^+$.

Compound 7-e (151.2 g), tert-butyl 2-[(1-tert-butyldimethylsilylpyrrolo[2,3-b]pyridin-5-yl)oxy]-4-bromobenzoate (compound 7-f, 197.1 g), tris(dibenzylideneacetone)dipalladium (2.7 g), [(4-(N,N-dimethylamino)phenyl]di-tert-butylphosphine (1.6 g), sodium tert-butoxide (187.4 g) and toluene (800 mL) were mixed, and the mixture was stirred, heated to 100° C. and reacted for 24 h under nitrogen atmosphere. After the reaction was completed, the reaction solution was extracted with water (1 L) and ethyl acetate (300 mL). The organic phase was collected, dried over anhydrous $Na_2SO_4$, filtered and concentrated to give compound 7-g (181.9 g).

Compound 7-g: $^1$H NMR (500 MHz, DMSO-d6), δ: 7.95 (s, 1H), 7.82 (s, 1H), 7.65 (t, 2H), 7.37 (m, 4H), 6.76 (d, 1H), 6.47 (s, 1H), 3.14 (s, 2H), 2.64 (d, 1H), 2.55 (d, 1H), 2.19 (m, 5H), 1.92 (m, 2H), 1.42 (t, 2H), 1.31 (t, 2H), 1.22 (m, 9H), 0.95 (d, 6H), 0.84 (s, 10H), 0.60 (s, 6H). $^{13}$C NMR (125 MHz, DMSO-d6), δ: 164.4 156.8, 155.1, 150.3, 149.8, 146.2, 133.6, 133.4, 133.2, 132.0, 131.9, 131.5, 129.5, 129.0, 128.8, 126.4, 126.1, 124.4, 122.8, 114.4, 113.8, 110.2, 106.8, 103.3, 80.1, 60.6, 52.6, 47.1, 44.7, 35.2, 29.4, 27.9, 27.2, 26.7, 25.4, 19.0. ESI-MS: m/z=809.4 [M+H]$^+$ 4) Preparation of Compound 7-h A mixture of compound 7-g (181.9 g), toluene (1.8 L) and trifluoroacetic acid (107 mL) was heated to 45° C. and reacted for 5 h. The reaction solution was concentrated, added with ethyl acetate (1.5 L), washed with saturated aqueous $NaHCO_3$ solution and saturated aqueous sodium chloride solution, dried over anhydrous sodium sulfate, filtered and concentrated. The concentrate was added with toluene (1 L) and ethyl acetate (200 mL), heated to dissolved clarification, cooled to precipitate a solid, filtered and dried to give compound 7-h (83.4 g).

Compound 7-h: $^1$H NMR (500 MHz, DMSO-d6), δ: 7.98 (s, 1H), 7.82 (s, 1H), 7.73 (d, 1H), 7.64 (d, 1H), 7.46 (s, 1H), 7.40 (s, 1H), 7.32 (d, 1H), 6.73 (d, 1H), 6.36 (d, 1H), 6.34 (s, 1H), 3.09 (s, 4H), 2.64 (d, 1H), 2.55 (d, 1H), 2.19 (m, 6H), 1.88 (m, 2H), 1.42 (m, 2H), 1.25 (m, 2H), 0.95 (m, 6H). $^{13}$C NMR (125 MHz, DMSO-d6), δ: 166.3, 158.9, 155.1, 148.9, 146.2, 145.3, 135.0, 133.8, 133.2, 132.0, 131.9, 131.4, 129.5, 129.2, 127.8, 126.4, 124.9, 124.4, 122.7, 120.2, 116.6, 112.0, 109.5, 105.3, 100.2, 60.5, 55.3, 52.7, 47.0, 44.7, 35.2, 29.4, 27.2, 25.4. ESI-MS: m/z=639.2 [M+H]$^+$.

5) Preparation of Compound 7-k 3-nitro-4-chlorobenzenesulfonamide (0.64 g), (R)-(1,4-dioxan)-2-methylamine hydrochloride (0.5 g) and N,N-diisopropylethylamine (1.58 g) were dissolved in acetonitrile (10 mL), and the solution was heated to 85° C. and reacted for 6.5 h. The reaction solution was cooled at room temperature, left to stand overnight, and filtered to give compound 7-k (0.65 g). ESI-MS: m/z=316.2 [M–H]$^-$.

6) Preparation of Compound 7-1

Compound 7-h (1 g) and dichloromethane (10 mL) were mixed, and the mixture was stirred at room temperature. Then 4-dimethylaminopyridine (0.28 g) and 1-ethyl-(3-dimethylaminopropyl)carbodiimide hydrochloride (0.44 g) were added and dissolved with stirring. The resulting mixture was added with compound 7-k (0.5 g) and triethylamine (0.44 g), and reacted at room temperature for 3 h. The reaction solution was washed successively with 5 wt % hydrochloric acid, saturated aqueous sodium bicarbonate solution and saturated aqueous sodium chloride solution, dried over anhydrous $Na_2SO_4$, filtered, concentrated, and purified by column chromatography to give compound 7-1 (0.8 g).

Compound 7-1: $^1$H NMR (500 MHz, DMSO-d6), δ: 11.66 (s, 1H), 11.37 (s, 1H), 8.59 (t, 1H), 8.57 (d, 1H), 8.05 (d, 1H), 7.88 (d, 1H), 7.83 (dd, 1H), 7.70 (d, 1H), 7.53 (d, 1H), 7.52 (m, 2H), 7.40 (m, 1H), 7.12 (d, 1H), 6.75 (dd, 1H), 6.40 (dd, 1H), 6.30 (d, 1H), 3.80 (m, 3H), 3.62 (m, 2H), 3.51 (m, 2H), 3.42 (m, 2H), 3.03 (m, 4H), 2.67 (d, 1H), 2.54 (d, 1H), 2.17 (m, 6H), 1.88 (dd, 2H), 1.42 (t, 2H), 0.97 (s, 6H).

$^{13}$C NMR (125 MHz, DMSO-d6), δ: 164.0, 159.2, 159.0, 158.7, 158.4, 158.2, 154.0, 147.8, 146.9, 145.8, 144.2, 139.0, 135.5, 134.3, 132.8, 132.6, 131.7, 130.1, 130.0, 128.3, 128.2, 127.0, 125.1, 124.9, 124.4, 122.75, 120.3, 118.3, 117.5, 115.7, 115.2, 114.2, 122.8, 109.7, 103.6, 100.4, 58.5, 45.2, 44.3, 43.8, 34.6, 29.2, 29.1, 27.1, 24.8. ESI-MS: m/z=938.5 [M+H]$^+$.

Example 8

(S)-4-(4-{[2-(2-chloro-4-trifluoromethylphenyl)-4,4-dimethylcyclohex-1-enyl]methyl}-piperazin-1-yl)-N-({3-nitro-4-[(1,4-dioxan-2-yl)methyl)amino]phenyl}sulfonyl)-2-(1H-pyrrolo[2,3-b]pyridin-5-yloxy)-benzamide

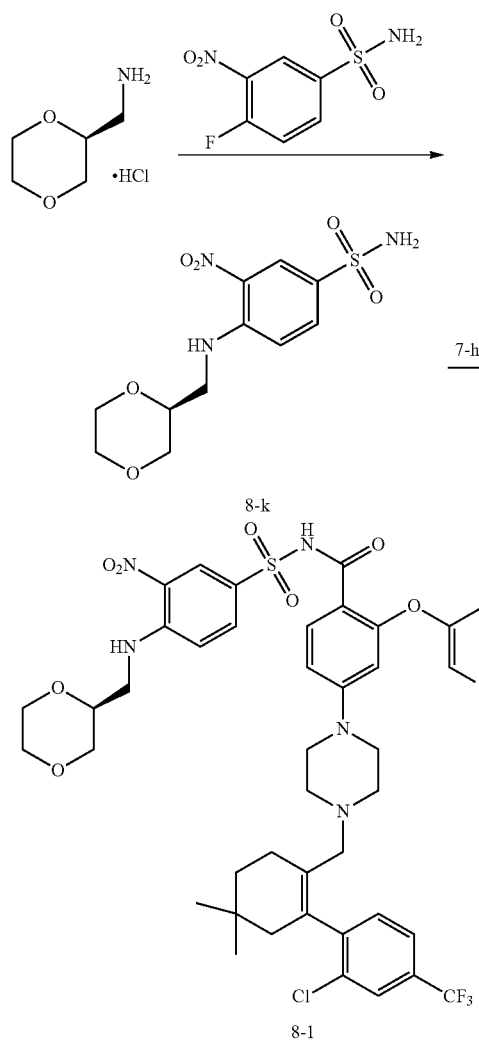

1) Preparation of Compound 8-k 3-nitro-4-fluorobenzenesulfonamide (3.58 g), (S)-2-(aminomethyl)-1,4-dioxane hydrochloride (3.0 g) and N,N-diisopropylethylamine (9.47 g) were dissolved in acetonitrile (50 mL), and the solution was heated to 85° C. and reacted for 5 h. The reaction solution was cooled at room temperature, left to stand overnight, and filtered under vacuum to give compound 8-k (4.70 g). ESI-MS: m/z=316.1 [M–H]⁻.

2) Preparation of compound 8-1

Compound 8-1 was obtained by reference to the preparation method for compound 7-1 in step 6) of Example 7, with compound 7-k being replaced by compound 8-k.

Compound 8-1: $^1$H NMR (500 MHz, DMSO-d6), δ: 11.66 (s, 1H), 11.37 (s, 1H), 8.59 (t, 1H), 8.57 (d, 1H), 8.04 (d, 1H), 7.89 (d, 1H), 7.84 (dd, 1H), 7.70 (d, 1H), 7.54 (d, 1H), 7.52 (m, 2H), 7.40 (m, 1H), 7.11 (d, 1H), 6.75 (dd, 1H), 6.40 (dd, 1H), 6.29 (d, 1H), 3.79 (m, 3H), 3.65 (m, 2H), 3.51 (m, 2H), 3.42 (m, 2H), 3.03 (m, 4H), 2.67 (d, 1H), 2.54 (d, 1H), 2.17 (m, 6H), 1.88 (dd, 2H), 1.42 (t, 2H), 0.96 (s, 6H).

$^{13}$C NMR (125 MHz, DMSO-d6), δ: 164.0, 158.2, 154.0, 147.9, 146.9, 145.9, 144.3, 135.6, 134.3, 132.9, 132.6, 131.8, 130.2, 130.0, 128.3, 128.2, 127.0, 125.2, 125.0, 122.8, 120.3, 118.3, 115.7, 114.1, 109.7, 103.6, 100.4, 73.4, 68.5, 66.4, 66.2, 58.6, 45.1, 44.4, 43.9, 34.6, 29.3, 29.1, 27.2, 24.8. ESI-MS: m/z=939.4 [M+H]⁺.

Example 9

4-(4-{[2-(2-chloro-4-trifluoromethylphenyl)-4,4-dimethylcyclohex-1-enyl]methyl}-piperazin-1-yl)-N-({3-nitro-4-[((4-acetylmorpholin-2-yl)methyl)amino]phenyl}sulfonyl)-2-(1H-pyrrolo[2,3-b]pyridin-5-yloxy)-benzamide

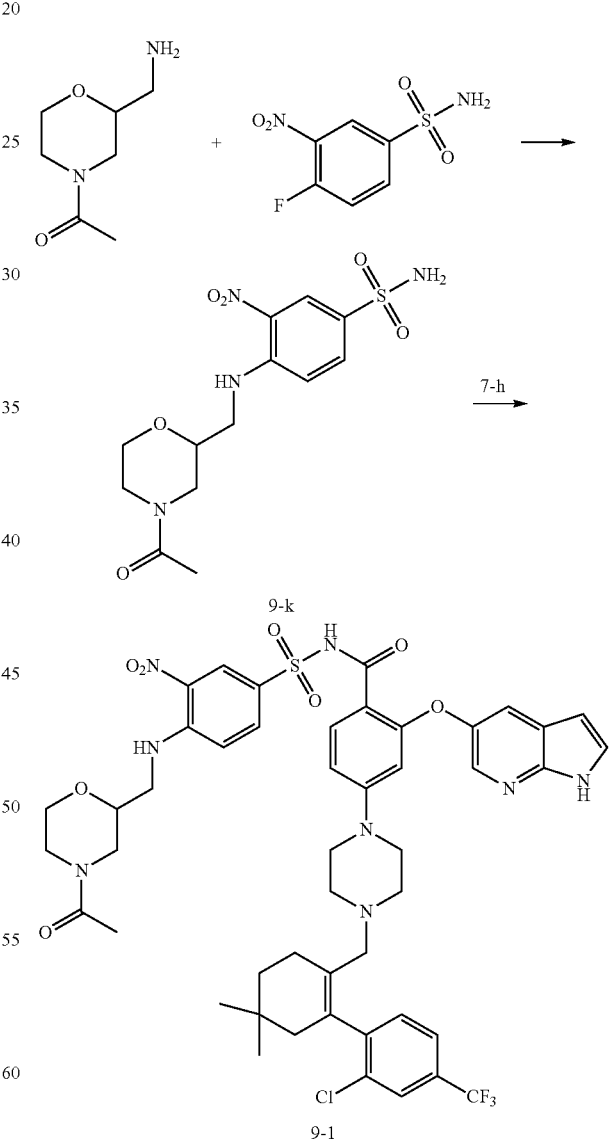

1) Preparation of Compound 9-k 3-nitro-4-fluorobenzenesulfonamide (0.56 g), [(4-acetylmorpholin-2-yl)methyl]amine (0.48 g) and N,N-diisopropylethylamine (0.65 g) were dissolved in acetonitrile (10 mL), and the solution was heated to 85° C. and reacted for 5 h. The reaction solution was cooled at room temperature, left to stand overnight, and filtered under vacuum to give compound 9-k (1.2 g). ESI-MS: m/z=359.0 [M+H]⁺.

2) Preparation of Compound 9-1

Compound 9-1 was obtained by reference to the preparation method for compound 7-1 in step 6) of Example 7, with compound 7-k being replaced by compound 9-k. Compound 9-1: ¹H NMR (500 MHz, DMSO-d6), δ:11.71 (s, 2H), 8.63 (t, 1H), 8.57 (d, 1H), 8.04 (d, 1H), 7.89 (s, 1H), 7.84 (dd, 1H), 7.70 (d, 1H), 7.53 (d, 3H), 7.39 (m, 1H), 7.15 (d, 1H), 6.75 (d, 1H), 6.40 (s, 1H), 6.30 (s, 1H), 3.87 (m, 3H), 3.68 (m, 2H), 3.60 (m, 3H), 3.48 (m, 2H), 3.40 (m, 2H), 3.30 (m, 2H), 3.18 (m, 1H), 3.02 (m, 2H), 2.29 (m, 1H), 2.19 (m, 1H), 1.96 (d, 2H), 1.49 (t, 2H), 1.24 (m, 1H), 0.97 (s, 9H).

¹³C NMR (125 MHz, DMSO-d6), δ: 169.1, 164.0, 158.9, 158.6, 158.2, 154.0, 147.9, 146.9, 145.9, 144.2, 135.5, 134.3, 132.8, 132.6, 131.7, 130.2, 128.3, 128.2, 127.0, 125.2, 124.9, 122.8, 120.3, 118.3, 117.4, 115.8, 115.1, 114.2, 109.7, 103.6, 100.4, 73.8, 66.4, 58.5, 48.5, 46.0, 45.1, 44.9, 44.3, 43.8, 34.6, 29.3, 29.1, 27.2, 24.8, 21.6, 21.6. ESI-MS: m/z=979.3 [M+H]⁺.

Example 10

4-(4-{[2-(2-chloro-4-trifluoromethylphenyl)-4,4-dimethylcyclohex-1-enyl]methyl}-piperazin-1-yl)-N-({3-nitro-4-[((4-isobutyrylmorpholin-2-yl)methyl)amino]phenyl}sulfonyl)-2-(1H-pyrrolo[2,3-b]pyridin-5-yloxy)-benzamide

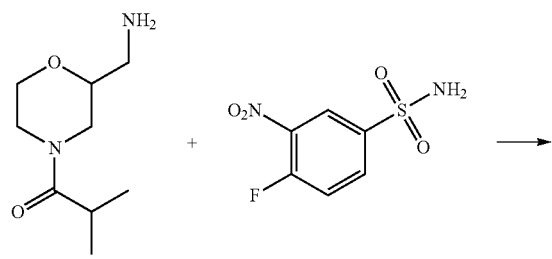

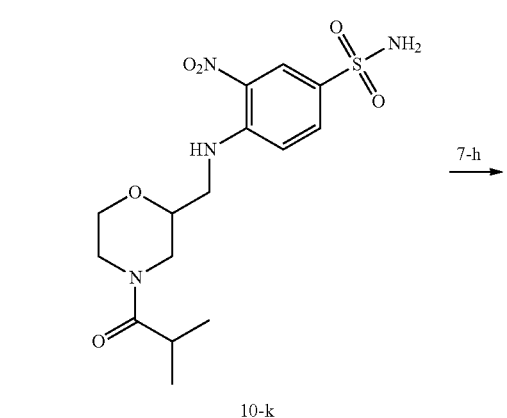

10-k

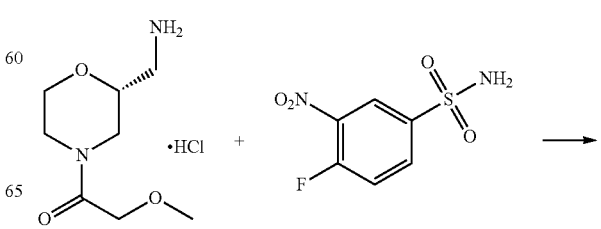

10-1

1) Preparation of Compound 10-k 3-nitro-4-fluorobenzenesulfonamide (1.48 g), [(4-isobutyrylmorpholin-2-yl)methyl]amine (1.5 g) and N,N-diisopropylethylamine (2.2 g) were dissolved in acetonitrile (10 mL), and the solution was heated to 85° C. and reacted for 5 h. The reaction solution was cooled at room temperature, left to stand overnight, and filtered under vacuum to give compound 10-k (1.8 g). ESI-MS: m/z=387.0 [M+H]⁺.

2) Preparation of Compound 10-1

Compound 10-1 was obtained by reference to the preparation method for compound 7-1 in step 6) of Example 7, with compound 7-k being replaced by compound 10-k.

Compound 10-1: ¹H NMR (500 MHz, DMSO-d6), δ: 11.71 (s, 2H), 8.64 (t, 1H), 8.58 (s, 1H), 8.04 (d, 1H), 7.89 (s, 1H), 7.84 (t, 1H), 7.70 (d, 1H), 7.53 (d, 3H), 7.40 (d, 1H), 7.16 (t, 1H), 6.75 (d, 1H), 6.40 (s, 1H), 6.30 (s, 1H), 4.36 (m, 1H), 3.86 (m, 2H), 3.58 (m, 4H), 3.47 (t, 2H), 3.39 (m, 2H), 3.19 (m, 1H), 3.02 (m, 2H), 2.87 (m, 2H), 2.71 (m, 1H), 2.57 (m, 1H), 2.29 (m, 1H), 2.20 (m, 1H), 1.96 (s, 2H), 1.49 (m, 2H), 1.24 (m, 1H), 0.97 (s, 12H).

¹³C NMR (125 MHz, DMSO-d6), δ: 175.2, 164.0, 158.8, 158.6, 158.2, 154.0, 147.9, 146.9, 145.9, 144.2, 135.6, 134.3, 132.8, 132.6, 131.8, 130.2, 130.0, 128.3, 128.2, 127.0, 125.2, 124.9, 122.8, 120.3, 118.3, 117.9, 115.8, 115.6, 114.1, 109.7, 103.6, 100.4, 74.2, 74.0, 66.6, 58.5, 47.8, 45.2, 45.1, 44.3, 44.1, 34.6, 29.5, 29.3, 29.1, 27.2, 24.8, 20.0, 19.5. ESI-MS: m/z=1007.3 [M+H]⁺.

Example 11

4-(4-{[2-(2-chloro-4-trifluoromethylphenyl)-4,4-dimethylcyclohex-1-enyl]methyl}-piperazin-1-yl)-N-({3-nitro-4-[(R)-(4-methoxyacetylmorpholin-2-yl)methyl)amino]phenyl}sulfonyl)-2-(1H-pyrrolo[2,3-b]pyridin-5-yloxy)-benzamide

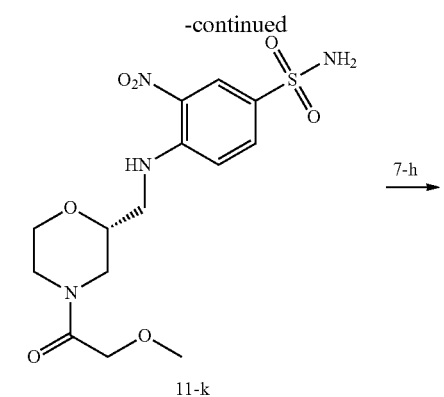

Example 12

4-(4-{[2-(2-chloro-4-trifluoromethylphenyl)-4,4-dimethylcyclohex-1-enyl]methyl}-piperazin-1-yl)-N-({3-nitro-4-[((4-methylsulfonylmorpholin-2-yl)methyl)amino]phenyl}sulfonyl)-2-(1H-pyrrolo[2,3-b]pyridin-5-yloxy)-benzamide

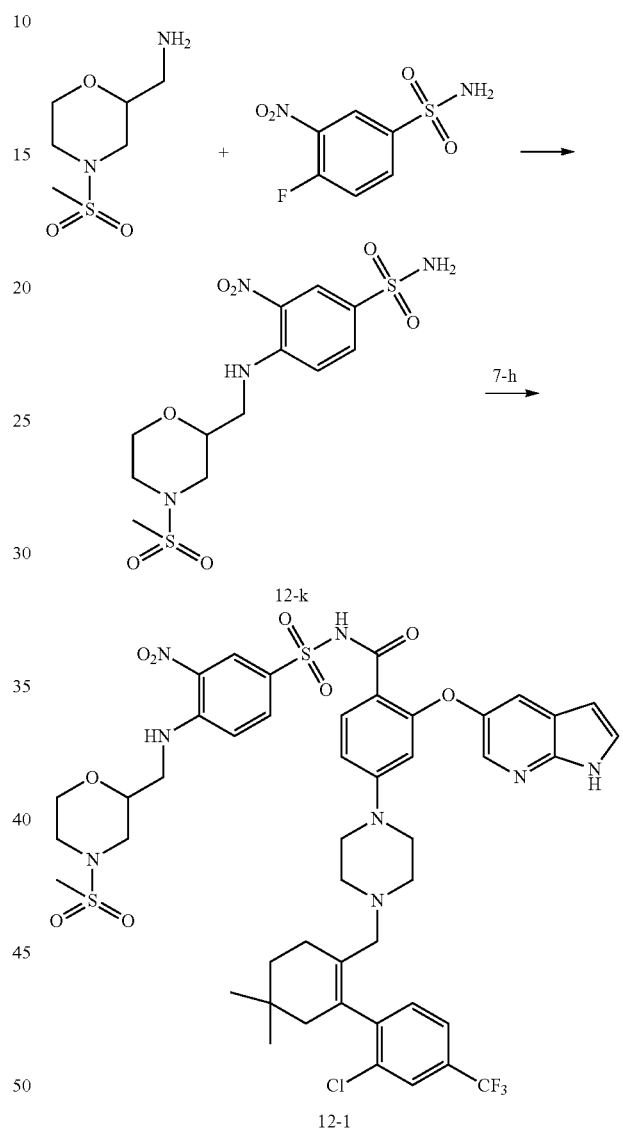

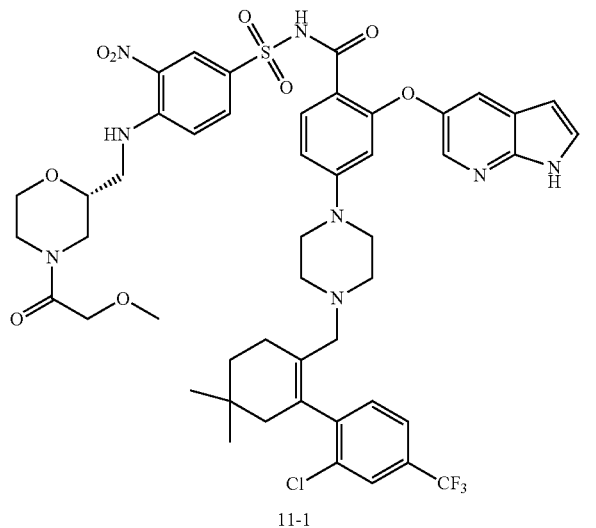

1) Preparation of Compound 11-k 3-nitro-4-fluorobenzenesulfonamide (0.36 g), (R)-2-(aminomethyl)-4-methoxyacetylmorpholine hydrochloride (0.45 g) and N,N-diisopropylethylamine (0.97 g) were dissolved in acetonitrile (20 mL), and the solution was heated to 85° C. and reacted for 5 h. The reaction solution was cooled at room temperature, left to stand overnight, and filtered under vacuum to give compound 11-k (0.39 g). ESI-MS: m/z=387.1 [M−H]⁻.

2) Preparation of Compound 11-1

Compound 11-1 was obtained by reference to the preparation method for compound 7-1 in step 6) of Example 7, with compound 7-k being replaced by compound 11-k.

Compound 11-1: $^1$H NMR (500 MHz, DMSO-d6), δ:11.72 (s, 2H), 8.64 (m, 1H), 8.57 (d, 1H), 8.04 (d, 1H), 7.89 (d, 1H), 7.84 (dd, 1H), 7.70 (d, 1H), 7.54 (d, 1H), 7.52 (m, 2H), 7.38 (m, 1H), 7.21 (d, 1H), 6.75 (dd, 1H), 6.38 (dd, 1H), 6.29 (d, 1H), 3.47 (m, 3H), 3.42 (m, 1H), 3.27 (m, 5H), 2.27 (m, 3H), 2.21 (m, 1H), 2.01 (m, 2H), 1.98 (m, 2H), 1.48 (t, 3H), 1.24 (m, 7H), 0.97 (s, 9H).

ESI-MS: m/z=1010.4 [M+H]⁺.

1) Preparation of Compound 12-k 3-nitro-4-fluorobenzenesulfonamide (0.66 g), [(4-methylsulfonylmorpholin-2-yl)methyl]amine (0.7 g) and N,N-diisopropylethylamine (0.97 g) were dissolved in acetonitrile (10 mL), and the solution was heated to 85° C. and reacted for 5 h. The reaction solution was cooled at room temperature, left to stand overnight, and filtered under vacuum to give compound 12-k (1.2 g). ESI-MS: m/z=395.0 [M+H]⁺.

2) Preparation of Compound 12-1

Compound 12-1 was obtained by reference to the preparation method for compound 7-1 in step 6) of Example 7, with compound 7-k being replaced by compound 12-k.

Compound 12-1: $^1$H NMR (500 MHz, DMSO-d6), δ: 11.71 (s, 2H), 8.64 (t, 1H), 8.58 (d, 1H), 8.05 (d, 1H), 7.89

(s, 1H), 7.84 (d, 1H), 7.70 (d, 1H), 7.54 (d, 3H), 7.39 (d, 1H), 7.17 (d, 1H), 6.75 (d, 1H), 6.40 (s, 1H), 6.30 (s, 1H), 3.99 (d, 1H), 3.79 (d, 2H), 3.63 (m, 5H), 3.50 (m, 1H), 3.38 (m, 3H), 2.92 (s, 3H), 2.86 (m, 2H), 2.70 (m, 2H), 2.29 (m, 1H), 2.19 (m, 1H), 1.96 (s, 3H), 1.50 (m, 2H), 1.24 (m, 1H), 0.97 (s, 6H).

$^{13}$C NMR (125 MHz, DMSO-d6), δ: 164.0, 158.9, 158.6, 158.3, 154.0, 147.8, 146.9, 145.9, 144.2, 139.0, 135.6, 134.3, 132.8, 132.6, 131.8, 130.3, 128.3, 128.2, 127.0, 125.2, 124.4, 122.8, 120.3, 118.3, 117.6, 115.8, 115.2, 114.1, 109.7, 103.6, 100.4, 73.7, 66.0, 58.5, 47.8, 45.4, 45.2, 45.0, 44.3, 34.6, 34.3, 29.3, 29.3, 29.1, 27.2, 24.8.

ESI-MS: m/z=1015.3 [M+H]$^+$.

Example 13

4-(4-{[2-(2-chloro-4-trifluoromethylphenyl)-4,4-dimethylcyclohex-1-enyl]methyl}-piperazin-1-yl)-N-({3-nitro-4-[(tetrahydro-2H-pyran-3-ylmethyl)amino]phenyl}sulfonyl)-2-(1H-pyrrolo[2,3-b]pyridin-5-yloxy)-benzamide

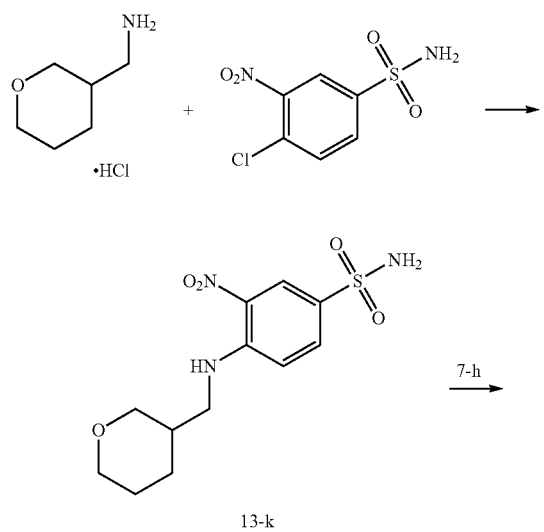

1) Preparation of Compound 13-k 3-nitro-4-chlorobenzenesulfonamide (1.0 g), 3-aminomethyl tetrahydropyran hydrochloride (0.77 g) and N,N-diisopropylethylamine (2.18 g) were dissolved in acetonitrile (20 mL), and the solution was heated to 85° C. and reacted for 5 h. The reaction solution was cooled at room temperature, left to stand overnight, and filtered under vacuum to give compound 13-k (1.3 g). ESI-MS: m/z=314.1 [M−H]$^−$.

2) Preparation of Compound 13-1

Compound 13-1 was obtained by reference to the preparation method for compound 7-1 in step 6) of Example 7, with compound 7-k being replaced by compound 13-k.

Compound 13-1: $^1$H NMR (500 MHz, DMSO-d6), δ: 11.71 (s, 1H), 11.69 (s, 1H), 8.59 (t, 1H), 8.57 (d, 1H), 8.05 (d, 1H), 7.88 (d, 1H), 7.82 (dd, 1H), 7.70 (d, 1H), 7.55 (d, 1H), 7.52 (m, 2H), 7.39 (m, 1H), 7.10 (d, 1H), 6.75 (dd, 1H), 6.40 (dd, 1H), 6.30 (d, 1H), 3.79 (m, 1H), 3.72 (m, 2H), 3.59 (m, 1H), 3.33 (m, 5H), 3.18 (m, 2H), 3.05 (m, 4H), 2.28 (m, 1H), 2.20 (m, 1H), 2.08 (m, 1H), 1.96 (d, 3H), 1.62 (m, 1H), 1.49 (t, 3H), 1.24 (m, 2H), 0.97 (s, 6H).

$^{13}$C NMR (125 MHz, DMSO-d6), δ: 158.2, 154.0, 147.8, 146.9, 145.9, 144.2, 139.0, 135.6, 134.3, 132.8, 132.6, 131.7, 130.2, 130.1, 130.0, 128.3, 127.0, 124.9, 124.8, 124.4, 122.8, 120.3, 118.3, 117.6, 115.5, 115.3, 114.2, 109.7, 103.6, 100.4, 70.5, 68.0, 58.5, 45.1, 44.9, 44.3, 35.3, 34.6, 29.3, 29.1, 27.2, 27.1, 25.0, 24.8.

ESI-MS: m/z=937.4 [M+H]$^+$.

Example 14

4-(4-{[2-(2-chloro-4-trifluoromethylphenyl)-4,4-dimethylcyclohex-1-enyl]methyl}-piperazin-1-yl)-N-({3-nitro-4-[(4-tetrahydro-2H-pyran-2-ylmethyl)amino]phenyl}sulfonyl)-2-(1H-pyrrolo[2,3-b]pyridin-5-yloxy)-benzamide

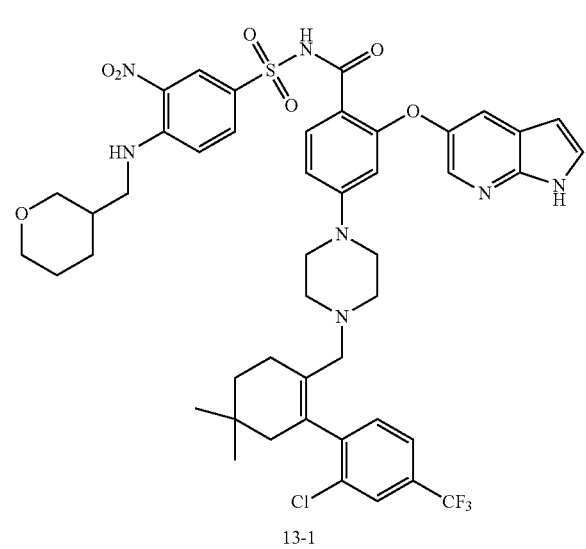

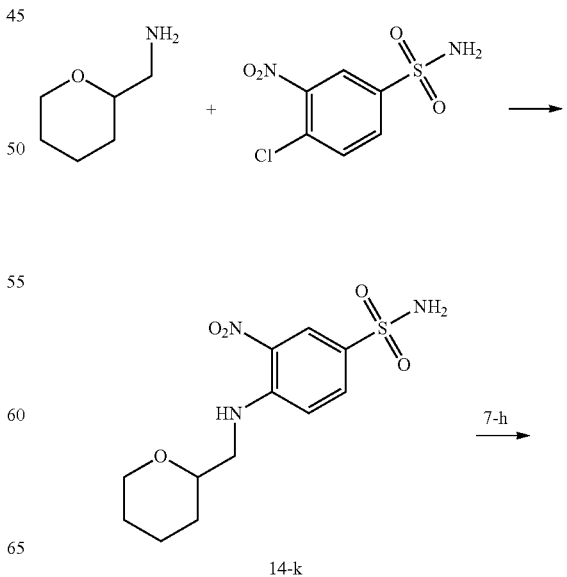

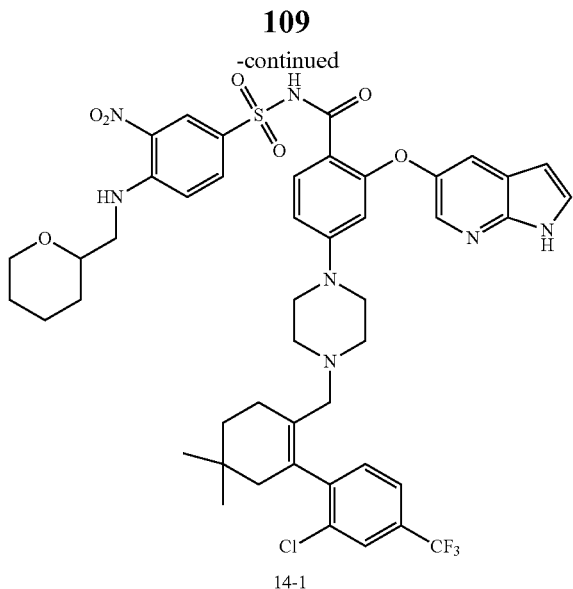

14-1

1) Preparation of Compound 14-k 3-nitro-4-chlorobenzenesulfonamide (1.2 g), 2-aminomethyl tetrahydropyran (0.7 g) and N,N-diisopropylethylamine (1.64 g) were dissolved in acetonitrile (10 mL), and the solution was heated to 85° C. and reacted for 8 h. The reaction solution was cooled at room temperature, left to stand overnight, and filtered under vacuum to give compound 14-k (1.92 g). ESI-MS: m/z=316.0 [M+H]$^+$.

2) Preparation of Compound 14-1

Compound 14-1 was obtained by reference to the preparation method for compound 7-1 in step 6) of Example 7, with compound 7-k being replaced by compound 14-k.

Compound 14-1: $^1$H NMR (500 MHz, DMSO-d6), δ: 11.72 (s, 2H), 8.62 (t, 1H), 8.57 (d, 1H), 8.05 (d, 1H), 7.89 (s, 1H), 7.83 (d, 1H), 7.70 (d, 1H), 7.54 (d, 3H), 7.39 (d, 1H), 7.11 (d, 1H), 6.75 (d, 1H), 6.40 (s, 1H), 6.30 (s, 1H), 3.92 (d, 1H), 3.56 (t, 2H), 3.48 (m, 1H), 3.37 (m, 5H), 2.85 (m, 4H), 2.23 (m, 1H), 2.20 (m, 1H), 1.96 (s, 2H), 1.80 (m, 1H), 1.65 (d, 1H), 1.50 (m, 5H), 1.28 (m, 2H), 0.97 (d, 6H).

$^{13}$C NMR (125 MHz, DMSO-d6), δ: 164.0, 158.9, 158.6, 158.2, 154.0, 147.9, 146.9, 145.9, 144.2, 139.0, 135.6, 134.3, 132.8, 132.6, 131.8, 130.2, 130.0, 128.3, 128.2, 127.0, 125.0, 124.4, 122.8, 120.3, 118.3, 115.8, 114.2, 109.7, 103.6, 100.4, 75.6, 68.0, 58.5, 47.9, 45.2, 44.3, 34.6, 29.3, 29.2, 29.1, 27.2, 26.0, 24.8, 22.9.

ESI-MS: m/z=936.4 [M+H]$^+$.

Example 15

4-(4-{[2-(2-chloro-4-trifluoromethylphenyl)-4,4-dimethylcyclohex-1-enyl]methyl}-piperazin-1-yl)-N-({3-nitro-4-[(1-(methylsulfonyl)piperidin-3-yl)methyl)amino]phenyl}sulfon yl)-2-(1H-pyrrolo[2,3-b]pyridin-5-yloxy)-benzamide

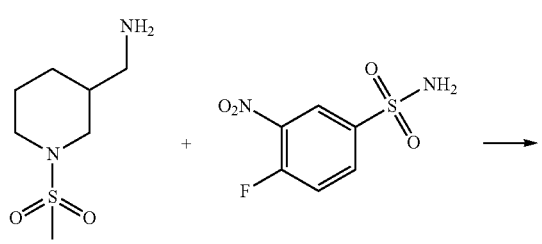

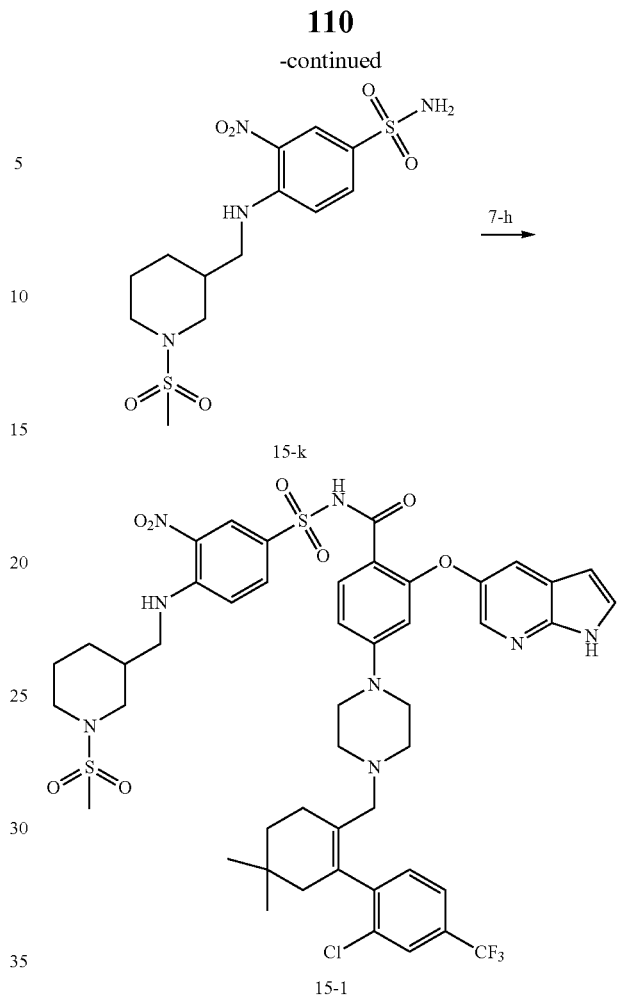

15-k 15-1

1) Preparation of Compound 15-k 3-nitro-4-fluorobenzenesulfonamide (1.57 g), 3-aminomethyl-1-methylsulfonylpiperidine (1.65 g) and N,N-diisopropylethylamine (2.31 g) were dissolved in acetonitrile (10 mL), and the solution was heated to 85° C. and reacted for 6 h. The reaction solution was cooled at room temperature, left to stand overnight, and filtered under vacuum to give compound 15-k (2.40 g). ESI-MS: m/z=393.1 [M+H]$^+$.

2) Preparation of Compound 15-1

Compound 15-1 was obtained by reference to the preparation method for compound 7-1 in step 6) of Example 7, with compound 7-k being replaced by compound 15-k.

Compound 15-1: $^1$H NMR (500 MHz, DMSO-d6), δ: 11.72 (d, 2H), 8.64 (t, 1H), 8.58 (s, 1H), 8.05 (s, 1H), 7.89 (s, 1H), 7.84 (d, 1H), 7.70 (d, 1H), 7.54 (t, 3H), 7.39 (d, 1H), 7.15 (d, 1H), 6.75 (d, 1H), 6.41 (s, 1H), 6.29 (s, 1H), 3.54 (d, 2H), 3.36 (m, 6H), 2.85 (s, 4H), 2.76 (t, 2H), 2.59 (t, 1H), 2.29 (m, 1H), 2.19 (m, 1H), 1.96 (s, 4H), 1.79 (m, 2H), 1.49 (m, 4H), 1.24 (m, 3H), 0.97 (d, 6H).

$^{13}$C NMR (125 MHz, DMSO-d6), δ: 164.0, 158.8, 158.2, 154.0, 147.8, 146.9, 145.9, 144.2, 135.6, 134.4, 132.8, 132.6, 131.8, 130.2, 128.3, 127.0, 125.0, 122.8, 120.3, 118.3, 115.6, 114.1, 109.7, 103.5, 100.4, 58.5, 49.3, 46.4, 45.7, 45.2, 44.4, 35.0, 34.6, 34.5, 29.3, 29.1, 27.4, 27.2, 24.8, 24.1.

ESI-MS: m/z=1013.3 [M+H]$^+$.

Example 16

4-(4-{[2-(2-chloro-4-trifluoromethylphenyl)-4,4-dimethylcyclohex-1-enyl]methyl}-piperazin-1-yl)-N-({3-nitro-4-[(2-(4-acetylmorpholin-2-yl)ethyl)amino]phenyl}sulfonyl)-2-(1H-pyrrolo[2,3-b]pyridin-5-yloxy)-benzamide

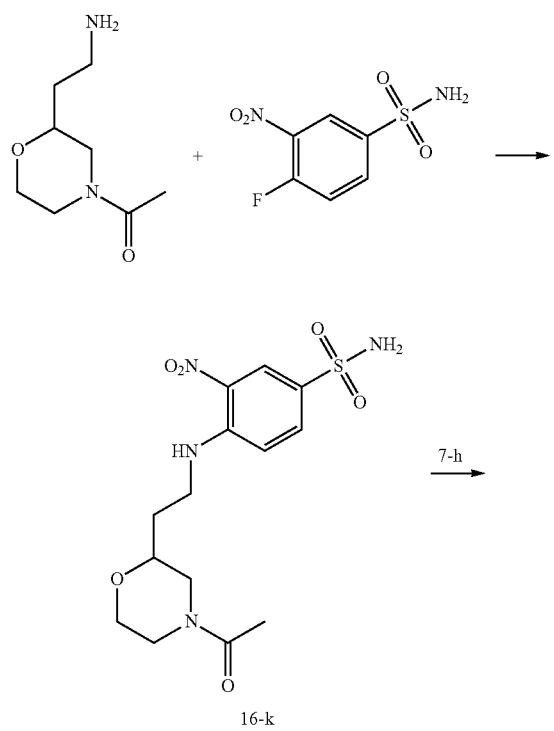

1) Preparation of Compound 16-k 3-nitro-4-fluorobenzenesulfonamide (2.13 g), 2-aminoethyl-4-acetylmorpholine (2 g) and N,N-diisopropylethylamine (3.13 g) were dissolved in acetonitrile (10 mL), and the solution was heated to 85° C. and reacted for 6 h. The reaction solution was cooled at room temperature, left to stand overnight, and filtered under vacuum to give compound 16-k (3.40 g). ESI-MS: m/z=373.1 [M+H]⁺.

2) Preparation of Compound 16-1

Compound 16-1 was obtained by reference to the preparation method for compound 7-1 in step 6) of Example 7, with compound 7-k being replaced by compound 16-k.

Compound 16-1: $^1$H NMR (500 MHz, DMSO-d6), δ: 11.70 (s, 2H), 8.78 (s, 1H), 8.57 (s, 1H), 8.04 (s, 1H), 7.82 (m, 2H), 7.69 (d, 1H), 7.52 (s, 1H), 7.44 (m, 2H), 7.38 (d, 1H), 7.23 (m, 1H), 6.75 (d, 1H), 6.39 (s, 1H), 6.29 (s, 1H), 4.87 (m, 2H), 3.89 (d, 2H), 3.43 (m, 8H), 3.03 (m, 4H), 2.90 (m, 2H), 2.67 (m, 2H), 2.20 (m, 4H), 1.96 (m, 3H), 1.47 (m, 2H), 1.24 (m, 1H), 0.96 (s, 6H).

$^{13}$C NMR (125 MHz, DMSO-d6), δ: 168.9, 163.9, 163.5, 153.9, 147.6, 145.9, 135.5, 134.4, 133.2, 132.8, 131.7, 130.1, 129.6, 128.3, 127.5, 124.9, 120.2, 115.2, 109.3, 100.4, 74.3, 66.6, 66.4, 58.5, 49.8, 50.4, 45.7, 45.3, 44.2, 41.2, 34.6, 31.6, 31.4, 29.3, 29.1, 27.2, 24.8, 21.6.

ESI-MS: m/z=993.3 [M+H]⁺.

Example 17

4-(4-{[2-(2-chloro-4-trifluoromethylphenyl)-4,4-dimethylcyclohex-1-enyl]methyl}-piperazin-1-yl)-N-({3-nitro-4-[(3-(1-methylpiperidin-4-yl)propyl)amino]phenyl}sulfonyl)-2-(1H-pyrrolo[2,3-b]pyridin-5-yloxy)-benzamide

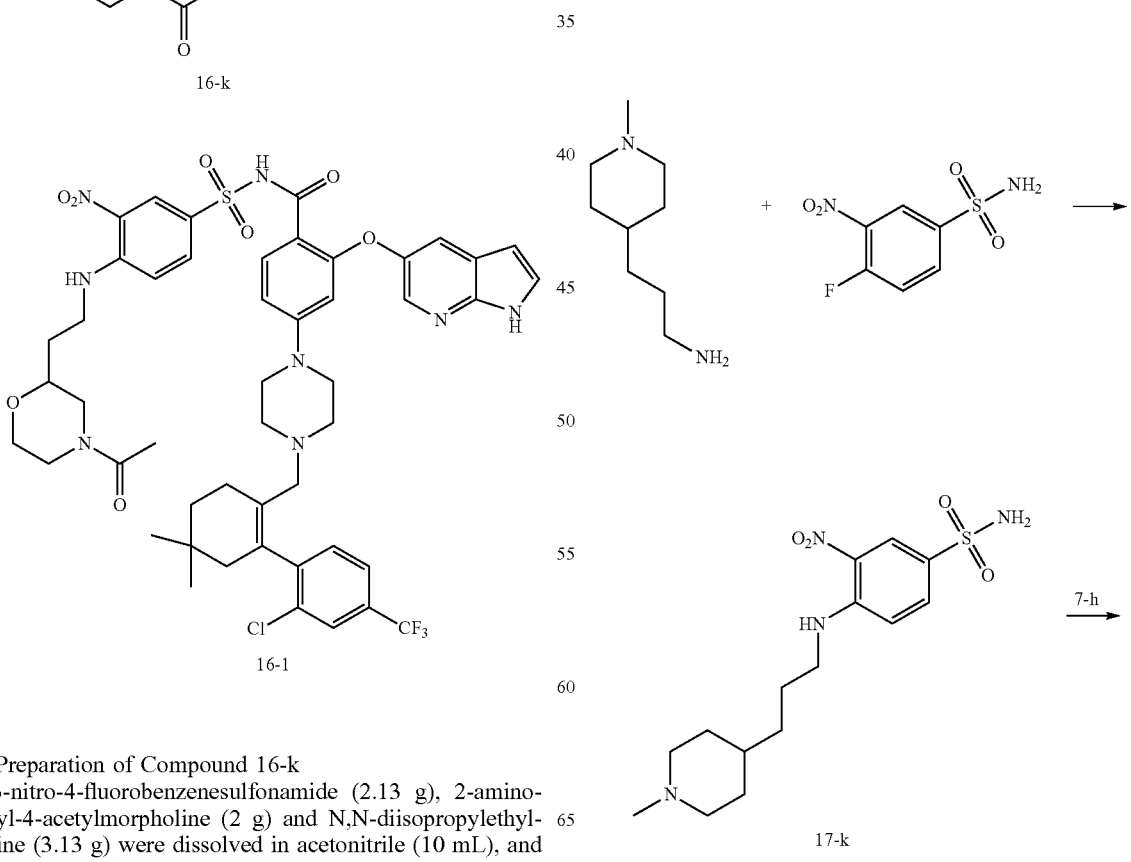

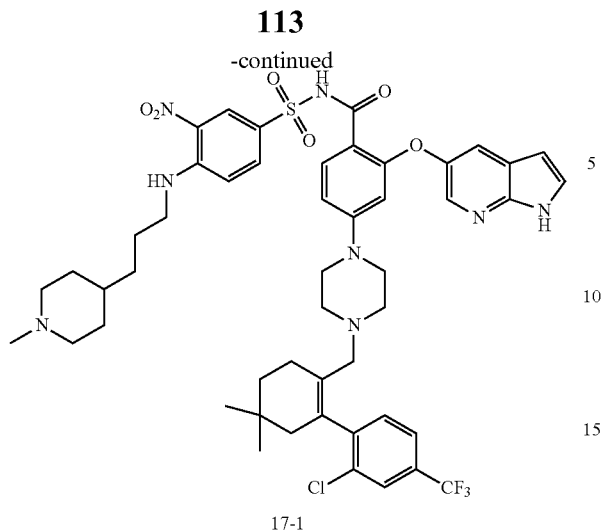

17-1

1) Preparation of Compound 17-k 3-nitro-4-fluorobenzenesulfonamide (2.34 g), 4-aminopropyl-1-methylpiperidine (2 g) and N,N-diisopropylethylamine (3.56 g) were dissolved in acetonitrile (10 mL), and the solution was heated to 85° C. and reacted for 6 h. The reaction solution was cooled at room temperature, left to stand overnight, and filtered under vacuum to give compound 17-k (3.56 g). ESI-MS: m/z=357.2 [M+H]$^+$.

2) Preparation of Compound 17-1

Compound 17-1 was obtained by reference to the preparation method for compound 7-1 in step 6) of Example 7, with compound 7-k being replaced by compound 17-k.

Compound 17-1: $^1$H NMR (500 MHz, DMSO-d6), δ: 11.54 (s, 2H), 8.43 (s, 1H), 8.30 (t, 1H), 8.19 (s, 1H), 7.94 (s, 1H), 7.82 (s, 1H), 7.67 (t, 2H), 7.58 (d, 1H), 7.33 (m, 2H), 6.82 (d, 1H), 6.63 (d, 1H), 6.31 (s, 1H), 6.24 (s, 1H), 3.34 (m, 3H), 2.98 (m, 6H), 2.75 (t, 2H), 2.65 (d, 1H), 2.54 (s, 1H), 2.20 (m, 6H), 1.90 (t, 4H), 1.56 (s, 3H), 1.35 (m, 4H), 1.23 (s, 1H), 1.17 (t, 3H), 0.96 (d, 6H).

$^{13}$C NMR (125 MHz, DMSO-d6), δ: 169.2, 164.0, 156.9, 153.4, 149.3, 146.2, 145.2, 135.3, 135.1, 133.2, 132.5, 132.0, 131.5, 129.8, 129.5, 129.2, 127.5, 126.5, 126.2, 125.0, 124.4, 122.8, 121.5, 120.1, 116.6, 114.1, 109.7, 105.8, 100.1, 60.6, 52.8, 51.4, 51.3, 47.7, 44.7, 35.3, 34.3, 31.3, 29.4, 29.3, 27.3, 25.4, 9.8.

ESI-MS: m/z=977.6 [M+H]$^+$.

Example 18

4-(4-{[2-(2-chloro-4-trifluoromethylphenyl)-4,4-dimethylcyclohex-1-enyl]methyl}-piperazin-1-yl)-N-({3-nitro-4-[(2-(1-methylpiperidin-4-yl)ethyl)amino]phenyl}sulfonyl)-2-(1H-pyrrolo[2,3-b]pyridin-5-yloxy)-benzamide

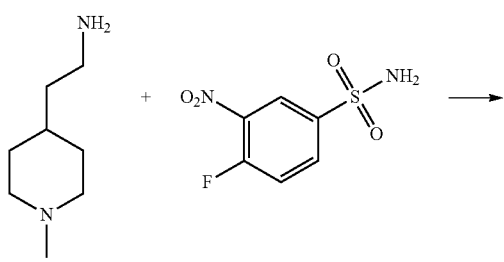

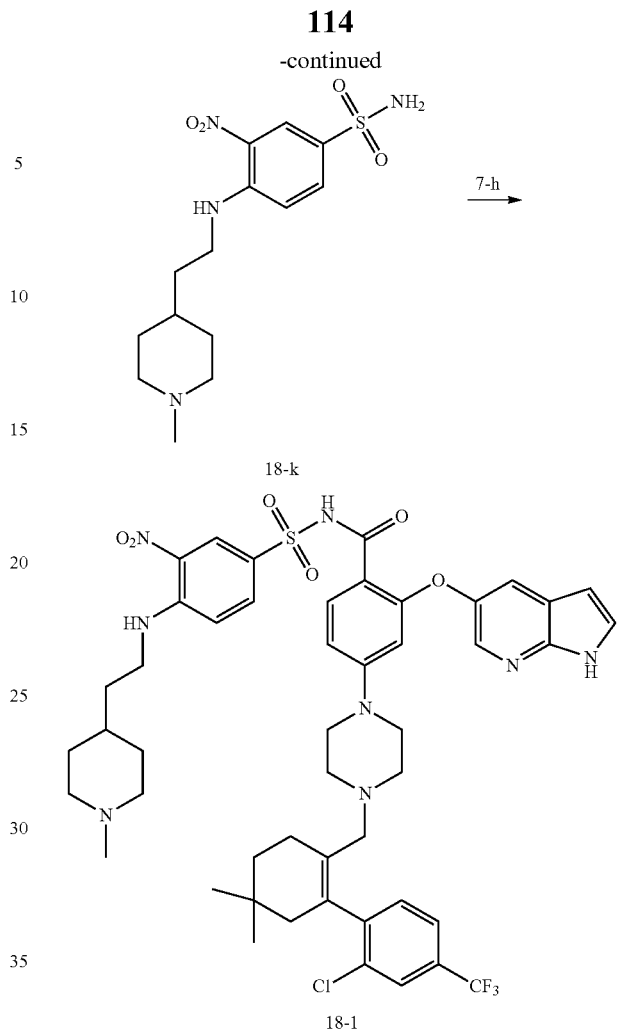

18-k 18-1

1) Preparation of Compound 18-k 3-nitro-4-fluorobenzenesulfonamide (2.58 g), 4-aminoethyl-1-methylpiperidine (2 g) and N,N-diisopropylethylamine (3.78 g) were dissolved in acetonitrile (10 mL), and the solution was heated to 85° C. and reacted for 6 h. The reaction solution was cooled at room temperature, left to stand overnight, and filtered under vacuum to give compound 18-k (3.68 g). ESI-MS: m/z=343.1 [M+H]$^+$.

2) Preparation of Compound 18-1

Compound 18-1 was obtained by reference to the preparation method for compound 7-1 in step 6) of Example 7, with compound 7-k being replaced by compound 18-k.

Compound 18-1: $^1$H NMR (500 MHz, DMSO-d6), δ: 11.72 (d, 2H), 8.58 (s, 2H), 8.04 (s, 1H), 7.88 (s, 1H), 7.84 (d, 1H), 7.70 (d, 1H), 7.53 (m, 3H), 7.40 (d, 1H), 7.08 (d, 1H), 6.75 (d, 1H), 6.40 (s, 1H), 6.29 (s, 1H), 3.56 (d, 1H), 3.42 (m, 6H), 3.10 (m, 1H), 2.91 (m, 3H), 2.77 (m, 4H), 2.21 (m, 2H), 1.94 (d, 4H), 1.53 (m, 4H), 1.36 (m, 2H), 1.24 (m, 2H), 0.97 (d, 9H).

$^{13}$C NMR (125 MHz, DMSO-d6), δ: 164.0, 158.9, 158.6, 158.2, 154.0, 147.6, 146.9, 145.9, 144.3, 135.6, 134.4, 132.9, 132.5, 131.8, 130.1, 128.3, 125.0, 124.8, 120.3, 118.3, 115.6, 115.4, 114.2, 109.7, 103.6, 100.4, 58.5, 53.9, 45.2, 44.3, 43.1, 34.6, 34.3, 30.8, 29.4, 29.3, 29.1, 28.0, 24.8.

ESI-MS: m/z=963.8 [M+H]$^+$.

Example 19

4-(4-{[2-(2-chloro-4-trifluoromethylphenyl)-4,4-dimethylcyclohex-1-enyl]methyl}-piperazin-1-yl)-N-({3-nitro-4-[(2-(1-ethylpiperidin-4-yl)ethyl)amino]phenyl}sulfonyl)-2-(1H-pyrrolo[2,3-b]pyridin-5-yloxy)-benzamide

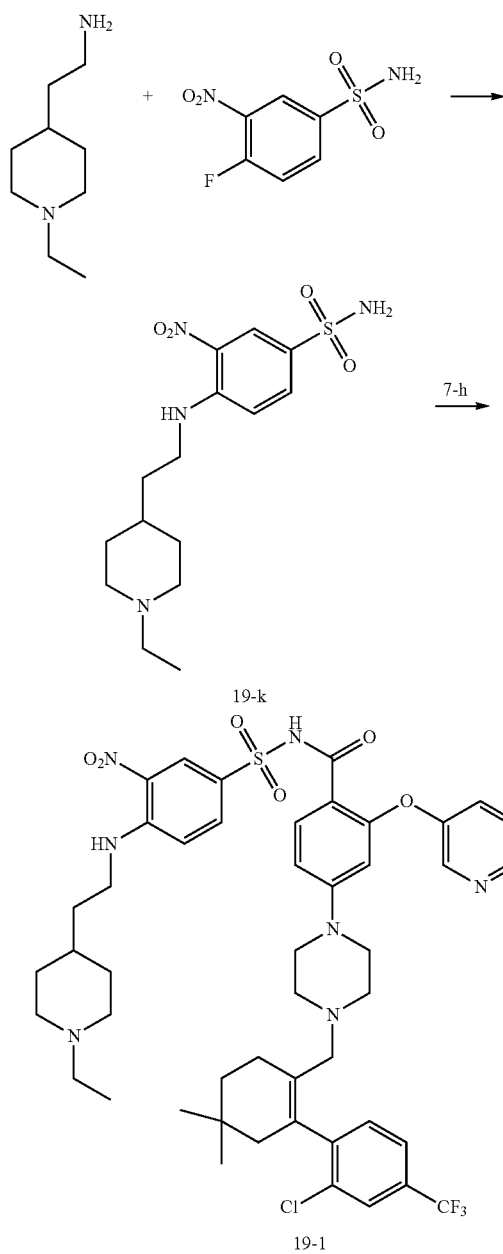

1) Preparation of Compound 19-k 3-nitro-4-fluorobenzenesulfonamide (2.34 g), 4-aminoethyl-1-ethylpiperidine (2 g) and N,N-diisopropylethylamine (3.43 g) were dissolved in acetonitrile (10 mL), and the solution was heated to 85° C. and reacted for 6 h. The reaction solution was cooled at room temperature, left to stand overnight, and filtered under vacuum to give compound 19-k (3.35 g). ESI-MS: m/z=357.2 [M+H]$^+$.

2) Preparation of Compound 19-1

Compound 19-1 was obtained by reference to the preparation method for compound 7-1 in step 6) of Example 7, with compound 7-k being replaced by compound 19-k.

Compound 19-1: $^1$H NMR (500 MHz, DMSO-d6), δ: 11.61 (s, 1H), 11.57 (s, 1H), 8.45 (s, 1H), 8.37 (t, 1H), 8.17 (s, 1H), 7.96 (s, 1H), 7.82 (s, 1H), 7.70 (d, 1H), 7.65 (d, 1H), 7.55 (d, 1H), 7.36 (s, 1H), 7.33 (d, 1H), 6.87 (d, 1H), 6.64 (d, 1H), 6.33 (s, 1H), 6.23 (s, 1H), 3.31 (m, 3H), 3.01 (s, 6H), 2.81 (t, 1H), 2.66 (m, 3H), 2.54 (s, 1H), 2.15 (m, 5H), 1.90 (d, 2H), 1.81 (d, 2H), 1.59 (m, 1H), 1.43 (m, 2H), 1.27 (m, 8H), 0.95 (d, 6H).

$^{13}$C NMR (125 MHz, DMSO-d6), δ: 168.1, 157.2, 153.8, 148.7, 146.6, 146.2, 145.3, 135.4, 135.0, 133.2, 132.5, 132.0, 131.5, 129.7, 129.5, 127.7, 126.6, 126.5, 125.0, 124.7, 124.5, 122.8, 120.1, 117.0, 114.3, 109.6, 105.1, 100.2, 53.8, 52.8, 47.6, 44.7, 43.1, 42.8, 35.3, 32.6, 31.8, 31.6, 30.3, 29.4, 29.2, 27.3, 25.7, 25.4, 22.6, 14.4. ESI-MS: m/z=977.7 [M+H]$^+$.

Example 20

4-(4-{[2-(2-chloro-4-trifluoromethylphenyl)-4,4-dimethylcyclohex-1-enyl]methyl}-piperazin-1-yl)-N-({3-nitro-4-[(2-(1-(2-fluoroethyl)piperidin-4-yl)ethyl)amino]phenyl}sulfonyl)-2-(1H-pyrrolo[2,3-b]pyridin-5-yloxy)-benzamide

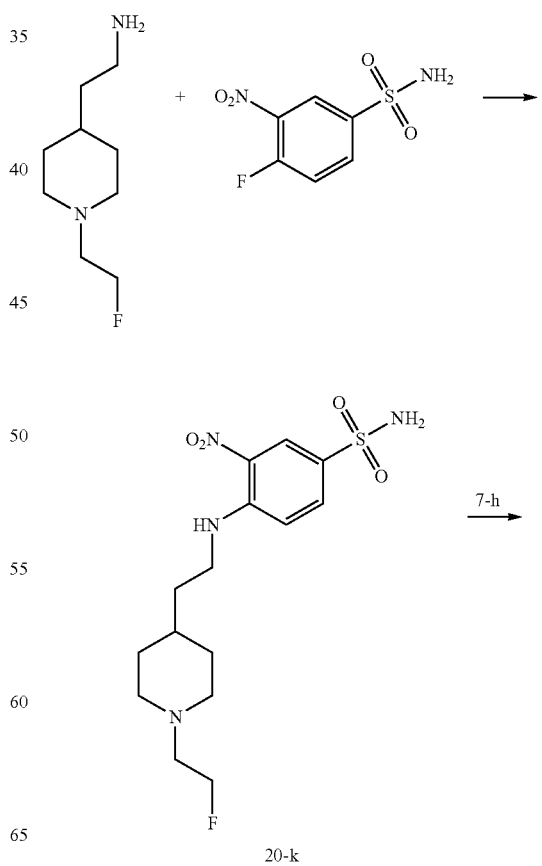

117
-continued

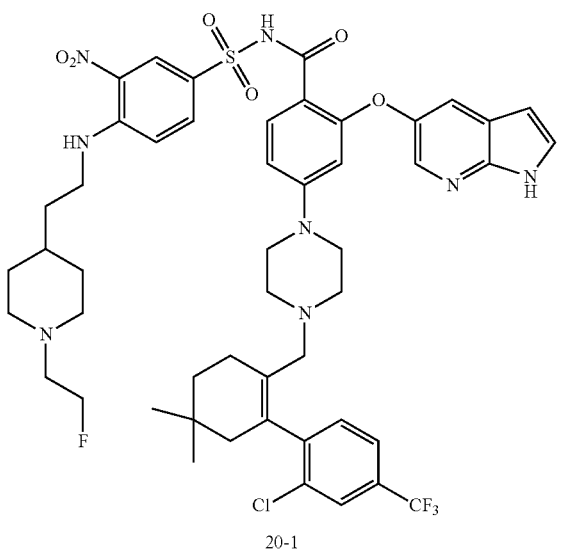

20-1

1) Preparation of Compound 20-k 3-nitro-4-fluorobenzenesulfonamide (2.11 g), 4-aminoethyl-1-(2-fluoroethyl)piperidine (2 g) and N,N-diisopropylethylamine (3.09 g) were dissolved in acetonitrile (10 mL), and the solution was heated to 85° C. and reacted for 6 h. The reaction solution was cooled at room temperature, left to stand overnight, and filtered under vacuum to give compound 20-k (3.29 g). ESI-MS: m/z=375.1 [M+H]⁺.

2) Preparation of Compound 20-1

Compound 20-1 was obtained by reference to the preparation method for compound 7-1 in step 6) of Example 7, with compound 7-k being replaced by compound 20-k.

Compound 20-1: $^{1}$H NMR (500 MHz, DMSO-d6), δ: 11.62 (s, 2H), 8.51 (s, 1H), 8.43 (t, 1H), 8.16 (s, 1H), 8.00 (s, 1H), 7.82 (s, 1H), 7.76 (d, 1H), 7.65 (d, 1H), 7.52 (d, 1H), 7.47 (s, 1H), 7.33 (d, 1H), 6.95 (d, 1H), 6.66 (d, 1H), 6.36 (s, 1H), 6.21 (s, 1H), 4.69 (s, 1H), 4.60 (s, 1H), 3.39 (m, 2H), 3.12 (d, 2H), 3.03 (s, 3H), 2.98 (s, 1H), 2.92 (s, 1H), 2.64 (d, 1H), 2.54 (s, 1H), 2.42 (t, 2H), 2.15 (m, 6H), 1.89 (d, 2H), 1.78 (d, 2H), 1.56 (m, 2H), 1.43 (m, 3H), 1.29 (m, 3H), 0.96 (d, 6H).

$^{13}$C NMR (125 MHz, DMSO-d6), δ: 163.6, 157.7, 154.4, 148.0, 147.0, 146.2, 145.6, 135.6, 134.8, 133.2, 132.5, 132.0, 131.4, 129.9, 129.5, 129.3, 128.2, 127.9, 127.3, 126.5, 124.9, 124.4, 122.8, 120.2, 117.6, 116.7, 114.7, 109.4, 104.1, 100.3, 81.6, 80.2, 60.5, 57.4, 57.3, 53.3, 52.7, 47.3, 44.7, 35.3, 34.7, 32.2, 30.7, 29.4, 25.4. ESI-MS: m/z=995.4 [M+H]⁺.

118

Example 21

4-(4-{[2-(2-chloro-4-trifluoromethylphenyl)-4,4-dimethylcyclohex-1-enyl]methyl}-piperazin-1-yl)-N-({3-nitro-4-[(2-(4-(methylsulfonyl)morpholin-2-yl)ethyl)amino]phenyl}sulfonyl)-2-(1H-pyrrolo[2,3-b]pyridin-5-yloxy)-benzamide

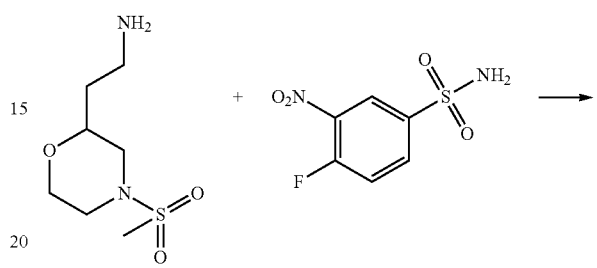

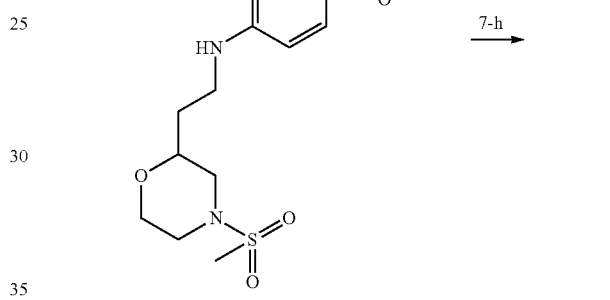

21-1

1) Preparation of Compound 21-k 3-nitro-4-fluorobenzenesulfonamide (2.2 g), 2-aminoethyl-4-methylsulfonylmorpholine (2.52 g) and N,N-diisopropylethylamine (3.26 g) were dissolved in acetonitrile (10 mL), and the solution was heated to 85° C. and reacted for 6 h. The reaction solution was cooled at room temperature, left to stand overnight, concentrated and dried to give compound 21-k (3.52 g). ESI-MS: m/z=409.1 [M+H]⁺.

2) Preparation of Compound 21-1

Compound 21-1 was obtained by reference to the preparation method for compound 7-1 in step 6) of Example 7, with compound 7-k being replaced by compound 21-k.

Compound 21-1: $^1$H NMR (500 MHz, DMSO-d6), δ: 11.72 (s, 2H), 8.59 (d, 1H), 8.18 (d, 1H), 8.04 (d, 1H), 7.89 (m, 2H), 7.69 (dd, 1H), 7.56 (d, 1H), 7.52 (m, 2H), 7.40 (m, 1H), 7.27 (m, 1H), 6.75 (d, 1H), 6.40 (m, 1H), 6.30 (m, 1H), 4.00 (m, 3H), 3.67 (m, 1H), 3.59 (m, 3H), 3.46 (m, 1H), 3.35 (m, 5H), 3.15 (m, 3H), 2.28 (m, 3H), 2.05 (m, 5H), 1.84 (m, 1H), 1.71 (m, 1H), 1.60 (m, 1H), 1.49 (m, 2H), 1.24 (m, 1H), 0.96 (s, 6H).

$^{13}$C NMR (125 MHz, DMSO-d6), δ: 164.0, 158.2, 154.0, 146.9, 146.6, 145.9, 144.2, 139.0, 135.6, 134.5, 132.9, 132.5, 131.8, 130.6, 130.0, 128.3, 128.2, 127.0, 125.7, 124.9, 124.5, 122.8, 120.3, 118.3, 115.6, 114.2, 109.7, 103.6, 100.5, 66.0, 62.1, 58.5, 58.5, 48.0, 47.9, 45.2, 44.3, 34.6, 29.3, 29.2, 29.1, 27.9, 27.5, 27.1, 24.8. ESI-MS: m/z=1029.4 [M+H]$^+$.

Example 22

4-(4-{[2-(2-chloro-4-trifluoromethylphenyl)-4,4-dimethylcyclohex-1-enyl]methyl}-piperazin-1-yl)-N-({3-nitro-4-[(2-(4-isobutyrylmorpholin-2-yl)ethyl)amino]phenyl}sulfonyl)-2-(1H-pyrrolo[2,3-b]pyridin-5-yloxy)-benzamide

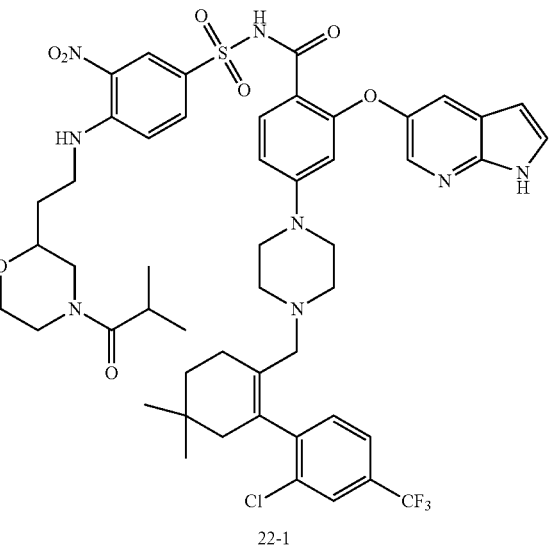

22-1

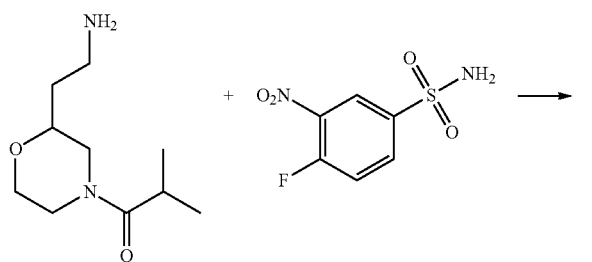

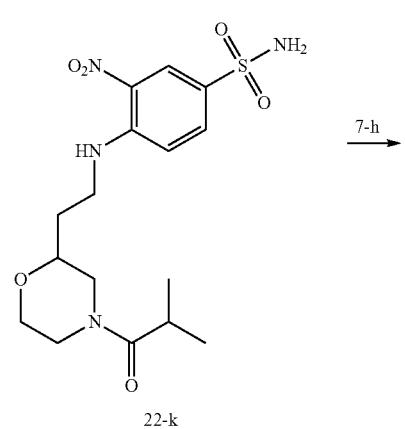

22-k

1) Preparation of Compound 22-k 3-nitro-4-fluorobenzenesulfonamide (2.2 g), 2-aminoethyl-4-isobutyrylmorpholine (2.42 g) and N,N-diisopropylethylamine (3.26 g) were dissolved in acetonitrile (10 mL), and the solution was heated to 85° C. and reacted for 6 h. The reaction solution was cooled at room temperature, left to stand overnight, concentrated and dried to give compound 22-k (3.42 g). ESI-MS: m/z=401.1 [M+H]$^+$.

2) Preparation of Compound 22-1

Compound 22-1 was obtained by reference to the preparation method for compound 7-1 in step 6) of Example 7, with compound 7-k being replaced by compound 22-k.

Compound 22-1: $^1$H NMR (500 MHz, DMSO-d6), δ: 11.69 (s, 2H), 8.79 (s, 1H), 8.58 (s, 1H), 8.05 (s, 1H), 7.82 (m, 2H), 7.65 (d, 1H), 7.55 (s, 1H), 7.50 (m, 2H), 7.33 (d, 1H), 7.06 (m, 1H), 6.69 (d, 1H), 6.39 (s, 1H), 6.20 (s, 1H), 3.89 (d, 2H), 3.42 (m, 8H), 3.17 (m, 4H), 2.88 (m, 2H), 2.66 (m, 2H), 2.22 (m, 4H), 1.92 (m, 3H), 1.42 (m, 2H), 1.23 (m, 1H), 0.96 (s, 12H).

$^{13}$C NMR (125 MHz, DMSO-d6), δ: 174.9, 163.9, 163.5, 158.3, 155.0, 147.6, 146.9, 145.9, 135.7, 134.4, 133.2, 132.6, 131.9, 130.1, 129.6, 129.3, 128.2, 126.5, 124.9, 124.5, 122.8, 120.2, 118.3, 115.2, 112.8, 109.3, 102.8, 100.4, 74.5, 74.4, 66.6, 66.4, 60.3, 52.4, 49.8, 46.7, 46.0, 45.3, 44.8, 41.5, 35.2, 31.6, 31.4, 29.4, 29.2, 27.3, 25.3, 20.1, 19.5. ESI-MS: m/z=1021.4 [M+H]$^+$.

Example 23

4-(4-{[2-(2-chloro-4-trifluoromethylphenyl)-4,4-dimethylcyclohex-1-enyl]methyl}-piperazin-1-yl)-N-({3-nitro-4-[(1-isobutyrylpiperidin-4-yl)methyl)amino]phenyl}sulfonyl)-2-(1H-pyrrolo[2,3-b]pyridin-5-yloxy)-benzamide

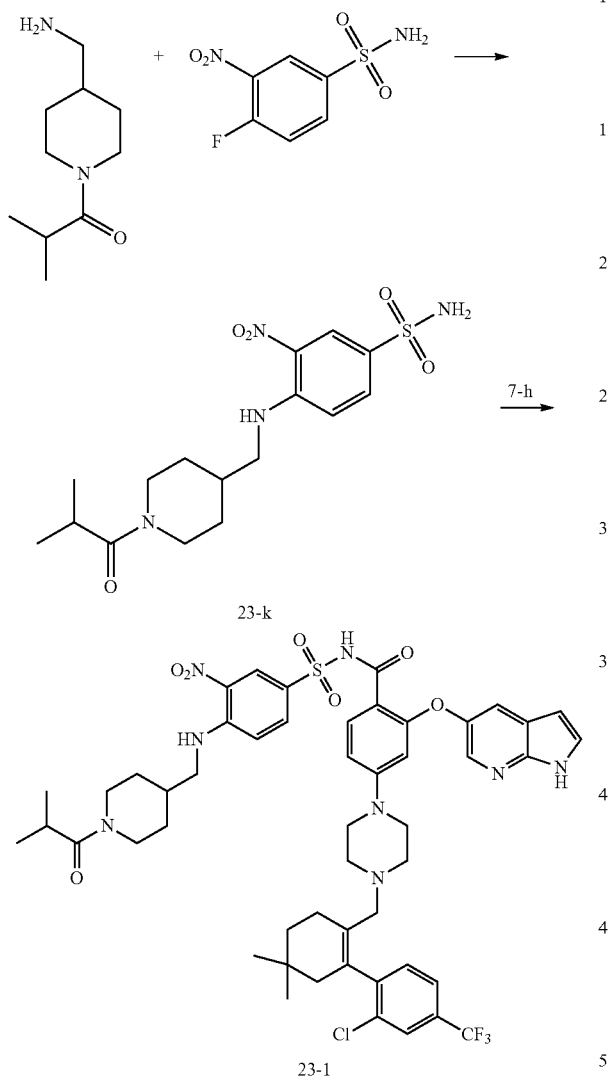

1) Preparation of Compound 23-k 3-nitro-4-fluorobenzenesulfonamide (1.99 g), 4-aminomethyl-1-isobutyrylpiperidine (2.0 g) and N,N-diisopropylethylamine (2.91 g) were dissolved in acetonitrile (10 mL), and the solution was heated to 85° C. and reacted for 6 h. The reaction solution was cooled at room temperature, left to stand overnight, concentrated and dried to give compound 23-k (3.24 g). ESI-MS: m/z=385.2 [M+H]$^+$.

2) Preparation of Compound 23-1

Compound 23-1 was obtained by reference to the preparation method for compound 7-1 in step 6) of Example 7, with compound 7-k being replaced by compound 23-k.

Compound 23-1: $^1$H NMR (500 MHz, DMSO-d6), δ: 11.73 (s, 1H), 11.68 (s, 1H), 8.64 (t, 1H), 8.58 (s, 1H), 8.05 (s, 1H), 7.89 (s, 1H), 7.82 (d, 1H), 7.70 (d, 1H), 7.54 (m, 3H), 7.39 (d, 1H), 7.14 (d, 1H), 6.75 (d, 1H), 6.40 (s, 1H), 6.29 (s, 1H), 4.42 (d, 1H), 3.96 (d, 2H), 3.74 (m, 1H), 3.58 (d, 1H), 3.40 (d, 1H), 3.32 (t, 4H), 2.98 (t, 3H), 2.86 (m, 2H), 2.47 (s, 1H), 2.29 (m, 1H), 2.20 (m, 1H), 1.93 (m, 4H), 1.74 (m, 2H), 1.49 (m, 2H), 1.24 (m, 1H), 1.14 (m, 1H), 0.97 (s, 12H).

$^{13}$C NMR (125 MHz, DMSO-d6), δ: 174.5, 164.0, 159.2, 158.9, 158.6, 154.0, 147.9, 146.9, 145.9, 144.2, 139.0, 135.6, 134.3, 132.8, 132.6, 131.7, 130.2, 130.1, 130.0, 128.3, 127.0, 124.8, 124.4, 122.8, 120.3, 118.4, 117.5, 115.6, 115.2, 114.2, 109.7, 103.5, 100.4, 58.5, 48.0, 45.2, 45.0, 44.3, 41.4, 35.5, 34.6, 30.7, 29.7, 29.5, 29.3, 29.1, 27.2, 24.8, 20.0, 19.9. ESI-MS: m/z=1005.4 [M+H]$^+$.

Example 24

4-(4-{[2-(2-chloro-4-trifluoromethylphenyl)-4,4-dimethylcyclohex-1-enyl]methyl}-piperazin-1-yl)-N-({3-nitro-4-[((4-ethylmorpholin-3-yl)methyl)amino]phenyl}sulfonyl)-2-(1H-pyrrolo[2,3-b]pyridin-5-yloxy)-benzamide

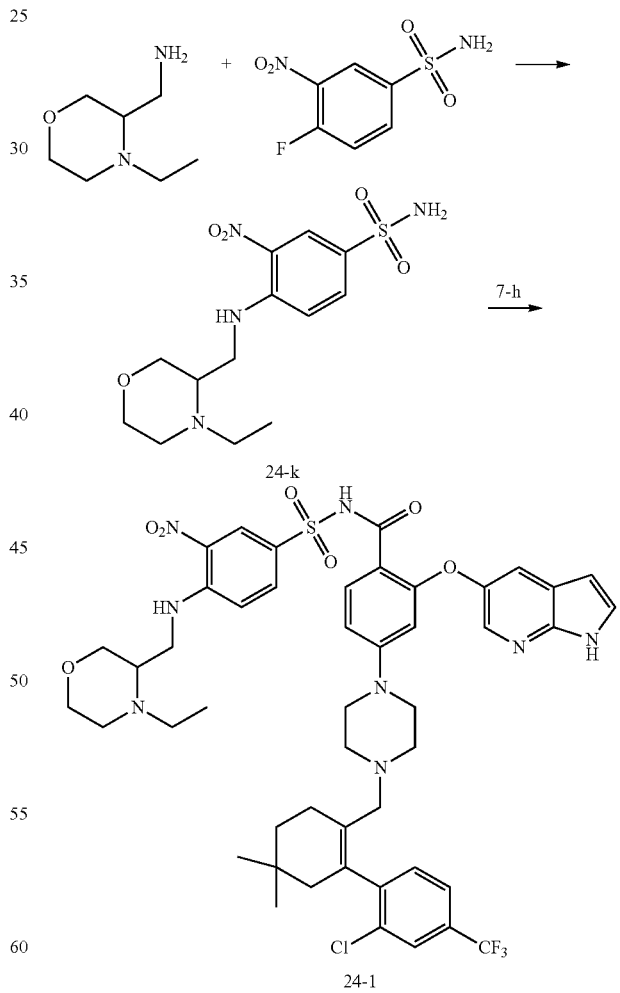

1) Preparation of Compound 24-k 3-nitro-4-fluorobenzenesulfonamide (2.54 g), 3-aminomethyl-4-ethylmorpholine (2.0 g) and N,N-diisopropylethylamine (3.72 g) were dissolved in acetonitrile (10 mL), and the solution was heated to 85° C. and reacted for 6 h. The reaction solution was cooled at room temperature, left to stand overnight, concentrated and dried to give compound 24-k (3.51 g). ESI-MS: m/z=345.1 [M+H]⁺.

2) Preparation of Compound 24-1

Compound 24-1 was obtained by reference to the preparation method for compound 7-1 in step 6) of Example 7, with compound 7-k being replaced by compound 24-k.

Compound 24-1: $^1$H NMR (500 MHz, DMSO-d6), δ: 11.73 (s, 2H), 8.68 (t, 1H), 8.61 (s, 1H), 8.05 (s, 1H), 7.92 (d, 1H), 7.88 (s, 1H), 7.70 (d, 1H), 7.58 (s, 1H), 7.53 (m, 2H), 7.40 (d, 1H), 6.75 (d, 2H), 6.41 (s, 1H), 6.29 (s, 1H), 4.05 (d, 3H), 3.61 (m, 8H), 3.35 (m, 6H), 3.12 (m, 3H), 2.25 (m, 2H), 2.00 (s, 2H), 1.49 (m, 2H), 1.23 (m, 4H), 0.97 (s, 6H).

$^{13}$C NMR (125 MHz, DMSO-d6), δ: 159.0, 158.7, 158.4, 158.3, 154.0, 146.8, 145.9, 144.2, 139.0, 135.6, 134.6, 132.8, 132.6, 131.8, 131.3, 130.2, 128.4, 128.1, 127.0, 125.9, 125.0, 124.4, 122.8, 120.3, 118.5, 117.5, 115.4, 115.2, 114.0, 109.6, 103.5, 100.5, 58.5, 47.9, 45.2, 44.3, 34.6, 29.5, 29.3, 29.1, 27.1, 24.8.

ESI-MS: m/z=965.4 [M+H]⁺.

Example 25

4-(4-{[2-(2-chloro-4-trifluoromethylphenyl)-4,4-dimethylcyclohex-1-enyl]methyl}-piperazin-1-yl)-N-({3-nitro-4-[(1-(tetrahydro-2H-pyran-4-yl)piperidin-4-yl)amino]phenyl}sulfonyl)-2-(1H-pyrrolo[2,3-b]pyridin-5-yloxy)-benzamide

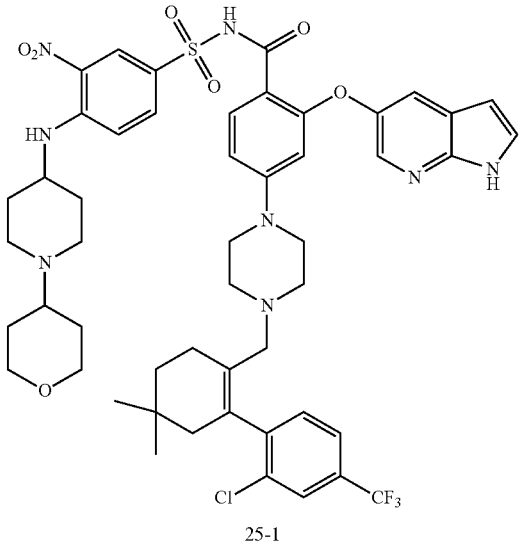

25-1

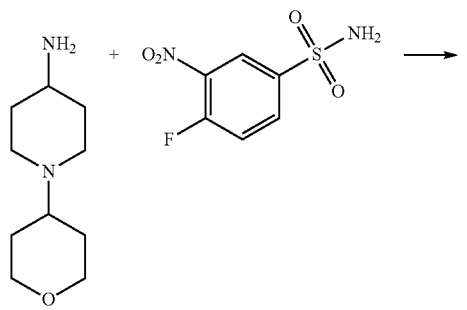

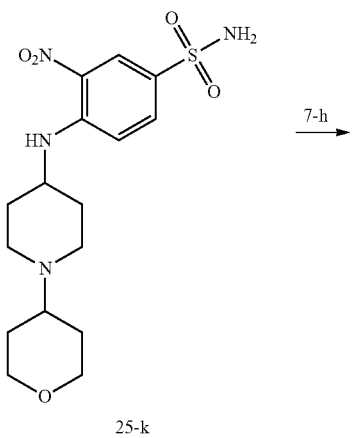

25-k

1) Preparation of Compound 25-k 3-nitro-4-fluorobenzenesulfonamide (1.67 g), 4-aminomethyl-1-(tetrahydro-2H-pyran)piperidine (2.0 g) and N,N-diisopropylethylamine (2.91 g) were dissolved in acetonitrile (10 mL), and the solution was heated to 85° C. and reacted for 6 h. The reaction solution was cooled at room temperature, left to stand overnight, concentrated and dried to give compound 25-k (2.91 g). ESI-MS: m/z=385.2 [M+H]⁺.

2) Preparation of Compound 25-1

Compound 25-1 was obtained by reference to the preparation method for compound 7-1 in step 6) of Example 7, with compound 7-k being replaced by compound 25-k.

Compound 25-1: $^1$H NMR (500 MHz, DMSO-d6), δ: 11.62 (s, 1H), 11.58 (s, 1H), 8.66 (s, 1H), 8.50 (s, 1H), 7.99 (s, 1H), 7.82 (s, 1H), 7.75 (d, 1H), 7.66 (d, 1H), 7.52 (d, 1H), 7.47 (s, 1H), 7.43 (s, 1H), 7.34 (d, 1H), 6.95 (d, 1H), 6.66 (d, 1H), 6.35 (s, 1H), 6.22 (s, 1H), 3.97 (d, 1H), 3.61 (t, 1H), 3.50 (m, 4H), 3.36 (d, 1H), 3.03 (s, 4H), 3.90 (s, 2H), 2.83 (t, 1H), 2.61 (m, 2H), 2.54 (s, 1H), 2.16 (m, 6H), 1.90 (m, 4H), 1.74 (m, 1H), 1.42 (t, 2H), 1.24 (m, 4H), 0.96 (s, 6H).

$^{13}$C NMR (125 MHz, DMSO-d6), δ: 146.2, 145.6, 135.5, 134.7, 133.2, 132.5, 132.1, 132.0, 131.4, 130.1, 130.0, 127.9, 126.5, 125.0, 124.5, 122.8, 120.2, 109.4, 100.3, 74.0, 65.9, 60.5, 52.7, 49.8, 47.3, 45.4, 44.7, 35.6, 35.3, 34.2, 31.5, 29.5, 29.4, 29.2, 29.0, 27.3, 25.4, 22.6, 14.4. ESI-MS: m/z=1005.4 [M+H]⁺.

Example 26

4-(4-{[2-(2-chloro-4-trifluoromethylphenyl)-4,4-dimethylcyclohex-1-enyl]methyl}-piperazin-1-yl)-N-({3-nitro-4-[((4-(3-oxetanyl)-morpholin-2-yl)methyl)amino]phenyl}sulfonyl)-2-(1H-pyrrolo[2,3-b]pyridin-5-yloxy)-benzamide

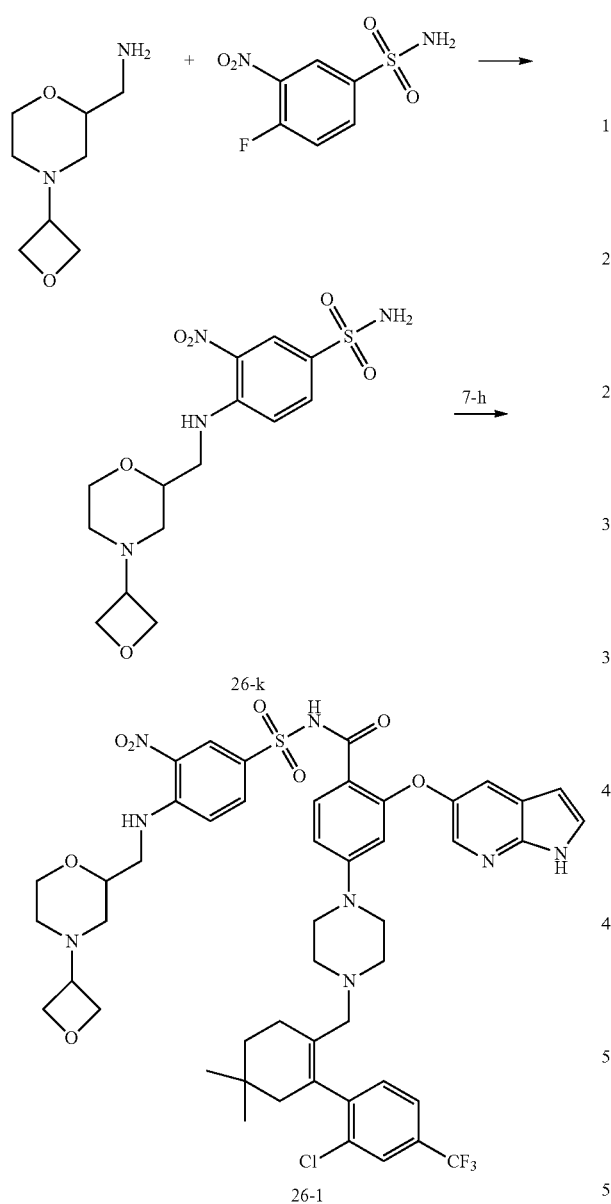

1) Preparation of Compound 26-k

Compound 26-k was obtained by reference to the preparation method for compound 25-k in step 1) of Example 25, with 4-aminomethyl-1-(tetrahydro-2H-pyran)piperidine being replaced by 4-(3-oxetanyl)-2-aminomethylmorpholine.

2) Preparation of Compound 26-1

Compound 26-1 was obtained by reference to the preparation method for compound 7-1 in step 6) of Example 7, with compound 7-k being replaced by compound 26-k.

Example 27

4-(4-{[2-(2-chloro-4-trifluoromethylphenyl)-4,4-dimethylcyclohex-1-enyl]methyl}-piperazin-1-yl)-N-({3-nitro-4-[((4-(tetrahydropyran-4-yl)morpholin-2-yl)methyl)amino]phen yl}sulfonyl)-2-(1H-pyrrolo[2,3-b]pyridin-5-yloxy)-benzamide

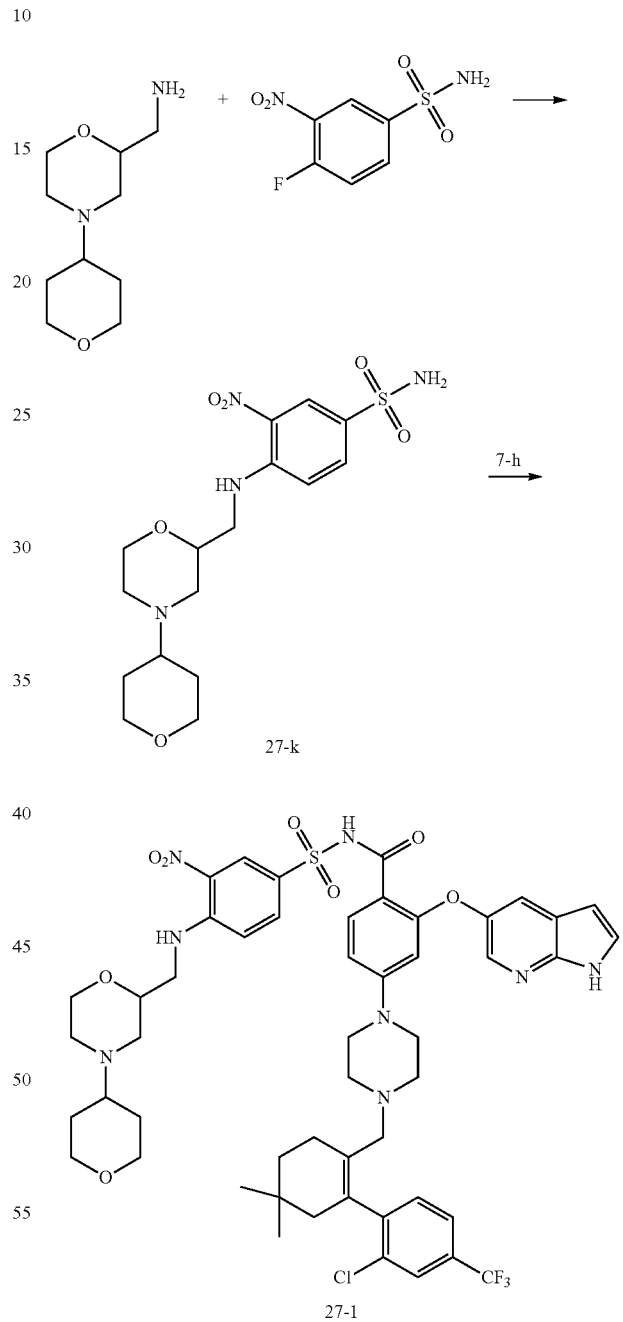

1) Preparation of Compound 27-k

Compound 27-k was obtained by reference to the preparation method for compound 25-k in step 1) of Example 25, with 4-aminomethyl-1-(tetrahydro-2H-pyran)piperidine being replaced by 4-(tetrahydropyran-4-yl)-2-aminomethylmorpholine.

2) Preparation of Compound 27-1

Compound 27-1 was obtained by reference to the preparation method for compound 7-1 in step 6) of Example 7, with compound 7-k being replaced by compound 27-k.

Example 28

4-(4-{[2-(2-chloro-4-trifluoromethylphenyl)-4,4-dimethylcyclohex-1-enyl]methyl}-piperazin-1-yl)-N-({3-nitro-4-[((4-cyclopropylsulfonylmorpholin-2-yl)methyl)amino]phenyl}sulfonyl)-2-(1H-pyrrolo[2,3-b]pyridin-5-yloxy)-benzamide

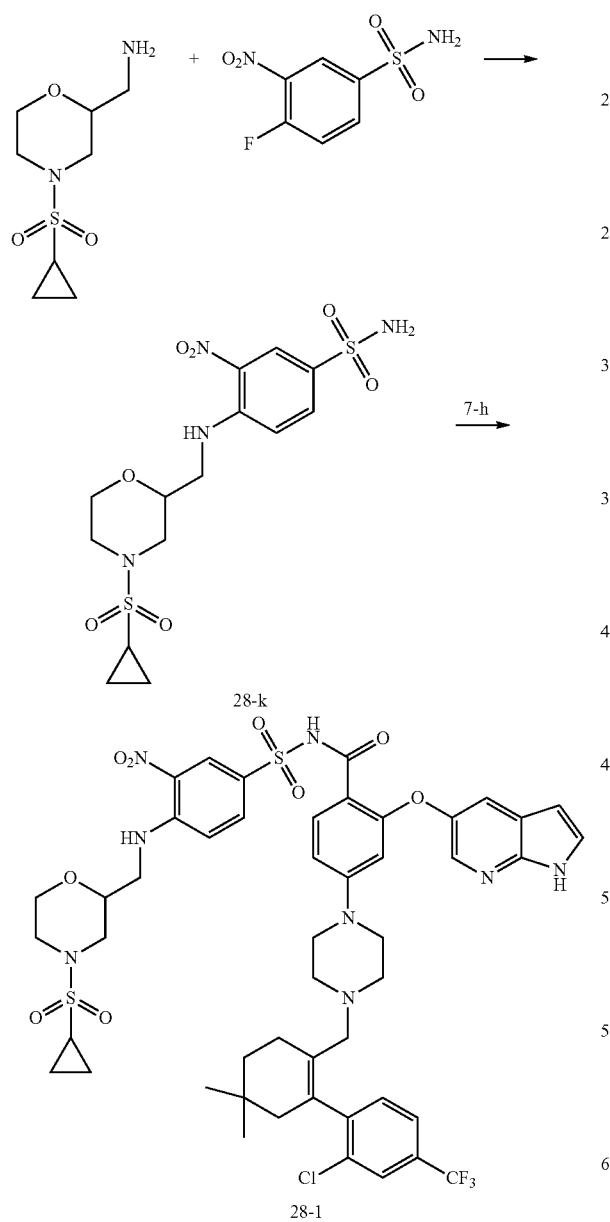

1) Preparation of Compound 28-k

Compound 28-k (1.01 g) was obtained by reference to the preparation method for compound 25-k in step 1) of Example 25, with 4-aminomethyl-1-(tetrahydro-2H-pyran) piperidine being replaced by 4-cyclopropylsulfonyl-2-aminomethylmorpholine.

2) Preparation of Compound 28-1

Compound 28-1 was obtained by reference to the preparation method for compound 7-1 in step 6) of Example 7, with compound 7-k being replaced by compound 28-k.

Compound 28-1: $^1$H NMR (500 MHz, DMSO-d6), δ: 11.71 (s, 1H), 11.67 (s, 1H), 8.64 (m, 1H), 8.58 (s, 1H), 8.05 (d, 1H), 7.89 (s, 1H), 7.84 (d, 1H), 7.70 (d, 1H), 7.55 (m, 3H), 7.38 (d, 1H), 7.17 (d, 1H), 6.76 (d, 1H), 6.40 (s, 1H), 6.29 (s, 1H), 3.55 (m, 7H), 3.42 (m, 4H), 2.99 (m, 4H), 2.83 (m, 2H), 2.65 (m, 1H), 2.27 (m, 2H), 1.96 (m, 2H), 1.50 (s, 2H), 1.24 (s, 1H), 0.98 (m, 10H).

$^{13}$C NMR (125 MHz, DMSO-d6), δ: 164.0, 158.9, 158.6, 158.2, 154.0, 147.9, 146.9, 145.9, 144.2, 139.0, 135.6, 134.3, 132.8, 132.6, 131.7, 130.3, 128.3, 128.2, 125.2, 124.9, 124.4, 120.3, 118.4, 117.4, 115.8, 115.1, 114.1, 109.7, 103.5, 100.4, 73.8, 66.1, 58.5, 48.3, 45.8, 45.1, 44.9, 44.3, 34.6, 29.3, 29.1, 27.2, 25.1, 24.8, 4.4, 4.3.

Example 29

4-(4-{[2-(2-chloro-4-trifluoromethylphenyl)-4,4-dimethylcyclohex-1-enyl]methyl}-piperazin-1-yl)-N-({3-nitro-4-[((4-cyclopropanoylmorpholin-2-yl)methyl)amino]phenyl}sulfonyl)-2-(1H-pyrrolo[2,3-b]pyridin-5-yloxy)-benzamide

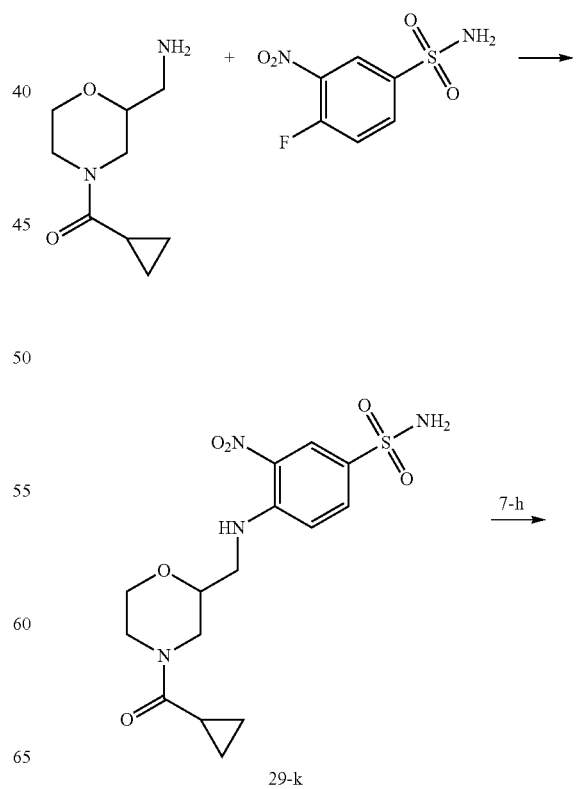

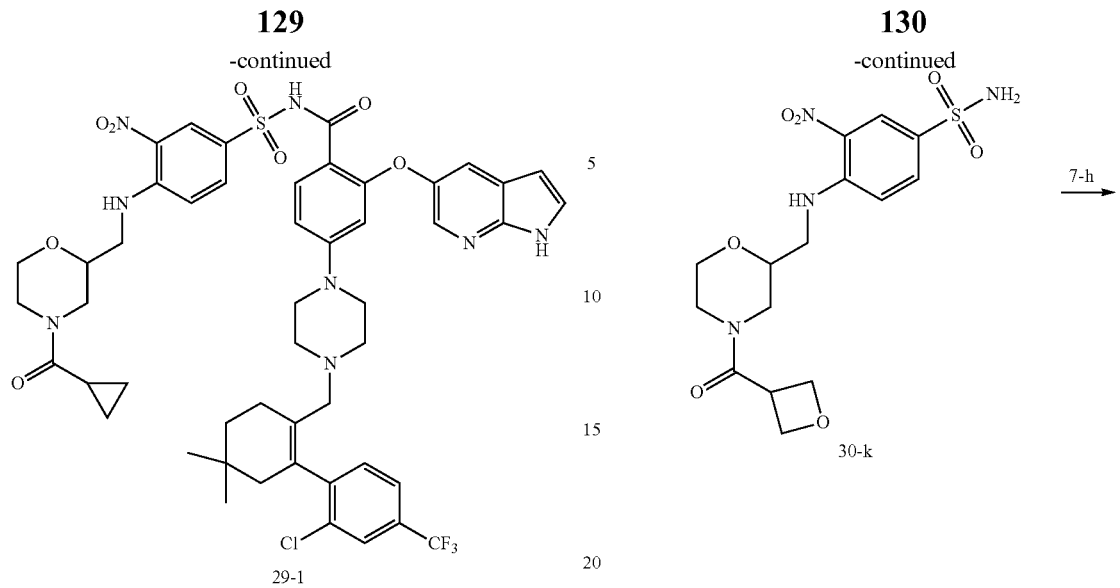

29-1

1) Preparation of Compound 29-k

Compound 29-k (0.85 g) was obtained by reference to the preparation method for compound 25-k in step 1) of Example 25, with 4-aminomethyl-1-(tetrahydro-2H-pyran) piperidine being replaced by 4-cyclopropanoyl-2-aminomethylmorpholine.

2) Preparation of Compound 29-1

Compound 29-1 was obtained by reference to the preparation method for compound 7-1 in step 6) of Example 7, with compound 7-k being replaced by compound 29-k.

Compound 29-1: $^1$H NMR (500 MHz, DMSO-d6), δ: 11.72 (s, 1H), 11.70 (s, 1H), 8.62 (m, 2H), 8.05 (s, 1H), 7.89 (s, 1H), 7.84 (d, 1H), 7.70 (d, 1H), 7.55 (m, 3H), 7.39 (d, 1H), 7.16 (d, 1H), 6.76 (d, 1H), 6.40 (s, 1H), 6.30 (s, 1H), 3.95 (d, 2H), 3.62 (m, 4H), 3.49 (m, 3H), 3.39 (m, 3H), 2.91 (m, 2H), 2.75 (m, 2H), 2.33 (m, 6H), 2.02 (m, 1H), 1.50 (s, 2H), 1.24 (s, 1H), 0.97 (s, 6H), 0.78 (d, 4H).

Example 30

4-(4-{[2-(2-chloro-4-trifluoromethylphenyl)-4,4-dimethylcyclohex-1-enyl]methyl}-piperazin-1-yl)-N-({3-nitro-4-[((4-(oxetan-3-yl)formylmorpholin-2-yl)methyl)amino]phenyl}sulfonyl)-2-(1H-pyrrolo[2,3-b]pyridin-5-yloxy)-benzamide

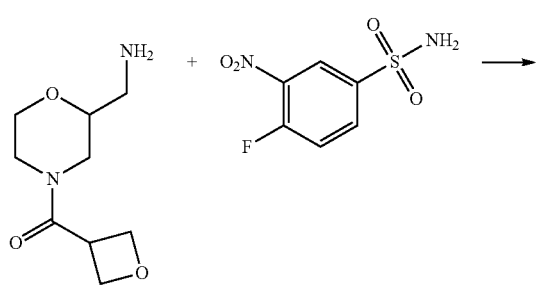

1) Preparation of Compound 30-k

Compound 30-k (0.85 g) was obtained by reference to the preparation method for compound 25-k in step 1) of Example 25, with 4-aminomethyl-1-(tetrahydro-2H-pyran) piperidine being replaced by 4-(oxetan-3-yl)formyl-2-aminomethylmorpholine.

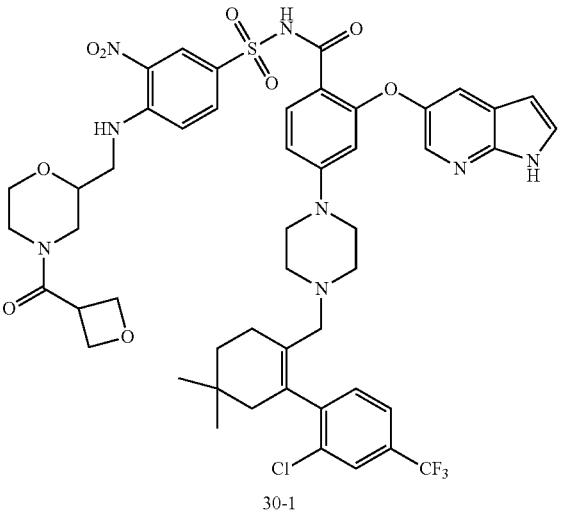

30-k

2) Preparation of Compound 30-1

Compound 30-1 was obtained by reference to the preparation method for compound 7-1 in step 6) of Example 7, with compound 7-k being replaced by compound 30-k.

30-1

Example 31

4-(4-{[2-(2-chloro-4-trifluoromethylphenyl)-4,4-dimethylcyclohex-1-enyl]methyl}-piperazin-1-yl)-N-({3-nitro-4-[((4-cyclobutylsulfonylmorpholin-2-yl)methyl)amino]phenyl}sulfonyl)-2-(1H-pyrrolo[2,3-b]pyridin-5-yloxy)-benzamide

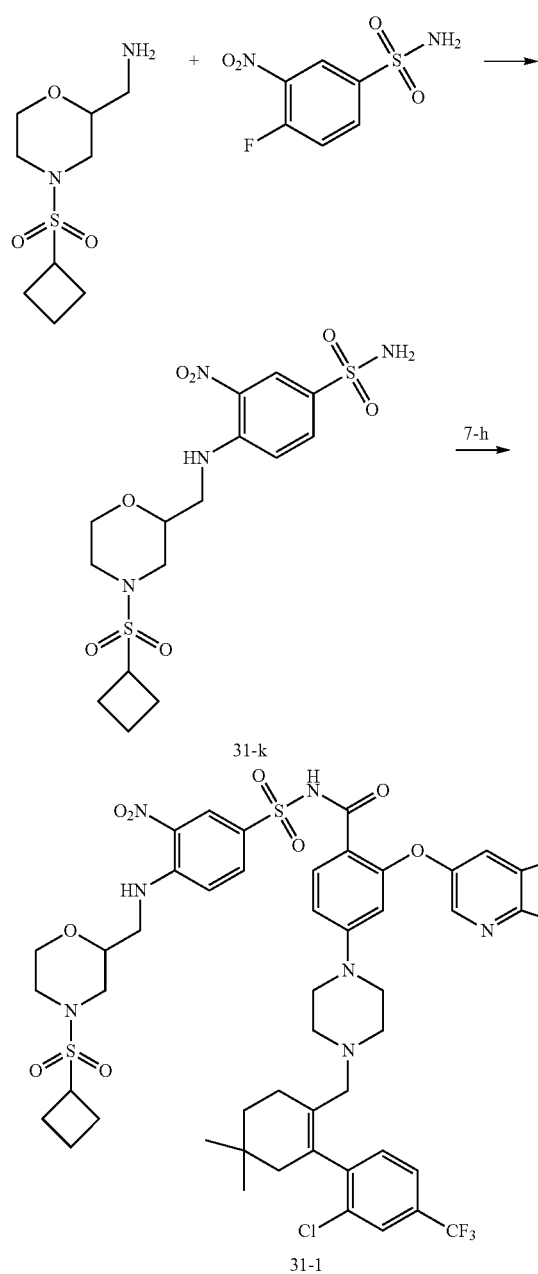

1) Preparation of Compound 31-k

Compound 31-k (0.98 g) was obtained by reference to the preparation method for compound 25-k in step 1) of Example 25, with 4-aminomethyl-1-(tetrahydro-2H-pyran) piperidine being replaced by 4-cyclobutylsulfonyl-2-aminomethylmorpholine.

2) Preparation of Compound 31-1

Compound 31-1 was obtained by reference to the preparation method for compound 7-1 in step 6) of Example 7, with compound 7-k being replaced by compound 31-k.

Compound 31-1: $^1$H NMR (500 MHz, DMSO-d6), δ: 11.71 (s, 1H), 11.69 (s, 1H), 8.61 (m, 2H), 8.05 (s, 1H), 7.89 (s, 1H), 7.83 (d, 1H), 7.71 (d, 1H), 7.54 (m, 3H), 7.39 (d, 1H), 7.17 (d, 1H), 6.76 (d, 1H), 6.40 (s, 1H), 6.29 (s, 1H), 3.95 (d, 2H), 3.62 (m, 6H), 3.49 (m, 3H), 3.39 (m, 3H), 2.91 (m, 2H), 2.75 (m, 2H), 2.33 (m, 6H), 2.02 (m, 4H), 1.50 (s, 2H), 1.24 (s, 1H), 0.97 (s, 6H).

$^{13}$C NMR (125 MHz, DMSO-d6), δ: 163.9, 158.2, 154.0, 147.8, 146.9, 145.9, 144.2, 135.6, 134.3, 132.8, 132.6, 131.8, 130.3, 128.3, 128.2, 127.0, 125.2, 124.9, 122.8, 120.3, 118.3, 115.8, 114.1, 109.7, 103.5, 100.4, 74.0, 66.3, 58.5, 50.9, 48.0, 45.6, 45.1, 44.9, 44.3, 34.6, 29.3, 29.1, 27.2, 24.8.

Example 32

4-(4-{[2-(2-chloro-4-trifluoromethylphenyl)-4,4-dimethylcyclohex-1-enyl]methyl}-piperazin-1-yl)-N-({3-nitro-4-[((4-(oxetan-3-yl)sulfonylmorpholin-2-yl)methyl)amino]phenyl}sulfonyl)-2-(1H-pyrrolo[2,3-b]pyridin-5-yloxy)-benzamide

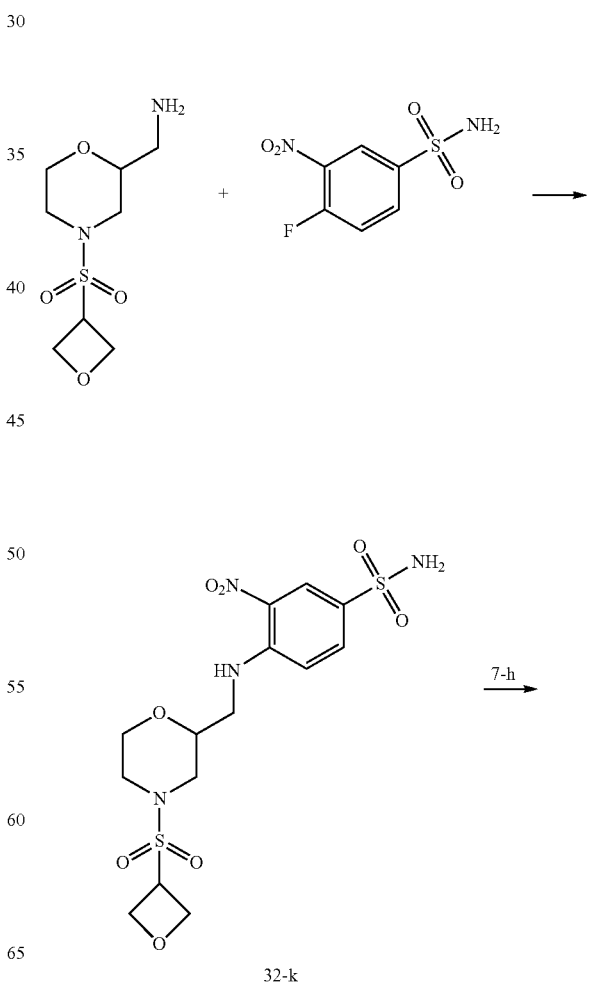

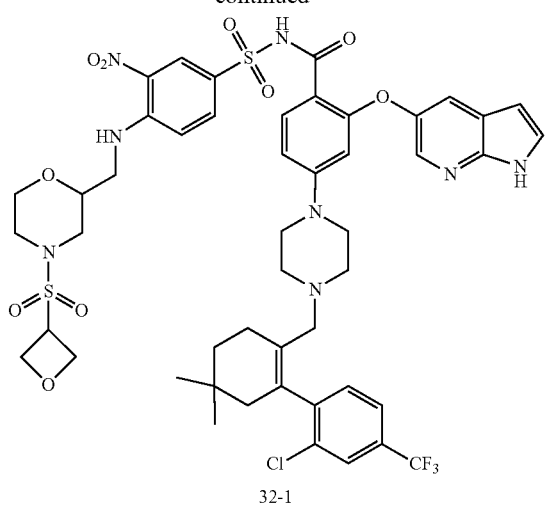

32-1

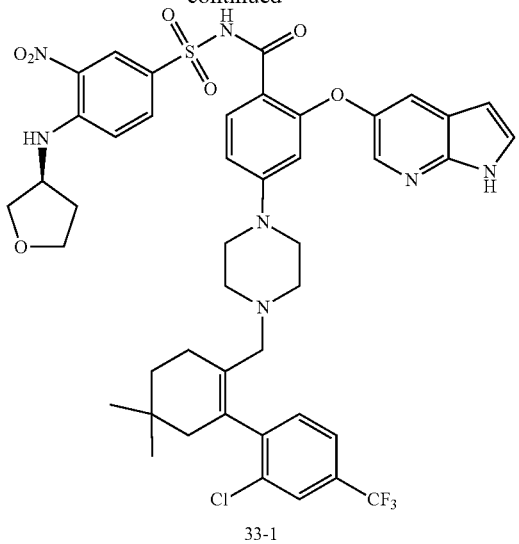

33-1

1) Preparation of Compound 32-k

Compound 32-k (1.01 g) was obtained by reference to the preparation method for compound 25-k in step 1) of Example 25, with 4-aminomethyl-1-(tetrahydro-2H-pyran) piperidine being replaced by 4-(oxetan-3-yl)sulfonyl-2-aminomethylmorpholine.

2) Preparation of Compound 32-l

Compound 32-l was obtained by reference to the preparation method for compound 7-l in step 6) of Example 7, with compound 7-k being replaced by compound 32-k.

Example 33

(S)-4-(4-{[2-(2-chloro-4-trifluoromethylphenyl)-4,4-dimethylcyclohex-1-enyl]methyl}-piperazin-1-yl)-N-({3-nitro-4-[(tetrahydrofuran-3-yl)amino]phenyl}sulfonyl)-2-(1H-pyrrolo[2,3-b]pyridin-5-yloxy)-benzamide

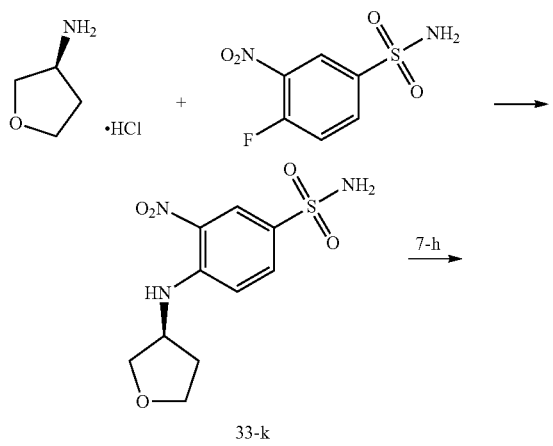

33-k

1) Preparation of Compound 33-k

Compound 33-k (1.72 g) was obtained by reference to the preparation method for compound 25-k in step 1) of Example 25, with 4-aminomethyl-1-(tetrahydro-2H-pyran) piperidine being replaced by (S)-4-aminotetrahydrofuran hydrochloride.

2) Preparation of Compound 33-l

Compound 33-l was obtained by reference to the preparation method for compound 7-l in step 6) of Example 7, with compound 7-k being replaced by compound 33-k.

Compound 33-l: $^1$H NMR (500 MHz, DMSO-d6), δ: 11.70 (s, 1H), 11.68 (s, 1H), 8.57 (s, 1H), 8.32 (d, 1H), 8.03 (s, 1H), 7.87 (t, 2H), 7.70 (d, 1H), 7.54 (d, 3H), 7.40 (d, 1H), 7.13 (d 1H), 6.76 (d, 1H), 6.39 (s, 1H), 6.31 (s, 1H), 3.93 (m, 3H), 3.78 (m, 2H), 3.73 (d, 2H), 3.58 (d, 1H), 3.41 (d, 1H), 3.04 (m, 3H), 2.78 (s, 1H), 2.34 (m, 2H), 2.28 (m, 1H), 2.08 (s, 1H), 1.96 (s, 2H), 1.90 (m, 1H), 1.49 (m, 2H), 1.24 (s, 1H), 0.97 (s, 6H).

$^{13}$C NMR (125 MHz, DMSO-d6), δ: 164.0, 159.1, 158.9, 158.6, 158.3, 158.1, 154.0, 147.0, 146.9, 145.9, 144.2, 135.5, 134.5, 132.8, 132.5, 131.8, 130.5, 128.3, 128.1, 127.0, 125.6, 125.0, 122.8, 120.2, 118.1, 115.8, 114.3, 109.7, 103.7, 100.4, 72.7, 66.9, 58.5, 53.7, 45.2, 44.3, 34.6, 33.0, 29.3, 29.1, 27.1, 24.8.

Example 34

(R)-4-(4-{[2-(2-chloro-4-trifluoromethylphenyl)-4,4-dimethylcyclohex-1-enyl]methyl}-piperazin-1-yl)-N-({3-nitro-4-[(tetrahydrofuran-3-yl)amino]phenyl}sulfonyl)-2-(1H-pyrrolo[2,3-b]pyridin-5-yloxy)-benzamide

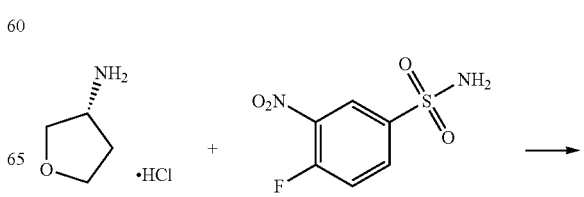

-continued

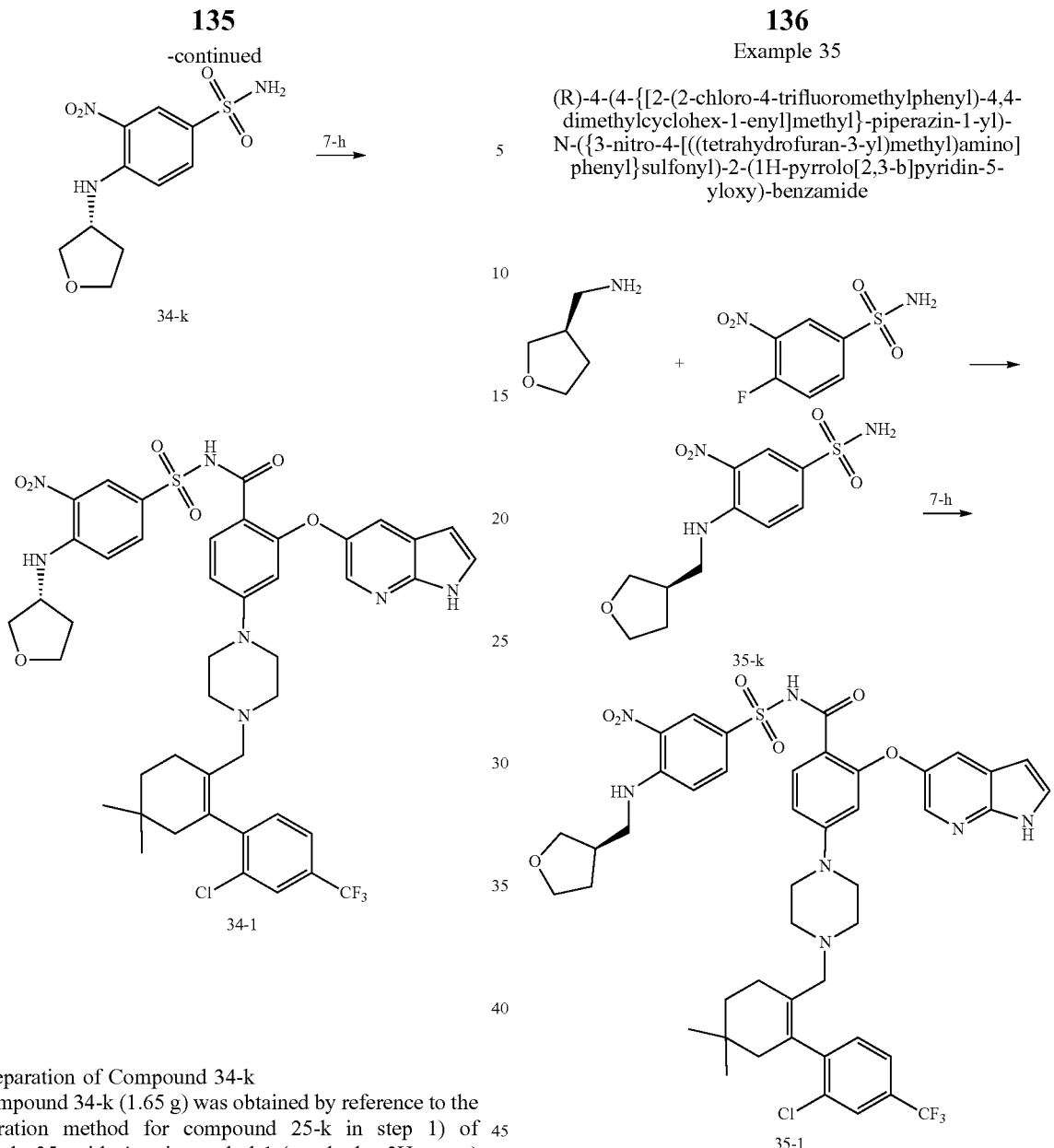

Example 35

(R)-4-(4-{[2-(2-chloro-4-trifluoromethylphenyl)-4,4-dimethylcyclohex-1-enyl]methyl}-piperazin-1-yl)-N-({3-nitro-4-[((tetrahydrofuran-3-yl)methyl)amino]phenyl}sulfonyl)-2-(1H-pyrrolo[2,3-b]pyridin-5-yloxy)-benzamide 1) Preparation of Compound 34-k Compound 34-k (1.65 g) was obtained by reference to the preparation method for compound 25-k in step 1) of Example 25, with 4-aminomethyl-1-(tetrahydro-2H-pyran)piperidine being replaced by (R)-4-aminotetrahydrofuran hydrochloride.

2) Preparation of Compound 34-1

Compound 34-1 was obtained by reference to the preparation method for compound 7-1 in step 6) of Example 7, with compound 7-k being replaced by compound 34-k.

Compound 34-1: $^1$H NMR (500 MHz, DMSO-d6), δ: 11.71 (s, 1H), 11.68 (s, 1H), 8.57 (s, 1H), 8.32 (d, 1H), 8.03 (s, 1H), 7.87 (t, 2H), 7.71 (d, 1H), 7.54 (d, 3H), 7.40 (d, 1H), 7.13 (s, 1H), 6.76 (d, 1H), 6.39 (s, 1H), 6.31 (s, 1H), 3.95 (m, 1H), 3.89 (m, 1H), 3.79 (m, 2H), 3.73 (d, 2H), 3.60 (d, 1H), 3.42 (d, 1H), 3.29 (m, 2H), 3.05 (m, 3H), 2.78 (m, 1H), 2.33 (m, 2H), 2.21 (m, 1H), 1.96 (s, 2H), 1.91 (m, 1H), 1.49 (m, 2H), 1.23 (s, 1H), 0.97 (s, 6H).

$^{13}$C NMR (125 MHz, DMSO-d6), δ: 159.2, 158.9, 158.7, 158.4, 158.1, 154.0, 147.0, 146.9, 145.8, 144.2, 139.0, 135.4, 134.5, 132.8, 132.5, 131.7, 130.5, 128.3, 128.1, 127.1, 125.6, 124.9, 124.4, 120.3, 118.1, 117.3, 115.8, 114.9, 114.4, 109.8, 103.7, 100.4, 72.7, 66.9, 58.5, 53.7, 45.1, 44.3, 34.6, 33.0, 29.2, 29.1, 27.1, 24.8.

1) Preparation of Compound 35-k

Compound 35-k (1.10 g) was obtained by reference to the preparation method for compound 25-k in step 1) of Example 25, with 4-aminomethyl-1-(tetrahydro-2H-pyran)piperidine being replaced by (3R)-tetrahydrofuran-3-methylamine.

2) Preparation of Compound 35-1

Compound 35-1 was obtained by reference to the preparation method for compound 7-1 in step 6) of Example 7, with compound 7-k being replaced by compound 35-k.

Compound 35-1: $^1$H NMR (500 MHz, DMSO-d6), δ: 11.72 (s, 1H), 11.69 (s, 1H), 8.64 (m, 1H), 8.58 (d, 1H), 8.05 (d, 1H), 7.88 (s, 1H), 7.82 (d, 1H), 7.70 (d, 1H), 7.54 (d, 3H), 7.39 (d, 1H), 7.12 (d, 1H), 6.75 (d, 1H), 6.40 (s, 1H), 6.30 (s, 1H), 3.80 (m, 2H), 3.71 (m, 2H), 3.63 (m, 2H), 3.52 (m, 2H), 3.40 (m, 4H), 2.58 (m, 1H), 2.28 (m, 2H), 2.08 (s, 2H), 1.98 (m, 4H), 1.67 (m, 1H), 1.50 (m, 2H), 1.24 (m, 1H), 0.97 (s, 6H).

$^{13}$C NMR (125 MHz, DMSO-d6), δ: 163.9, 158.9, 158.6, 158.2, 154.0, 147.8, 146.9, 145.9, 144.2, 138.9, 135.6, 134.3, 132.9, 132.5, 131.8, 130.2, 130.1, 128.3, 127.0, 124.9, 124.5, 122.8, 120.3, 118.5, 118.3, 117.8, 115.5, 114.2, 109.7, 103.6, 100.4, 70.8, 67.3, 58.5, 45.8, 45.2, 44.3, 38.1, 34.6, 29.8, 29.3, 29.1, 27.2, 24.8, 1.6.

Example 36

(S)-4-(4-{[2-(2-chloro-4-trifluoromethylphenyl)-4,4-dimethylcyclohex-1-enyl]methyl}-piperazin-1-yl)-N-({3-nitro-4-[((tetrahydrofuran-3-yl)methyl)amino]phenyl}sulfonyl)-2-(1H-pyrrolo[2,3-b]pyridin-5-yloxy)-benzamide

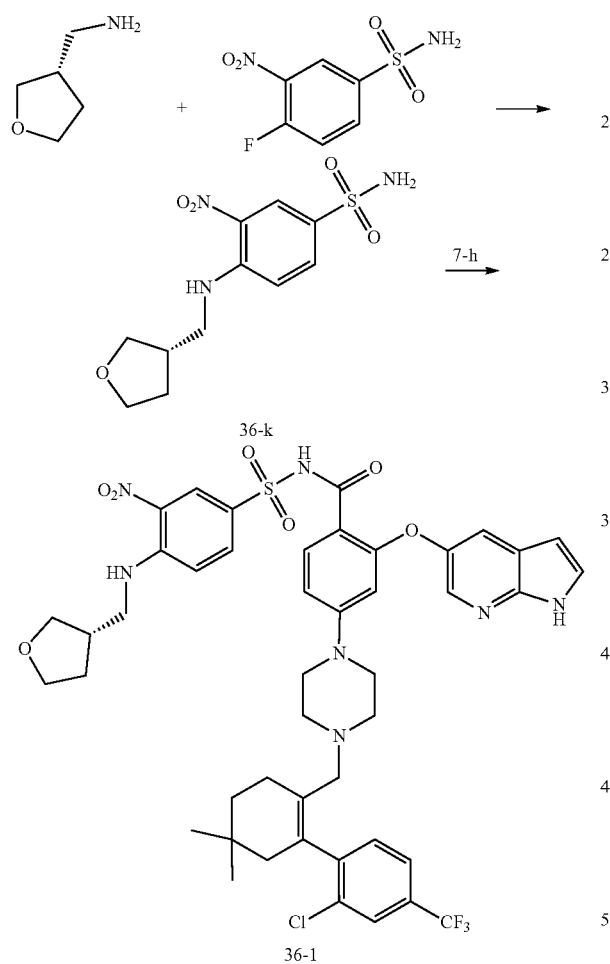

1) Preparation of Compound 36-k

Compound 36-k (1.39 g) was obtained by reference to the preparation method for compound 25-k in step 1) of Example 25, with 4-aminomethyl-1-(tetrahydro-2H-pyran)piperidine being replaced by (3S)-tetrahydrofuran-3-methylamine (0.64 g).

2) Preparation of Compound 36-1

Compound 36-1 was obtained by reference to the preparation method for compound 7-1 in step 6) of Example 7, with compound 7-k being replaced by compound 36-k.

Compound 36-1: $^1$H NMR (500 MHz, DMSO-d6), δ: 11.72 (s, 1H), 11.69 (s, 1H), 8.65 (s, 1H), 8.58 (s, 1H), 8.05 (s, 1H), 7.89 (s, 1H), 7.83 (d, 1H), 7.71 (d, 1H), 7.54 (d, 3H), 7.40 (d, 1H), 7.12 (d, 1H), 6.76 (d, 1H), 6.40 (s, 1H), 6.30 (s, 1H), 3.81 (m, 1H), 3.73 (m, 2H), 3.61 (m, 3H), 3.53 (m, 1H), 3.41 (m, 4H), 3.05 (m, 3H), 2.58 (m, 1H), 2.31 (m, 1H), 2.27 (m, 1H), 2.08 (s, 1H), 1.96 (m, 3H), 1.65 (m, 1H), 1.49 (s, 2H), 1.24 (s, 1H), 0.97 (s, 6H).

$^{13}$C NMR (125 MHz, DMSO-d6), δ: 159.2, 158.9, 158.6, 158.4, 158.1, 154.0, 147.7, 146.9, 145.9, 144.2, 139.0, 135.5, 134.3, 132.8, 132.5, 131.7, 130.1, 128.3, 128.2, 127.0, 124.9, 124.4, 122.7, 120.3, 118.3, 117.5, 115.4, 115.1, 114.2, 109.7, 103.6, 100.4, 70.8, 67.3, 58.5, 45.8, 45.1, 44.3, 38.1, 34.6, 29.8, 29.3, 29.1, 27.1, 24.8.

Example 37

(S)-4-(4-{[2-(2-chloro-4-trifluoromethylphenyl)-4,4-dimethylcyclohex-1-enyl]methyl}-piperazin-1-yl)-N-({3-nitro-4-[((tetrahydrofuran-2-yl)methyl)amino]phenyl}sulfonyl)-2-(1H-pyrrolo[2,3-b]pyridin-5-yloxy)-benzamide

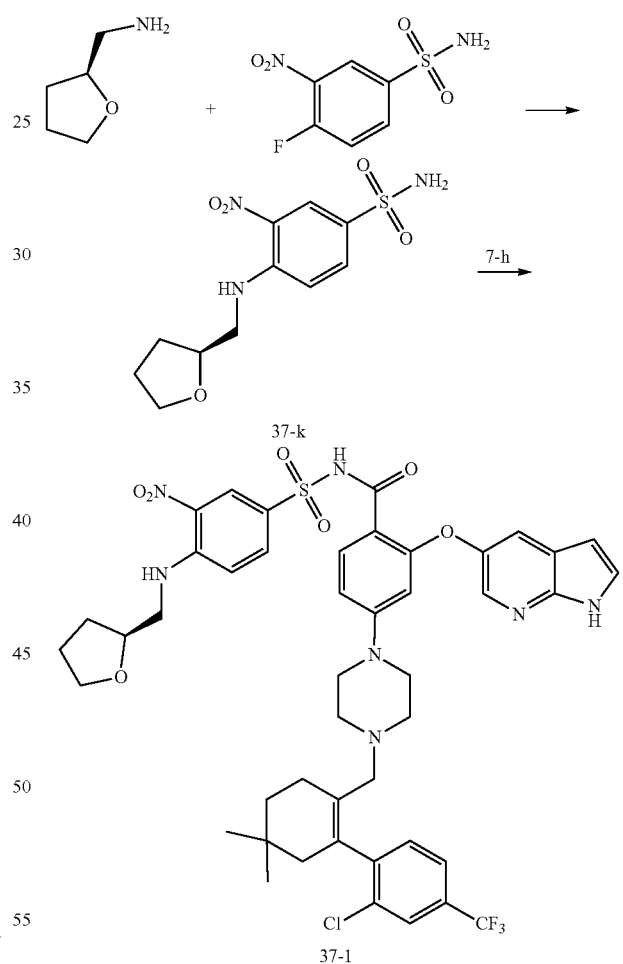

1) Preparation of Compound 37-k

Compound 37-k (1.35 g) was obtained by reference to the preparation method for compound 25-k in step 1) of Example 25, with 4-aminomethyl-1-(tetrahydro-2H-pyran)piperidine being replaced by (S)-2-tetrahydrofurfurylamine.

2) Preparation of Compound 37-1

Compound 37-1 was obtained by reference to the preparation method for compound 7-1 in step 6) of Example 7, with compound 7-k being replaced by compound 37-k.

Compound 37-1: ¹H NMR (500 MHz, DMSO-d6), δ: 11.71 (s, 2H), 8.62 (s, 1H), 8.58 (m, 1H), 8.04 (s, 1H), 7.89 (d, 1H), 7.81 (m, 1H), 7.70 (d, 1H), 7.52 (m, 3H), 7.40 (m, 1H), 7.13 (d, 1H), 6.75 (d, 1H), 6.40 (s, 1H), 6.30 (s, 1H), 3.83 (m, 2H), 3.69 (m, 2H), 3.55 (m, 2H), 3.40 (m, 2H), 3.29 (m, 2H), 3.04 (m, 3H), 2.77 (m, 1H), 2.27 (m, 1H), 2.21 (m, 1H), 2.00 (m, 1H), 1.96 (m, 2H), 1.87 (m, 2H), 1.66 (m, 2H), 1.50 (m, 2H), 0.97 (s, 6H).

¹³C NMR (125 MHz, DMSO-d6), δ: 164.0, 159.2, 158.9, 158.1, 154.0, 148.0, 146.2, 145.9, 144.2, 139.0, 135.5, 134.3, 132.8, 130.2, 130.0, 128.3, 127.0, 125.0, 122.8, 118.3, 117.5, 115.8, 115.2, 114.2, 109.7, 100.4, 76.9, 67.9, 58.5, 46.9, 45.2, 44.3, 34.6, 29.3, 27.1, 24.8.

Example 38

(R)-4-(4-{[2-(2-chloro-4-trifluoromethylphenyl)-4,4-dimethylcyclohex-1-enyl]methyl}-piperazin-1-yl)-N-({3-nitro-4-[((tetrahydrofuran-2-yl)methyl)amino]phenyl}sulfonyl)-2-(1H-pyrrolo[2,3-b]pyridin-5-yloxy)-benzamide

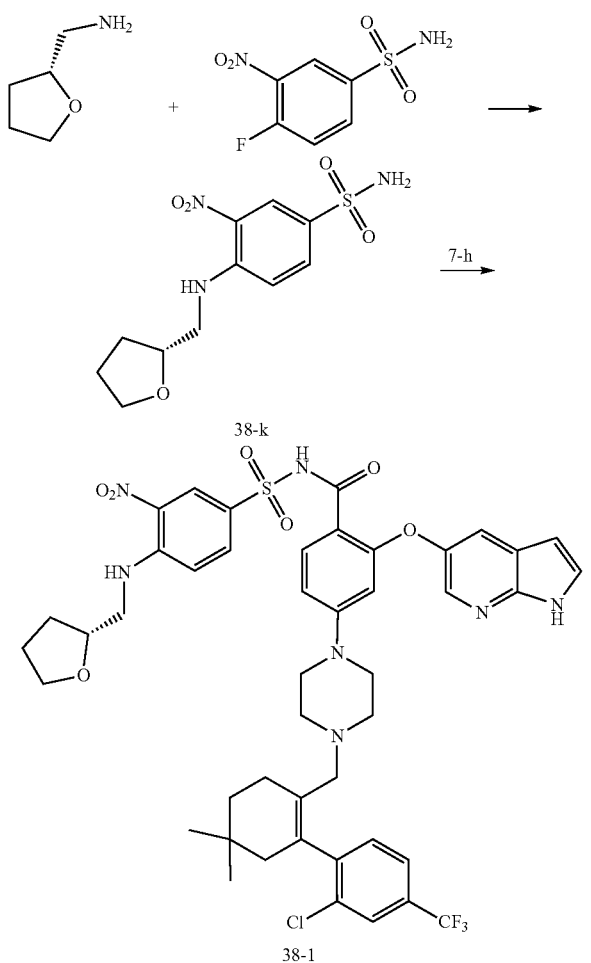

1) Preparation of Compound 38-k

Compound 38-k (1.38 g) was obtained by reference to the preparation method for compound 25-k in step 1) of Example 25, with 4-aminomethyl-1-(tetrahydro-2H-pyran)piperidine being replaced by (R)-2-tetrahydrofurfurylamine.

2) Preparation of Compound 38-1

Compound 38-1 was obtained by reference to the preparation method for compound 7-1 in step 6) of Example 7, with compound 7-k being replaced by compound 38-k.

Compound 38-1: ¹H NMR (500 MHz, DMSO-d6), δ: 11.72 (s, 1H), 11.69 (s, 1H), 8.61 (m, 2H), 8.04 (d, 1H), 7.88 (s, 1H), 7.82 (d, 1H), 7.70 (d, 1H), 7.54 (m, 3H), 7.39 (d, 1H), 7.13 (d, 1H), 6.76 (d, 1H), 6.39 (s, 1H), 6.29 (s, 1H), 3.82 (m, 2H), 3.70 (m, 2H), 3.56 (m, 2H), 3.41 (m, 2H), 3.38 (m, 1H), 3.04 (m, 3H), 2.79 (m, 1H), 2.31 (m, 2H), 2.18 (s, 1H), 1.98 (m, 3H), 1.89 (m, 2H), 1.65 (m, 1H), 1.49 (m, 2H), 1.24 (s, 1H), 0.97 (s, 6H).

¹³C NMR (125 MHz, DMSO-d6), δ: 164.0, 158.9, 158.7, 158.1, 154.0, 147.9, 146.9, 145.9, 144.2, 139.0, 135.5, 134.3, 132.6, 131.7, 130.0, 128.3, 127.0, 125.0, 124.9, 124.4, 122.7, 120.3, 118.3, 117.5, 115.8, 114.2, 109.7, 103.6, 100.4, 76.9, 67.9, 58.5, 46.9, 45.1, 44.3, 34.6, 29.2, 27.1, 25.7, 24.8.

Example 39

4-(4-{[2-(2-chloro-4-trifluoromethylphenyl)-4,4-dimethylcyclohex-1-enyl]methyl}-piperazin-1-yl)-N-({3-nitro-4-[(tetrahydropyran-4-yl)amino]phenyl}sulfonyl)-2-(1H-pyrrolo[2,3-b]pyridin-5-yloxy)-benzamide

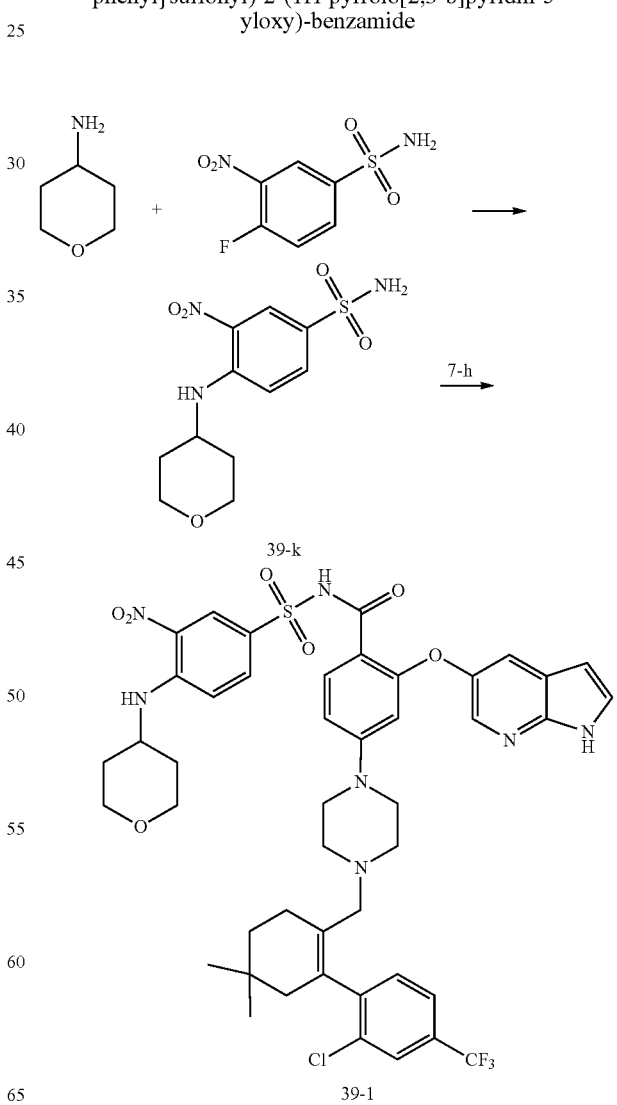

1) Preparation of Compound 39-k

Compound 39-k (1.70 g) was obtained by reference to the preparation method for compound 25-k in step 1) of Example 25, with 4-aminomethyl-1-(tetrahydro-2H-pyran) piperidine being replaced by 4-aminotetrahydropyran.

2) Preparation of Compound 39-1

Compound 39-1 was obtained by reference to the preparation method for compound 7-1 in step 6) of Example 7, with compound 7-k being replaced by compound 39-k.

Compound 39-1: $^1$H NMR (500 MHz, DMSO-d6), δ: 11.72 (s, 2H), 8.58 (m, 1H), 8.26 (m, 1H), 8.04 (s, 1H), 7.88 (d, 1H), 7.82 (m, 1H), 7.70 (d, 1H), 7.52 (m, 3H), 7.40 (m, 1H), 7.20 (d, 1H), 6.75 (d, 1H), 6.40 (s, 1H), 6.30 (s, 1H), 3.88 (m, 3H), 3.58 (m, 2H), 3.47 (m, 2H), 3.39 (m, 2H), 3.30 (m, 2H), 3.04 (m, 3H), 2.77 (m, 1H), 2.27 (m, 1H), 2.21 (m, 1H), 1.96 (m, 2H), 1.90 (m, 2H), 1.65 (m, 2H), 1.50 (m, 2H), 0.97 (s, 6H).

$^{13}$C NMR (125 MHz, DMSO-d6), δ: 164.0, 159.2, 158.9, 158.1, 154.0, 146.9, 146.7, 145.8, 144.2, 139.0, 135.5, 134.4, 132.8, 131.7, 130.1, 128.4, 127.1, 125.1, 122.8, 118.3, 117.3, 115.7, 115.0, 114.3, 109.7, 103.6, 100.4, 66.0, 58.5, 49.0, 45.1, 44.3, 34.6, 29.3, 27.1, 24.8.

Example 40

(S)-4-(4-{[2-(2-chloro-4-trifluoromethylphenyl)-4,4-dimethylcyclohex-1-enyl]methyl}-piperazin-1-yl)-N-({3-nitro-4-[(tetrahydropyran-3-yl)amino]phenyl}sulfonyl)-2-(1H-pyrrolo[2,3-b]pyridin-5-yloxy)-benzamide

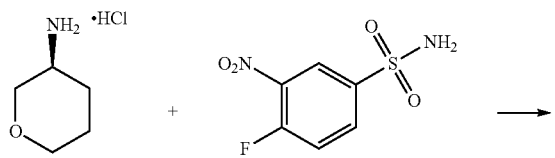

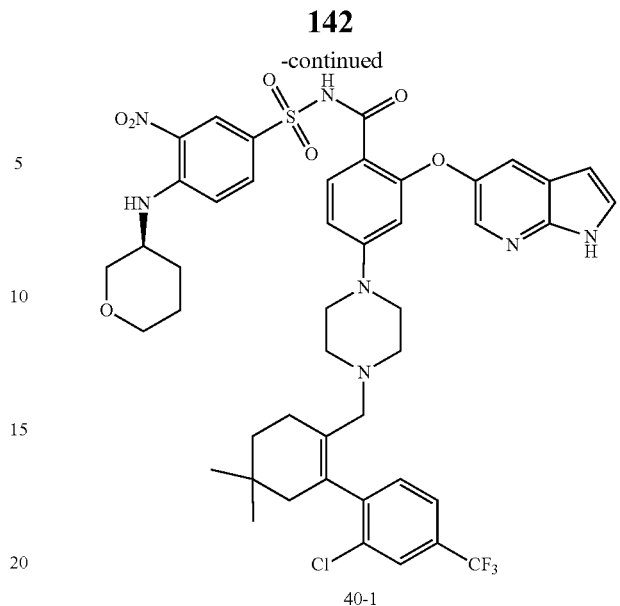

40-1

1) Preparation of Compound 40-k

Compound 40-k (1.08 g) was obtained by reference to the preparation method for compound 25-k in step 1) of Example 25, with 4-aminomethyl-1-(tetrahydro-2H-pyran) piperidine being replaced by (S)-3-aminotetrahydropyran hydrochloride.

2) Preparation of Compound 40-1

Compound 40-1 was obtained by reference to the preparation method for compound 7-1 in step 6) of Example 7, with compound 7-k being replaced by compound 40-k.

Compound 40-1: $^1$H NMR (500 MHz, DMSO-d6), δ: 11.72 (s, 1H), 11.69 (s, 1H), 8.59 (s, 1H), 8.52 (d, 1H), 8.05 (s, 1H), 7.85 (m, 2H), 7.70 (s, 1H), 7.53 (m, 3H), 7.40 (d, 1H), 7.16 (d, 1H), 6.74 (d, 1H), 6.40 (s, 1H), 6.29 (s, 1H), 3.85 (m, 3H), 3.59 (m, 4H), 3.41 (d, 1H), 3.05 (m, 5H), 2.28 (m, 2H), 2.08 (s, 1H), 1.96 (s, 3H), 1.74 (m, 2H), 1.52 (m, 3H), 1.24 (s, 1H), 0.97 (s, 6H).

$^{13}$C NMR (125 MHz, DMSO-d6), δ: 164.0, 158.9, 158.6, 158.2, 154.0, 146.9, 145.9, 144.2, 135.6, 134.6, 132.8, 131.8, 130.2, 130.0, 128.4, 127.0, 125.3, 124.9, 124.4, 120.3, 118.3, 117.6, 115.7, 115.3, 114.2, 109.7, 103.5, 100.4, 70.1, 67.8, 58.5, 48.1, 45.2, 44.3, 34.6, 29.3, 29.1, 27.7, 27.1, 24.8, 23.0, 1.6.

Example 41

(R)-4-(4-{[2-(2-chloro-4-trifluoromethylphenyl)-4,4-dimethylcyclohex-1-enyl]methyl}-piperazin-1-yl)-N-({3-nitro-4-[(tetrahydropyran-3-yl)amino]phenyl}sulfonyl)-2-(1H-pyrrolo[2,3-b]pyridin-5-yloxy)-benzamide

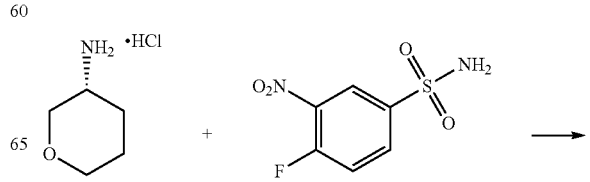

143

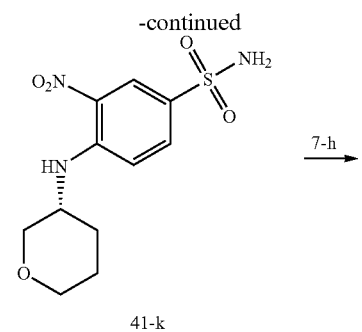

41-k

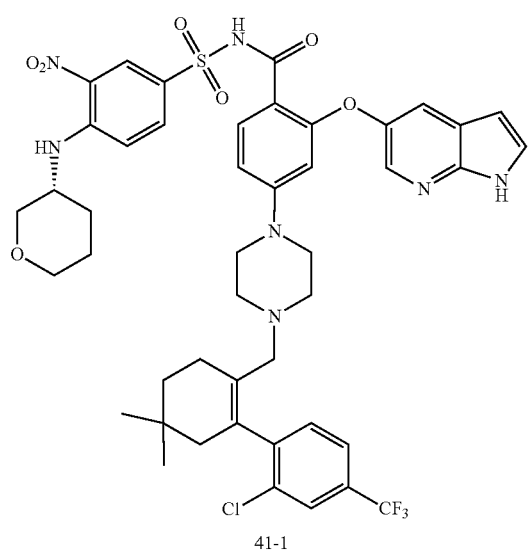

41-1

1) Preparation of Compound 41-k

Compound 41-k (0.95 g) was obtained by reference to the preparation method for compound 25-k in step 1) of Example 25, with 4-aminomethyl-1-(tetrahydro-2H-pyran) piperidine being replaced by (R)-3-aminotetrahydropyran hydrochloride.

2) Preparation of Compound 41-1

Compound 41-1 was obtained by reference to the preparation method for compound 7-1 in step 6) of Example 7, with compound 7-k being replaced by compound 41-k.

Compound 41-1: $^1$H NMR (500 MHz, DMSO-d6), δ: 11.72 (s, 2H), 8.59 (m, 1H), 8.53 (m, 1H), 8.05 (s, 1H), 7.88 (d, 1H), 7.83 (m, 1H), 7.70 (d, 1H), 7.53 (m, 3H), 7.40 (m, 1H), 7.17 (d, 1H), 6.75 (d, 1H), 6.40 (s, 1H), 6.30 (s, 1H), 3.85 (m, 3H), 3.59 (m, 2H), 3.47 (m, 2H), 3.39 (m, 2H), 3.30 (m, 2H), 3.04 (m, 2H), 2.27 (m, 1H), 2.21 (m, 1H), 2.08 (m, 2H), 1.96 (m, 2H), 1.90 (m, 2H), 1.69 (m, 2H), 1.50 (m, 2H), 0.97 (s, 6H).

$^{13}$C NMR (125 MHz, DMSO-d6), δ: 164.0, 158.9, 158.6, 158.2, 154.0, 146.9, 145.9, 144.2, 135.6, 134.6, 132.8, 131.8, 130.2, 128.4, 127.0, 125.3, 125.0, 120.3, 118.5, 118.3, 115.7, 114.2, 109.7, 103.5, 100.4, 70.1, 67.8, 58.5, 48.2, 45.2, 44.3, 34.6, 29.3, 27.7, 24.8, 23.0.

144

Example 42

(R)-4-(4-{[2-(2-chloro-4-trifluoromethylphenyl)-4,4-dimethylcyclohex-1-enyl]methyl}-piperazin-1-yl)-N-({3-nitro-4-[((tetrahydropyran-3-yl)methyl)amino]phenyl}sulfonyl)-2-(1H-pyrrolo[2,3-b]pyridin-5-yloxy)-benzamide

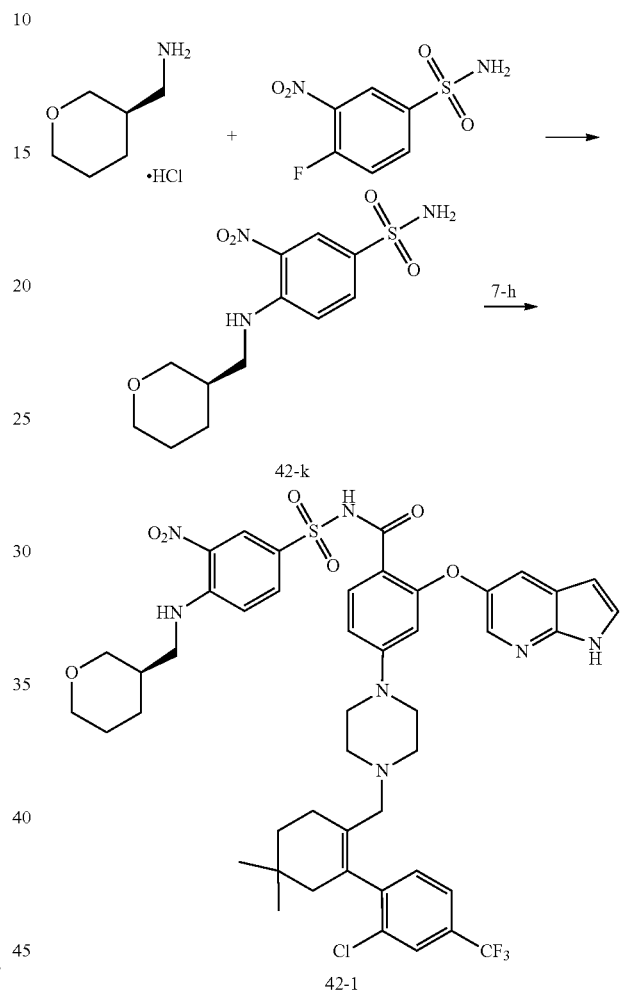

1) Preparation of Compound 42-k

Compound 42-k (0.36 g) was obtained by reference to the preparation method for compound 25-k in step 1) of Example 25, with 4-aminomethyl-1-(tetrahydro-2H-pyran) piperidine being replaced by (R)-3-aminomethyltetrahydropyran hydrochloride.

2) Preparation of Compound 42-1

Compound 42-1 was obtained by reference to the preparation method for compound 7-1 in step 6) of Example 7, with compound 7-k being replaced by compound 42-k.

Compound 42-1: $^1$H NMR (500 MHz, DMSO-d6), δ: 11.72 (s, 1H), 11.68 (s, 1H), 8.57 (m, 2H), 8.05 (d, 1H), 7.88 (s, 1H), 7.81 (d, 1H), 7.70 (d, 1H), 7.53 (d, 3H), 7.40 (d, 1H), 7.10 (d, 1H), 6.75 (d, 1H), 6.40 (s, 1H), 6.29 (s, 1H), 3.78 (m, 3H), 3.59 (m, 1H), 3.32 (m, 7H), 2.92 (m, 3H), 2.28 (m, 2H), 2.08 (s, 1H), 1.95 (m, 4H), 1.63 (m, 1H), 1.49 (m, 3H), 1.31 (m, 2H), 0.98 (s, 6H).

$^{13}$C NMR (125 MHz, DMSO-d6), δ: 163.9, 158.9, 158.6, 158.2, 154.0, 147.8, 146.9, 145.9, 144.2, 139.0, 135.6, 134.3, 132.9, 132.6, 131.8, 130.2, 130.0, 128.3, 127.0, 124.9, 124.8, 122.8, 120.3, 118.3, 117.7, 115.5, 115.4, 114.2, 109.7, 103.6, 100.4, 70.6, 68.0, 58.5, 45.2, 44.9, 44.3, 35.3, 34.6, 29.3, 29.1, 27.2, 27.1, 25.0, 24.8, 1.6.

Example 43

(S)-4-(4-{[2-(2-chloro-4-trifluoromethylphenyl)-4,4-dimethylcyclohex-1-enyl]methyl}-piperazin-1-yl)-N-({3-nitro-4-[((tetrahydropyran-3-yl)methyl)amino]phenyl}sulfonyl)-2-(1H-pyrrolo[2,3-b]pyridin-5-yloxy)-benzamide

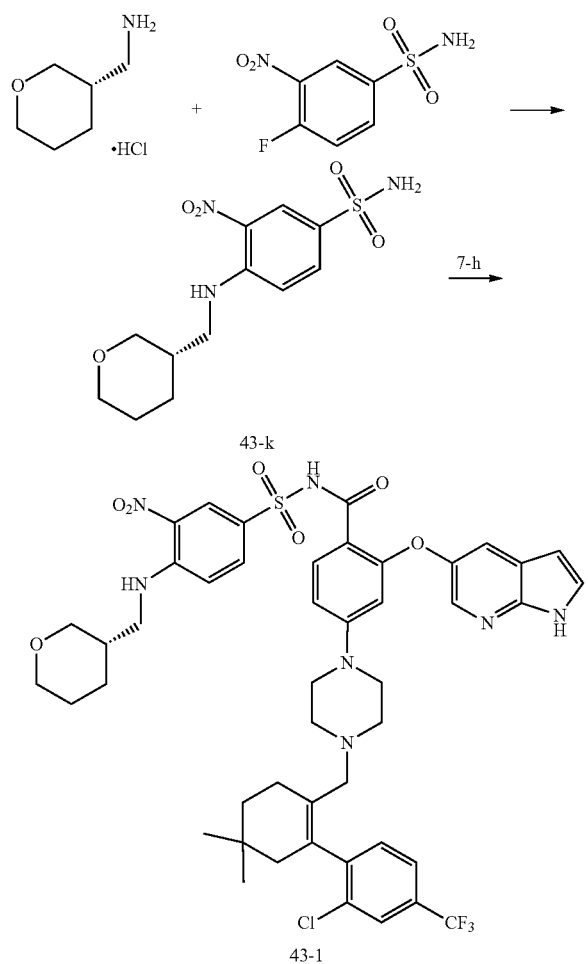

1) Preparation of Compound 43-k

Compound 43-k (0.39 g) was obtained by reference to the preparation method for compound 25-k in step 1) of Example 25, with 4-aminomethyl-1-(tetrahydro-2H-pyran)piperidine being replaced by (S)-3-aminomethyltetrahydropyran hydrochloride.

2) Preparation of Compound 43-1

Compound 43-1 was obtained by reference to the preparation method for compound 7-1 in step 6) of Example 7, with compound 7-k being replaced by compound 43-k.

Compound 43-1: $^1$H NMR (500 MHz, DMSO-d6), δ: 11.71 (s, 1H), 11.68 (s, 1H), 8.58 (m, 2H), 8.05 (s, 1H), 7.87 (s, 1H), 7.83 (d, 1H), 7.69 (d, 1H), 7.53 (m, 3H), 7.39 (d, 1H), 7.11 (d, 1H), 6.75 (d, 1H), 6.40 (s, 1H), 6.28 (s, 1H), 3.78 (m, 4H), 3.34 (m, 6H), 3.15 (m, 2H), 2.30 (m, 1H), 2.20 (m, 1H), 2.08 (s, 2H), 1.95 (m, 4H), 1.84 (m, 1H), 1.63 (m, 1H), 1.48 (s, 3H), 1.31 (m, 2H), 0.98 (d, 6H).

$^{13}$C NMR (125 MHz, DMSO-d6), δ: 163.9, 158.7, 158.2, 154.2, 147.8, 146.9, 146.0, 135.7, 134.3, 132.9, 132.6, 131.8, 130.2, 128.3, 127.0, 124.9, 124.8, 122.8, 120.3, 118.5, 118.3, 115.5, 109.6, 103.4, 100.4, 70.5, 68.0, 44.9, 35.3, 29.3, 29.2, 27.2, 27.1, 25.0, 1.6.

Example 44

4-(4-{[2-(2-chloro-4-trifluoromethylphenyl)-4,4-dimethylcyclohex-1-enyl]methyl}-piperazin-1-yl)-N-({3-nitro-4-[((2-tetrahydropyran-2-yl)ethyl)amino]phenyl}sulfonyl)-2-(1H-pyrrolo[2,3-b]pyridin-5-yloxy)-benzamide

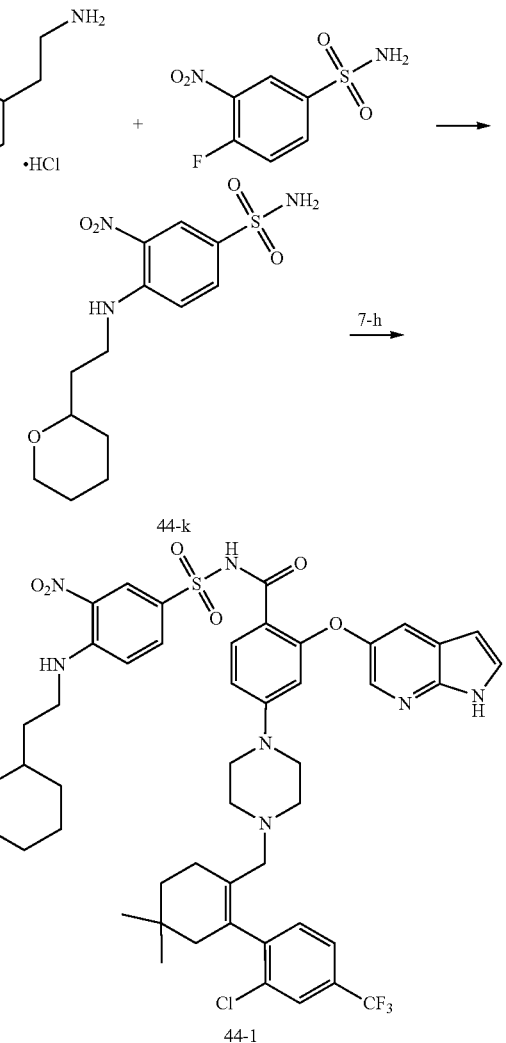

1) Preparation of Compound 44-k

Compound 44-k (1.18 g) was obtained by reference to the preparation method for compound 25-k in step 1) of Example 25, with 4-aminomethyl-1-(tetrahydro-2H-pyran)piperidine being replaced by 2-(tetrahydro-2H-pyran-2-yl)ethylamine hydrochloride.

2) Preparation of Compound 44-1

Compound 44-1 was obtained by reference to the preparation method for compound 7-1 in step 6) of Example 7, with compound 7-k being replaced by compound 44-k.

Compound 44-1: $^1$H NMR (500 MHz, DMSO-d6), δ: 11.72 (s, 1H), 11.68 (s, 1H), 8.86 (s, 1H), 8.58 (s, 1H), 8.05 (s, 1H), 7.88 (s, 1H), 7.83 (d, 1H), 7.71 (m, 1H), 7.54 (m, 3H), 7.40 (m, 1H), 7.03 (m, 1H), 6.76 (d, 1H), 6.40 (s, 1H), 6.29 (s, 1H), 3.93 (m, 1H), 3.78 (m, 1H), 3.59 (d, 1H), 3.41 (m, 7H), 3.05 (m, 4H), 2.55 (s, 2H), 2.31 (m, 1H), 2.21 (m, 1H), 1.96 (s, 2H), 1.76 (m, 3H), 1.59 (d, 1H), 1.49 (m, 4H), 1.29 (m, 1H), 0.97 (s, 6H).

$^{13}$C NMR (125 MHz, DMSO-d6), δ: 163.9, 158.9, 158.6, 158.4, 158.2, 154.0, 147.7, 146.9, 145.9, 144.2, 139.0, 135.5, 134.4, 132.8, 132.6, 131.7, 130.2, 130.0, 128.3, 127.0, 124.9, 124.6, 124.4, 122.8, 120.3, 118.3, 117.5, 115.2, 114.2, 109.7, 103.6, 100.4, 76.3, 67.9, 58.5, 45.2, 44.3, 34.7, 34.6, 31.8, 29.3, 29.1, 27.1, 26.0, 24.8, 23.4.

Example 45

4-(4-{[2-(2-chloro-4-trifluoromethylphenyl)-4,4-dimethylcyclohex-1-enyl]methyl}-piperazin-1-yl)-N-({3-nitro-4-[((2-tetrahydropyran-3-yl)ethyl)amino]phenyl}sulfonyl)-2-(1H-pyrrolo[2,3-b]pyridin-5-yloxy)-benzamide

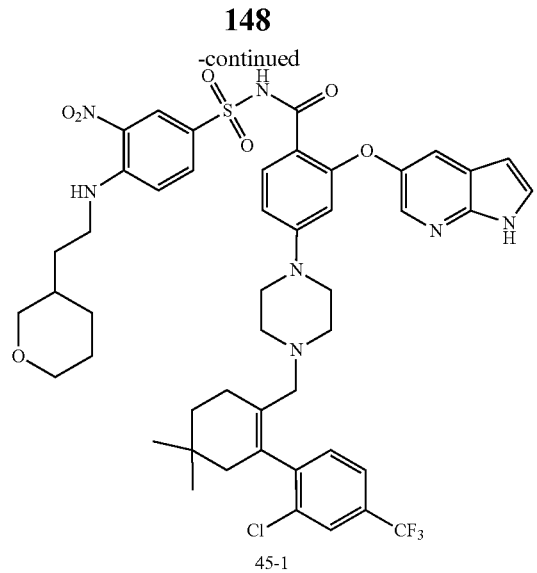

45-1

1) Preparation of Compound 45-k

Compound 45-k (1.06 g) was obtained by reference to the preparation method for compound 25-k in step 1) of Example 25, with 4-aminomethyl-1-(tetrahydro-2H-pyran)piperidine being replaced by 2-(tetrahydro-2H-pyran-3-yl)ethylamine.

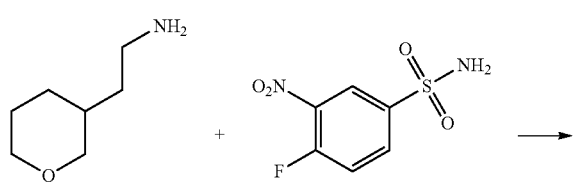

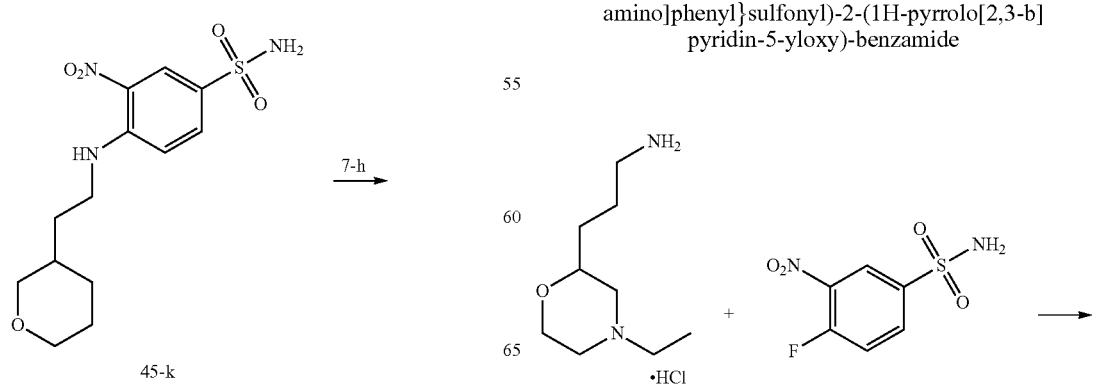

45-k

2) Preparation of Compound 45-1

Compound 45-1 was obtained by reference to the preparation method for compound 7-1 in step 6) of Example 7, with compound 7-k being replaced by compound 45-k.

Compound 45-1: $^1$H NMR (500 MHz, DMSO-d6), δ: 11.71 (s, 2H), 8.56 (m, 2H), 8.05 (s, 1H), 7.84 (t, 2H), 7.68 (d, 1H), 7.52 (m, 3H), 7.37 (d, 1H), 7.05 (d, 1H), 6.72 (d, 1H), 6.40 (s, 1H), 6.25 (s, 1H), 3.37 (m, 10H), 3.28 (m, 2H), 3.03 (m, 2H), 2.28 (d, 1H), 2.17 (d, 1H), 1.93 (s, 2H), 1.85 (d, 1H), 1.51 (m, 8H), 1.23 (m, 2H), 0.96 (s, 6H).

$^{13}$C NMR (125 MHz, DMSO-d6), δ: 163.9, 158.4, 158.3, 154.5, 147.6, 146.9, 146.0, 135.7, 134.4, 133.0, 132.5, 131.8, 130.0, 128.3, 128.2, 126.8, 124.9, 124.8, 122.8, 120.3, 118.3, 115.4, 109.5, 103.2, 100.4, 72.5, 67.9, 51.6, 45.0, 34.9, 33.9, 31.2, 29.7, 29.3, 29.2, 27.2, 25.7, 25.1.

Example 46

4-(4-{[2-(2-chloro-4-trifluoromethylphenyl)-4,4-dimethylcyclohex-1-enyl]methyl}-piperazin-1-yl)-N-({3-nitro-4-[(3-(N-ethylmorpholin-2-yl)propyl)amino]phenyl}sulfonyl)-2-(1H-pyrrolo[2,3-b]pyridin-5-yloxy)-benzamide

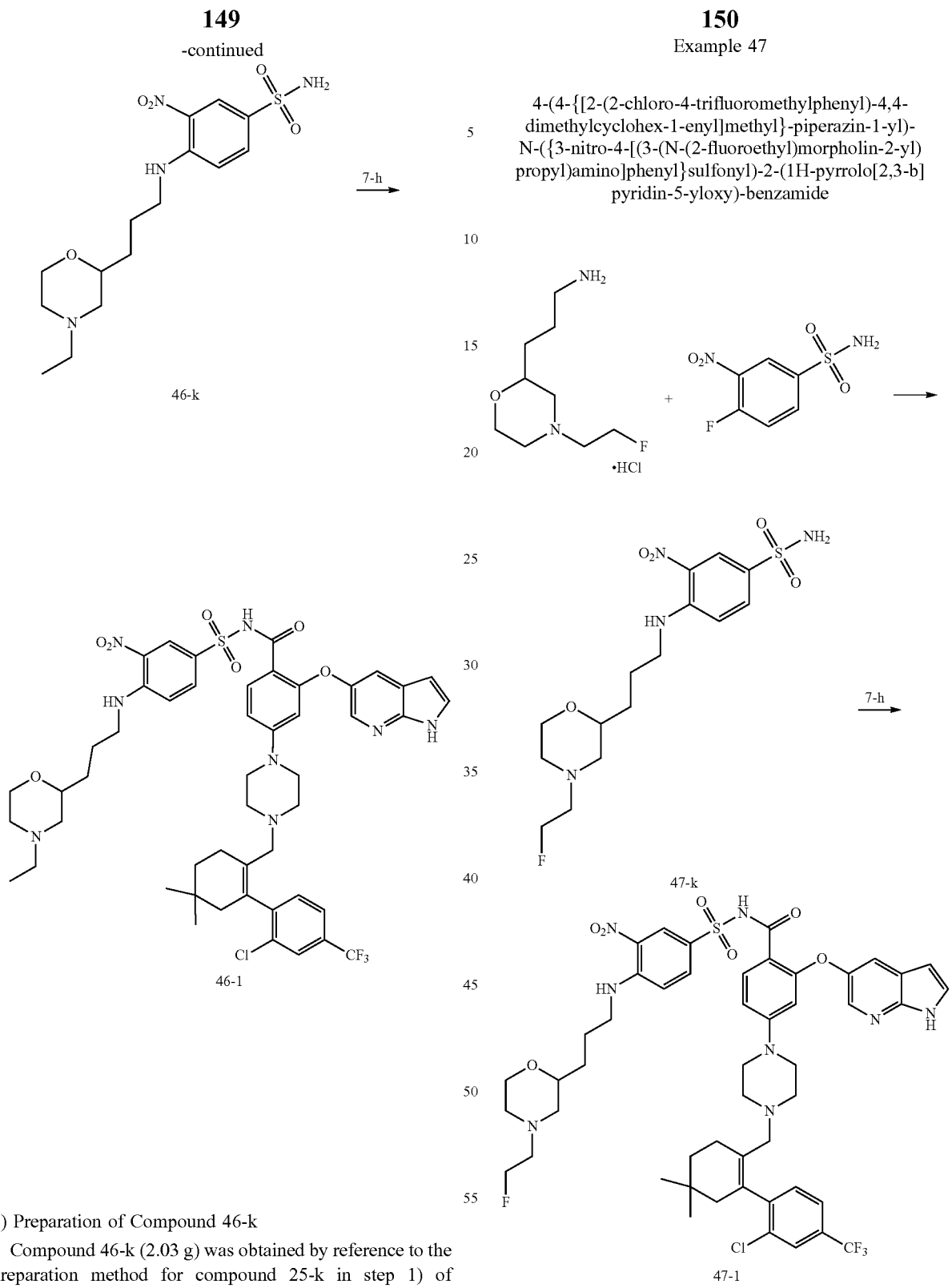

Example 47

4-(4-{[2-(2-chloro-4-trifluoromethylphenyl)-4,4-dimethylcyclohex-1-enyl]methyl}-piperazin-1-yl)-N-({3-nitro-4-[(3-(N-(2-fluoroethyl)morpholin-2-yl)propyl)amino]phenyl}sulfonyl)-2-(1H-pyrrolo[2,3-b]pyridin-5-yloxy)-benzamide 1) Preparation of Compound 46-k Compound 46-k (2.03 g) was obtained by reference to the preparation method for compound 25-k in step 1) of Example 25, with 4-aminomethyl-1-(tetrahydro-2H-pyran) piperidine being replaced by N-ethyl-2-propylaminomorpholine hydrochloride.

2) Preparation of Compound 46-1

Compound 46-1 was obtained by reference to the preparation method for compound 7-1 in step 6) of Example 7, with compound 7-k being replaced by compound 46-k.

1) Preparation of Compound 47-k

Compound 47-k (2.03 g) was obtained by reference to the preparation method for compound 25-k in step 1) of Example 25, with 4-aminomethyl-1-(tetrahydro-2H-pyran) piperidine being replaced by N-(2-fluoroethyl)-2-propylaminomorpholine hydrochloride.

2) Preparation of Compound 47-1

Compound 47-1 was obtained by reference to the preparation method for compound 7-1 in step 6) of Example 7, with compound 7-k being replaced by compound 47-k.

Example 48

4-(4-{[2-(2-chloro-4-trifluoromethylphenyl)-4,4-dimethylcyclohex-1-enyl]methyl}-piperazin-1-yl)-N-({3-nitro-4-[((N-formylmorpholin-2-yl)methyl)amino]phenyl}sulfonyl)-2-(1H-pyrrolo[2,3-b]pyridin-5-yloxy)-benzamide

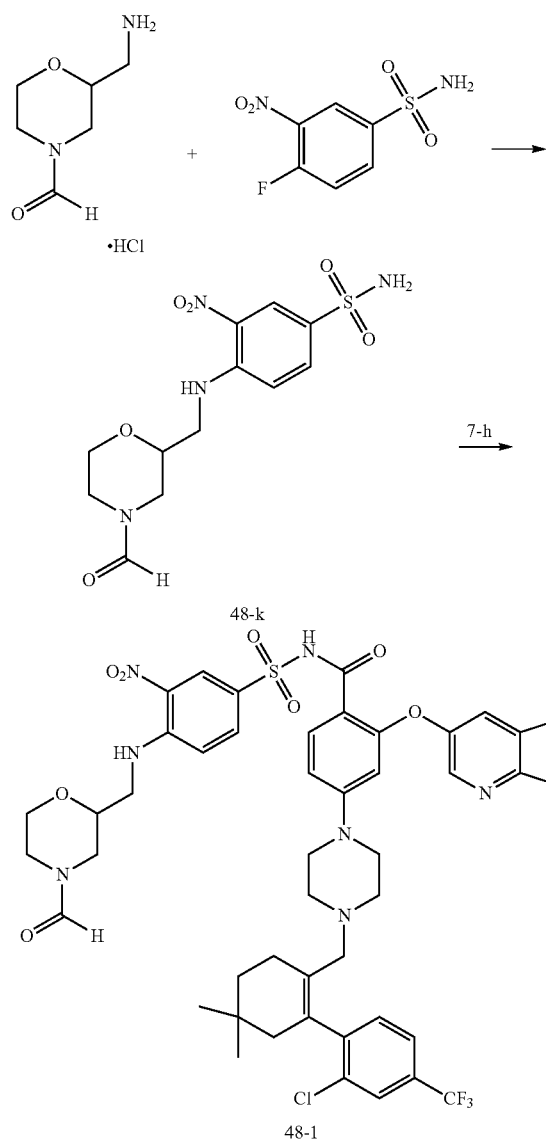

1) Preparation of Compound 48-k

Compound 48-k (0.50 g) was obtained by reference to the preparation method for compound 25-k in step 1) of Example 25, with 4-aminomethyl-1-(tetrahydro-2H-pyran) piperidine being replaced by N-formyl-2-aminomethylmorpholine hydrochloride.

2) Preparation of Compound 48-1

Compound 48-1 was obtained by reference to the preparation method for compound 7-1 in step 6) of Example 7, with compound 7-k being replaced by compound 48-k.

Compound 48-1: $^1$H NMR (500 MHz, DMSO-d6), δ: 11.72 (s, 2H), 8.65 (s, 1H), 8.57 (m, 1H), 8.04 (s, 1H), 7.88 (d, 1H), 7.83 (m, 1H), 7.70 (d, 1H), 7.54 (m, 3H), 7.39 (m, 1H), 7.16 (d, 1H), 6.75 (d, 1H), 6.40 (s, 1H), 6.30 (s, 1H), 3.90 (m, 1H), 3.75 (m, 2H), 3.60 (m, 4H), 3.51 (m, 1H), 3.45 (m, 1H), 3.21 (m, 1H), 3.06 (m, 2H), 2.81 (m, 1H), 2.67 (m, 1H), 2.27 (m, 2H), 2.07 (m, 4H), 1.96 (m, 2H), 1.50 (m, 2H), 1.24 (m, 2H), 0.97 (s, 6H).
$^{13}$C NMR (125 MHz, DMSO-d6), δ: 162.4, 160.1, 157.4, 156.6, 152.4, 146.3, 145.3, 144.2, 142.6, 137.5, 133.9, 132.7, 131.2, 130.2, 130.1, 128.7, 126.8, 123.6, 122.8, 118.8, 116.8, 115.6, 114.1, 108.1, 98.7, 72.8, 65.4, 56.9, 46.1, 43.6, 42.7, 33.0, 27.5, 23.2.

Example 49

4-(4-{[2-(2-chloro-4-trifluoromethylphenyl)-4,4-dimethylcyclohex-1-enyl]methyl}-piperazin-1-yl)-N-({3-nitro-4-[((N-methylsulfonylmorpholin-3-yl)methyl)amino]phenyl}sulfonyl)-2-(1H-pyrrolo[2,3-b]pyridin-5-yloxy)-benzamide

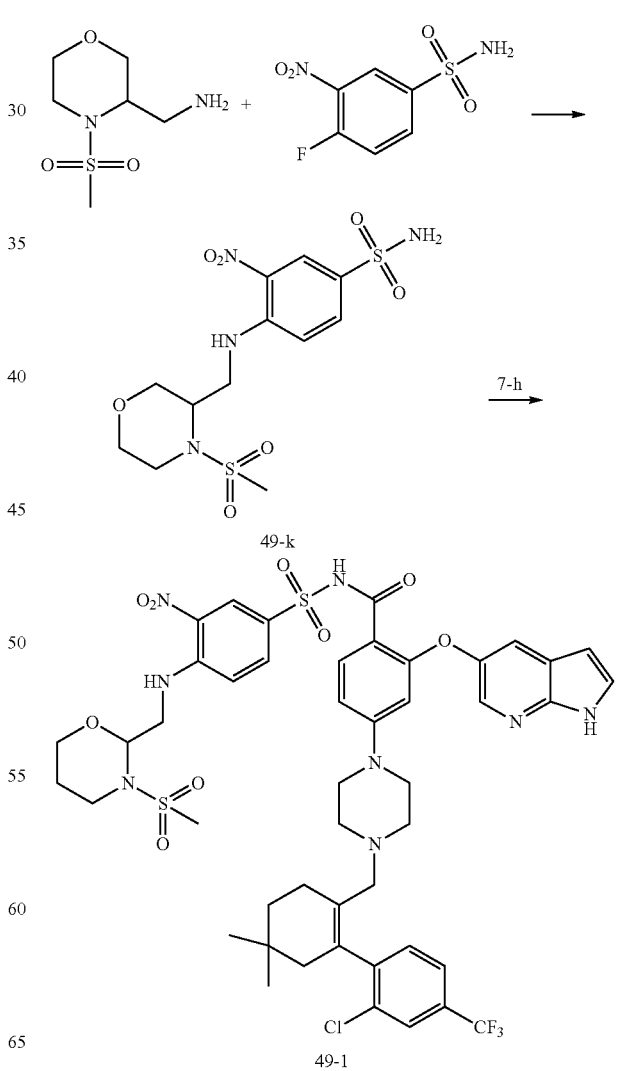

1) Preparation of Compound 49-k

Compound 49-k (0.63 g) was obtained by reference to the preparation method for compound 25-k in step 1) of Example 25, with 4-aminomethyl-1-(tetrahydro-2H-pyran)piperidine being replaced by N-methylsulfonyl-3-aminomethylmorpholine.

2) Preparation of Compound 49-1

Compound 49-1 was obtained by reference to the preparation method for compound 7-1 in step 6) of Example 7, with compound 7-k being replaced by compound 49-k.

Example 50

4-(4-{[2-(2-chloro-4-trifluoromethylphenyl)-4,4-dimethylcyclohex-1-enyl]methyl}-piperazin-1-yl)-N-({3-nitro-4-[((4-pivaloylmorpholin-2-yl)methyl)amino]phenyl}sulfonyl)-2-(1H-pyrrolo[2,3-b]pyridin-5-yloxy)-benzamide

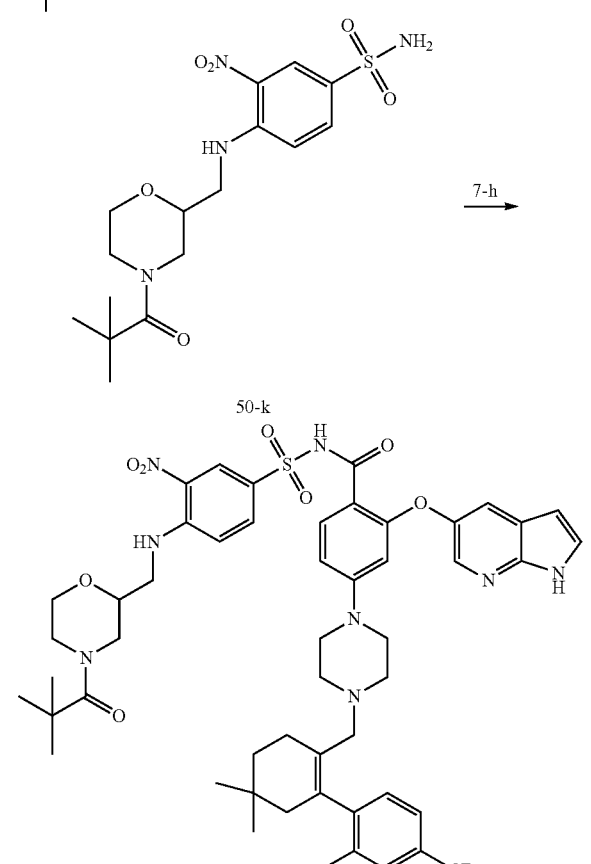

1) Preparation of Compound 50-k

Compound 50-k (1.71 g) was obtained by reference to the preparation method for compound 25-k in step 1) of Example 25, with 4-aminomethyl-1-(tetrahydro-2H-pyran)piperidine being replaced by 2-aminomethyl-4-pivaloylmorpholine.

2) Preparation of Compound 50-1

Compound 50-1 was obtained by reference to the preparation method for compound 7-1 in step 6) of Example 7, with compound 7-k being replaced by compound 50-k.

Compound 50-1: $^1$H NMR (500 MHz, DMSO-d6), δ: 11.72 (s, 1H), 11.67 (s, 1H), 8.78 (m, 1H), 8.57 (s, 1H), 8.04 (s, 1H), 7.88 (s, 1H), 7.83 (t, 1H), 7.70 (d, 1H), 7.52 (d, 3H), 7.39 (d, 1H), 7.06 (t, 1H), 6.74 (d, 1H), 6.39 (s, 1H), 6.30 (s, 1H), 4.25 (d, 1H), 4.10 (d, 1H), 3.88 (d, 1H), 3.59 (m, 6H), 3.50 (m, 6H), 3.02 (m, 2H), 2.82 (m, 2H), 2.21 (m, 2H), 1.98 (s, 2H), 1.49 (m, 2H), 1.18 (s, 9H), 0.87 (s, 6H).

$^{13}$C NMR (125 MHz, DMSO-d6), δ: 175.8, 163.9, 159.2, 158.9, 158.6, 158.3, 158.2, 154.0, 147.9, 146.9, 145.9, 144.2, 139.0, 135.6, 134.3, 132.8, 132.6, 131.8, 130.2, 129.9, 128.3, 128.2, 127.0, 125.2, 124.9, 124.5, 122.8, 120.3, 118.4, 117.7, 115.8, 115.4, 114.1, 113.0, 109.7, 103.5, 100.4, 74.1, 66.5, 58.5, 45.2, 45.0, 44.3, 34.6, 29.3, 29.1.

Example 51

4-(4-{[2-(2-chloro-4-trifluoromethylphenyl)-4,4-dimethylcyclohex-1-enyl]methyl}-piperazin-1-yl)-N-({3-nitro-4-[((4-(2-cyanoacetyl)morpholin-2-yl)methyl)amino]phenyl}sulfonyl)-2-(1H-pyrrolo[2,3-b]pyridin-5-yloxy)-benzamide

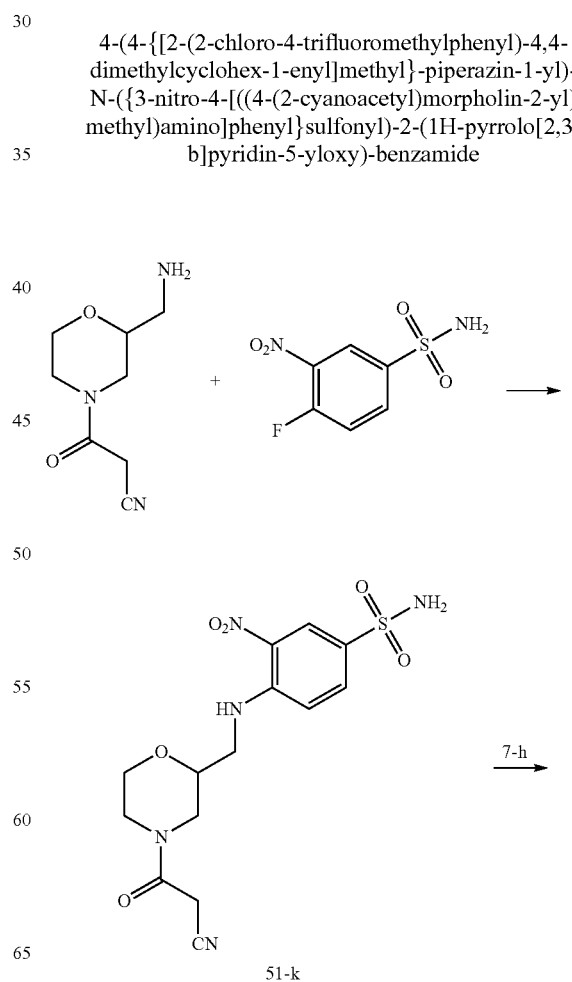

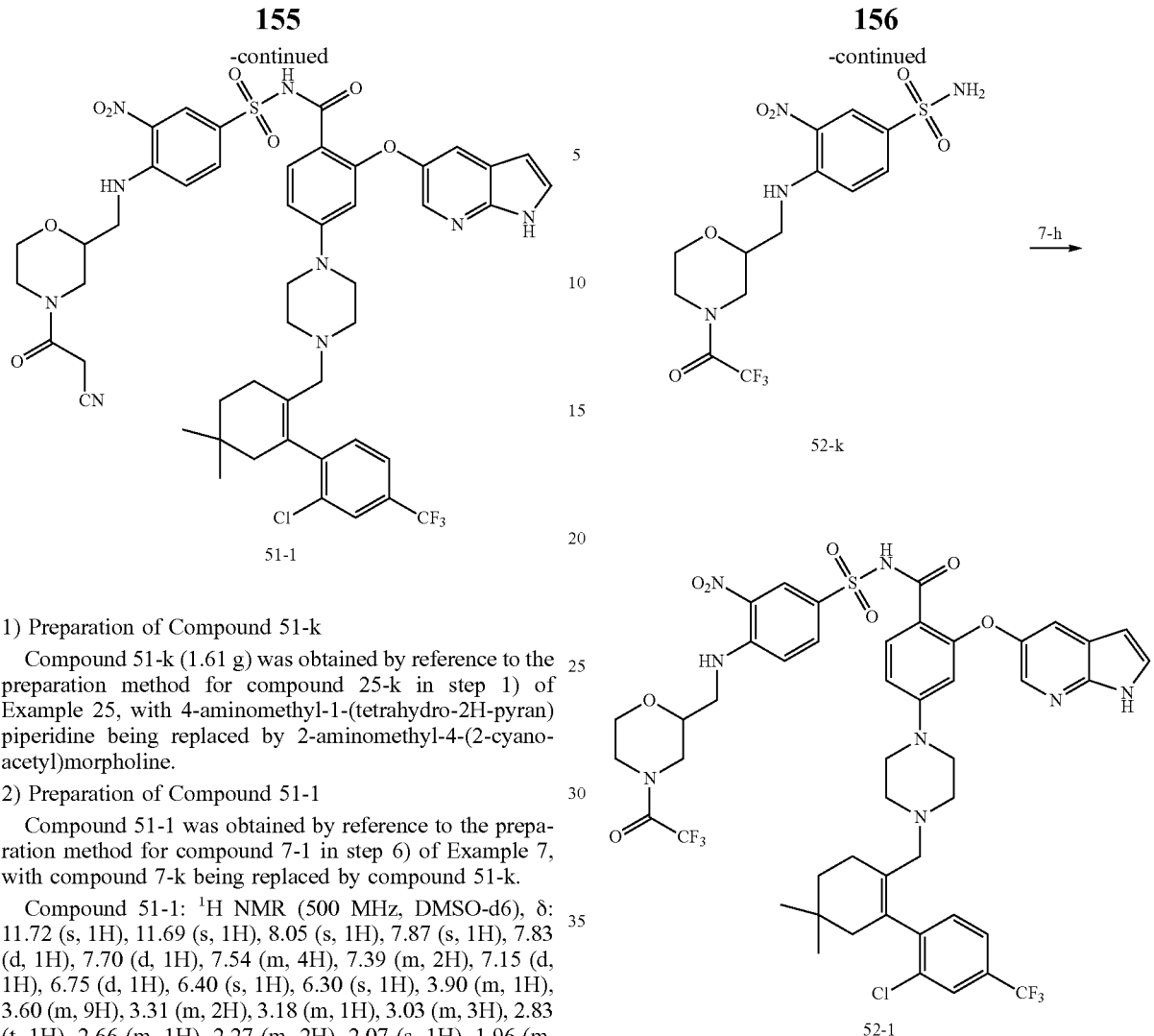

51-1

1) Preparation of Compound 51-k

Compound 51-k (1.61 g) was obtained by reference to the preparation method for compound 25-k in step 1) of Example 25, with 4-aminomethyl-1-(tetrahydro-2H-pyran) piperidine being replaced by 2-aminomethyl-4-(2-cyanoacetyl)morpholine.

2) Preparation of Compound 51-1

Compound 51-1 was obtained by reference to the preparation method for compound 7-1 in step 6) of Example 7, with compound 7-k being replaced by compound 51-k.

Compound 51-1: $^1$H NMR (500 MHz, DMSO-d6), δ: 11.72 (s, 1H), 11.69 (s, 1H), 8.05 (s, 1H), 7.87 (s, 1H), 7.83 (d, 1H), 7.70 (d, 1H), 7.54 (m, 4H), 7.39 (m, 2H), 7.15 (d, 1H), 6.75 (d, 1H), 6.40 (s, 1H), 6.30 (s, 1H), 3.90 (m, 1H), 3.60 (m, 9H), 3.31 (m, 2H), 3.18 (m, 1H), 3.03 (m, 3H), 2.83 (t, 1H), 2.66 (m, 1H), 2.27 (m, 2H), 2.07 (s, 1H), 1.96 (m, 2H), 1.50 (m, 2H), 1.24 (t, 2H), 0.97 (s, 6H).

$^{13}$C NMR (125 MHz, DMSO-d6), δ: 163.9, 162.3, 159.0, 154.0, 146.9, 145.8, 139.1, 135.4, 134.3, 132.8, 132.6, 131.7, 130.3, 130.2, 128.2, 127.0, 125.2, 124.9, 124.3, 120.4, 117.1, 109.7, 103.6, 100.5, 73.7, 66.0, 58.5, 48.2, 45.7, 44.9, 44.5, 34.6, 29.3, 29.1, 27.1, 25.3, 24.8.

Example 52

4-(4-{[2-(2-chloro-4-trifluoromethylphenyl)-4,4-dimethylcyclohex-1-enyl]methyl}-piperazin-1-yl)-N-({3-nitro-4-[((4-(2,2,2-trifluoroacetyl)morpholin-2-yl)methyl)amino]phenyl}sulfonyl)-2-(1H-pyrrolo[2,3-b]pyridin-5-yloxy)-benzamide

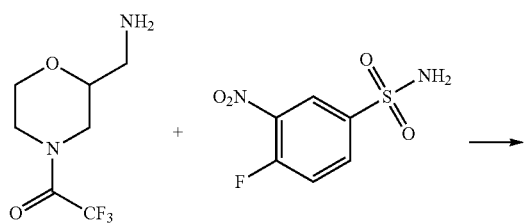

1) Preparation of Compound 52-k

Compound 52-k (1.75 g) was obtained by reference to the preparation method for compound 25-k in step 1) of Example 25, with 4-aminomethyl-1-(tetrahydro-2H-pyran) piperidine being replaced by 2-aminomethyl-4-(2,2,2-trifluoroacetyl)morpholine.

2) Preparation of Compound 52-1

Compound 52-1 was obtained by reference to the preparation method for compound 7-1 in step 6) of Example 7, with compound 7-k being replaced by compound 52-k.

Compound 52-1: $^1$H NMR (500 MHz, DMSO-d6), δ: 11.71 (s, 2H), 8.65 (s, 1H), 8.58 (m, 1H), 8.05 (s, 1H), 7.85 (d, 1H), 7.83 (m, 1H), 7.70 (d, 1H), 7.54 (m, 3H), 7.39 (m, 1H), 7.17 (d, 1H), 6.75 (d, 1H), 6.40 (s, 1H), 6.30 (s, 1H), 3.79 (m, 4H), 3.58 (m, 3H), 3.32 (m, 4H), 3.05 (m, 4H), 2.66 (m, 1H), 2.27 (m, 2H), 1.96 (m, 3H), 1.50 (m, 2H), 1.24 (t, 2H), 0.97 (s, 6H).

$^{13}$C NMR (125 MHz, DMSO-d6), δ: 164.0, 158.6, 154.0, 147.9, 145.9, 144.2, 139.0, 135.6, 134.3, 132.8, 132.6, 131.8, 130.3, 130.0, 128.3, 127.0, 125.3, 125.0, 120.3, 118.3, 117.5, 115.8, 109.7, 103.5, 100.4, 73.9, 66.0, 58.5, 51.1, 48.0, 45.5, 44.6, 43.1, 40.3, 34.6, 29.3.

Example 53

4-(4-{[2-(2-chloro-4-trifluoromethylphenyl)-4,4-dimethylcyclohex-1-enyl]methyl}-piperazin-1-yl)-N-({3-nitro-4-[((4-(trifluoromethyl)morpholin-2-yl)methyl)amino]phenyl}sulfonyl)-2-(1H-pyrrolo[2,3-b]pyridin-5-yloxy)-benzamide

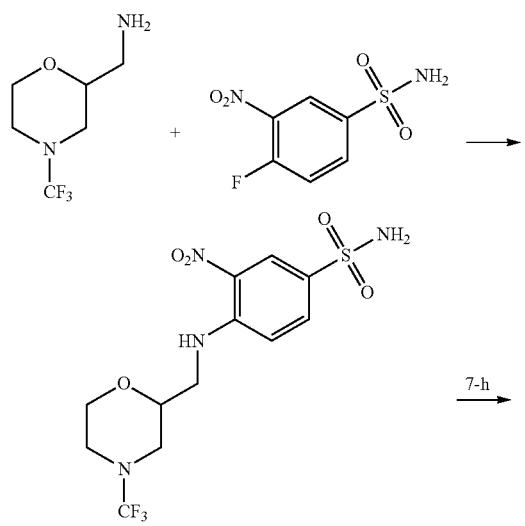

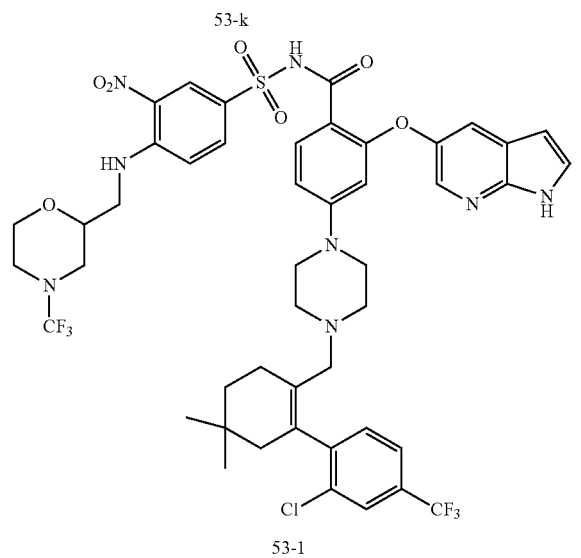

1) Preparation of Compound 53-k

Compound 53-k (1.64 g) was obtained by reference to the preparation method for compound 25-k in step 1) of Example 25, with 4-aminomethyl-1-(tetrahydro-2H-pyran) piperidine being replaced by 2-aminomethyl-4-(trifluoromethyl)morpholine.

2) Preparation of Compound 53-1

Compound 53-1 was obtained by reference to the preparation method for compound 7-1 in step 6) of Example 7, with compound 7-k being replaced by compound 53-k.

Example 54

4-(4-{[2-(2-chloro-4-trifluoromethylphenyl)-4,4-dimethylcyclohex-1-enyl]methyl}-piperazin-1-yl)-N-({3-nitro-4-[((4-(perfluoroethyl)morpholin-2-yl)methyl)amino]phenyl}sulfonyl)-2-(1H-pyrrolo[2,3-b]pyridin-5-yloxy)-benzamide

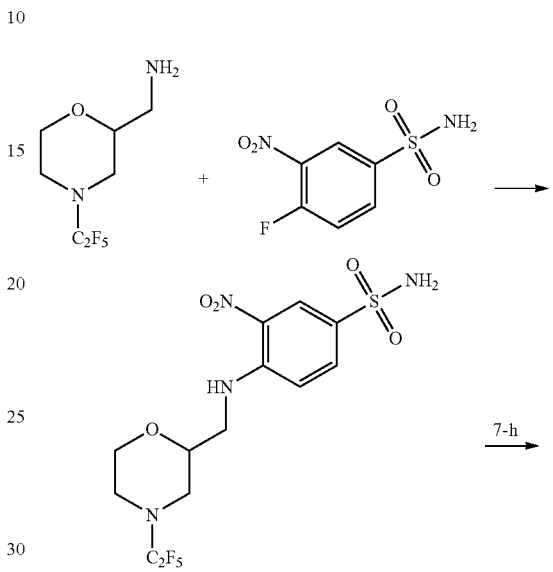

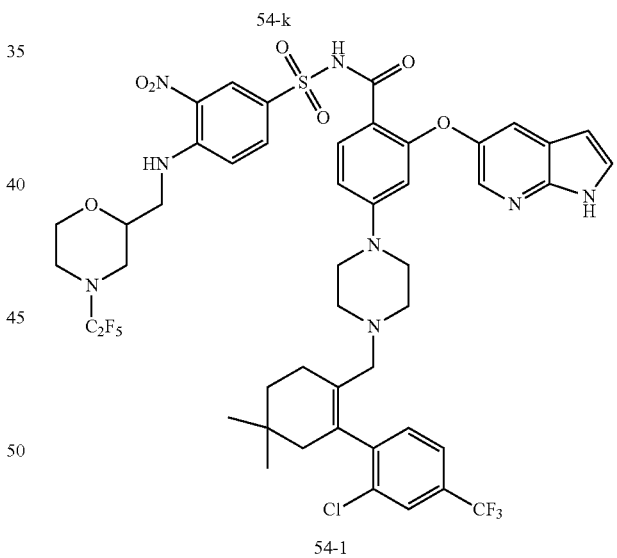

1) Preparation of Compound 54-k

Compound 54-k (1.93 g) was obtained by reference to the preparation method for compound 25-k in step 1) of Example 25, with 4-aminomethyl-1-(tetrahydro-2H-pyran) piperidine being replaced by 2-aminomethyl-4-(perfluoroethyl)morpholine.

2) Preparation of Compound 54-1

Compound 54-1 was obtained by reference to the preparation method for compound 7-1 in step 6) of Example 7, with compound 7-k being replaced by compound 54-k.

Example 55

4-(4-{[2-(2-chloro-4-trifluoromethylphenyl)-4,4-dimethylcyclohex-1-enyl]methyl}-piperazin-1-yl)-N-({3-nitro-4-[(4-(((perfluoroethyl)sulfonyl)morpholin-2-yl)methyl)amino]phenyl}sulfonyl)-2-(1H-pyrrolo[2,3-b]pyridin-5-yloxy)-benzamide

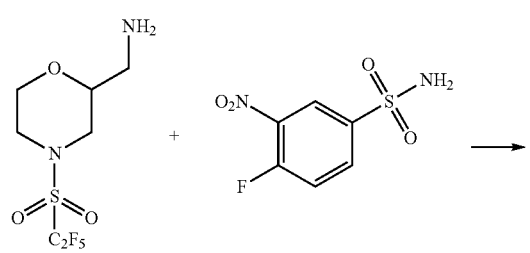

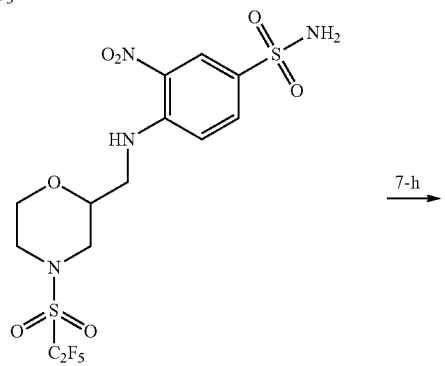

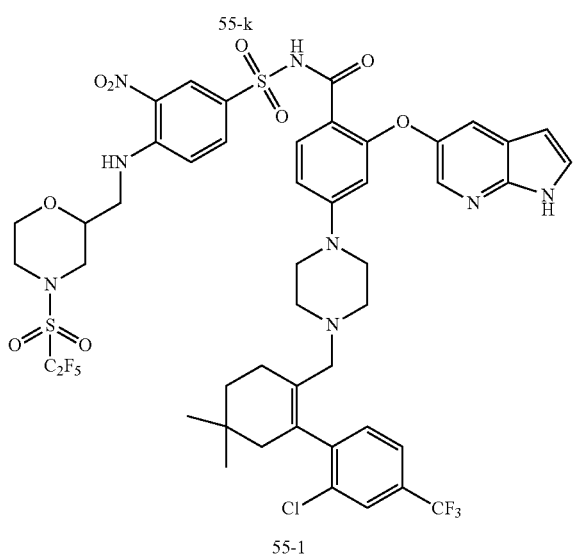

Example 56

4-(4-{[2-(2-chloro-4-trifluoromethylphenyl)-4,4-dimethylcyclohex-1-enyl]methyl}-piperazin-1-yl)-N-({3-nitro-4-[(4-(((trifluoromethyl)sulfonyl)morpholin-2-yl)methyl)amino]phenyl}sulfonyl)-2-(1H-pyrrolo[2,3-b]pyridin-5-yloxy)-benzamide

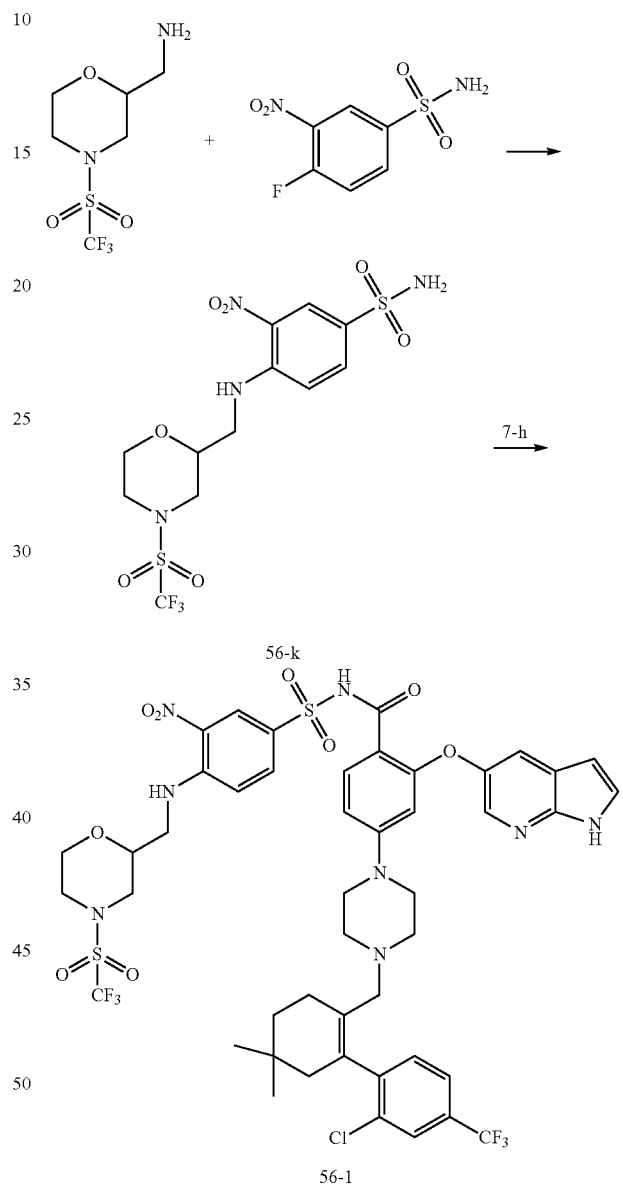

1) Preparation of Compound 55-k

Compound 55-k (2.05 g) was obtained by reference to the preparation method for compound 25-k in step 1) of Example 25, with 4-aminomethyl-1-(tetrahydro-2H-pyran) piperidine being replaced by 2-aminomethyl-4-((perfluoroethyl)sulfonyl)morpholine.

2) Preparation of Compound 55-1

Compound 55-1 was obtained by reference to the preparation method for compound 7-1 in step 6) of Example 7, with compound 7-k being replaced by compound 55-k.

1) Preparation of Compound 56-k

Compound 56-k (1.75 g) was obtained by reference to the preparation method for compound 25-k in step 1) of Example 25, with 4-aminomethyl-1-(tetrahydro-2H-pyran) piperidine being replaced by 2-aminomethyl-4-((perfluoroethyl)sulfonyl)morpholine.

2) Preparation of Compound 56-1

Compound 56-1 was obtained by reference to the preparation method for compound 7-1 in step 6) of Example 7, with compound 7-k being replaced by compound 56-k.

Compound 56-1: $^1$H NMR (500 MHz, DMSO-d6), δ: 11.71 (s, 2H), 8.64 (t, 1H), 8.59 (d, 1H), 8.05 (d, 1H), 7.89

(s, 1H), 7.84 (d, 1H), 7.71 (d, 1H), 7.55 (d, 3H), 7.40 (d, 1H), 7.16 (d, 1H), 6.75 (d, 1H), 6.40 (s, 1H), 6.29 (s, 1H), 3.80 (d, 2H), 3.64 (m, 5H), 3.52 (m, 1H), 3.38 (m, 3H), 2.91 (s, 3H), 2.86 (m, 2H), 2.72 (m, 2H), 2.27 (m, 1H), 2.21 (m, 1H), 1.96 (s, 2H), 1.50 (m, 2H), 1.24 (m, 1H), 0.96 (s, 6H).

Example 57

4-(4-{[2-(2-chloro-4-trifluoromethylphenyl)-4,4-dimethylcyclohex-1-enyl]methyl}-piperazin-1-yl)-N-({3-nitro-4-[((4-(ethylsulfonyl)morpholin-2-yl)methyl)amino]phenyl}sulfon yl)-2-(1H-pyrrolo[2,3-b]pyridin-5-yloxy)-benzamide

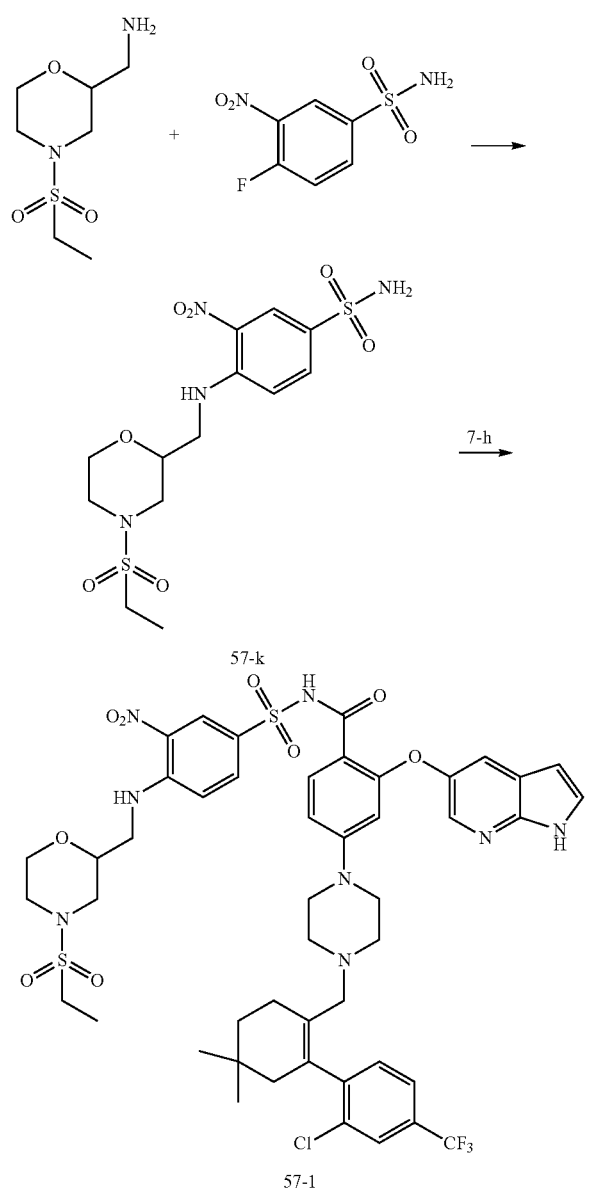

57-1

1) Preparation of Compound 57-k

Compound 57-k was obtained by reference to the preparation method for compound 25-k in step 1) of Example 25, with 4-aminomethyl-1-(tetrahydro-2H-pyran)piperidine being replaced by 2-aminomethyl-4-(ethylsulfonyl)morpholine.

2) Preparation of Compound 57-1

Compound 57-1 was obtained by reference to the preparation method for compound 7-1 in step 6) of Example 7, with compound 7-k being replaced by compound 57-k.

Compound 57-1: $^1$H NMR (500 MHz, DMSO-d6), δ: 11.72 (s, 2H), 8.64 (s, 1H), 8.58 (m, 1H), 8.05 (s, 1H), 7.89 (d, 1H), 7.83 (m, 1H), 7.70 (d, 1H), 7.54 (m, 3H), 7.39 (m, 1H), 7.16 (d, 1H), 6.75 (d, 1H), 6.40 (s, 1H), 6.30 (s, 1H), 3.95 (m, 1H), 3.75 (m, 2H), 3.52 (m, 6H), 3.42 (m, 2H), 3.39 (m, 2H), 3.12 (m, 3H), 2.96 (m, 2H), 2.77 (m, 1H), 2.28 (m, 2H), 2.08 (m, 1H), 1.96 (m, 2H), 1.50 (m, 2H), 1.24 (t, 4H), 0.97 (s, 6H).

$^{13}$C NMR (125 MHz, DMSO-d6), δ: 164.0, 158.9, 154.0, 147.9, 145.9, 144.2, 139.0, 135.5, 134.3, 132.8, 132.6, 131.7, 130.3, 130.0, 128.3, 127.0, 125.2, 124.9, 120.3, 118.5, 117.3, 115.8, 109.7, 103.6, 100.5, 73.9, 66.3, 58.5, 47.7, 45.3, 44.9, 42.9, 34.6, 29.3, 27.4, 24.8.

Example 58

4-(4-{[2-(2-chloro-4-trifluoromethylphenyl)-4,4-dimethylcyclohex-1-enyl]methyl}-piperazin-1-yl)-N-({3-nitro-4-[((1-(2-methoxyacetyl)piperidin-3-yl)methyl)amino]phenyl}sulfonyl)-2-(1H-pyrrolo[2,3-b]pyridin-5-yloxy)-benzamide

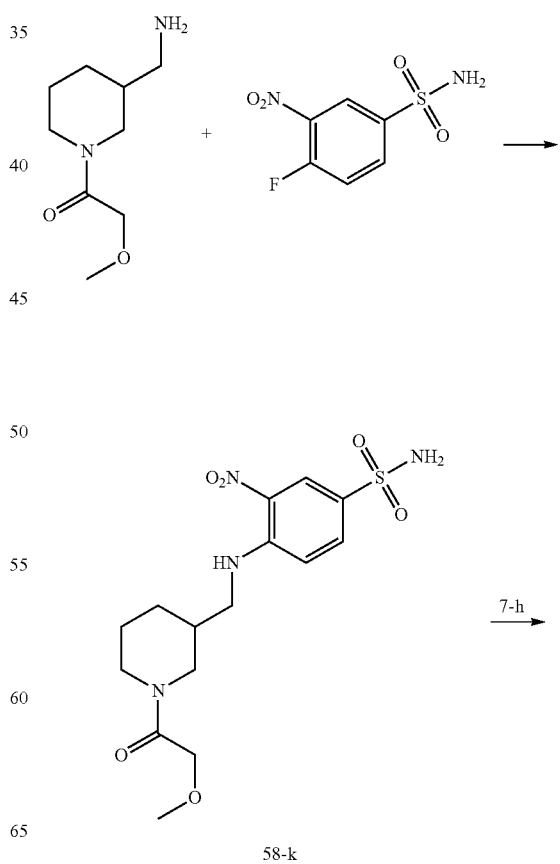

58-k

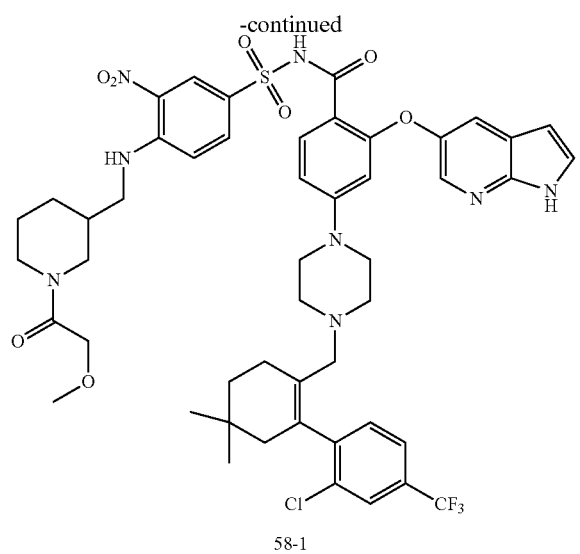

58-1

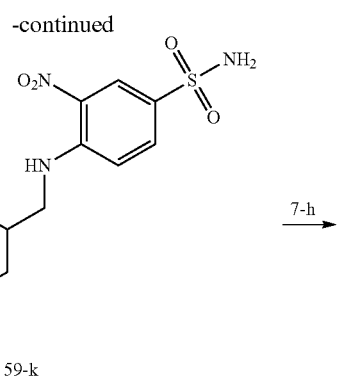

59-k

1) Preparation of Compound 58-k 3-nitro-4-fluorobenzenesulfonamide (1.03 g), 3-aminomethyl-1-(2-methoxyacetyl)piperidine (1.04 g) and N,N-diisopropylethylamine (1.51 g) were dissolved in acetonitrile (10 mL), and the solution was heated to 85° C. and reacted for 6 h. The reaction solution was cooled at room temperature, left to stand overnight, concentrated and dried to give compound 58-k (1.51 g). ESI-MS: m/z=387.0 [M+H]⁺.

2) Preparation of Compound 58-1

Compound 58-1 was obtained by reference to the preparation method for compound 7-1 in step 6) of Example 7, with compound 7-k being replaced by compound 58-k.

Compound 58-1: ¹H NMR (500 MHz, DMSO-d6), δ: 11.71 (s, 1H), 11.68 (s, 1H), 8.64 (m, 1H), 8.58 (d, 1H), 8.05 (d, 1H), 7.88 (s, 1H), 7.83 (m, 1H), 7.71 (d, 1H), 7.55 (m, 3H), 7.40 (d, 1H), 7.16 (d, 1H), 6.76 (m, 1H), 6.40 (m, 1H), 6.30 (d, 1H), 3.93 (m, 2H), 3.76 (m, 8H), 3.39 (m, 4H), 3.05 (m, 4H), 2.79 (m, 2H), 2.27 (m, 2H), 2.09 (s, 1H), 1.96 (s, 2H), 1.62 (m, 2H), 1.50 (m, 2H), 1.37 (m, 2H), 1.24 (s, 1H), 0.97 (s, 6H). ESI-MS: m/z=1007.4 [M+H]⁺.

Example 59

4-(4-{[2-(2-chloro-4-trifluoromethylphenyl)-4,4-dimethylcyclohex-1-enyl]methyl}-piperazin-1-yl)-N-({3-nitro-4-[((1-(methylglycyl)piperidin-4-yl)methyl)amino]phenyl}sulfonyl)-2-(1H-pyrrolo[2,3-b]pyridin-5-yloxy)-benzamide

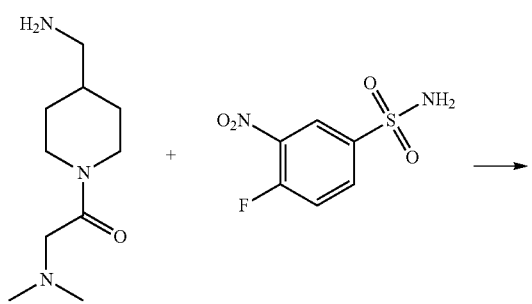

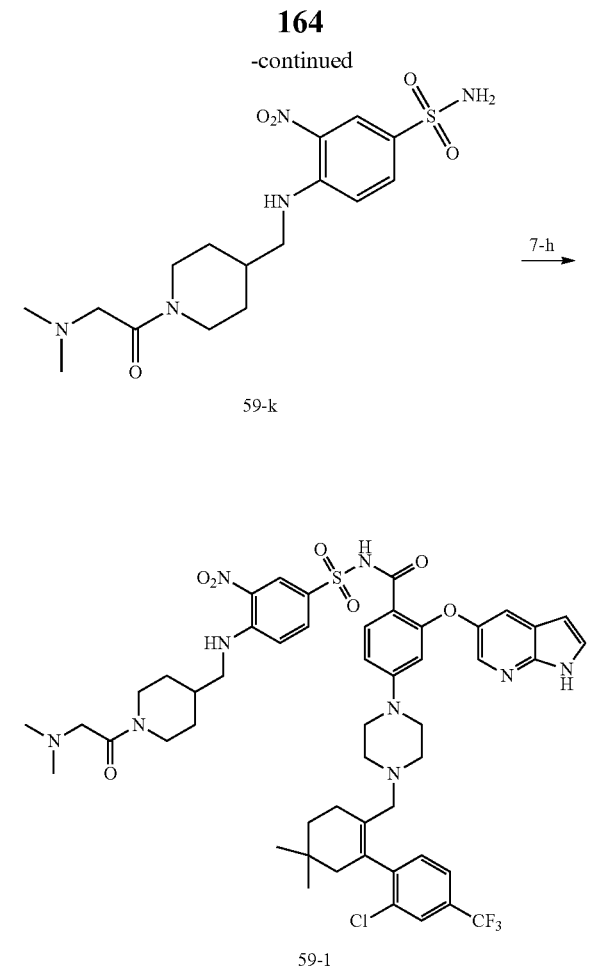

59-1

1) Preparation of Compound 59-k 3-nitro-4-fluorobenzenesulfonamide (0.91 g), 4-aminomethyl-1-(methylglycyl)piperidine (0.99 g) and N,N-diisopropylethylamine (1.34 g) were dissolved in acetonitrile (10 mL), and the solution was heated to 85° C. and reacted for 6 h. The reaction solution was cooled at room temperature, left to stand overnight, concentrated and dried to give compound 59-k (1.62 g). ESI-MS: m/z=400.1 [M+H]⁺.

2) Preparation of Compound 59-1

Compound 59-1 was obtained by reference to the preparation method for compound 7-1 in step 6) of Example 7, with compound 7-k being replaced by compound 59-k.

ESI-MS: m/z=1020.4 [M+H]⁺.

Compound 59-1: ¹H NMR (500 MHz, DMSO-d6), δ: 11.74 (s, 2H), 8.67 (s, 1H), 8.59 (m, 1H), 8.05 (s, 1H), 7.88 (d, 1H), 7.83 (m, 1H), 7.69 (d, 1H), 7.54 (m, 3H), 7.39 (m, 1H), 7.16 (d, 1H), 6.75 (d, 1H), 6.40 (s, 1H), 6.30 (s, 1H), 3.61 (m, 4H), 3.38 (m, 5H), 3.02 (m, 4H), 2.81 (m, 7H), 2.67 (m, 2H), 2.28 (m, 2H), 2.02 (m, 3H), 1.78 (m, 2H), 1.49 (m, 2H), 1.20 (m, 4H), 0.97 (s, 6H).

¹³C NMR (125 MHz, DMSO-d6), δ: 158.9, 154.0, 147.9, 145.9, 144.2, 139.0, 135.6, 134.3, 132.8, 132.6, 131.8, 130.2, 130.1, 128.3, 127.0, 124.9, 124.5, 120.3, 118.4, 117.6, 115.6, 114.2, 109.7, 103.5, 100.4, 58.5, 47.7, 45.3, 44.9, 41.7, 34.6, 29.4, 27.1, 24.8.

Example 60

4-(4-{[2-(2-chloro-4-trifluoromethylphenyl)-4,4-dimethylcyclohex-1-enyl]methyl}-piperazin-1-yl)-N-({3-nitro-4-[((1-(methylglycyl)piperidin-3-yl)methyl)amino]phenyl}sulfonyl)-2-(1H-pyrrolo[2,3-b]pyridin-5-yloxy)-benzamide

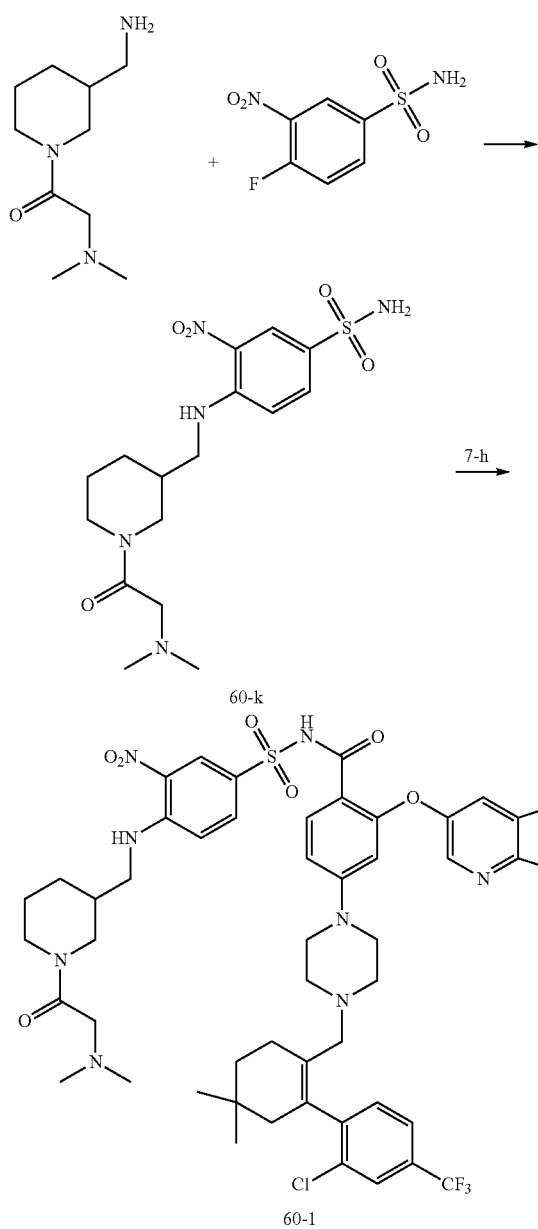

1) Preparation of Compound 60-k 3-nitro-4-fluorobenzenesulfonamide (0.90 g), 3-aminomethyl-1-(methylglycyl)piperidine (0.98 g) and N,N-diisopropylethylamine (1.32 g) were dissolved in acetonitrile (10 mL), and the solution was heated to 85° C. and reacted for 6 h. The reaction solution was cooled at room temperature, left to stand overnight, concentrated and dried to give compound 60-k (1.58 g). ESI-MS: m/z=400.0 [M+H]$^+$.

2) Preparation of Compound 60-1

Compound 60-1 was obtained by reference to the preparation method for compound 7-1 in step 6) of Example 7, with compound 7-k being replaced by compound 60-k.

Compound 60-1: $^1$H NMR (500 MHz, DMSO-d6), δ: 11.72 (s, 2H), 8.63 (m, 1H), 8.59 (d, 1H), 8.04 (d, 1H), 7.88 (s, 1H), 7.84 (m, 1H), 7.70 (d, 1H), 7.54 (m, 3H), 7.40 (d, 1H), 7.17 (d, 1H), 6.76 (m, 1H), 6.40 (m, 1H), 6.29 (d, 1H), 3.89 (m, 2H), 3.66 (m, 7H), 3.33 (m, 4H), 3.04 (m, 4H), 2.89 (s, 6H), 2.27 (m, 3H), 2.09 (s, 1H), 1.96 (s, 2H), 1.62 (m, 2H), 1.50 (m, 2H), 1.24 (s, 2H), 0.97 (s, 6H). ESI-MS: m/z=1020.4[M+H]$^+$.

Example 61

(S)-4-(4-{[2-(2-chloro-4-trifluoromethylphenyl)-4,4-dimethylcyclohex-1-enyl]methyl}-piperazin-1-yl)-N-({3-nitro-4-[((4-acetylmorpholin-2-yl)methyl)amino]phenyl}sulfonyl)-2-(1H-pyrrolo[2,3-b]pyridin-5-yloxy)-benzamide

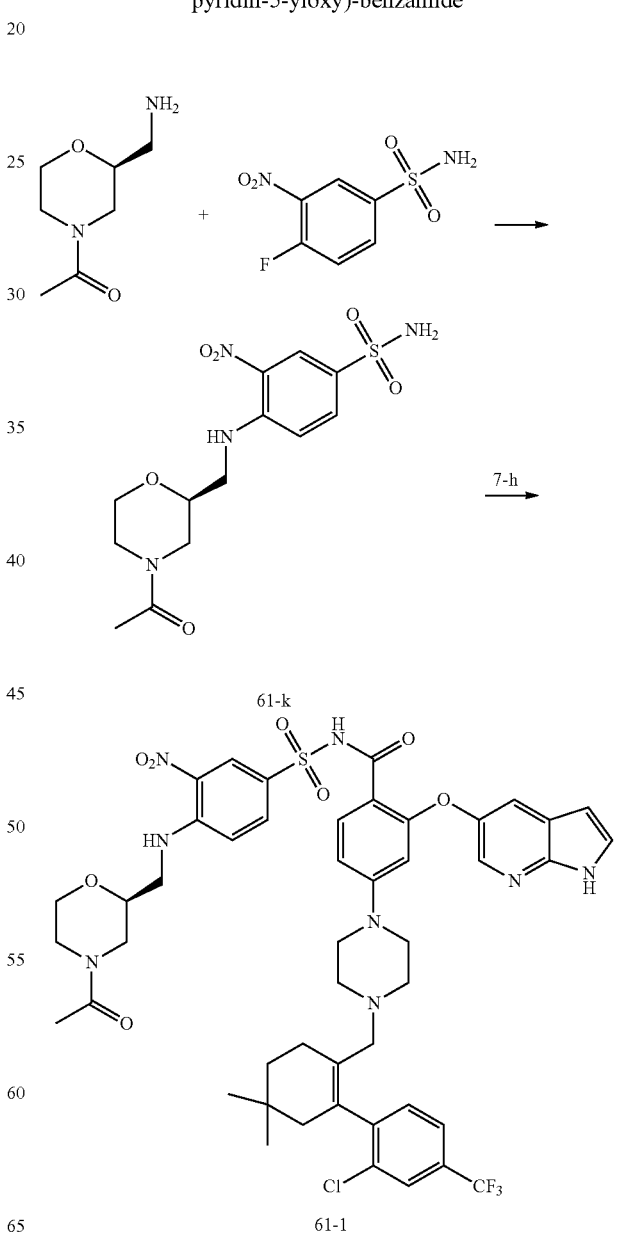

1) Preparation of Compound 61-k 3-nitro-4-fluorobenzenesulfonamide (0.68 g), (S)-2-aminomethyl-4-acetylmorpholine (0.59 g) and N,N-diisopropylethylamine (2.59 g) were dissolved in acetonitrile (10 mL), and the solution was heated to 85° C. and reacted for 6 h. The reaction solution was cooled at room temperature, left to stand overnight, concentrated and dried to give compound 61-k (0.89 g). ESI-MS: m/z=359.0 [M+H]$^+$.

2) Preparation of Compound 61-1

Compound 61-1 was obtained by reference to the preparation method for compound 7-1 in step 6) of Example 7, with compound 7-k being replaced by compound 61-k.

Compound 61-1: $^1$H NMR (500 MHz, DMSO-d6), δ: 11.71 (s, 2H), 8.64 (s, 1H), 8.58 (m, 1H), 8.05 (s, 1H), 7.87 (d, 1H), 7.84 (m, 1H), 7.70 (d, 1H), 7.54 (m, 3H), 7.39 (m, 1H), 7.15 (d, 1H), 6.75 (d, 1H), 6.40 (s, 1H), 6.30 (s, 1H), 3.91 (m, 1H), 3.67 (m, 2H), 3.60 (m, 4H), 3.47 (m, 2H), 3.42 (m, 2H), 3.30 (m, 2H), 3.17 (m, 1H), 3.02 (m, 2H), 2.72 (m, 1H), 2.55 (m, 1H), 2.27 (m, 1H), 2.21 (m, 2H), 2.01 (m, 3H), 1.96 (m, 2H), 1.50 (m, 2H), 0.97 (s, 6H).

$^{13}$C NMR (125 MHz, DMSO-d6), δ: 169.1, 164.0, 158.9, 158.6, 154.0, 147.9, 146.9, 145.9, 144.2, 135.5, 132.8, 131.7, 130.2, 128.3, 128.2, 125.2, 120.3, 118.3, 117.4, 115.8, 114.2, 109.7, 103.6, 100.4, 73.8, 66.4, 58.5, 48.5, 45.2, 44.3, 41.2, 34.6, 29.3, 27.1, 24.8, 21.6. ESI-MS: m/z=979.4 [M+H]$^+$.

Example 62

(S)-4-(4-{[2-(2-chloro-4-trifluoromethylphenyl)-4,4-dimethylcyclohex-1-enyl]methyl}-piperazin-1-yl)-N-({3-nitro-4-[((4-isobutyrylmorpholin-2-yl)methyl)amino]phenyl}sulfonyl)-2-(1H-pyrrolo[2,3-b]pyridin-5-yloxy)-benzamide

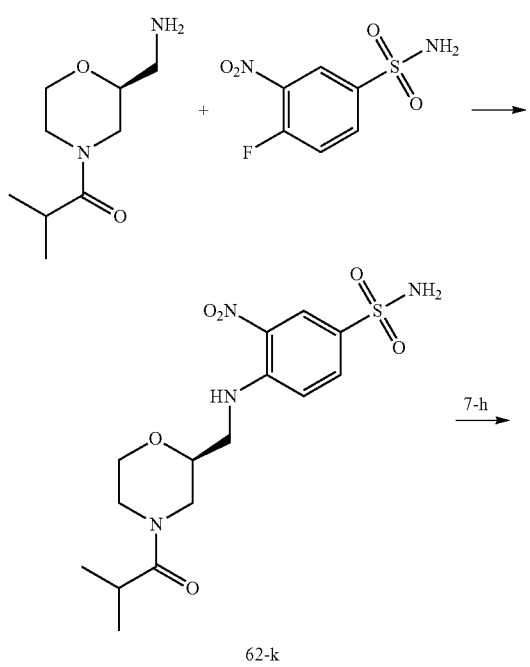

62-k

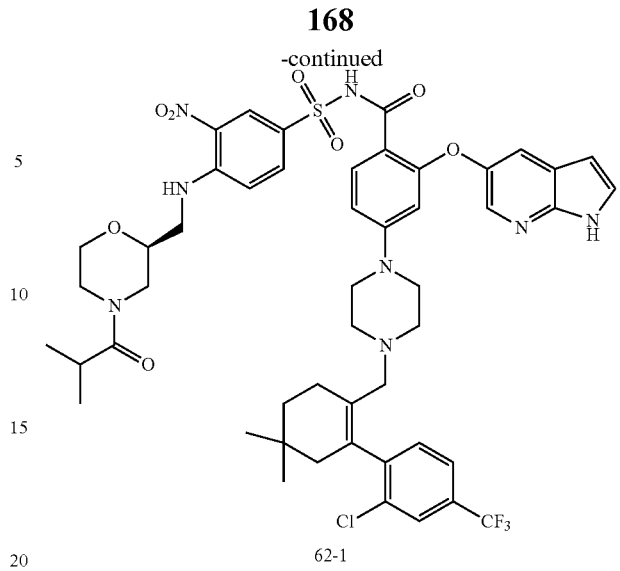

62-1

1) Preparation of Compound 62-k 3-nitro-4-fluorobenzenesulfonamide (0.68 g), (S)-2-aminomethyl-4-isobutyrylmorpholine (0.69 g) and N,N-diisopropylethylamine (2.59 g) were dissolved in acetonitrile (10 mL), and the solution was heated to 85° C. and reacted for 6 h. The reaction solution was cooled at room temperature, left to stand overnight, concentrated and dried to give compound 62-k (0.87 g). ESI-MS: m/z=387.0 [M+H]$^+$.

2) Preparation of Compound 62-1

Compound 62-1 was obtained by reference to the preparation method for compound 7-1 in step 6) of Example 7, with compound 7-k being replaced by compound 62-k.

Compound 62-1: $^1$H NMR (500 MHz, DMSO-d6), δ: 11.72 (s, 1H), 11.69 (s, 1H), 8.64 (s, 1H), 8.58 (m, 1H), 8.05 (s, 1H), 7.88 (d, 1H), 7.83 (m, 1H), 7.70 (d, 1H), 7.54 (m, 3H), 7.39 (m, 1H), 7.16 (d, 1H), 6.75 (d, 1H), 6.40 (s, 1H), 6.30 (s, 1H), 3.92 (m, 1H), 3.80 (m, 1H), 3.60 (m, 4H), 3.47 (m, 2H), 3.39 (m, 2H), 3.30 (m, 2H), 3.19 (m, 1H), 2.86 (m, 5H), 2.72 (m, 1H), 2.57 (m, 1H), 2.27 (m, 2H), 1.96 (m, 2H), 1.50 (m, 2H), 1.00 (s, 6H), 0.97 (s, 6H).

$^{13}$C NMR (125 MHz, DMSO-d6), δ: 158.9, 154.0, 147.9, 145.6, 144.2, 139.0, 135.5, 134.3, 132.8, 132.6, 131.7, 130.2, 130.0, 128.3, 127.0, 125.2, 125.0, 120.3, 118.4, 117.3, 115.8, 109.7, 103.6, 100.4, 74.0, 66.6, 58.5, 45.3, 44.3, 42.9, 34.6, 29.3, 27.1, 24.8, 20.0. ESI-MS: m/z=1007.4 [M+H]$^+$.

Example 63

(S)-4-(4-{[2-(2-chloro-4-trifluoromethylphenyl)-4,4-dimethylcyclohex-1-enyl]methyl}-piperazin-1-yl)-N-({3-nitro-4-[(((4-(methylsulfonyl)morpholin)-2-yl)methyl)amino]phenyl}sulfonyl)-2-(1H-pyrrolo[2,3-b]pyridin-5-yloxy)-benzamide

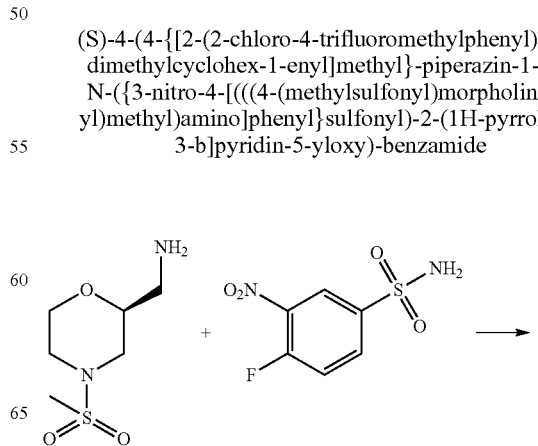

169

-continued

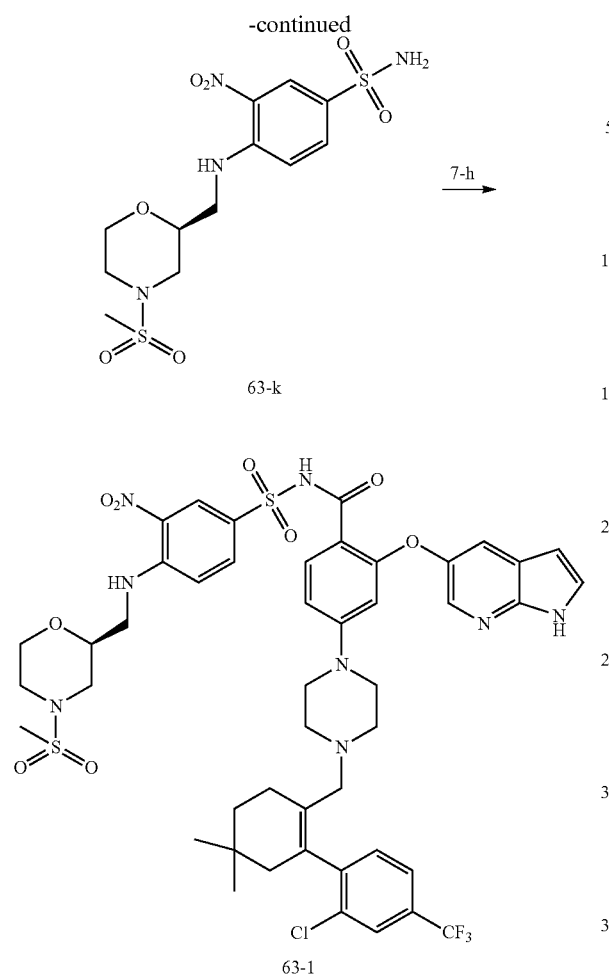

1) Preparation of Compound 63-k 3-nitro-4-fluorobenzenesulfonamide (0.68 g), (S)-2-aminomethyl-4-(methylsulfonyl)morpholine (0.72 g) and N,N-diisopropylethylamine (2.59 g) were dissolved in acetonitrile (10 mL), and the solution was heated to 85° C. and reacted for 6 h. The reaction solution was cooled at room temperature, left to stand overnight, concentrated and dried to give compound 63-k (0.68 g). ESI-MS: m/z=395.0 [M+H]⁺.

2) Preparation of Compound 63-1

Compound 63-1 was obtained by reference to the preparation method for compound 7-1 in step 6) of Example 7, with compound 7-k being replaced by compound 63-k.

Compound 63-1: ¹H NMR (500 MHz, DMSO-d6), δ: 11.71 (s, 1H), 11.69 (s, 1H), 8.65 (s, 1H), 8.58 (m, 1H), 8.05 (s, 1H), 7.89 (d, 1H), 7.84 (m, 1H), 7.70 (d, 1H), 7.54 (m, 3H), 7.39 (m, 1H), 7.16 (d, 1H), 6.75 (d, 1H), 6.40 (s, 1H), 6.30 (s, 1H), 3.98 (m, 1H), 3.79 (m, 3H), 3.66 (m, 2H), 3.58 (m, 3H), 3.49 (m, 1H), 3.44 (m, 1H), 3.35 (m, 2H), 2.92 (m, 4H), 2.85 (m, 2H), 2.69 (m, 2H), 2.27 (m, 1H), 2.21 (m, 1H), 1.96 (m, 3H), 1.50 (m, 2H), 0.97 (s, 6H).

¹³C NMR (125 MHz, DMSO-d6), δ: 164.0, 158.9, 158.6, 154.0, 147.8, 146.9, 145.9, 144.2, 135.6, 132.8, 131.7, 130.3, 128.3, 128.2, 125.2, 120.3, 118.3, 115.8, 115.1, 114.1, 109.7, 103.6, 100.4, 73.7, 66.0, 58.5, 47.9, 45.4, 44.3, 34.6, 29.3, 27.2, 24.8. ESI-MS: m/z=1015.3 [M+H]⁺.

170

Example 64

(S)-4-(4-{[2-(2-chloro-4-trifluoromethylphenyl)-4,4-dimethylcyclohex-1-enyl]methyl}-piperazin-1-yl)-N-({3-nitro-4-[((4-(2-methoxyacetyl)morpholin-2-yl)methyl)amino]phenyl}sulfonyl)-2-(1H-pyrrolo[2,3-b]pyridin-5-yloxy)-benzamide

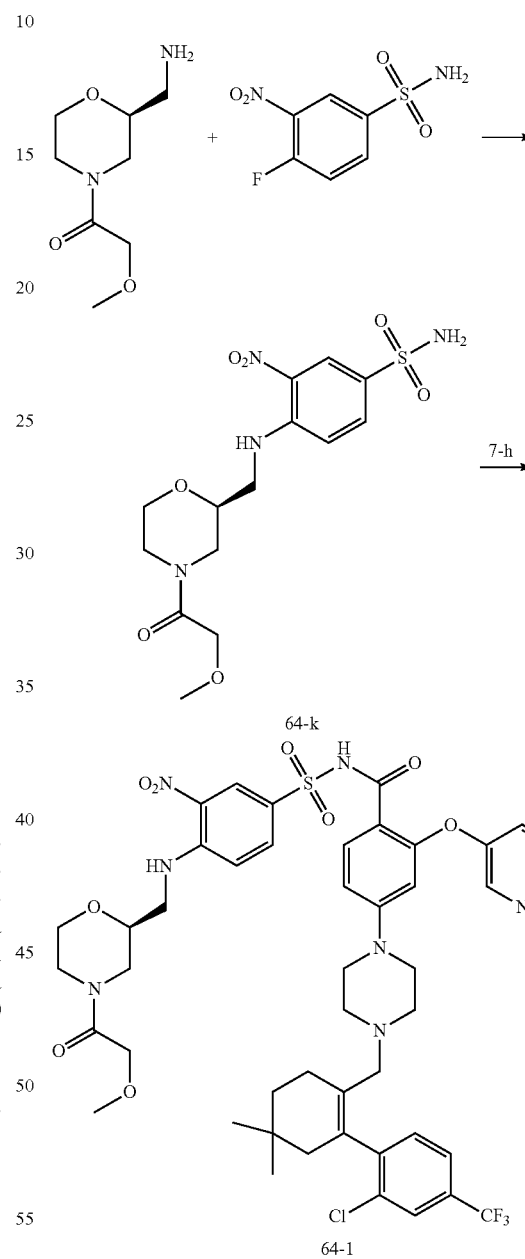

1) Preparation of Compound 64-k 3-nitro-4-fluorobenzenesulfonamide (0.68 g), (S)-2-aminomethyl-4-(2-methoxyacetyl)morpholine (0.70 g) and N,N-diisopropylethylamine (2.59 g) were dissolved in acetonitrile (10 mL), and the solution was heated to 85° C. and reacted for 6 h. The reaction solution was cooled at room temperature, left to stand overnight, concentrated and dried to give compound 64-k (0.68 g). ESI-MS: m/z=389.0 [M+H]⁺.

2) Preparation of Compound 64-1

Compound 64-1 was obtained by reference to the preparation method for compound 7-1 in step 6) of Example 7, with compound 7-k being replaced by compound 64-k.

Compound 64-1: $^1$H NMR (500 MHz, DMSO-d6), δ: 11.76 (s, 1H), 11.73 (s, 1H), 8.65 (s, 1H), 8.58 (m, 1H), 8.05 (s, 1H), 7.88 (d, 1H), 7.85 (m, 1H), 7.70 (d, 1H), 7.54 (m, 3H), 7.40 (m, 1H), 7.15 (d, 1H), 6.75 (d, 1H), 6.40 (s, 1H), 6.30 (s, 1H), 3.67 (m, 5H), 3.36 (m, 7H), 2.99 (m, 5H), 2.78 (m, 1H), 2.28 (m, 3H), 1.96 (m, 3H), 1.50 (m, 3H), 0.97 (s, 9H).

$^{13}$C NMR (125 MHz, DMSO-d6), δ: 164.9, 159.3, 158.9, 158.7, 158.4, 153.0, 147.9, 145.9, 144.2, 139.1, 135.5, 134.3, 132.8, 131.7, 130.2, 128.4, 127.1, 125.0, 124.9, 124.4, 122.8, 120.5, 119.4, 117.0, 115.1, 114.8, 112.4, 109.6, 100.5, 76.7, 66.6, 58.5, 45.2, 44.7, 40.9, 34.6, 29.3, 29.1, 27.2, 24.9. ESI-MS: m/z=1009.4 [M+H]$^+$.

Example 65

(R)-4-(4-{[2-(2-chloro-4-trifluoromethylphenyl)-4,4-dimethylcyclohex-1-enyl]methyl}-piperazin-1-yl)-N-({3-nitro-4-[((4-acetylmorpholin-2-yl)methyl)amino]phenyl}sulfonyl)-2-(1H-pyrrolo[2,3-b]pyridin-5-yloxy)-benzamide

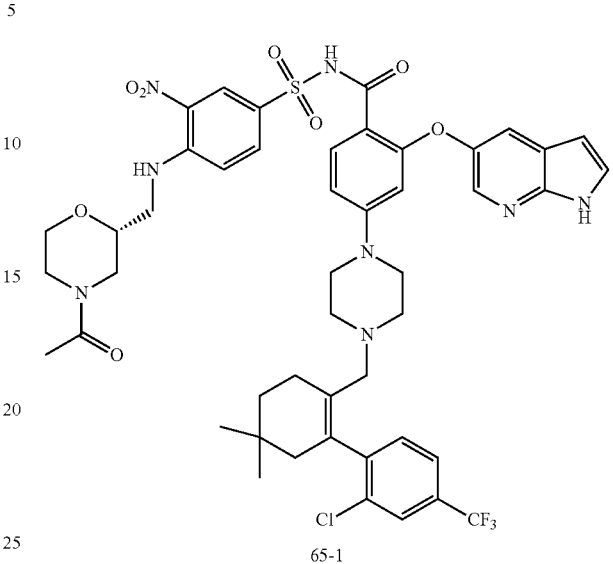

65-1

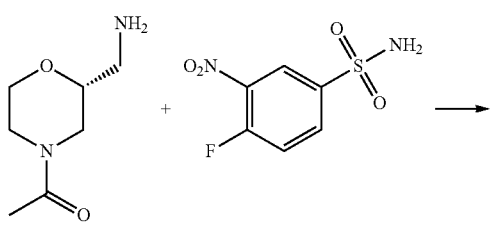

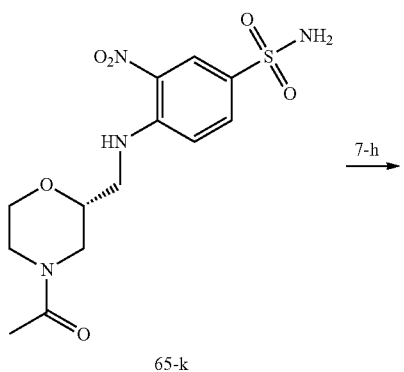

65-k

1) Preparation of Compound 65-k 3-nitro-4-fluorobenzenesulfonamide (0.68 g), (R)-2-aminomethyl-4-acetylmorpholine (0.59 g) and N,N-diisopropylethylamine (2.59 g) were dissolved in acetonitrile (10 mL), and the solution was heated to 85° C. and reacted for 6 h. The reaction solution was cooled at room temperature, left to stand overnight, concentrated and dried to give compound 65-k (0.89 g). ESI-MS: m/z=359.0 [M+H]$^+$.

2) Preparation of Compound 65-1

Compound 65-1 was obtained by reference to the preparation method for compound 7-1 in step 6) of Example 7, with compound 7-k being replaced by compound 65-k.

Compound 65-1: $^1$H NMR (500 MHz, DMSO-d6), δ: 11.71 (s, 1H), 11.69 (s, 1H), 8.64 (s, 1H), 8.58 (m, 1H), 8.05 (s, 1H), 7.88 (d, 1H), 7.84 (m, 1H), 7.70 (d, 1H), 7.55 (m, 3H), 7.39 (m, 1H), 7.15 (d, 1H), 6.75 (d, 1H), 6.40 (s, 1H), 6.30 (s, 1H), 3.89 (m, 2H), 3.67 (m, 2H), 3.58 (m, 3H), 3.49 (m, 3H), 3.30 (m, 2H), 3.17 (m, 2H), 3.02 (m, 2H), 2.72 (m, 1H), 2.56 (m, 1H), 2.27 (m, 2H), 2.21 (m, 1H), 2.02 (m, 3H), 1.96 (m, 2H), 1.50 (m, 2H), 0.97 (s, 6H).

$^{13}$C NMR (125 MHz, DMSO-d6), δ: 169.1, 164.0, 158.9, 158.6, 158.2, 154.0, 147.8, 146.9, 145.8, 144.2, 139.0, 135.5, 132.8, 131.7, 130.2, 128.3, 128.2, 124.4, 120.3, 118.3, 115.8, 114.9, 114.1, 109.7, 103.6, 100.4, 73.8, 66.4, 58.5, 48.5, 45.4, 44.3, 41.2, 34.6, 29.3, 29.1, 27.1, 24.8, 21.6. ESI-MS: m/z=979.4[M+H]$^+$.

Example 66

(R)-4-(4-{[2-(2-chloro-4-trifluoromethylphenyl)-4,4-dimethylcyclohex-1-enyl]methyl}-piperazin-1-yl)-N-({3-nitro-4-[((4-isobutyrylmorpholin-2-yl)methyl)amino]phenyl}sulfonyl)-2-(1H-pyrrolo[2,3-b]pyridin-5-yloxy)-benzamide

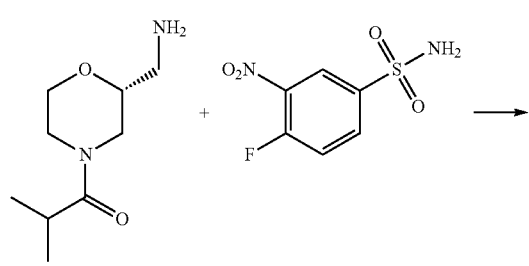

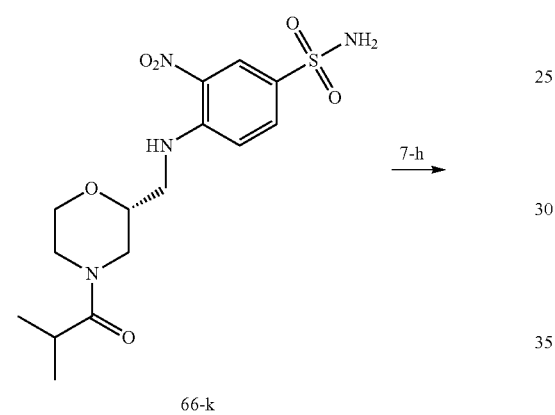

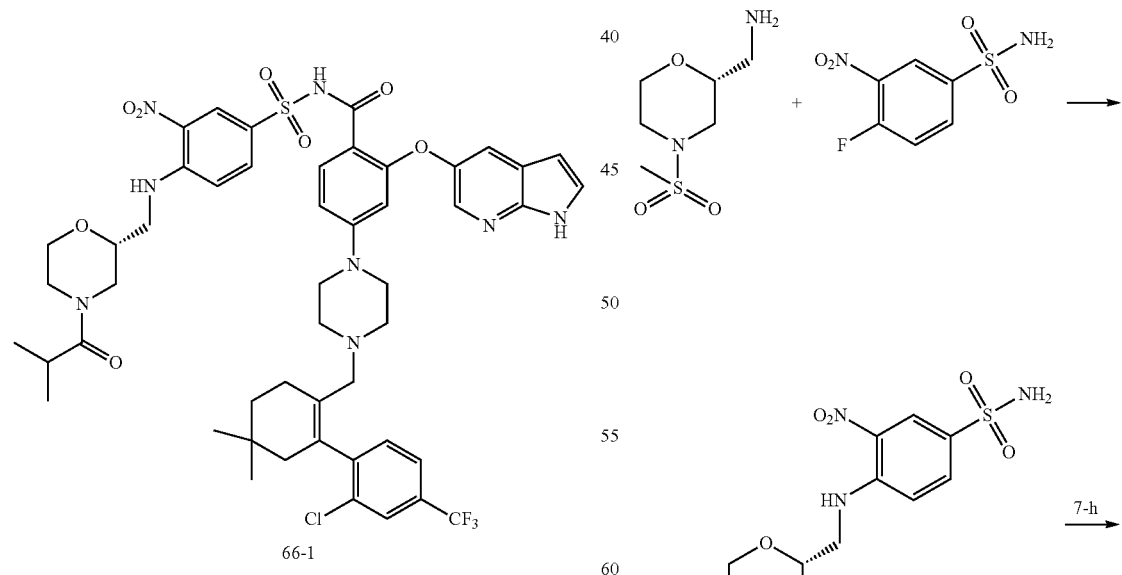

1) Preparation of Compound 66-k 3-nitro-4-fluorobenzenesulfonamide (0.68 g), (R)-2-aminomethyl-4-acetylmorpholine (0.69 g) and N,N-diisopropylethylamine (2.59 g) were dissolved in acetonitrile (10 mL), and the solution was heated to 85° C. and reacted for 6 h. The reaction solution was cooled at room temperature, left to stand overnight, concentrated and dried to give compound 66-k (0.87 g). ESI-MS: m/z=387.0 [M+H]$^+$.

2) Preparation of Compound 66-1

Compound 66-1 was obtained by reference to the preparation method for compound 7-1 in step 6) of Example 7, with compound 7-k being replaced by compound 66-k.

Compound 66-1: $^1$H NMR (500 MHz, DMSO-d6), δ: 11.72 (s, 1H), 11.69 (s, 1H), 8.64 (s, 1H), 8.58 (m, 1H), 8.05 (s, 1H), 7.88 (d, 1H), 7.84 (m, 1H), 7.70 (d, 1H), 7.56 (m, 3H), 7.40 (m, 1H), 7.16 (d, 1H), 6.75 (d, 1H), 6.40 (s, 1H), 6.30 (s, 1H), 3.91 (m, 2H), 3.81 (m, 1H), 3.60 (m, 4H), 3.45 (m, 2H), 3.39 (m, 2H), 3.30 (m, 2H), 3.18 (m, 1H), 3.03 (m, 2H), 2.87 (m, 2H), 2.72 (m, 1H), 2.57 (m, 1H), 2.27 (m, 1H), 2.21 (m, 1H), 1.96 (m, 2H), 1.50 (m, 2H), 1.00 (s, 6H), 0.97 (s, 6H).

$^{13}$C NMR (125 MHz, DMSO-d6), δ: 175.2, 164.0, 158.2, 154.0, 147.8, 146.9, 145.9, 144.2, 139.0, 135.5, 134.3, 132.8, 132.6, 131.7, 130.2, 128.3, 125.2, 124.4, 120.3, 118.3, 115.8, 114.1, 109.7, 103.6, 100.4, 74.0, 66.6, 58.5, 56.5, 45.3, 44.3, 41.5, 34.6, 29.4, 29.3, 27.1, 24.3, 20.0. ESI-MS: m/z=1007.4[M+H]$^+$.

Example 67

(R)-4-(4-{[2-(2-chloro-4-trifluoromethylphenyl)-4,4-dimethylcyclohex-1-enyl]methyl}-piperazin-1-yl)-N-({3-nitro-4-[(((4-(methylsulfonyl)morpholin)-2-yl)methyl)amino]phenyl}sulfonyl)-2-(1H-pyrrolo[2,3-b]pyridin-5-yloxy)-benzamide

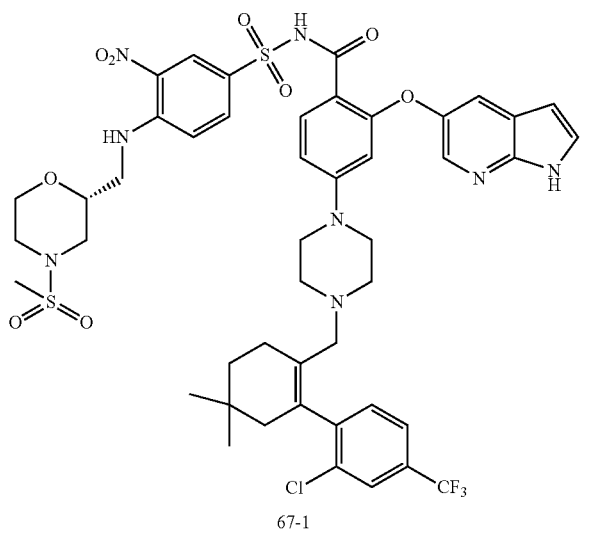

67-1

1) Preparation of Compound 67-k 3-nitro-4-fluorobenzenesulfonamide (0.68 g), (R)-2-aminomethyl-4-(methylsulfonyl)morpholine (0.72 g) and N,N-diisopropylethylamine (2.59 g) were dissolved in acetonitrile (10 mL), and the solution was heated to 85° C. and reacted for 6 h. The reaction solution was cooled at room temperature, left to stand overnight, concentrated and dried to give compound 67-k (0.68 g). ESI-MS: m/z=395.0 [M+H]$^+$.

2) Preparation of Compound 67-1

Compound 67-1 was obtained by reference to the preparation method for compound 7-1 in step 6) of Example 7, with compound 7-k being replaced by compound 67-k.

Compound 67-1: $^1$H NMR (500 MHz, DMSO-d6), δ: 11.72 (s, 1H), 11.69 (s, 1H), 8.64 (s, 1H), 8.58 (m, 1H), 8.05 (s, 1H), 7.88 (d, 1H), 7.85 (m, 1H), 7.70 (d, 1H), 7.54 (m, 3H), 7.39 (m, 1H), 7.16 (d, 1H), 6.75 (d, 1H), 6.40 (s, 1H), 6.30 (s, 1H), 3.98 (m, 2H), 3.79 (m, 2H), 3.66 (m, 2H), 3.56 (m, 3H), 3.49 (m, 2H), 3.38 (m, 3H), 2.92 (m, 3H), 2.88 (m, 2H), 2.70 (m, 2H), 2.27 (m, 1H), 2.21 (m, 1H), 1.96 (m, 2H), 1.50 (m, 2H), 1.24 (t, 1H), 0.97 (s, 6H).

$^{13}$C NMR (125 MHz, DMSO-d6), δ: 159.3, 159.0, 158.7, 158.2, 154.0, 147.8, 146.9, 145.8, 144.2, 139.0, 135.5, 132.8, 131.7, 130.2, 128.3, 128.2, 124.3, 120.4, 118.4, 115.8, 114.8, 114.1, 109.7, 103.6, 100.5, 73.7, 66.0, 58.5, 47.8, 45.4, 44.3, 34.6, 29.3, 29.1, 27.1, 24.8. ESI-MS: m/z=1015.3 [M+H]$^+$.

Example 68

4-(4-{[2-(2-chloro-4-trifluoromethylphenyl)-4,4-dimethylcyclohex-1-enyl]methyl}-piperazin-1-yl)-N-({3-nitro-4-[(3-(4-acetylmorpholin-2-yl)propyl)amino]phenyl}sulfonyl)-2-(1H-pyrrolo[2,3-b]pyridin-5-yloxy)-benzamide

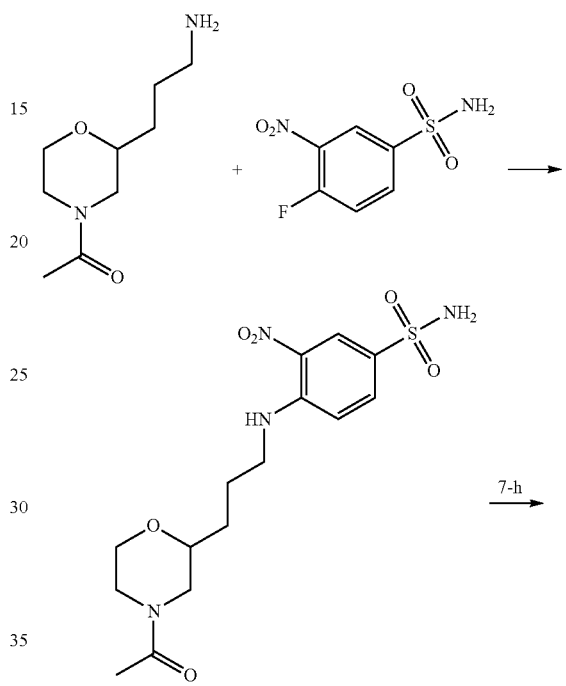

68-k

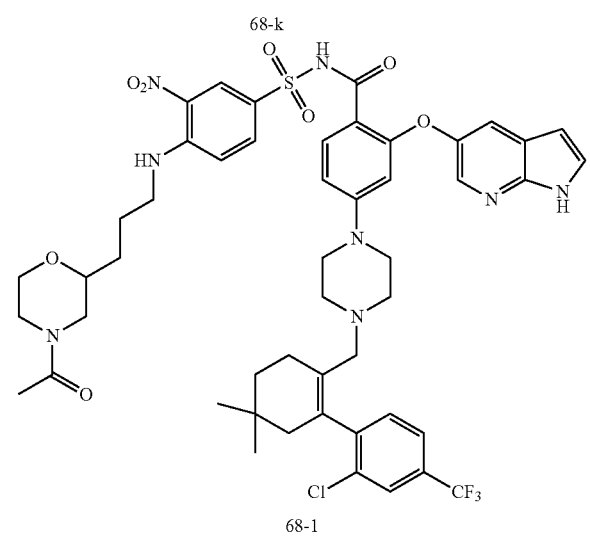

68-1

1) Preparation of Compound 68-k 3-nitro-4-fluorobenzenesulfonamide (1.20 g), 2-aminopropyl-3-(4-acetyl)morpholine (1.22 g) and N,N-diisopropylethylamine (4.59 g) were dissolved in acetonitrile (10 mL), and the solution was heated to 85° C. and reacted for 6 h. The reaction solution was cooled at room temperature, left to stand overnight, concentrated and dried to give compound 68-k (1.67 g). ESI-MS: m/z=387.0 [M+H]$^+$.

2) Preparation of Compound 68-1

Compound 68-1 was obtained by reference to the preparation method for compound 7-1 in step 6) of Example 7, with compound 7-k being replaced by compound 68-k.

Compound 68-1: $^1$H NMR (500 MHz, DMSO-d6), δ: 11.74 (s, 2H), 8.61 (s, 1H), 8.58 (m, 1H), 8.05 (s, 1H), 7.88 (d, 1H), 7.85 (m, 1H), 7.70 (d, 1H), 7.54 (m, 3H), 7.39 (m, 1H), 7.07 (d, 1H), 6.75 (d, 1H), 6.40 (s, 1H), 6.30 (s, 1H), 3.83 (m, 1H), 3.66 (m, 2H), 3.59 (m, 1H), 3.40 (m, 4H), 3.32 (m, 2H), 3.10 (m, 2H), 3.05 (m, 2H), 2.83 (m, 1H), 2.63 (m, 1H), 2.27 (m, 2H), 2.21 (m, 1H), 2.00 (m, 3H), 1.71 (m, 3H), 1.96 (m, 2H), 1.50 (m, 4H), 1.24 (t, 1H), 0.97 (s, 6H).

$^{13}$C NMR (125 MHz, DMSO-d6), δ: 168.8, 164.0, 159.3, 159.0, 158.7, 154.0, 147.7, 145.8, 144.2, 139.0, 135.5, 132.8, 131.7, 130.1, 128.3, 124.4, 120.4, 117.3, 115.4, 114.9, 109.7, 100.5, 75.1, 66.3, 58.5, 46.1, 45.1, 44.3, 42.8, 41.3, 34.6, 29.3, 29.1, 27.1, 24.8, 21.6. ESI-MS: m/z=1007.4 [M+H]$^+$.

Example 69

4-(4-{[2-(2-chloro-4-trifluoromethylphenyl)-4,4-dimethylcyclohex-1-enyl]methyl}-piperazin-1-yl)-N-({3-nitro-4-[(3-(4-isobutyrylmorpholin-2-yl)propyl)amino]phenyl}sulfonyl)-2-(1H-pyrrolo[2,3-b]pyridin-5-yloxy)-benzamide

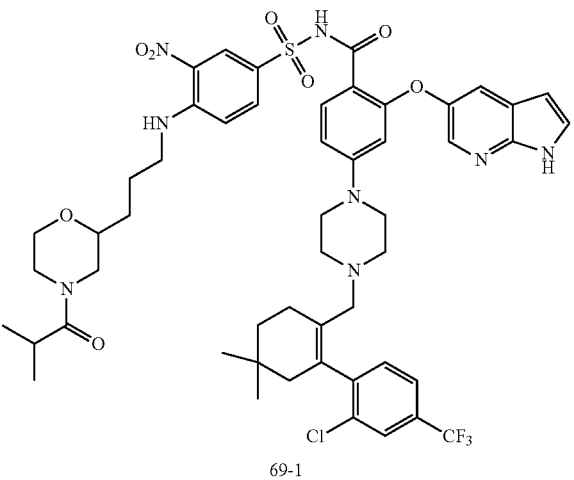

69-1

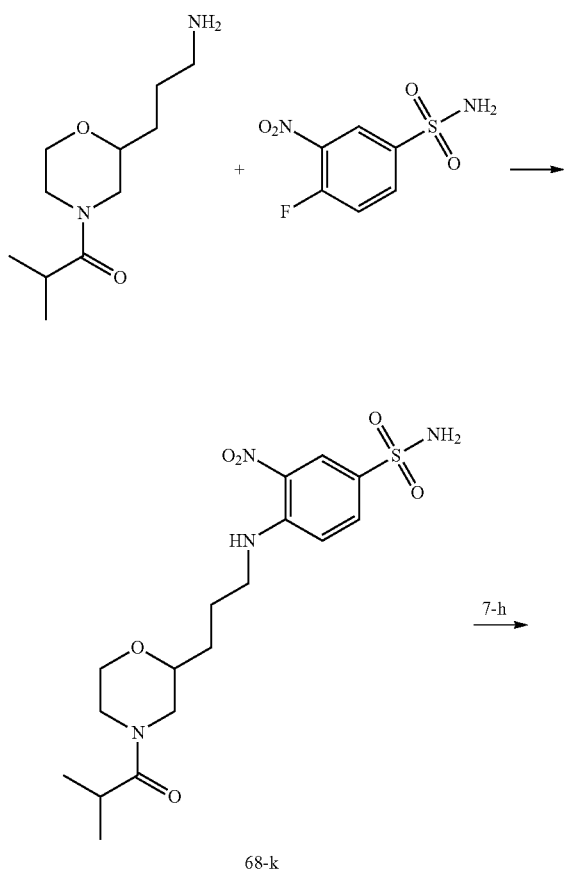

1) Preparation of Compound 69-k 3-nitro-4-fluorobenzenesulfonamide (1.20 g), 2-aminopropyl-3-(4-isobutyryl)morpholine (1.40 g) and N,N-diisopropylethylamine (4.59 g) were dissolved in acetonitrile (10 mL), and the solution was heated to 85° C. and reacted for 6 h. The reaction solution was cooled at room temperature, left to stand overnight, concentrated and dried to give compound 69-k (1.69 g). ESI-MS: m/z=415.1 [M+H]$^+$.

2) Preparation of Compound 69-1

Compound 69-1 was obtained by reference to the preparation method for compound 7-1 in step 6) of Example 7, with compound 7-k being replaced by compound 69-k.

Compound 69-1: $^1$H NMR (500 MHz, DMSO-d6), δ: 11.73 (s, 1H), 11.67 (s, 1H), 8.60 (s, 1H), 8.58 (m, 1H), 8.05 (s, 1H), 7.88 (d, 1H), 7.83 (m, 1H), 7.70 (d, 1H), 7.54 (m, 3H), 7.39 (m, 1H), 7.07 (d, 1H), 6.75 (d, 1H), 6.40 (s, 1H), 6.30 (s, 1H), 3.83 (m, 3H), 3.58 (m, 2H), 3.40 (m, 5H), 3.32 (m, 3H), 3.15 (m, 1H), 3.05 (m, 3H), 2.85 (m, 1H), 2.64 (m, 1H), 2.40 (m, 1H), 2.27 (m, 1H), 2.21 (m, 1H), 1.96 (m, 2H), 1.70 (m, 2H), 1.50 (m, 4H), 1.01 (s, 6H), 0.97 (s, 6H).

$^{13}$C NMR (125 MHz, DMSO-d6), δ: 174.9, 164.0, 159.0, 158.7, 158.2, 154.0, 147.7, 146.9, 145.8, 144.2, 139.0, 135.5, 132.8, 131.7, 130.0, 128.3, 124.9, 124.4, 120.3, 118.4, 115.4, 109.7, 100.4, 75.2, 66.6, 58.5, 46.3, 45.2, 44.3, 42.9, 34.6, 29.4, 29.1, 27.1, 24.8, 24.3, 20.6. ESI-MS: m/z=1035.3 [M+H]$^+$.

Example 70

4-(4-{[2-(2-chloro-4-trifluoromethylphenyl)-4,4-dimethylcyclohex-1-enyl]methyl}-piperazin-1-yl)-N-({3-nitro-4-[(3-(4-(2-methoxyacetyl)morpholin-2-yl)propyl)amino]phenyl}sulfonyl)-2-(1H-pyrrolo[2,3-b]pyridin-5-yloxy)-benzamide

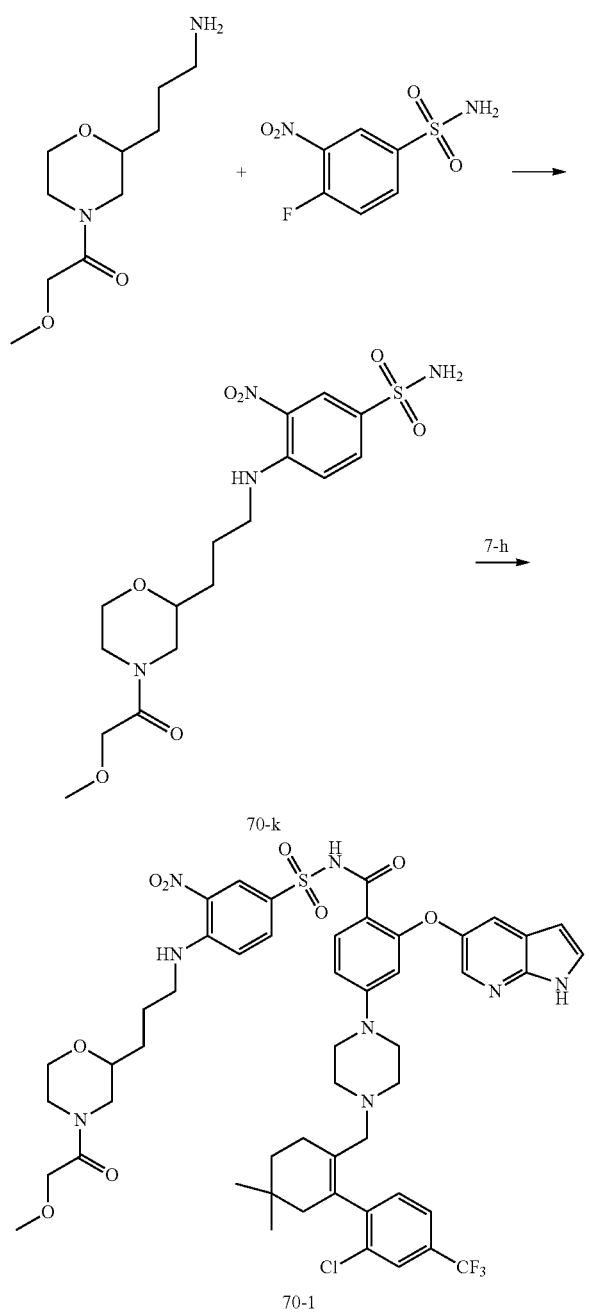

1) Preparation of Compound 70-k 3-nitro-4-fluorobenzenesulfonamide (1.20 g), 2-aminopropyl-3-(4-(2-methoxyacetyl))morpholine (1.42 g) and N,N-diisopropylethylamine (4.59 g) were dissolved in acetonitrile (10 mL), and the solution was heated to 85° C. and reacted for 6 h. The reaction solution was cooled at room temperature, left to stand overnight, concentrated and dried to give compound 70-k (1.71 g). ESI-MS: m/z=417.1 [M+H]$^+$.

2) Preparation of Compound 70-1

Compound 70-1 was obtained by reference to the preparation method for compound 7-1 in step 6) of Example 7, with compound 7-k being replaced by compound 70-k.

Compound 70-1: $^1$H NMR (500 MHz, DMSO-d6), δ: 11.73 (s, 1H), 11.69 (s, 1H), 8.64 (m, 1H), 8.58 (d, 1H), 8.05 (d, 1H), 7.89 (s, 1H), 7.83 (m, 1H), 7.71 (d, 1H), 7.54 (m, 3H), 7.40 (d, 1H), 7.18 (d, 1H), 6.76 (m, 1H), 6.39 (m, 1H), 6.30 (d, 1H), 4.26 (m, 2H), 3.64 (m, 6H), 3.54 (m, 2H), 3.49 (m, 2H), 3.39 (m, 4H), 3.05 (m, 4H), 2.79 (m, 2H), 2.27 (m, 1H), 2.21 (m, 1H), 2.09 (s, 1H), 1.96 (s, 2H), 1.62 (m, 2H), 1.50 (m, 2H), 1.37 (m, 2H), 1.24 (s, 1H), 0.97 (s, 6H).

ESI-MS: m/z=1037.2 [M+H]$^+$.

Example 71

4-(4-{[2-(2-chloro-4-trifluoromethylphenyl)-4,4-dimethylcyclohex-1-enyl]methyl}-piperazin-1-yl)-N-({3-nitro-4-[(3-(4-(2-methylsulfonyl)morpholin-2-yl)propyl)amino]phenyl}sulfonyl)-2-(1H-pyrrolo[2,3-b]pyridin-5-yloxy)-benzamide

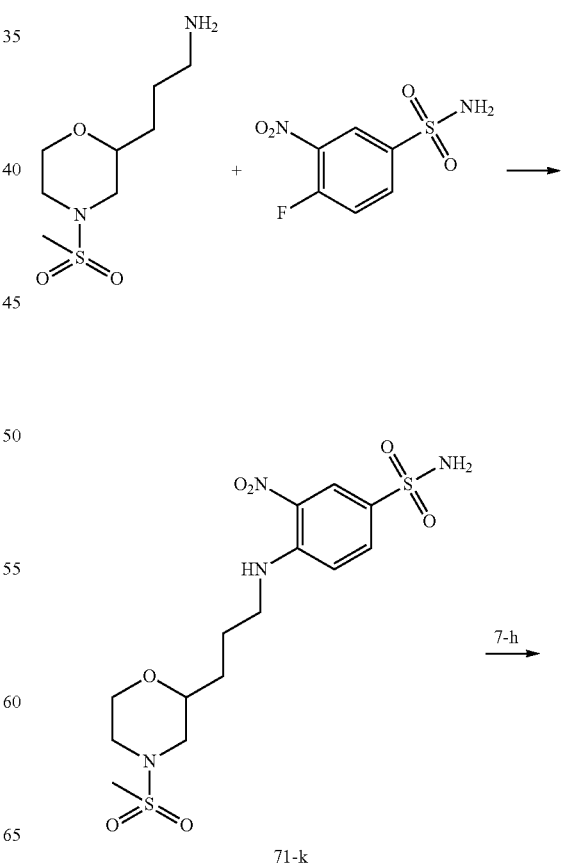

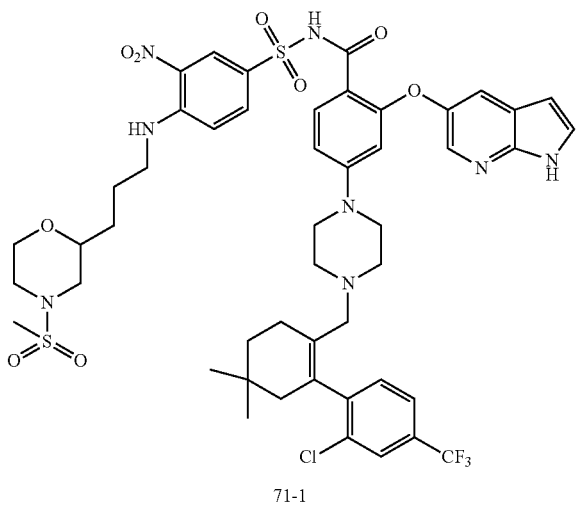

71-1

1) Preparation of Compound 71-k 3-nitro-4-fluorobenzenesulfonamide (1.13 g), 2-aminopropyl-3-(4-(2-methylsulfonyl))morpholine (1.36 g) and N,N-diisopropylethylamine (4.59 g) were dissolved in acetonitrile (10 mL), and the solution was heated to 85° C. and reacted for 6 h. The reaction solution was cooled at room temperature, left to stand overnight, concentrated and dried to give compound 71-k (1.51 g). ESI-MS: m/z=423.0 [M+H]$^+$.

2) Preparation of Compound 71-1

Compound 71-1 was obtained by reference to the preparation method for compound 7-1 in step 6) of Example 7, with compound 7-k being replaced by compound 71-k.

Compound 71-1: $^1$H NMR (500 MHz, DMSO-d6), δ: 11.72 (s, 2H), 8.62 (s, 1H), 8.57 (m, 1H), 8.05 (s, 1H), 7.89 (d, 1H), 7.83 (m, 1H), 7.70 (d, 1H), 7.54 (m, 3H), 7.39 (m, 1H), 7.07 (d, 1H), 6.75 (d, 1H), 6.40 (s, 1H), 6.30 (s, 1H), 3.92 (m, 1H), 3.78 (m, 2H), 3.53 (m, 4H), 3.35 (m, 7H), 2.89 (m, 7H), 2.55 (m, 1H), 2.21 (m, 2H), 1.96 (m, 2H), 1.70 (m, 2H), 1.52 (m, 4H), 0.97 (s, 6H).

$^{13}$C NMR (125 MHz, DMSO-d6), δ: 164.0, 158.9, 154.0, 147.7, 145.9, 144.2, 136.0, 134.3, 132.9, 132.6, 131.8, 130.2, 130.0, 128.4, 127.0, 125.0, 124.7, 122.8, 120.3, 118.3, 115.4, 114.2, 109.7, 103.6, 100.4, 74.7, 65.9, 58.5, 50.1, 45.1, 44.3, 42.8, 34.6, 29.3, 27.2, 24.8. ESI-MS: m/z=1043.2 [M+H]$^+$.

Example 72

4-(4-{[2-(2-chloro-4-trifluoromethylphenyl)-4,4-dimethylcyclohex-1-enyl]methyl}-piperazin-1-yl)-N-({3-nitro-4-[(2-(4-(2-methoxyacetyl)morpholin-2-yl)ethyl)amino]phenyl}sulfonyl)-2-(1H-pyrrolo[2,3-b]pyridin-5-yloxy)-benzamide

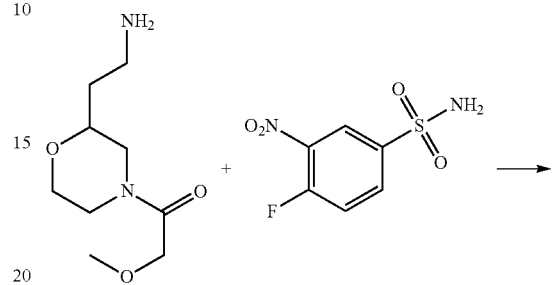

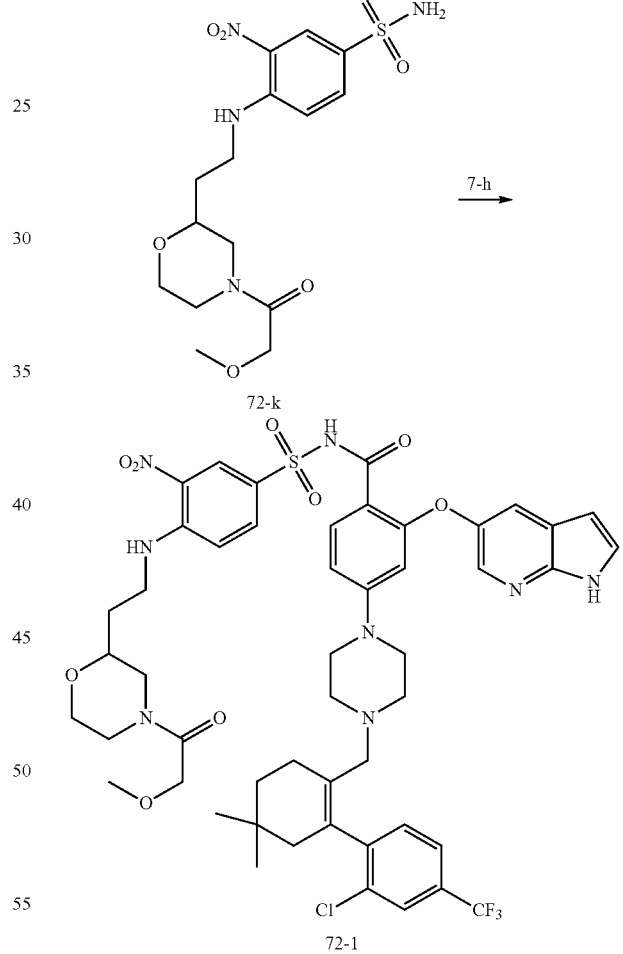

72-1

1) Preparation of Compound 72-k 3-nitro-4-fluorobenzenesulfonamide (1.20 g), 2-aminoethyl-2-(4-(2-methoxyacetyl))morpholine (1.33 g) and N,N-diisopropylethylamine (4.59 g) were dissolved in acetonitrile (10 mL), and the solution was heated to 85° C. and reacted for 6 h. The reaction solution was cooled at room temperature, left to stand overnight, concentrated and dried to give compound 72-k (1.56 g). ESI-MS: m/z=403.0 [M+H]$^+$.

2) Preparation of Compound 72-1

Compound 72-1 was obtained by reference to the preparation method for compound 7-1 in step 6) of Example 7, with compound 7-k being replaced by compound 72-k.

Compound 72-1: $^1$H NMR (500 MHz, DMSO-d6), δ: 11.72 (s, 2H), 8.64 (m, 1H), 8.58 (d, 1H), 8.04 (d, 1H), 7.88 (s, 1H), 7.84 (m, 1H), 7.70 (d, 1H), 7.55 (m, 3H), 7.39 (d, 1H), 7.16 (d, 1H), 6.76 (m, 1H), 6.39 (m, 1H), 6.29 (d, 1H), 3.89 (m, 2H), 3.70 (m, 6H), 3.55 (m, 2H), 3.51 (m, 2H), 3.40 (m, 4H), 3.04 (m, 4H), 2.79 (m, 2H), 2.28 (m, 1H), 2.21 (m, 1H), 2.11 (s, 1H), 1.96 (s, 2H), 1.62 (m, 2H), 1.35 (m, 2H), 1.24 (s, 1H), 0.97 (s, 6H). ESI-MS: m/z=1023.3 [M+H]$^+$.

Example 73

4-(4-{[2-(2-chloro-4-trifluoromethylphenyl)-4,4-dimethylcyclohex-1-enyl]methyl}-piperazin-1-yl)-N-({3-nitro-4-[((1-(2-methoxyacetyl)piperidin-4-yl)methyl)amino]phenyl}sulfonyl)-2-(1H-pyrrolo[2,3-b]pyridin-5-yloxy)-benzamide

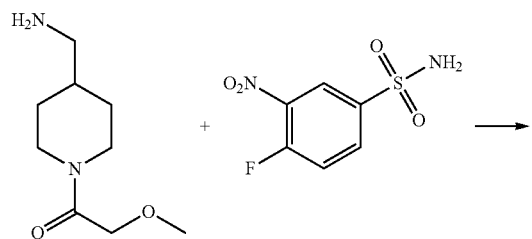

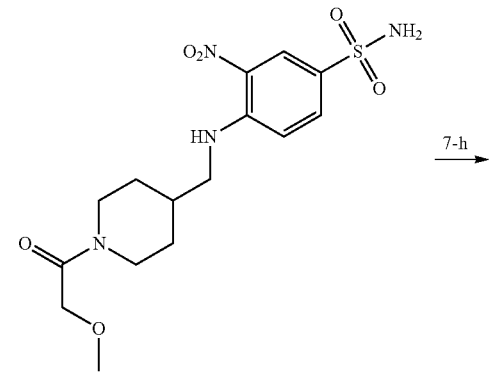

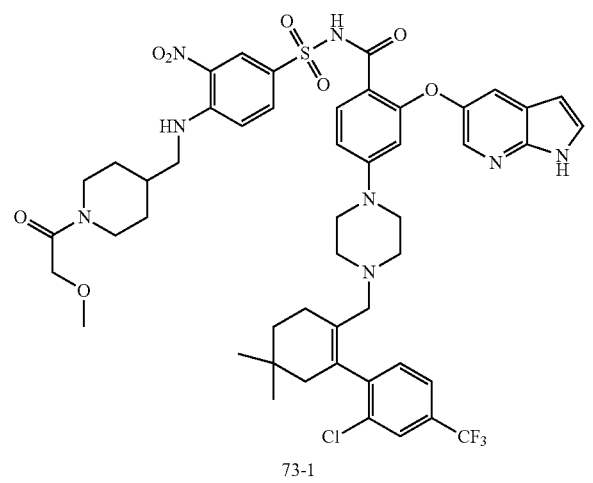

1) Preparation of Compound 73-k 3-nitro-4-fluorobenzenesulfonamide (1.56 g), 4-aminomethyl-1-(2-methoxyacetyl)piperidine (1.59 g) and N,N-diisopropylethylamine (2.30 g) were dissolved in acetonitrile (10 mL), and the solution was heated to 85° C. and reacted for 6 h. The reaction solution was cooled at room temperature, left to stand overnight, concentrated and dried to give compound 73-k (2.58 g). ESI-MS: m/z=387.0 [M+H]$^+$.

2) Preparation of Compound 73-1

Compound 73-1 was obtained by reference to the preparation method for compound 7-1 in step 6) of Example 7, with compound 7-k being replaced by compound 73-k.

Compound 73-1: $^1$H NMR (500 MHz, DMSO-d6), δ: 11.74 (s, 1H), 11.69 (s, 1H), 8.64 (s, 1H), 8.58 (m, 1H), 8.05 (s, 1H), 7.89 (d, 1H), 7.82 (m, 1H), 7.70 (d, 1H), 7.54 (m, 3H), 7.39 (m, 1H), 7.14 (d, 1H), 6.75 (d, 1H), 6.40 (s, 1H), 6.30 (s, 1H), 4.08 (m, 2H), 3.76 (m, 3H), 3.58 (m, 1H), 3.31 (m, 6H), 2.93 (m, 4H), 2.54 (m, 2H), 2.27 (m, 2H), 1.96 (m, 4H), 1.74 (m, 2H), 1.50 (m, 2H), 1.24 (m, 4H), 0.97 (s, 6H).

$^{13}$C NMR (125 MHz, DMSO-d6), δ: 164.0, 158.9, 154.0, 147.9, 146.9, 145.8, 144.2, 139.0, 135.5, 134.3, 132.8, 132.6, 131.7, 130.2, 130.1, 128.3, 127.0, 124.8, 120.4, 118.5, 117.2, 115.8, 114.9, 109.7, 103.6, 100.5, 71.2, 58.7, 48.0, 45.2, 44.4, 41.3, 35.3, 30.3, 29.6, 27.4. ESI-MS: m/z=1007.3 [M+H]$^+$.

Example 74

4-(4-{[2-(2-chloro-4-trifluoromethylphenyl)-4,4-dimethylcyclohex-1-enyl]methyl}-piperazin-1-yl)-N-({3-nitro-4-[((4-(ethoxyformyl)morpholin-2-yl)methyl)amino]phenyl}sulfon yl)-2-(1H-pyrrolo[2,3-b]pyridin-5-yloxy)-benzamide (Compound 74-1)

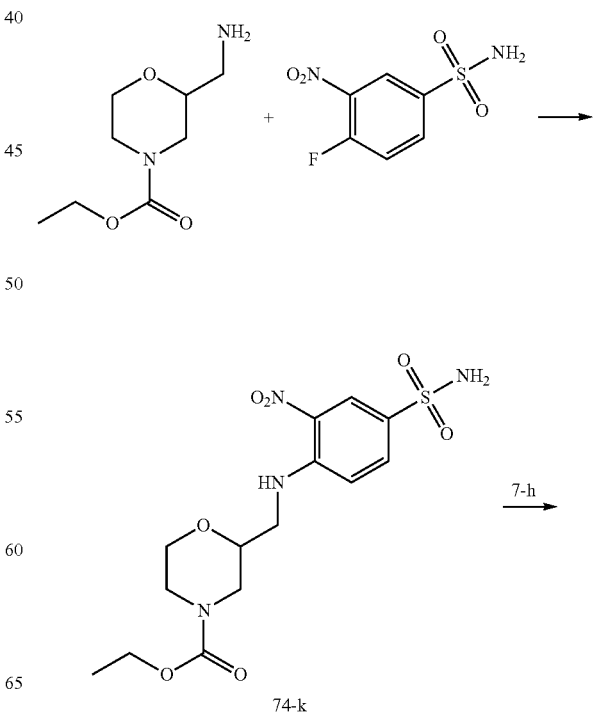

185

-continued 74-1

1) Preparation of Compound 74-k 3-nitro-4-fluorobenzenesulfonamide (1.20 g), 2-aminomethyl-4-(ethoxyformyl)morpholine (1.23 g) and N,N-diisopropylethylamine (4.59 g) were dissolved in acetonitrile (10 mL), and the solution was heated to 85° C. and reacted for 6 h. The reaction solution was cooled at room temperature, left to stand overnight, concentrated and dried to give compound 74-k (1.80 g). ESI-MS: m/z=387.1 [M−H]−.

2) Preparation of Compound 74-1

Compound 74-1 was obtained by reference to the preparation method for compound 7-1 in step 6) of Example 7, with compound 7-k being replaced by compound 74-k.

Compound 74-1: $^1$H NMR (500 MHz, DMSO-d6), δ: 11.70 (s, 2H), 8.64 (s, 1H), 8.57 (m, 1H), 8.04 (s, 1H), 7.88 (d, 1H), 7.83 (m, 1H), 7.70 (d, 1H), 7.53 (m, 3H), 7.39 (m, 1H), 7.15 (d, 1H), 6.75 (d, 1H), 6.40 (s, 1H), 6.30 (s, 1H), 4.08 (m, 2H), 3.89 (m, 3H), 3.65 (m, 2H), 3.51 (m, 7H), 2.96 (m, 3H), 2.79 (m, 2H), 2.21 (m, 2H), 2.02 (m, 1H), 1.95 (m, 2H), 1.50 (m, 2H), 1.23 (m, 1H), 1.18 (m, 3H), 0.97 (s, 6H).

$^{13}$C NMR (125 MHz, DMSO-d6), δ: 162.4, 156.0, 153.6, 152.5, 146.3, 145.3, 144.3, 142.8, 134.0, 132.7, 131.3, 131.0, 130.2, 128.6, 126.7, 126.6, 125.4, 123.6, 123.3, 118.7, 116.7, 114.2, 108.1, 101.9, 98.8, 72.1, 64.5, 59.8, 56.9, 43.5, 42.8, 33.1, 27.5, 25.6, 23.3. ESI-MS: m/z=1009.3 [M+H]+.

Example 75

4-(4-{[2-(2-chloro-4-trifluoromethylphenyl)-4,4-dimethylcyclohex-1-enyl]methyl}-piperazin-1-yl)-N-({3-nitro-4-[((4-(methoxyformyl)morpholin-2-yl)methyl)amino]phenyl}sulfonyl)-2-(1H-pyrrolo[2,3-b]pyridin-5-yloxy)-benzamide (Compound 75-1)

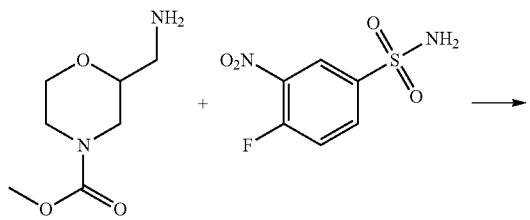

186

-continued 75-k

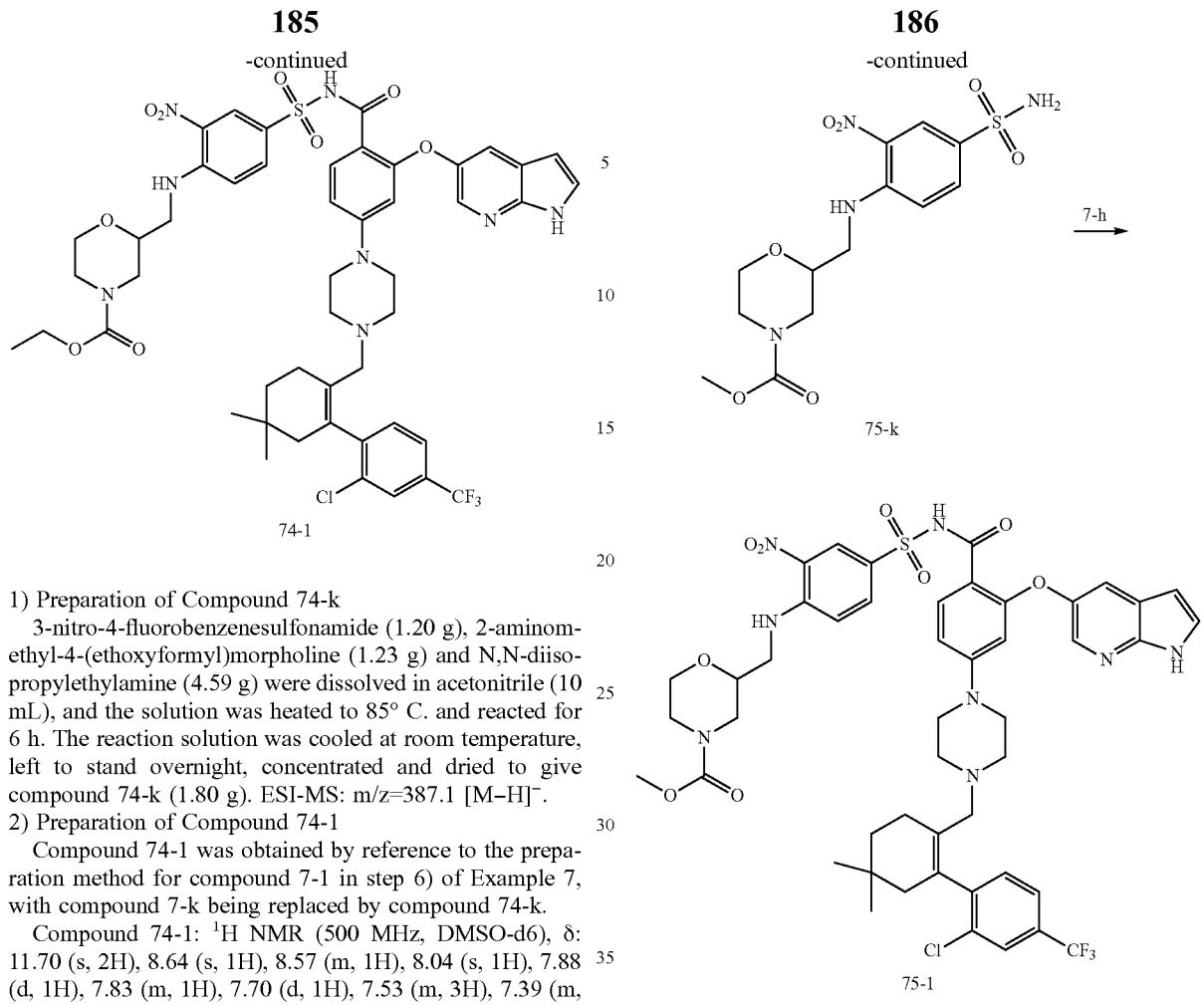

75-1

1) Preparation of Compound 75-k 3-nitro-4-fluorobenzenesulfonamide (1.20 g), 2-aminomethyl-4-(methoxyformyl)morpholine (1.14 g) and N,N-diisopropylethylamine (4.59 g) were dissolved in acetonitrile (10 mL), and the solution was heated to 85° C. and reacted for 6 h. The reaction solution was cooled at room temperature, left to stand overnight, concentrated and dried to give compound 75-k (1.73 g). ESI-MS: m/z=373.1 [M−H]+.

2) Preparation of Compound 75-1

Compound 75-1 was obtained by reference to the preparation method for compound 7-1 in step 6) of Example 7, with compound 7-k being replaced by compound 75-k.

Compound 75-1: $^1$H NMR (500 MHz, DMSO-d6), δ: 11.71 (s, 1H), 11.68 (s, 1H), 8.64 (m, 1H), 8.58 (d, 1H), 8.05 (d, 1H), 7.88 (s, 1H), 7.83 (m, 1H), 7.71 (d, 1H), 7.55 (m, 3H), 7.40 (d, 1H), 7.16 (d, 1H), 6.76 (m, 1H), 6.40 (m, 1H), 6.30 (d, 1H), 3.93 (m, 2H), 3.76 (m, 8H), 3.49 (m, 4H), 3.02 (m, 4H), 2.79 (m, 2H), 2.28 (m, 2H), 2.08 (s, 1H), 1.96 (s, 2H), 1.51 (m, 2H), 1.24 (s, 1H), 0.97 (s, 6H).

$^{13}$C NMR (125 MHz, DMSO-d6), δ: 162.4, 157.6, 157.3, 157.0, 156.6, 154.0, 152.4, 146.3, 145.3, 144.3, 142.6, 137.4, 133.9, 132.7, 131.2, 131.0, 130.1, 128.6, 126.7, 126.6, 123.6, 123.4, 122.8, 118.7, 116.7, 115.9, 114.2, 113.6, 112.6, 108.1, 102.0, 98.8, 72.1, 64.5, 56.9, 51.3, 43.6, 43.4, 42.7, 33.0, 27.7, 27.5, 25.5, 23.2.

ESI-MS: m/z=995.3 [M+H]+.

Example 76-Example 82

The following compounds were obtained by reference to the preparation procedure of Example 7:

| Number | Structure | Characterization |
|---|---|---|
| 76-1 | 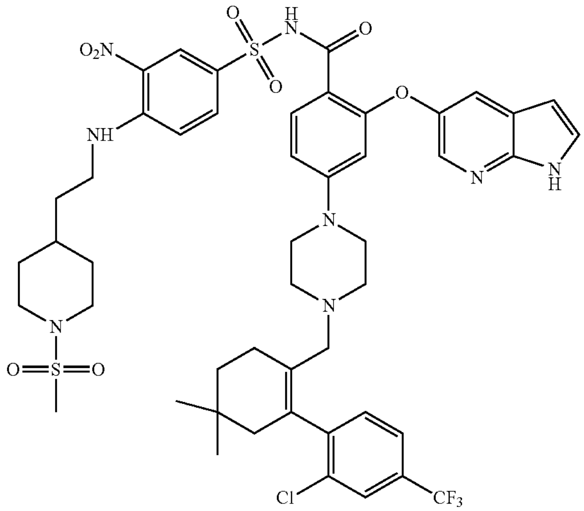 [SMILES: CC1(C)CCC(CN2CCN(c3ccc(C(=O)NS(=O)(=O)c4ccc(NCCC5CCN(S(C)(=O)=O)CC5)c([N+](=O)[O-])c4)c(Oc4cnc5[nH]ccc5c4)c3)CC2)=C(c2ccc(C(F)(F)F)cc2Cl)C1] | $^1$H NMR(500 MHz, DMSO-d6), δ: 11.62 (s, 1H), 11.58 (s, 1H), 8.45 (s, 1H), 8.37 (t, 1H), 8.17 (s, 1H), 7.96 (s, 1H), 7.82 (s, 1H), 7.70 (d, 1H), 7.65 (d, 1H), 7.55 (d, 1H), 7.36 (s, 1H), 7.33 (d, 1H), 6.87 (d, 1H), 6.64 (d, 1H), 6.33 (s, 1H), 6.23 (s, 1H), 3.31 (m, 4H), 3.01 (m, 6H), 2.87 (s, 1H), 2.81 (t, 1H), 2.66 (m, 3H), 2.54 (s, 1H), 1.90 (d, 2H), 1.81 (d, 2H), 1.59 (m, 2H), 1.43 (m, 2H), 1.27 (m, 8H), 0.97 (s, 6H). ESI-MS: m/z = 1027.3 [M + H]$^+$. |
| 77-1 | 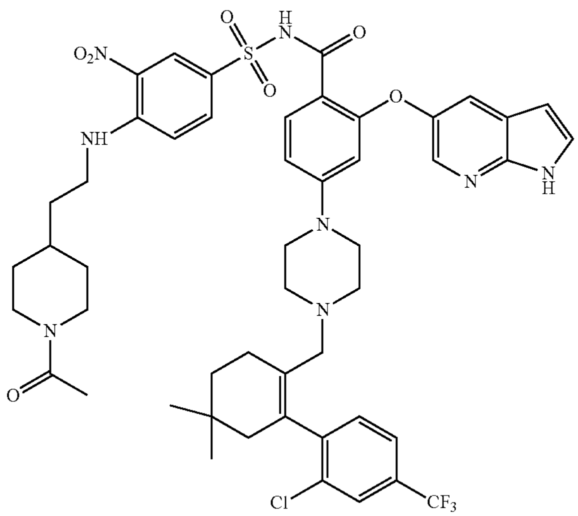 [SMILES: CC(=O)N1CCC(CCNc2ccc(S(=O)(=O)NC(=O)c3ccc(N4CCN(CC5=C(c6ccc(C(F)(F)F)cc6Cl)CC(C)(C)CC5)CC4)cc3Oc3cnc4[nH]ccc4c3)cc2[N+](=O)[O-])CC1] | $^1$H NMR(500 MHz, DMSO-d6), δ: 11.61 (s, 1H), 11.57 (s, 1H), 8.45 (s, 1H), 8.37 (t, 1H), 8.17 (s, 1H), 7.97 (s, 1H), 7.82 (s, 1H), 7.71 (d, 1H), 7.66 (d, 1H), 7.54 (d, 1H), 7.36 (s, 1H), 7.33 (d, 1H), 6.86 (d, 1H), 6.65 (d, 1H), 6.32 (s, 1H), 6.23 (s, 1H), 3.31 (m, 3H), 3.01 (m, 6H), 2.81 (t, 1H), 2.66 (m, 3H), 2.54 (s, 1H), 2.10 (s, 3H), 1.90 (d, 2H), 1.81 (d, 2H), 1.59 (m, 2H), 1.43 (m, 2H), 1.27 (m, 7H), 0.97 (s, 6H). ESI-MS: m/z = 991.4 [M + H]$^+$. |
| 78-1 | 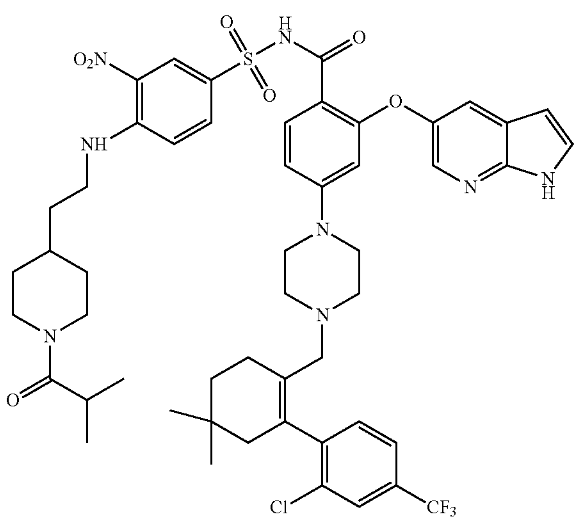 [SMILES: CC(C)C(=O)N1CCC(CCNc2ccc(S(=O)(=O)NC(=O)c3ccc(N4CCN(CC5=C(c6ccc(C(F)(F)F)cc6Cl)CC(C)(C)CC5)CC4)cc3Oc3cnc4[nH]ccc4c3)cc2[N+](=O)[O-])CC1] | $^1$H NMR(500 MHz, DMSO-d6), δ: 11.62 (s, 1H), 11.56 (s, 1H), 8.44 (s, 1H), 8.36 (t, 1H), 8.18 (s, 1H), 7.98 (s, 1H), 7.83 (s, 1H), 7.71 (d, 1H), 7.67 (d, 1H), 7.55 (d, 1H), 7.36 (s, 1H), 7.33 (d, 1H), 6.87 (d, 1H), 6.66 (d, 1H), 6.33 (s, 1H), 6.23 (s, 1H), 3.54 (m, 4H), 3.30 (m, 6H), 2.69 (t, 1H), 2.66 (m, 3H), 2.54 (s, 1H), 1.96 (m, 1H), 1.84 (d, 2H), 1.74 (d, 2H), 1.59 (m, 2H), 1.45 (m, 6H), 1.27 (m, 2H), 1.10 (s, 6H), 0.97 (s, 6H). ESI-MS: m/z = 1019.4 [M + H]$^+$. |

| Number | Structure | Characterization |
|---|---|---|
| 79-1 | 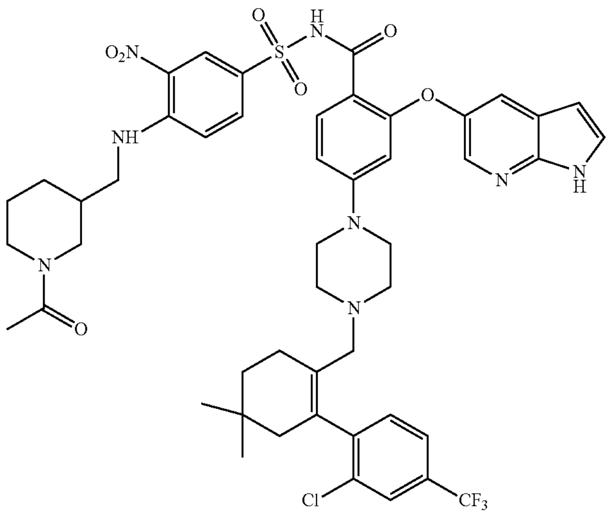 [SMILES: CC(=O)N1CCCC(CNc2ccc(S(=O)(=O)NC(=O)c3ccc(N4CCN(CC5=C(c6ccc(C(F)(F)F)cc6Cl)CC(C)(C)CC5)CC4)cc3Oc3cnc4[nH]ccc4c3)cc2[N+](=O)[O-])C1] | ¹H NMR(500 MHz, DMSO-d6), δ: 11.61 (s, 1H), 11.57 (s, 1H), 8.45 (s, 1H), 8.37 (t, 1H), 8.17 (s, 1H), 7.97 (s, 1H), 7.82 (s, 1H), 7.71 (d, 1H), 7.66 (d, 1H), 7.54 (d, 1H), 7.36 (s, 1H), 7.33 (d, 1H), 6.86 (d, 1H), 6.65 (d, 1H), 6.32 (s, 1H), 6.23 (s, 1H), 3.40 (m, 2H), 2.86 (m, 4H), 2.81 (t, 1H), 2.66 (m, 4H), 2.54 (s, 1H), 2.10 (s, 3H), 1.90 (d, 2H), 1.81 (d, 2H), 1.59 (m, 3H), 1.43 (m, 3H), 1.27 (m, 5H), 0.97 (s, 6H).<br>ESI-MS: m/z = 977.3 [M + H]⁺. |
| 80-1 | 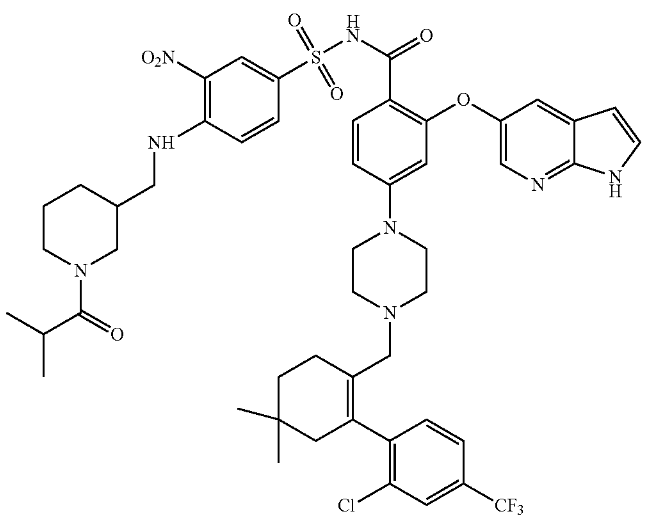 [SMILES: CC(C)C(=O)N1CCCC(CNc2ccc(S(=O)(=O)NC(=O)c3ccc(N4CCN(CC5=C(c6ccc(C(F)(F)F)cc6Cl)CC(C)(C)CC5)CC4)cc3Oc3cnc4[nH]ccc4c3)cc2[N+](=O)[O-])C1] | ¹H NMR(500 MHz, DMSO-d6), δ: 11.63 (s, 1H), 11.57 (s, 1H), 8.44 (s, 1H), 8.36 (t, 1H), 8.16 (s, 1H), 7.98 (s, 1H), 7.83 (s, 1H), 7.70 (d, 1H), 7.67 (d, 1H), 7.55 (d, 1H), 7.36 (s, 1H), 7.33 (d, 1H), 6.87 (d, 1H), 6.66 (d, 1H), 6.33 (s, 1H), 6.23 (s, 1H), 3.54 (m, 4H), 3.30 (m, 6H), 2.69 (t, 1H), 2.66 (m, 3H), 2.54 (s, 1H), 1.96 (m, 1H), 1.84 (d, 2H), 1.74 (d, 2H), 1.59 (m, 2H), 1.45 (m, 4H), 1.27 (m, 2H), 1.10 (s, 6H), 0.97 (s, 6H).<br>ESI-MS: m/z = 1005.4 [M + H]⁺. |
| 81-1 | 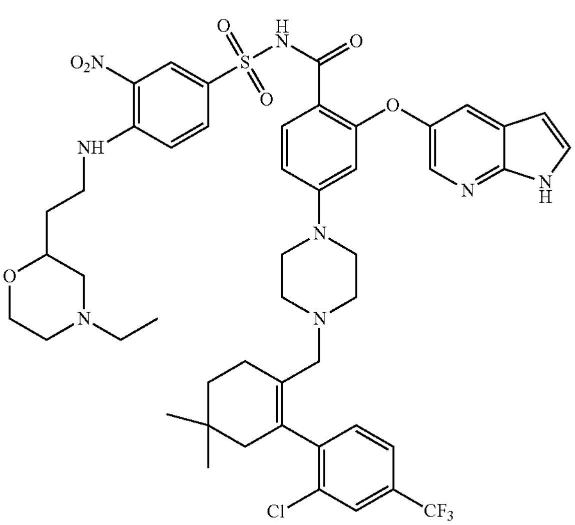 [SMILES: CCN1CCOC(CCNc2ccc(S(=O)(=O)NC(=O)c3ccc(N4CCN(CC5=C(c6ccc(C(F)(F)F)cc6Cl)CC(C)(C)CC5)CC4)cc3Oc3cnc4[nH]ccc4c3)cc2[N+](=O)[O-])C1] | ¹H NMR (500 MHz, DMSO-d6), δ: 11.72 (s, 2H), 8.64 (m, 1H), 8.58 (d, 1H), 8.04 (d, 1H), 7.88 (s, 1H), 7.84 (m, 1H), 7.70 (d, 1H), 7.55 (m, 3H), 7.39 (d, 1H), 7.16 (d, 1H), 6.76 (m, 1H), 6.39 (m, 1H), 6.29 (d, 1H), 3.89 (m, 2H), 3.70 (m, 4H), 3.55 (m, 3H), 3.51 (m, 2H), 3.40 (m, 4H), 3.04 (m, 4H), 2.79 (m, 2H), 2.28 (m, 1H), 2.21 (m, 1H), 1.96 (s, 2H), 1.62 (m, 2H), 1.35 (m, 2H), 1.15 (s, 3H), 0.97 (s, 6H).<br>ESI-MS: m/z = 979.4 [M + H]⁺. |

| Number | Structure | Characterization |
|---|---|---|
| 82-1 | (structure) | $^1$H NMR (500 MHz, DMSO-d6), δ: 11.71 (s, 2H), 8.65 (m, 1H), 8.59 (d, 1H), 8.04 (d, 1H), 7.88 (s, 1H), 7.85 (m, 1H), 7.71 (d, 1H), 7.56 (m, 3H), 7.40 (d, 1H), 7.16 (d, 1H), 6.76 (m, 1H), 6.40 (m, 1H), 6.30 (d, 1H), 3.89 (m, 2H), 3.70 (m, 4H), 3.57 (m, 3H), 3.51 (m, 2H), 3.38 (m, 4H), 3.04 (m, 2H), 2.32 (s, 3H), 2.27 (m, 1H), 2.20 (m, 1H), 1.96 (s, 2H), 1.62 (m, 2H), 1.35 (m, 2H), 0.97 (s, 6H). ESI-MS: m/z = 979.3 [M + H]$^+$. |

Experimental Example 1: Inhibitory Activity for In Vitro Protein Binding 1.1 Screening on Inhibitory Activity for BCL-2/BAK Binding 500 nM Tag1-BCL-2 protein stock solution and 20 μM Tag2-BAK protein stock solution were diluted to 5 nM and 120 nM respectively with dilution buffer in kit (model: BCL-2/BAK (BH3) BINDING ASSAY KITS, from Cisbio). 5 μL of Tag1-BCL-2 protein diluent was added to each well, then different compounds dissolved with DMSO were added to the wells with a nanoliter pipettor, allowing the final compound concentrations to be 200 nM to 0.0488 nM (4-fold gradient for 7 concentrations in total). Blank control wells (without enzyme) and negative control wells (with enzyme, plus vehicle DMSO) were set, and 2 replicate wells were set. Finally, 5 μL of Tag2-BAK protein diluent was added to each well, and the mixture was mixed well by centrifugation and incubated at 25° C. for 15 min. 100× anti-Tag1-Eu$^{3+}$ and 100× anti-Tag2-XL665 were both diluted to 1× working concentration with the detection buffer in the kit. Anti-Tag1-Eu$^{3+}$ and anti-Tag2-XL665 were mixed well in a 1:1 ratio, and the mixture was added to wells at 5 μL/well, and incubated at 25° C. for 2 h or more. The plate was read using a PE Envision multi-functional microplate reader (excitation: 620 nm, emission: 665 nm) and IC$_{50}$ (shown in table 1) was calculated by four-parameter fitting.

1.2 Screening on Inhibitory Activity for BCL-XL/BAK Binding 300 nM Tag1-BCL-XL protein stock solution and 10 μM Tag2-BAK protein stock solution were diluted to 2 nM and 80 nM respectively with dilution buffer in kit (model: BCL-XL/BAK (BH3) BINDING ASSAY KITS, from Cisbio). 5 μL of Tag1-BCL-XL protein diluent was added to each well, then different compounds dissolved with DMSO were added to the wells with a nanoliter pipettor, allowing the final compound concentrations to be 2000 nM to 0.488 nM (4-fold gradient for 7 concentrations in total). Blank control wells (without enzyme) and negative control wells (with enzyme, plus vehicle DMSO) were set, and 2 replicate wells were set. Finally, 5 μL of Tag2-BAK protein diluent was added to each well, and the mixture was mixed well by centrifugation and incubated at 25° C. for 15 min 100× anti-Tag1-Eu$^{3+}$ and 100× anti-Tag2-XL665 were both diluted to 1× working concentration with the detection buffer in the kit. Anti-Tag1-Eu$^{3+}$ and anti-Tag2-XL665 were mixed well in a 1:1 ratio, and the mixture was added to wells at 5 μL/well, and incubated at 25° C. for 2 h or more. The plate was read using a PE Envision multi-functional microplate reader (excitation: 620 nm, emission: 665 nm) and IC$_{50}$ (shown in table 1) was calculated by four-parameter fitting.

TABLE 1

Inhibitory activity of compounds for BCL-2/BAK and BCL-XL/BAK bindings

| Compound | BCL-2/BAK IC$_{50}$(nM) | BCL-XL/BAK IC$_{50}$(nM) |
|---|---|---|
| 1-1 | 2.7 | 133 |
| 3-1 | 0.86 | >2000 |
| 4-1 | 0.80 | >2000 |
| 6-1 | 5.7 | 1972 |
| 7-1 | 3.5 | 289 |
| 8-1 | 2.8 | 155 |
| 9-1 | 1.8 | |
| 10-1 | 2.8 | 194 |
| 11-1 | 1.6 | 140 |
| 12-1 | 1.4 | 113 |
| 13-1 | 3.6 | 387 |
| 14-1 | 5.1 | 338 |
| 15-1 | 3.83 | 729 |
| 16-1 | 3.09 | 653 |
| 17-1 | 2.0 | |
| 18-1 | 2.7 | |
| 19-1 | 2.5 | |
| 20-1 | 2.1 | |
| 21-1 | 2.40 | |
| 23-1 | 5.10 | 302 |
| 24-1 | 5.11 | 556 |
| 28-1 | 3.7 | 266 |
| 29-1 | 2.1 | |
| 31-1 | 4.6 | 485 |
| 35-1 | 1.61 | 232.5 |
| 36-1 | 1.78 | 157.4 |
| 37-1 | 1.59 | 142.1 |
| 38-1 | 2.81 | 187 |
| 42-1 | 2.81 | 220.3 |

TABLE 1-continued

Inhibitory activity of compounds for
BCL-2/BAK and BCL-XL/BAK bindings

| Compound | BCL-2/BAK IC$_{50}$(nM) | BCL-XL/BAK |
|---|---|---|
| 43-1 | 1.8 | 121 |
| 45-1 | 2.18 | 242.7 |
| 48-1 | 1.4 | 118 |
| 50-1 | 2.59 | 211.1 |
| 51-1 | 1.9 | |
| 52-1 | 3.9 | 175 |
| 56-1 | 3.55 | 381 |
| 57-1 | 3.4 | 268 |
| 58-1 | 2.35 | 145.2 |
| 59-1 | 1.1 | |
| 60-1 | 1.1 | |
| 61-1 | 1.52 | |
| 62-1 | 2.35 | 144.9 |
| 63-1 | 2.3 | 217 |
| 65-1 | 1.5 | 134 |
| 66-1 | 2.6 | 273 |
| 67-1 | 0.6 | 199 |
| 71-1 | 0.76 | 109 |
| 72-1 | 2.32 | 121.6 |
| 73-1 | 1.6 | 204 |
| 74-1 | 1.66 | 252.3 |
| 75-1 | 3.5 | 322 |

Experimental Example 2: Inhibitory Effect of Compounds on Proliferation of RS4;11 Cells RS4;11 cells (from Nanjing Cobioer) in logarithmic growth phase and good cell condition were added to a centrifuge tube and centrifuged at 1500 rpm for 3 min in a low speed centrifuge. The supernatant was discarded, and 5 mL of complete medium (RPMI basic medium+10 wt % fetal bovine serum (FBS)) was added using a pipette for cell resuspension. The cells were counted using a cell counter, diluted with complete medium to a cell density of 2×10$^5$ cells/mL, and added with an equivalent amount of RPMI basic medium to adjust the serum concentration to 5% and the cell density to 1×10$^5$ cells/mL for plate seeding. The cells were seeded on a 96-well plate at 100 μL/well using a pipettor, and incubated in an incubator at 37° C., 5% CO$_2$ with saturated humidity. After 24 h of incubation, compounds were loaded using a nanoliter pipettor, 2 duplicate wells were set for each concentration, and cells without compound were used as negative controls. After 72 h, CCK-8 reagent was added at 10 μL/well for incubation for 4 h, then absorbance was measured at 450 nm with an Envision plate reader, and inhibition rate was calculated. Inhibition rate (%)=(mean value of negative control group−mean value of experimental group)/(mean value of negative control group−mean value of blank group)×100%. A dose-response curve was fitted by four-parameter analysis, with the logarithm of compound concentration serving as abscissa and inhibition rate serving as ordinate, so that IC$_{50}$ was calculated (FIG. 2).

TABLE 2

Inhibitory effect of compounds on proliferation of RS4;11 cells

| Compound | RS4;11 cells IC$_{50}$(nM) |
|---|---|
| 1-1 | 2.3 |
| 6-1 | 2.4 |
| 7-1 | 4.6 |
| 8-1 | 2.5 |
| 9-1 | 2.7 |
| 10-1 | 5.6 |
| 11-1 | 2.5 |
| 12-1 | 1.7 |
| 13-1 | 8.1 |
| 14-1 | 8.6 |
| 15-1 | 7.2 |
| 16-1 | 7.8 |
| 17-1 | 2.9 |
| 18-1 | 4.3 |
| 19-1 | 3.5 |
| 20-1 | 3.9 |
| 21-1 | 4.1 |
| 23-1 | 10 |
| 28-1 | 3.0 |
| 29-1 | 1.3 |
| 74-1 | 6.9 |
| 75-1 | 3.9 |
| 31-1 | 3.0 |
| 35-1 | 9.6 |
| 38-1 | 6.6 |
| 42-1 | 6.8 |
| 43-1 | 1.9 |
| 48-1 | 1.4 |
| 50-1 | 4.3 |
| 51-1 | 1.1 |
| 52-1 | 0.9 |
| 57-1 | 2.3 |
| 58-1 | 5.3 |
| 59-1 | 1.0 |
| 60-1 | 1.3 |
| 61-1 | 3.2 |
| 62-1 | 4.1 |
| 63-1 | 1.4 |
| 65-1 | 1.8 |
| 66-1 | 3.3 |
| 67-1 | 0.8 |
| 71-1 | 6.1 |
| 73-1 | 1.5 |

Experimental Example 3: In Vitro Stability in Liver Microsome

300 μL of the final incubation system contains 30 μL of liver microsomes (protein concentration: 5 mg/mL), 30 μL of NADPH+MgCl$_2$, 3 μL of the test compound (in acetonitrile), and 237 μL of PBS buffer (pH 7.4), wherein the proportion of the organic solvent (acetonitrile) is 1% (volume ratio). Two duplicate samples were prepared for each specie (mouse, rat and human), and each sample was 0.3 mL. Each tube which was added with 270 μL of a mixed solution of substrate and enzyme, and NADPH, after being pre-incubated at 37° C. for 5 min, was added with 30 μL of NADPH+MgCl$_2$ and mixed. Then 50 μL of the mixture was taken at 0 min, 15 min, 30 min and 60 min, and added with 300 μL of glacial acetonitrile containing an internal standard to terminate the reaction. 50 μL of the incubated sample was added with 300 μL of glacial acetonitrile containing an internal standard (20 ng/mL diazepam) for precipitation, vortexed for 5 min, and centrifuged (13,000 rpm, 20° C.) for 10 min. 70 μL of supernatant was taken and diluted with 70 μL of ultrapure water. After being mixed well, 1 μL of the resulting sample was injected for analysis. The parameters for the elimination of compounds in liver microsomes of humans, rats and mice are shown in Table 3.

TABLE 3

In vitro metabolic stability of compounds in liver microsomes (1 μM)

| Compound number | Mouse Residual content after 60 min (%) | Rat Residual content after 60 min (%) | Human Residual content after 60 min (%) |
|---|---|---|---|
| 1-1 | 78.9% | 88.4% | 70.8% |
| 6-1 | 65.3% | 61.2% | 65.9% |
| 8-1 | 73.9% | 90.9% | 86.3% |
| 9-1 | 55.7% | 101.7% | 69.8% |
| 10-1 | 30.1% | 69.9% | 78.0% |
| 11-1 | 62.9% | 66.3% | 67.4% |
| 12-1 | 93.4% | 80.2% | 91.3% |

Experimental Example 4: In Vivo Pharmacokinetics 4.1 Pharmacokinetics in Rats

SD rats weighing 180-220 g were randomly grouped with 3 rats in each group after 3-5 days of adaptive feeding, and intragastrically administered with compounds 1-1 and 8-1 at a dosage of 5 mg/kg.

The animals to be tested (SD rats) were fasted for 12 h before administration and fed 4 h after administration, and water was freely drunk before, after and during the experiment.

After intragastric administration, about 0.2 mL of blood was collected from the orbit at 0 min, 15 min, 30 min, 1 h, 2 h, 4 h, 6 h, 8 h, 10 h and 24 h, and after anticoagulation with EDTA-K2, blood samples were transferred to a centrifuge within 30 min, and centrifuged at 4000 rpm for 10 min at 4° C. to separate the plasma. All plasma samples were collected and immediately stored at −20° C. for testing.

50 μL of the plasma sample to be tested was added with 300 μL of acetonitrile solution containing an internal standard (20 mg/mL diazepam), shaken and mixed well for 5 min, and centrifuged at 13,000 rpm for 10 min. 75 μL of supernatant was taken and diluted with 75 μL of ultrapure water. After being mixed well, 2 μL of the resulting sample was taken for LC/MS/MS determination, and a chromatogram was recorded.

Oral exposure of the compounds disclosed herein was evaluated by in vivo pharmacokinetic experiments in rats. The pharmacokinetic parameters for the compounds fitted using DAS3.2.5 software are shown in the table below.

The pharmacokinetic data of the compounds 1-1 and 8-1 are shown in Table 4-1 below.

TABLE 4-1

Pharmacokinetic parameters for compounds

| PK parameters | 1-1 IG 5 mg/kg | 8-1 IG 5 mg/kg |
|---|---|---|
| $T_{max}$ (h) | 4.00 ± 0.00 | 4.00 ± 0.00 |
| $C_{max}$ (ng/mL) | 378 ± 83.5 | 739 ± 226 |
| AUC(0-24 h) (ng*h/mL) | 3705 ± 848 | 5973 ± 2021 |
| AUC(0-∞) (ng*h/mL) | 4456 ± 1335 | 6558 ± 1805 |
| $t_{1/2}$(h) | 8.73 ± 0.31 | 7.62 ± 2.78 |
| MRT(0-t) (h) | 8.95 ± 4.99 | 7.35 ± 0.45 |

4.2 Pharmacokinetics in Beagle Dogs 3 male beagle dogs weighing 9-12 kg were intragastrically administered with the test compounds at a dosage of 2.5 mg/kg after adaptive feeding for a period of time.

The animals to be tested (male beagle dogs) were fasted for 12 h before administration and fed 4 h after administration, and water was freely drunk before, after and during the experiment.

After intragastric administration, about 0.5 mL of blood was collected from forelimb vein at 0.25 h (15 min), 0.5 h (30 min), 1 h, 1.5 h, 2 h, 4 h, 6 h, 8 h, 10 h, 24 h, 30 h, 48 h and 72 h, and placed in an EDTA-K2 anticoagulation tube. Blood samples were transferred to a centrifuge within 30 min, and centrifuged at 4000 rpm for 10 min at 4° C. to separate the plasma. All plasma samples were collected and immediately stored at −20° C. for testing.

50 μL of the plasma sample to be tested was added with 300 μL of acetonitrile solution containing an internal standard (20 ng/mL diazepam), shaken and mixed well for 5 min, and centrifuged at 13,000 rpm for 10 min. 75 μL of supernatant was taken and diluted with 75 μL of ultrapure water. After being mixed well, 1 μL of the resulting sample was taken for LC/MS/MS determination, and a chromatogram was recorded.

Oral exposure of the compounds disclosed herein was evaluated by in vivo pharmacokinetic experiments in beagle dogs. The pharmacokinetic parameters for the compounds fitted using DAS3.2.5 software are shown in table 4-2 below.

TABLE 4-2

Pharmacokinetic parameters for compounds in beagle dogs

| Test compound | | 8-1 |
|---|---|---|
| Dosage | | 2.5 mg/kg |
| T½ | (h) | 19.47 ± 1.64 |
| Tmax | (h) | 3.33 ± 1.16 |
| Cmax | (ng/mL) | 1429 ± 769 |
| AUC0-72 h | (h*ng/mL) | 26269 ± 13586 |
| AUC0-∞ | (h*ng/mL) | 27692 ± 14182 |
| MRTlast | (h) | 17.2 ± 1.62 |

Experimental Example 5: Pharmacodynamics of Compounds in Human B-Cell Leukemia RS4; 11 Subcutaneous Xenograft Model NOD/SCID mice, female, 9-10 weeks old (ages upon tumor cell grafting), body weight of 16.3-22.0 g, purchased from Beijing AniKeeper Biotech Co., Ltd.; production license number: SCXK (Jing) 2017-0006, and animal certification number: 11402400013155. Breeding environment: SPF grade. Mice were grafted subcutaneously on the right anterior dorsal side with $1 \times 10^7$ RS4;11 cells. The day of grafting was defined as day 0. When the mean tumor volume was 240 mm³, the mice were randomly grouped according to the tumor size. The administration was performed as per Table 5 below.

TABLE 5

Administration route, dosage and regimen for human B-cell leukemia RS4;11 subcutaneous xenograft model

| Group | n | Administration group | Dosage (mg/kg) | Administration route | Time of administration |
|---|---|---|---|---|---|
| 1 | 6 | Vehicle | | p.o. | One dose |
| 2 | 6 | 1-1 | 25 | p.o. | One dose |

TABLE 5-continued

Administration route, dosage and regimen for human
B-cell leukemia RS4;11 subcutaneous xenograft model

| Group | n | Administration group | Dosage (mg/kg) | Administration route | Time of administration |
|---|---|---|---|---|---|
| 3 | 6 | 1-1 | 50 | p.o. | One dose |
| 4 | 6 | 8-1 | 25 | p.o. | One dose |

Note:
n: the number of animals; the administration volume was 10 μL/g.

Clinical symptoms observed during the experiment were recorded in the raw data. The calculation formula for tumor volume: Tumor volume $(mm^3)=\frac{1}{2}\times(a\times b^2)$ (where a represents long diameter and b represents short diameter). The data were collected using StudyDirector™ software (version No. 3.1.399.19, supplier: Studylog System, Inc., S. San Francisco, CA, USA) in the experiment, including measurements of the long and short diameters of the tumor and weighing results of the animals. The raw data obtained from a balance and a vernier caliper were directly imported into the software, and any change in the data was recorded. Relative tumor proliferation rate (T/C %) refers to the percentage of the relative tumor volume or tumor weight of the treatment and control groups at a certain time point. The calculation formula is as follows:

T/C %=$T_{RTV}/CR_{TV}\times 100\%$ ($T_{RTV}$: mean RTV for treatment group; $C_{RTV}$: mean RTV for vehicle control group; RTV=$V_t/V_0$, where $V_0$ is the tumor volume of the animal upon grouping, and $V_t$ is the tumor volume of the animal after treatment).

Tumor growth inhibition rate (TGI %) is calculated according to the following formula: TGI %=(1−T/C)×100%. (T and C are the relative tumor volume (RTV) or tumor weight (TW) at a particular time point for the treatment and control groups, respectively).

All experimental results were expressed as mean tumor volume±SEM (standard error of mean). The relative tumor volume of the treatment group was compared with that of the control group for any significant difference by the independent sample T test. All data were analyzed using SPSS 18.0. p<0.05 was defined as a significant difference. The results are shown in Table 6.

TABLE 6

Pharmacodynamics for each group of human
B-cell leukemia RS4;11 subcutaneous model

| | | Day 17 after the end of administration | | | | |
|---|---|---|---|---|---|---|
| Experimental group | Dosage mg/kg | Tumor volume ($\bar{x} \pm S$) | Relative tumor volume ($\bar{x} \pm S$) | TGI (%) | T/C (%) | P Value (compared to control group) |
| Vehicle control group | | 2086.72 ± 368.80 | 8.51 ± 1.21 | | | |
| 1-1 | 25 | 1024.97 ± 160.59 | 4.39 ± 0.83 | 48.5 | 51.5 | 0.35 |
| 1-1 | 50 | 465.78 ± 95.68 | 1.92 ± 0.36 | 77.5 | 22.5 | <0.001 |
| 8-1 | 25 | 600.39 ± 32.88 | 2.54 ± 0.19 | 70.2 | 29.8 | <0.001 |

Note:
1. Data were expressed as "mean ± standard error";
2. T/C % = $T_{RTV}/C_{RTV} \times 100\%$; TGI % = (1 − T/C) × 100%.

Experimental Example 6: Human Platelet Toxicity Experiment (Caspase-3 Activity Assay)

10 mL of human whole blood was collected using a heparin sodium anticoagulation tube, mixed well by turning upside down, and centrifuged at 90 g for 10 min. The supernatant was collected and centrifuged at 1950 g for 10 min. The supernatant was discarded, and the residue was resuspended in 4 mL of PBS, and centrifuged at 1190 g for 5 min, and the procedure was repeated once. The supernatant was discarded, and the platelets were resuspended in PBS and adjusted to the density of $2-3\times10^8$ cells/mL. Cells were seeded into a 96-well plate at a density of $2-3\times10^7$ cells/mL and at 100 μL/well. 50 μL of control buffer was added to each negative control well, and 50 μL of compound at a corresponding concentration was added to each compound well, so that the final concentration of the compound was 2.5 μM, 2 μM, 1 μM or 0.5 μM, followed by incubation in an incubator at 37° C. for 90 min. The liquids in the 96-well plate were transferred to 1.5 mL centrifuge tubes, respectively. The tubes were centrifuged at 4° C. and 6000 g for 5 min, and placed on ice for later use after the supernatant was discarded. 5× lysis buffer was diluted into 1× lysis buffer with water in the kit, and protease inhibitor cocktail was added at a 1:200 ratio to prepare a lysis mixture for later use. 40 μL of lysis mixture was added to each centrifuge tube, and the platelets at the bottom were resuspended using a pipette. The suspension was lysed on ice for 15-20 min and centrifuged at 4° C. and 14,000 g for 10 min. The sample was sub-packaged for later use. 10× assay buffer was diluted into 1× assay buffer with water in the kit, and substrate Ac-DEVD-AMC was added at a 1:600 ratio to prepare a reaction mixture. 5 μL of assay buffer and 40 μL of reaction mixture were added to each blank control well. 5 μL of control platelet lysate and 40 μL of reaction mixture were added to each negative control well. 5 μL of platelet lysate and 40 μL of reaction mixture were added to each compound well. In this procedure, 40 L of reaction mixture was added at last. The resulting mixture was mixed gently, and the plate was read by a PE Envision multi-functional microplate reader (excitation: 360 nm, emission: 460 nm) once every 10 min for 6 times. Caspase-3 activity was determined based on the intensity of the released AMC fluorescence, that is the slope of the fitted line to which each well corresponds represents Caspase activity (all data were normalized and the reference was ABT-199). The results are shown in Tables 7-8.

TABLE 7

Effect of compounds on human platelet Caspase-3 activity

| | Slope | |
| --- | --- | --- |
| Compound | Compound concentration 2.5 μM | Compound concentration 1 μM |
| Negative | 0.03 | 0.04 |
| 1-1 | 0.28 | 0.67 |
| 6-1 | 0.22 | 0.45 |
| 8-1 | 0.94 | 0.59 |
| 7-1 | 0.67 | 0.48 |
| 17-1 | 0.43 | 0.48 |
| 18-1 | 0.46 | 0.31 |
| 19-1 | 0.18 | 0.12 |
| 20-1 | 0.71 | 0.37 |

Note:
Data were normalized.

TABLE 8

Effect of compounds on human platelet Caspase-3 activity

| | Slope | |
| --- | --- | --- |
| Compound | Compound concentration 0.5 μM | Compound concentration 2 μM |
| Negative | 0.15 | 0.09 |
| 11-1 | 0.42 | 0.57 |
| 12-1 | 0.27 | 0.33 |
| 28-1 | 0.04 | 0.03 |
| 43-1 | 0.19 | 0.09 |
| 57-1 | 0.08 | 0.04 |
| 65-1 | 0.44 | 0.43 |

Note:
Data were normalized.

The invention claimed is:

1. A compound of formula I, a stereoisomer thereof or a pharmaceutically acceptable salt thereof:

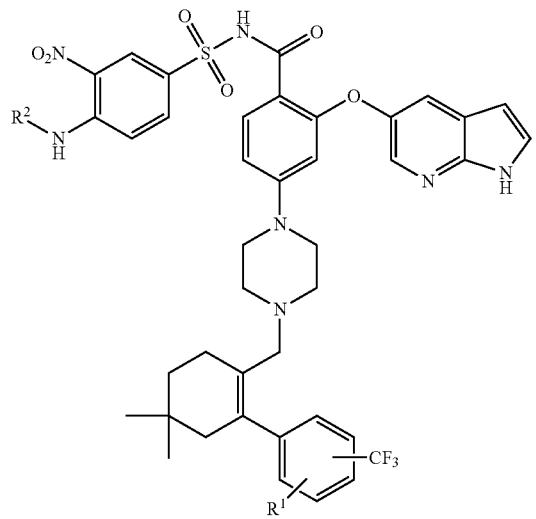

I wherein,
$R^1$ is chlorine;
$R^2$ is —$(CH_2)_n$—$R^3$, wherein n is 1;
$R^3$ is a 6 membered heterocycloalkyl, and the heteroatom in the 6 membered heterocycloalkyl is selected from the group consisting of N and O, and the number of the heteroatom is 1 or 2, wherein the 6 membered heterocycloalkyl is optionally substituted with one or two groups selected from the group consisting of 3-6 membered heterocycloalkyl, $C_{3-6}$ cycloalkyl, —$COR^a$, —$SO_2R^b$, —$COOC_{1-6}$ alkyl, and $C_{1-6}$ alkyl optionally substituted with halogen; and
$R^a$ or $R^b$ is each independently selected from the group consisting of H, 3-6 membered heterocycloalkyl, $C_{3-6}$ cycloalkyl and $C_{1-6}$ alkyl, wherein the $C_{1-6}$ alkyl is optionally substituted with halogen, —CN, —$N(C_{1-6}$ alkyl$)_2$, —$NHC_{1-6}$ alkyl or —$OC_{1-6}$ alkyl,
wherein the heteroatom in the 3-6 membered heterocycloalkyl is selected from the group consisting of N and O, and the number of the heteroatom is 1 or 2;
wherein the structural fragment

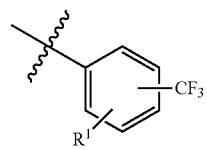

is

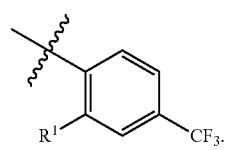

2. The compound of formula I, the stereoisomer thereof or the pharmaceutically acceptable salt thereof according to claim 1, wherein $R^3$ is a 6-membered heterocycloalkyl, and wherein the 6-membered heterocycloalkyl is optionally substituted with one or two groups at ring N atom.

3. The compound of formula I, the stereoisomer thereof or the pharmaceutically acceptable salt thereof according to claim 1, wherein $R^3$ is 6-membered heterocycloalkyl, and wherein the 6-membered heterocycloalkyl is optionally substituted with one or two groups selected from the group consisting of 3-6 membered heterocycloalkyl, —$COR^a$, —$SO_2R^b$, —$COOC_{1-4}$ alkyl, and $C_{1-6}$ alkyl optionally substituted with halogen.

4. The compound of formula I, the stereoisomer thereof or the pharmaceutically acceptable salt thereof according to claim 1, wherein $R^a$ or $R^b$ is each independently selected from the group consisting of H, 3-6 membered heterocycloalkyl, $C_{3-6}$ cycloalkyl and $C_{1-4}$ alkyl, and wherein the $C_{1-4}$ alkyl is optionally substituted with halogen, —CN, —$N(C_{1-4}$ alkyl$)_2$, —$NHC_{1-4}$ alkyl or —$OC_{1-4}$ alkyl.

5. The compound of formula I, the stereoisomer thereof or the pharmaceutically acceptable salt thereof according to claim 4, wherein $R^a$ or $R^b$ is each independently selected from $C_{1-4}$ alkyl optionally substituted with —$OC_{1-4}$ alkyl.

6. The compound of formula I, the stereoisomer thereof or the pharmaceutically acceptable salt thereof according to claim 1, wherein $R^3$ is a 6-membered heterocycloalkyl, and wherein the 6-membered heterocycloalkyl is optionally substituted with —C(O)H, —$COCH_3$, —$COCH(CH_3)_2$, —$COC(CH_3)_3$, —$COCF_3$, —$COCH_2CN$, —$COCH_2OCH_3$, —$COCH_2N(CH_3)_2$, —$SO_2CH_3$, —$SO_2CH_2CH_3$, —$SO_2CF_3$, —$SO_2C_2F_5$, methyl, ethyl, —$CF_3$, —$CH_2CH_2F$, —$C_2F_5$, tetrahydropyran, monooxacyclobutane, —$SO_2$-cyclopropane, —CO-cyclopropane, —CO-monooxacyclobutane, —$SO_2$-monooxacyclobutane, —$SO_2$-cyclobutane, —$COOCH_2CH_3$ or —$COOCH_3$.

7. The compound of formula I, the stereoisomer thereof or the pharmaceutically acceptable salt thereof according to claim 1, wherein $R^3$ is selected from the group consisting of

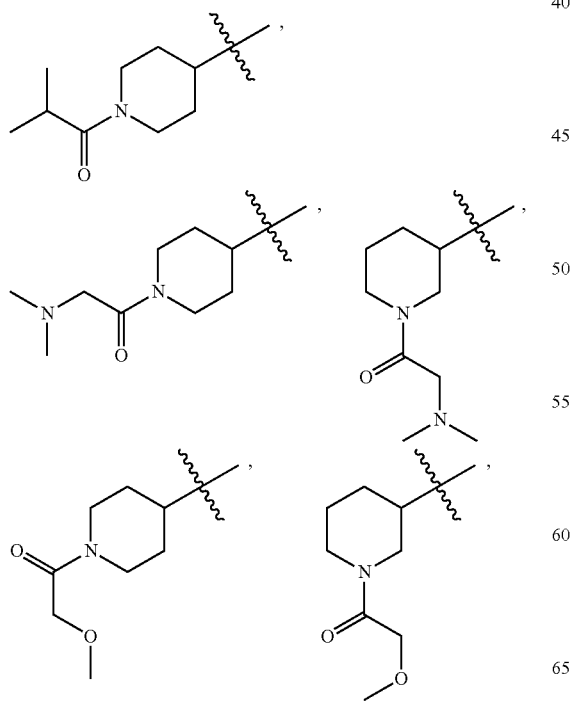

-continued

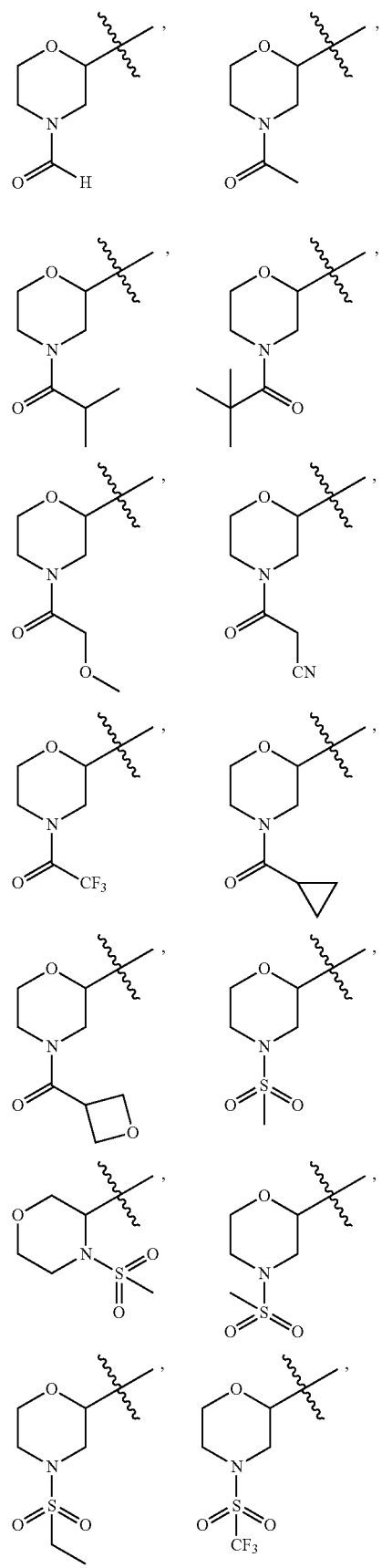

203
-continued
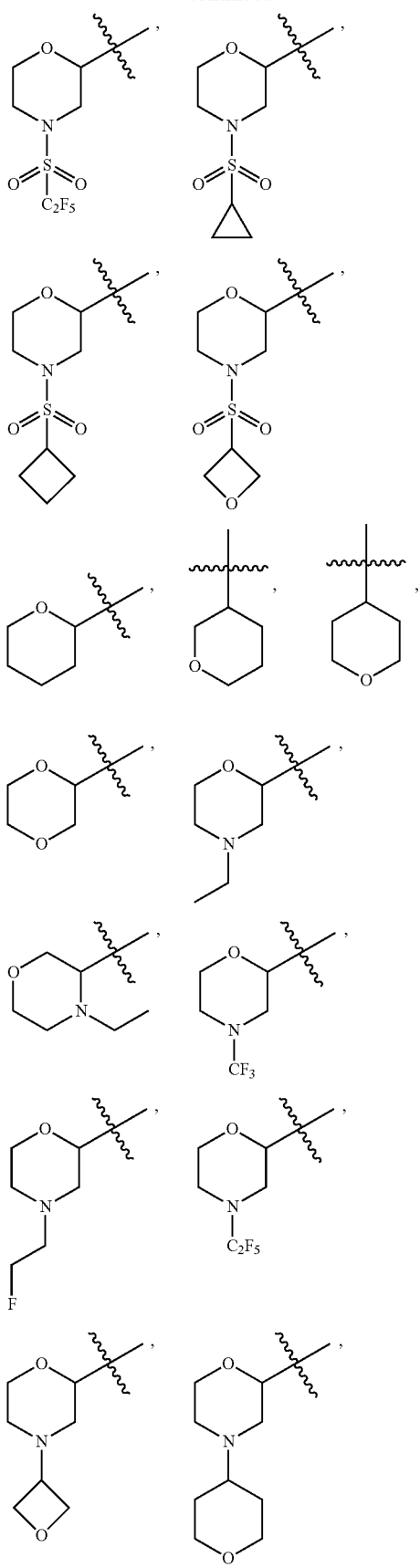
204
-continued
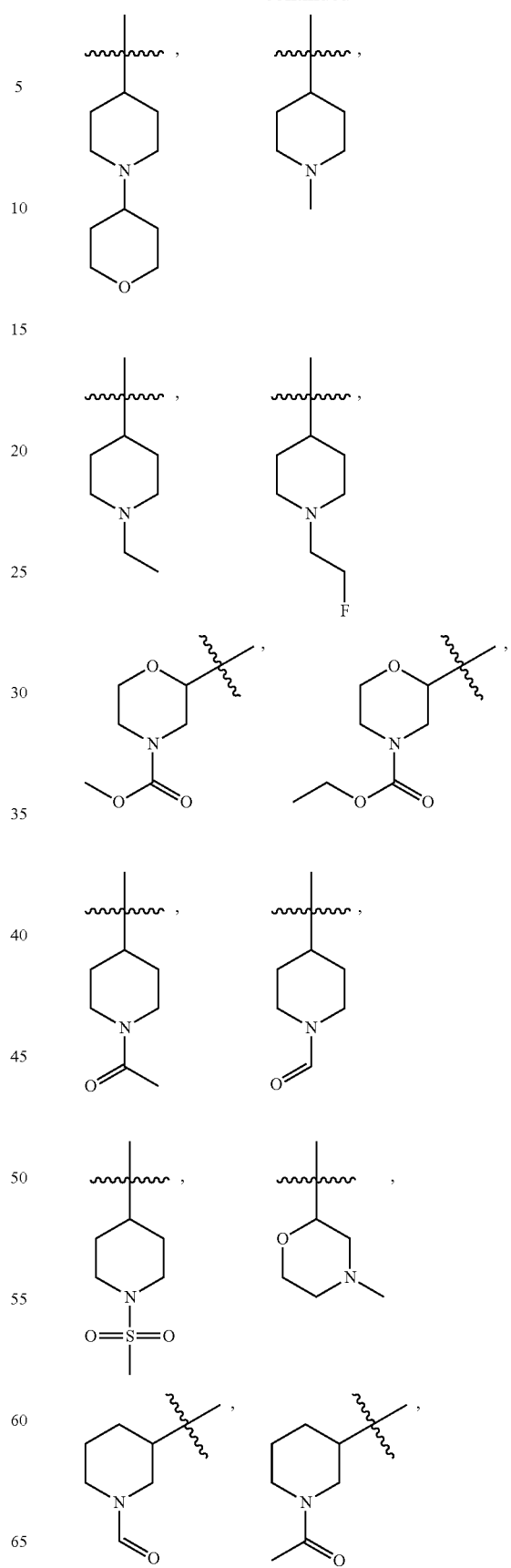

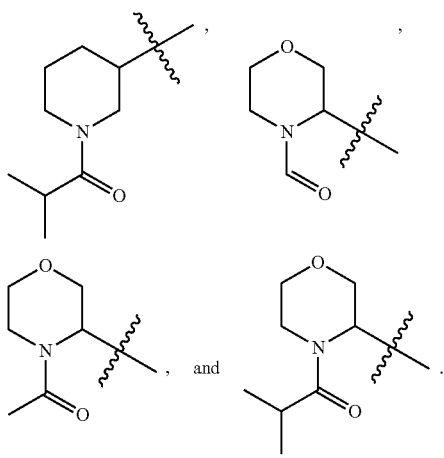

8. A pharmaceutical composition comprising the compound, the stereoisomer thereof or the pharmaceutically acceptable salt thereof according to claim 1.

9. The compound of formula I, the stereoisomer thereof or the pharmaceutically acceptable salt thereof according to claim 4, wherein $R^a$ or $R^b$ is each independently selected from the group consisting of H, methyl, ethyl, isopropyl, tert-butyl, trifluoromethyl, pentafluoroethyl, —CH$_2$OCH$_3$, —CH$_2$CN and —CH$_2$N(CH$_3$)$_2$, cyclopropyl, cyclobutyl and monooxacyclobutyl.

10. The compound of formula I, the stereoisomer thereof or the pharmaceutically acceptable salt thereof according to claim 9, wherein $R^a$ or $R^b$ is each independently selected from the group consisting of methyl, isopropyl, and —CH$_2$OCH$_3$.

11. The compound of formula I, the stereoisomer thereof or the pharmaceutically acceptable salt thereof according to claim 2, wherein $R^3$ is a 6-membered heterocycloalkyl, and wherein the 6-membered heterocycloalkyl is optionally substituted with one or two groups selected from the group consisting of —COR$^a$, —SO$_2$R$^b$, and C$_{1-6}$ alkyl optionally substituted with halogen.

12. The compound of formula I, the stereoisomer thereof or the pharmaceutically acceptable salt thereof according to claim 6, wherein $R^3$ is selected from the group consisting of tetrahydropyran, piperidine, morpholine and dioxane, and wherein the tetrahydropyran, piperidine, morpholine or dioxane is optionally substituted with —COCH$_3$, —COCH(CH$_3$)$_2$, —COCH$_2$OCH$_3$, —SO$_2$CH$_3$, methyl, ethyl, —CH$_2$CH$_2$F, —COOCH$_2$CH$_3$ or —COOCH$_3$.

13. The compound of formula I, the stereoisomer thereof or the pharmaceutically acceptable salt thereof according to claim 6, wherein $R^3$ is selected from the group consisting of

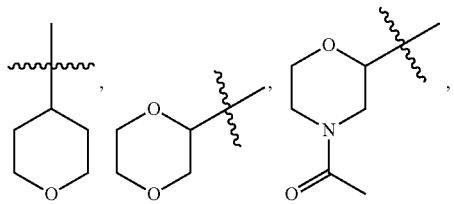

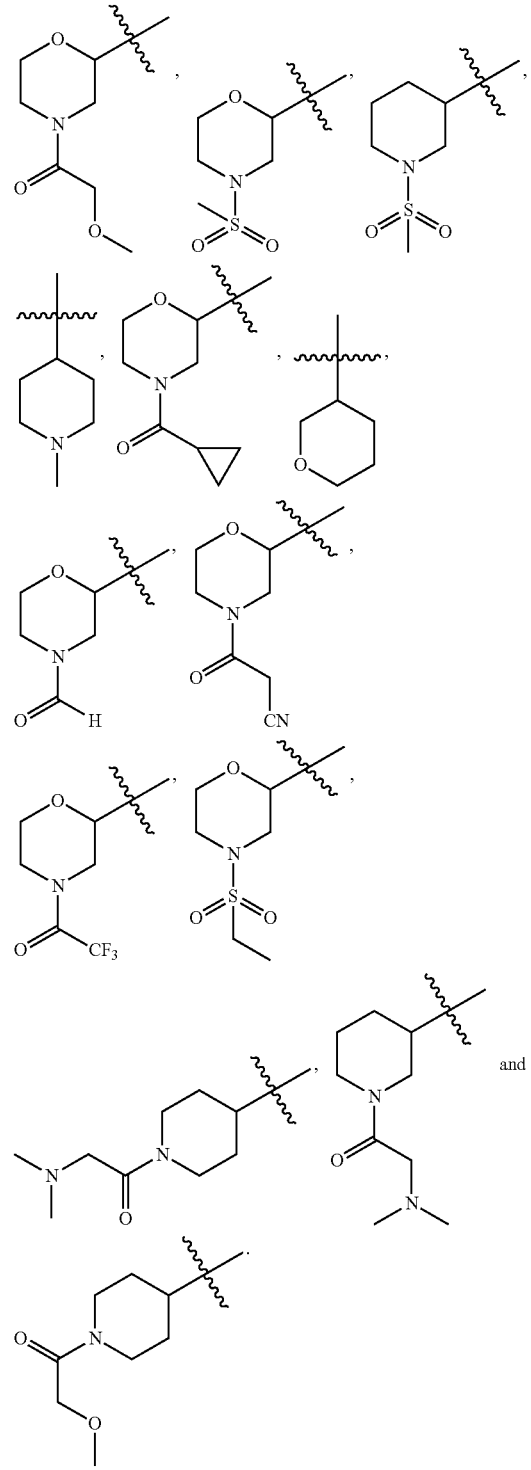

14. The compound of formula I, the stereoisomer thereof or the pharmaceutically acceptable salt thereof according to claim 1, wherein $R^3$ is selected from the group consisting of tetrahydropyran and dioxane.

15. The compound of formula I, the stereoisomer thereof or the pharmaceutically acceptable salt thereof according to claim 1, selected from a compound of the following formulas:

207
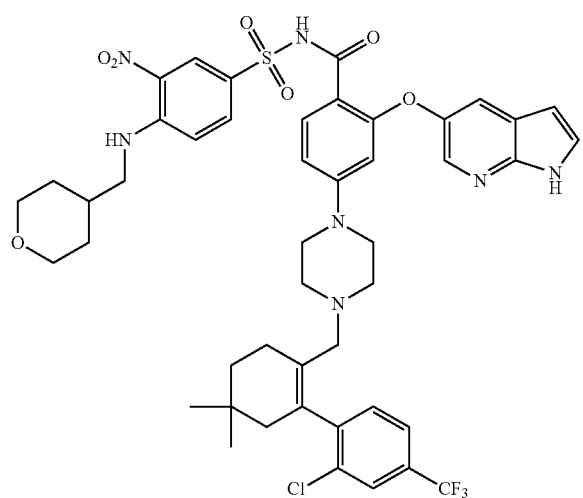
208
-continued
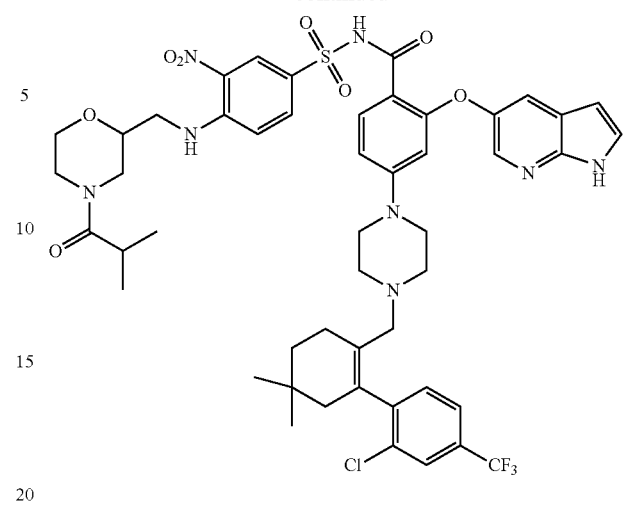
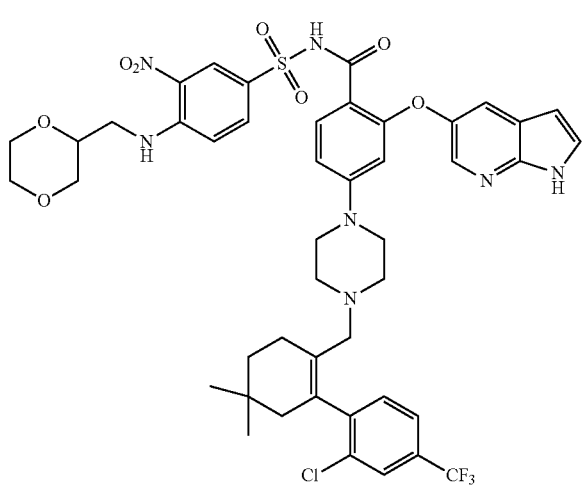
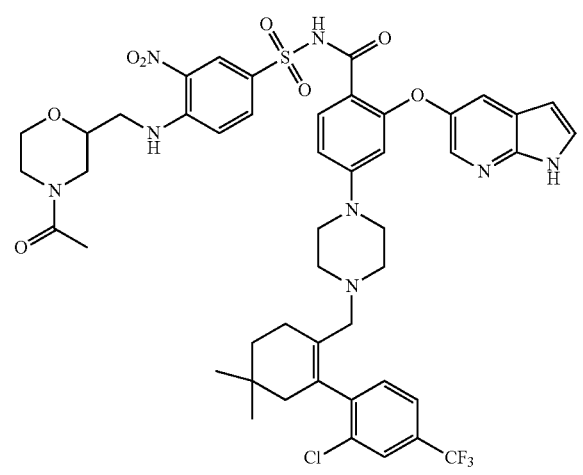
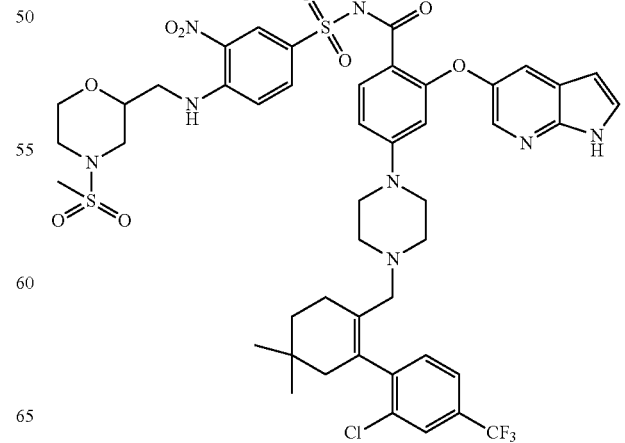

or a compound of the following formula:

wherein R is independently selected from the group consisting of:
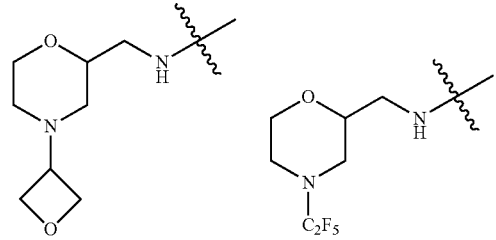
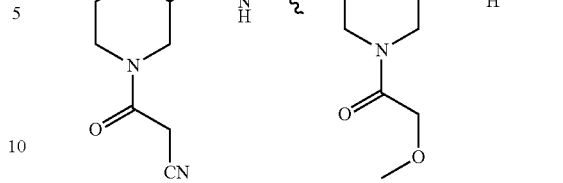
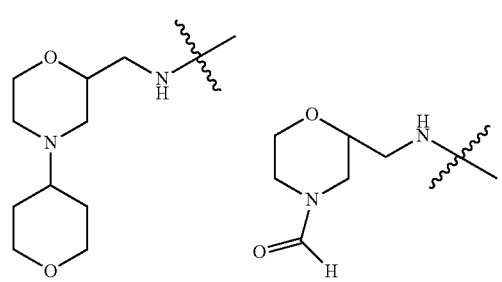
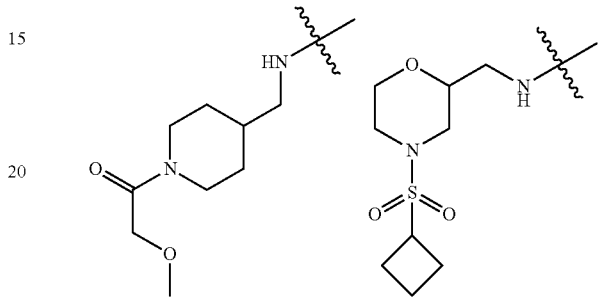
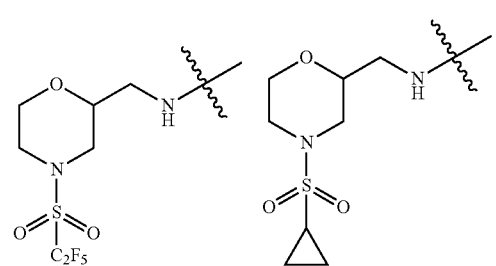
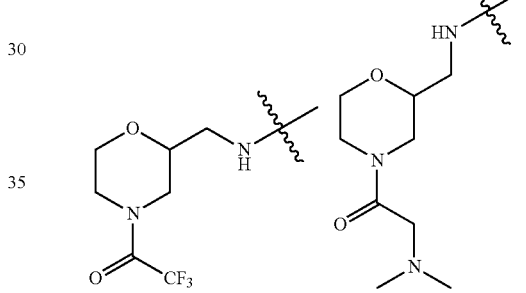
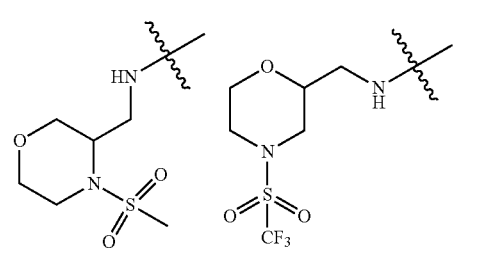
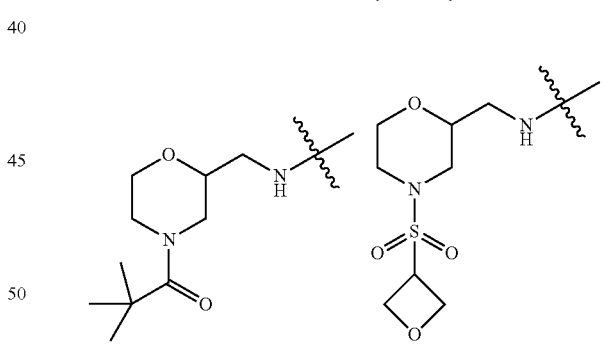
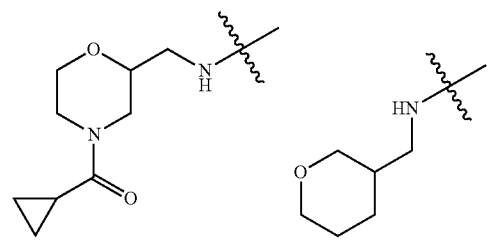
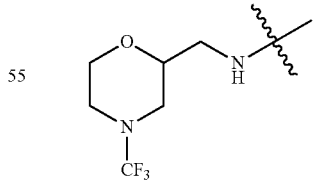
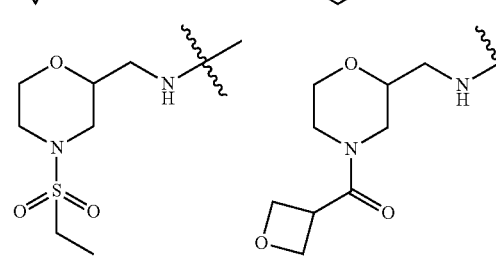
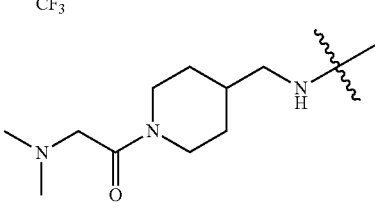

213
-continued
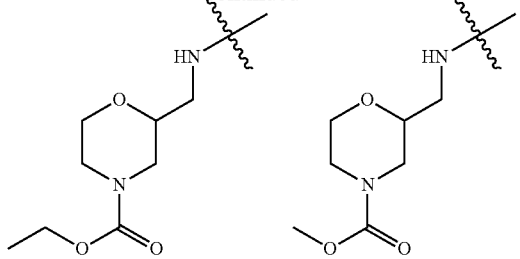
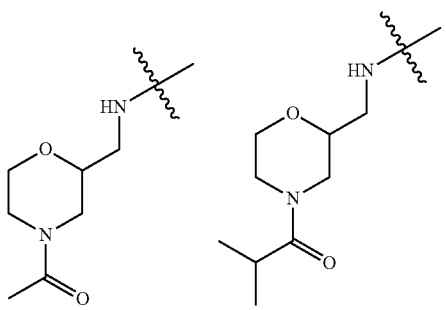
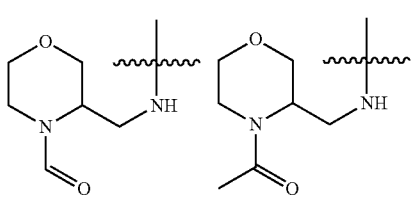
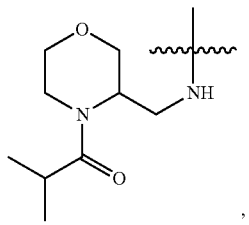
,
or a stereoisomer thereof or a pharmaceutically acceptable salt thereof.
16. The compound of formula I, the stereoisomer thereof or the pharmaceutically acceptable salt thereof according to claim 1, selected from a compound of the following formulas:
214
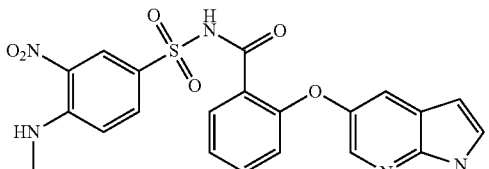
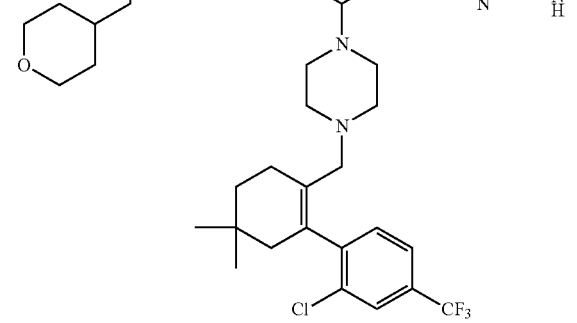
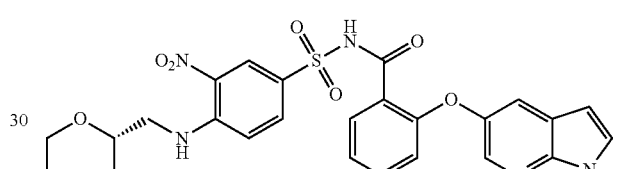
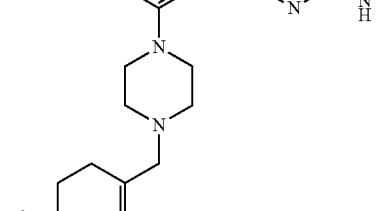
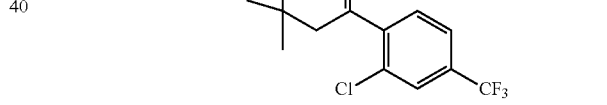
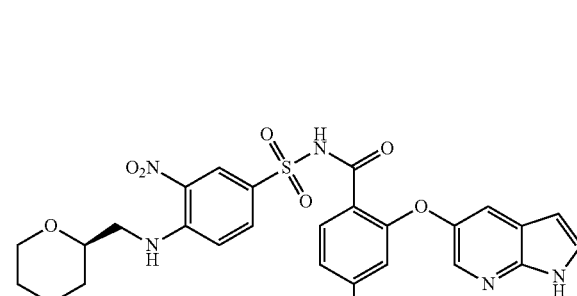
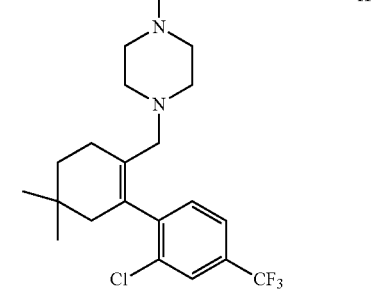

215
-continued
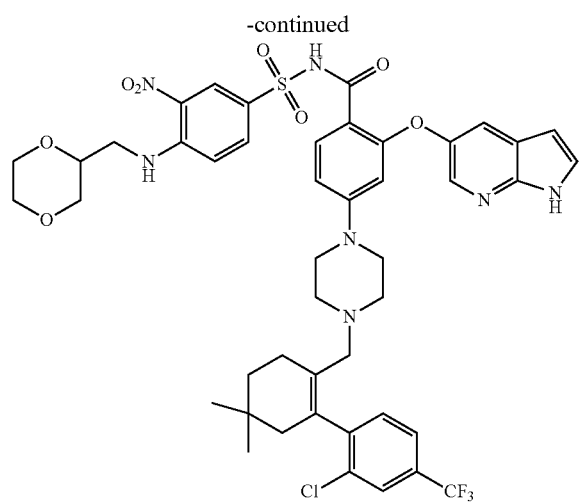
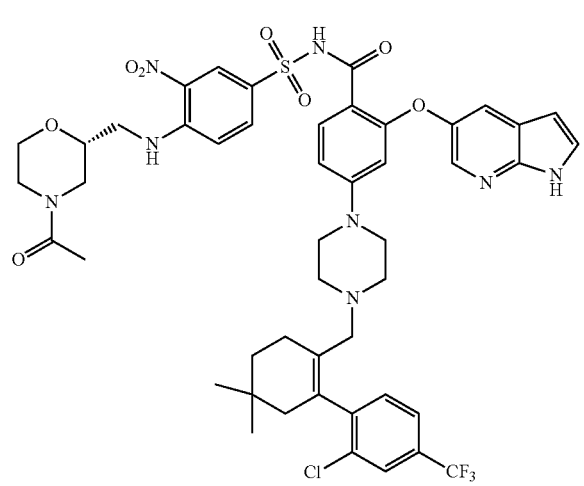
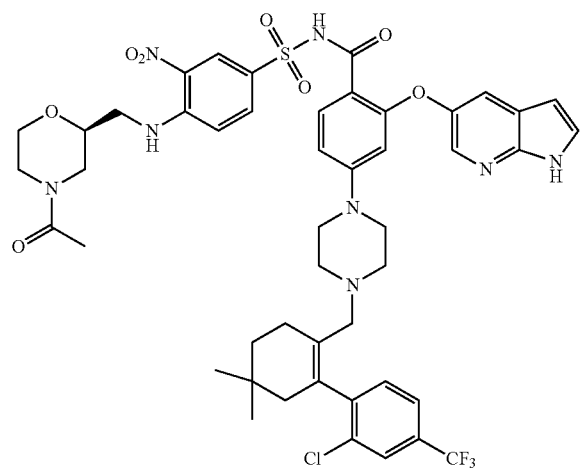
216
-continued
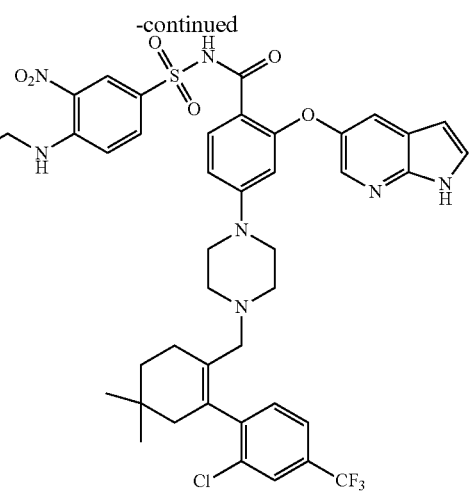
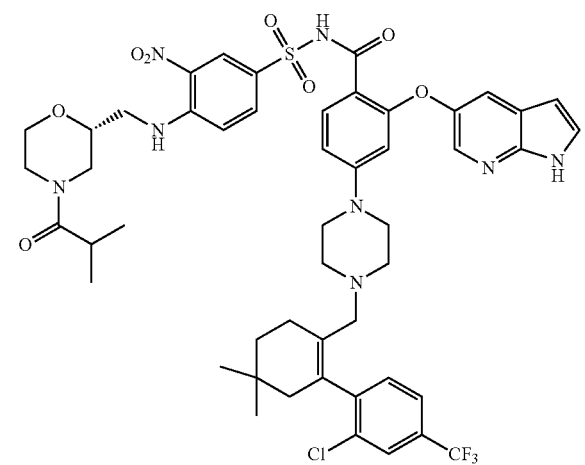
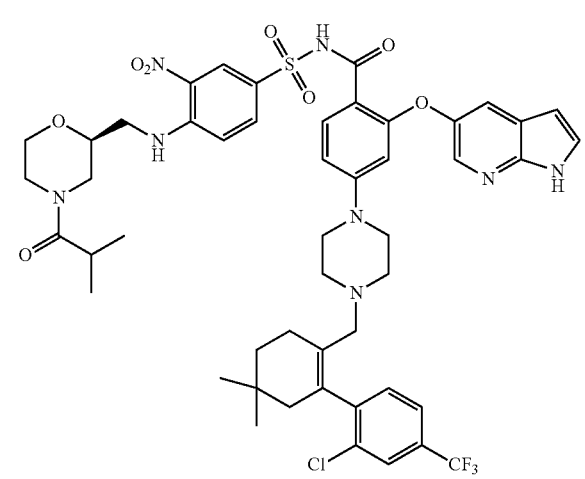

217
-continued
218
-continued
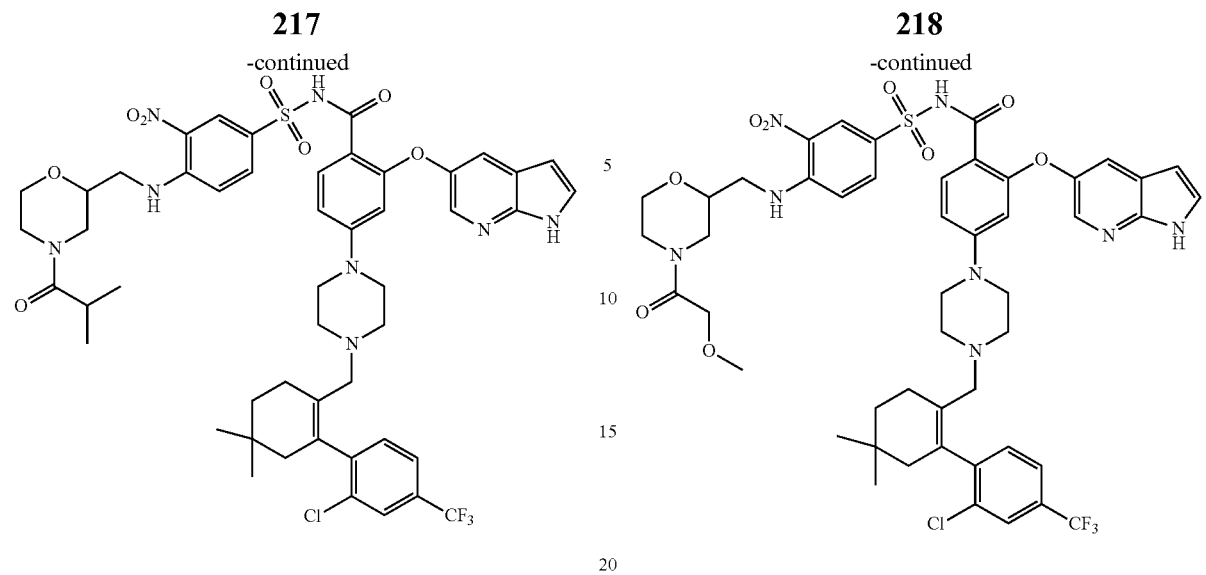
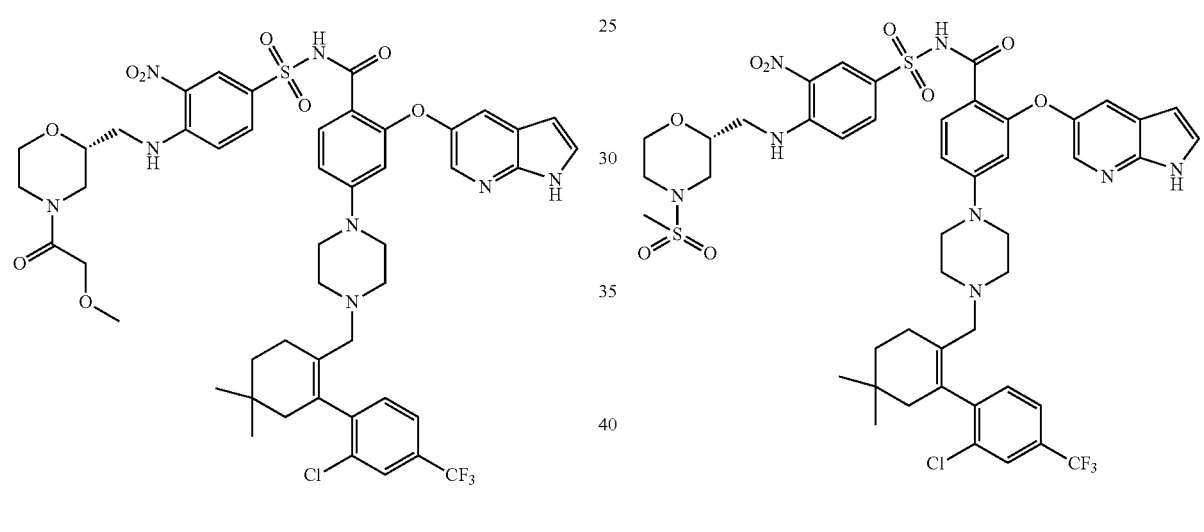
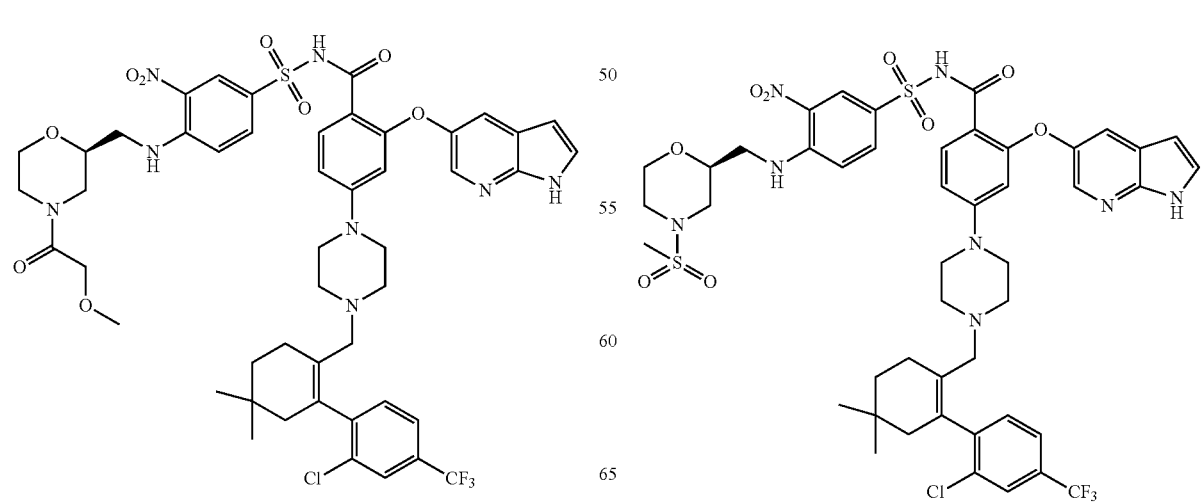

219
-continued
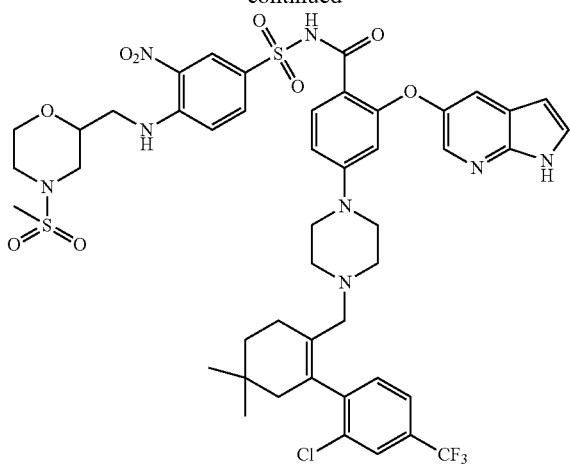
220
-continued
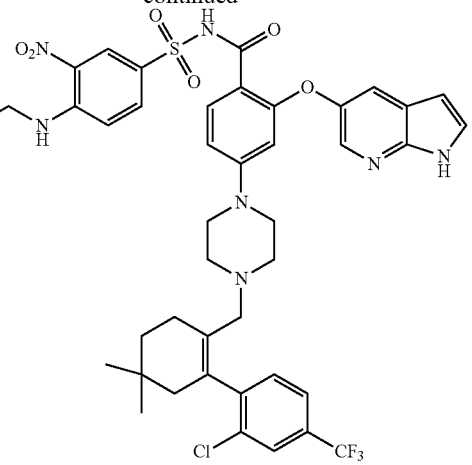
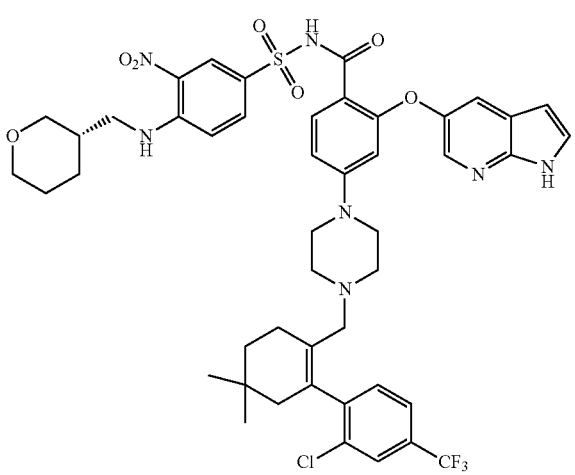
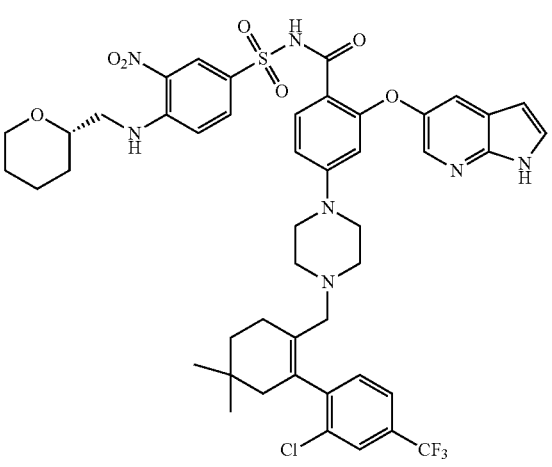
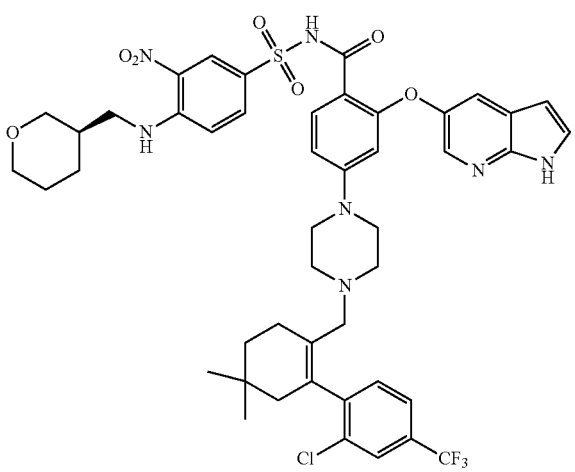
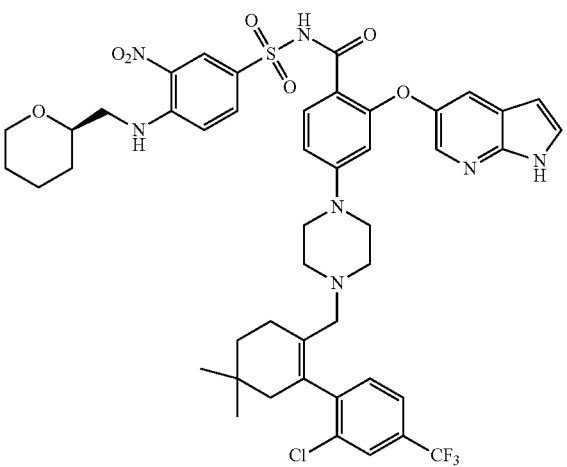

221
-continued
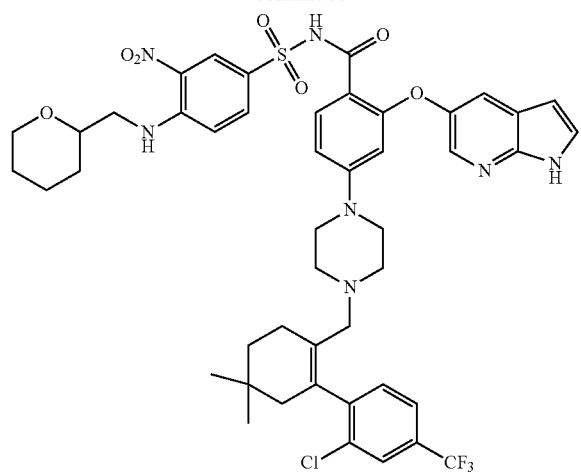
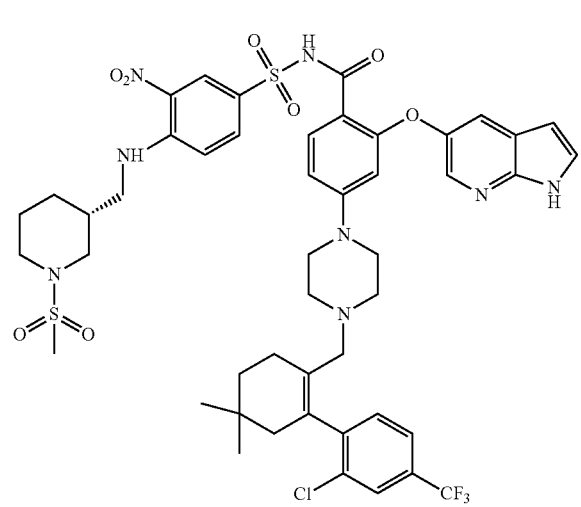 [SMILES: CC(=O)N1CCOCC1CNc1ccc(S(=O)(=O)NC(=O)c2ccc(N3CCN(CC4=C(c5ccc(C(F)(F)F)cc5Cl)CC(C)(C)CC4)CC3)cc2Oc2cnc3[nH]ccc3c2)cc1[N+](=O)[O-]]
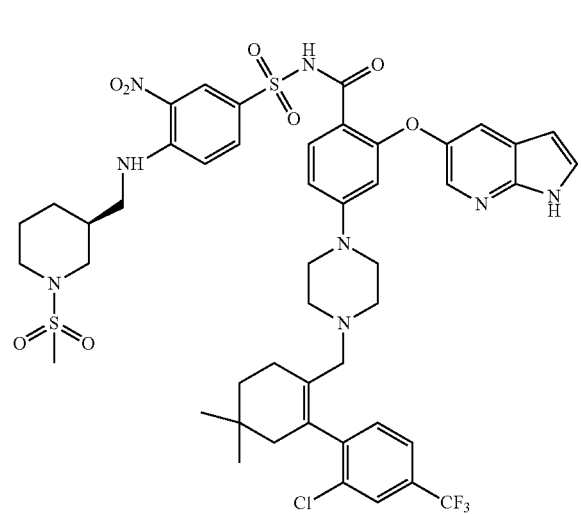
222
-continued
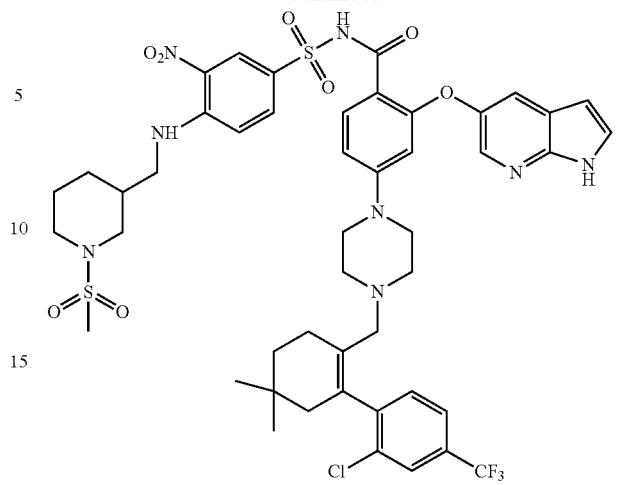
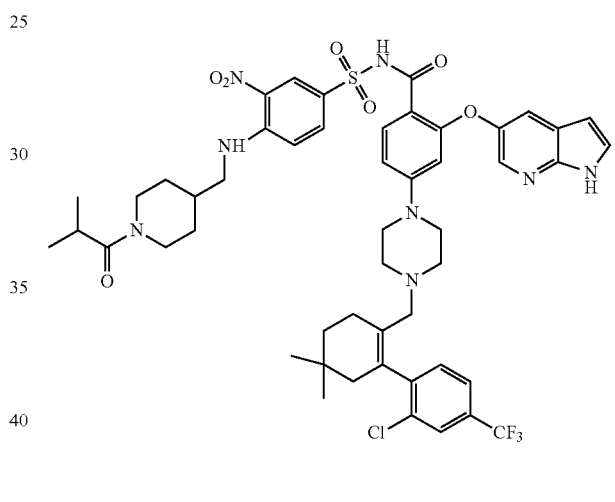
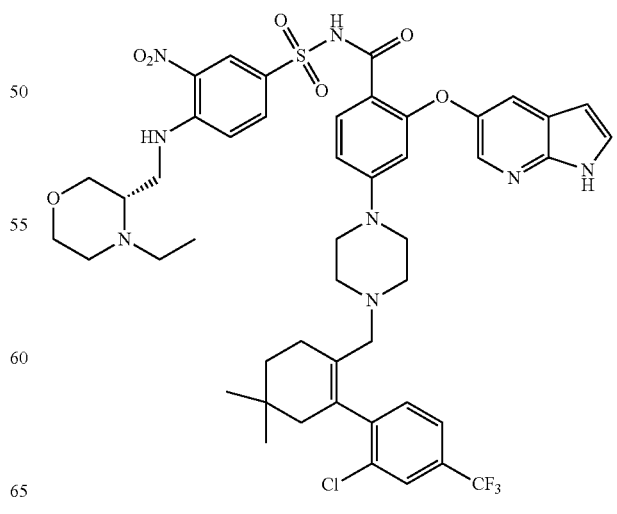

223
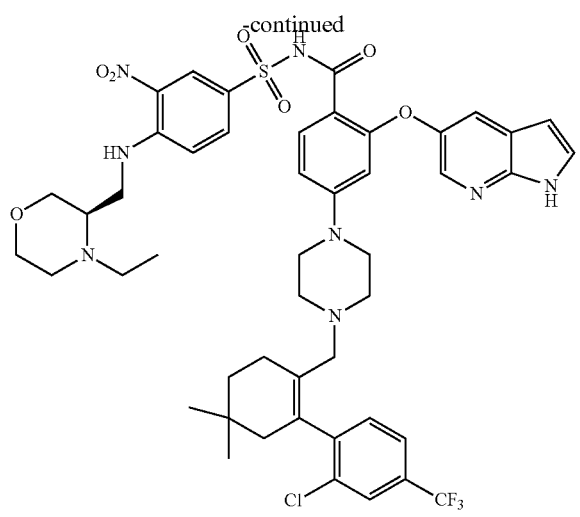
or a compound of the following formula:
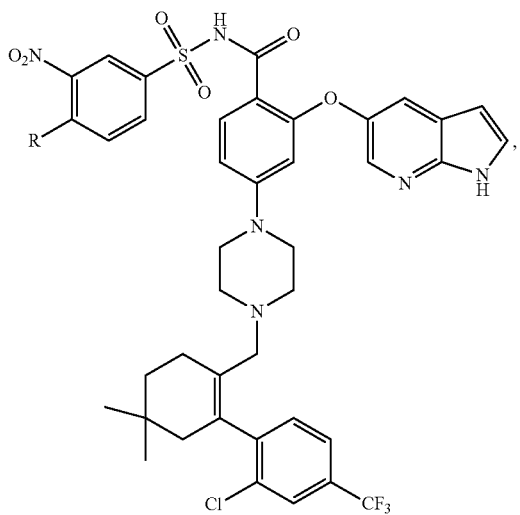
224
wherein R is independently selected from the group consisting of:
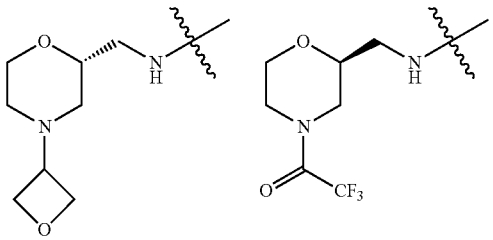
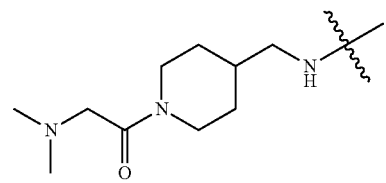
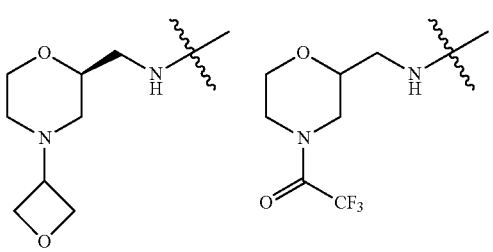
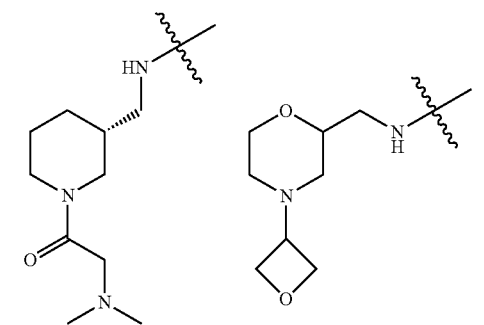
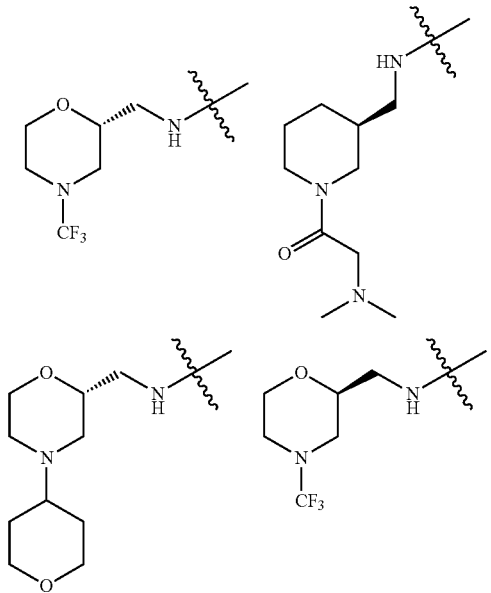

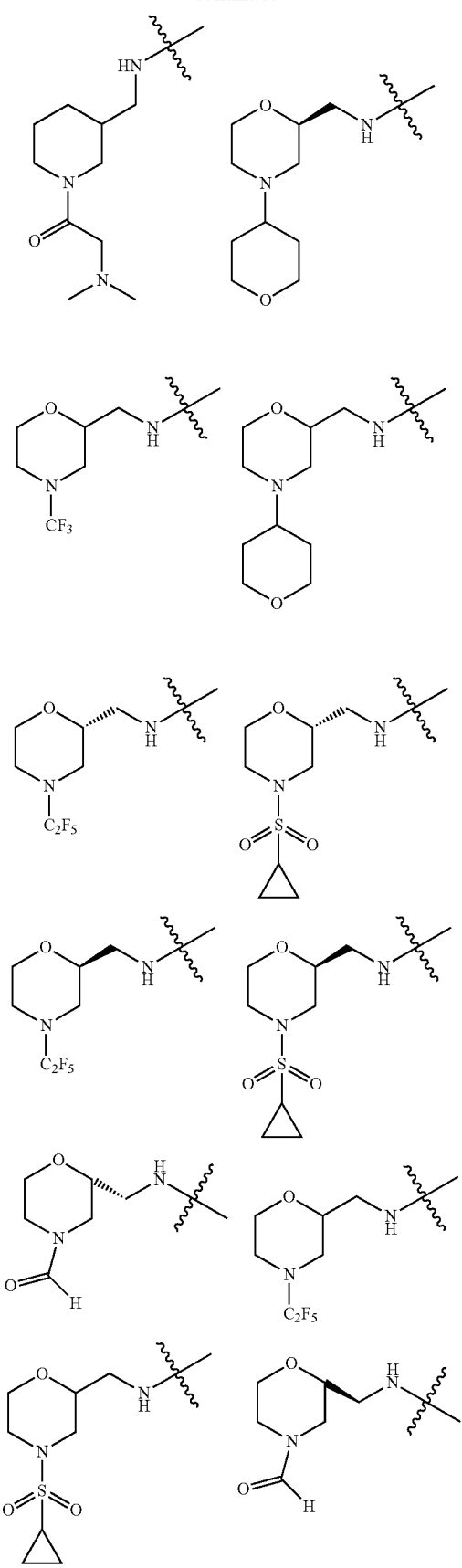
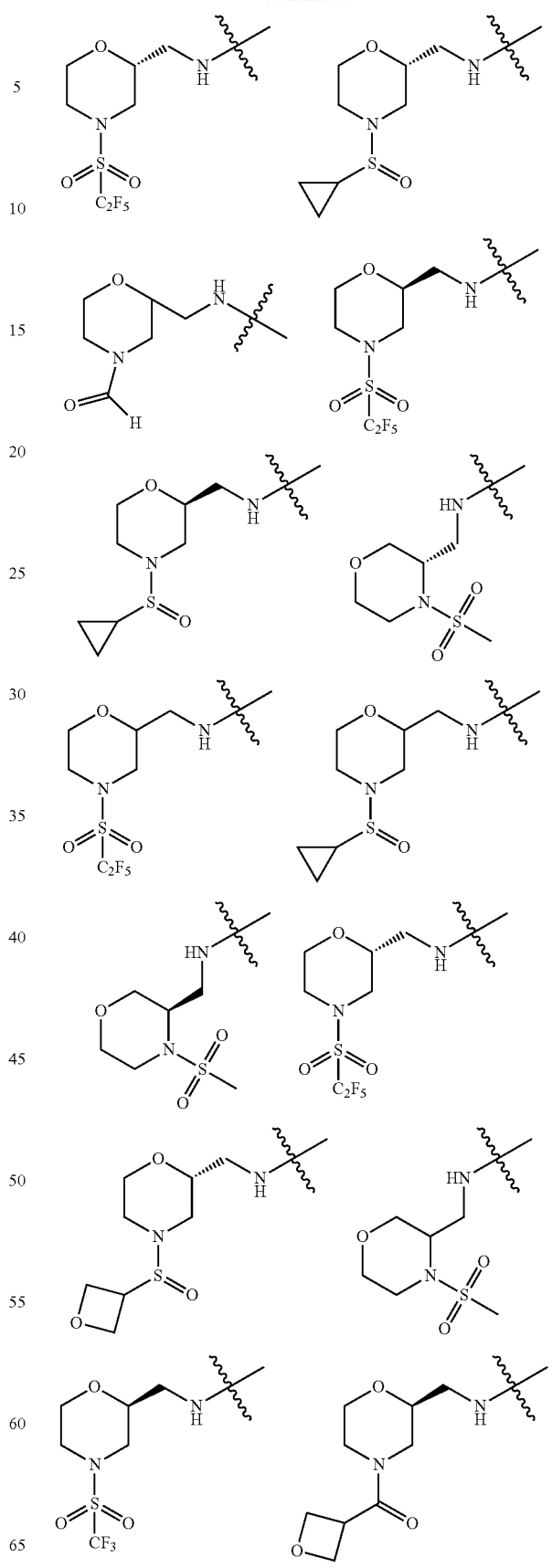

227
-continued
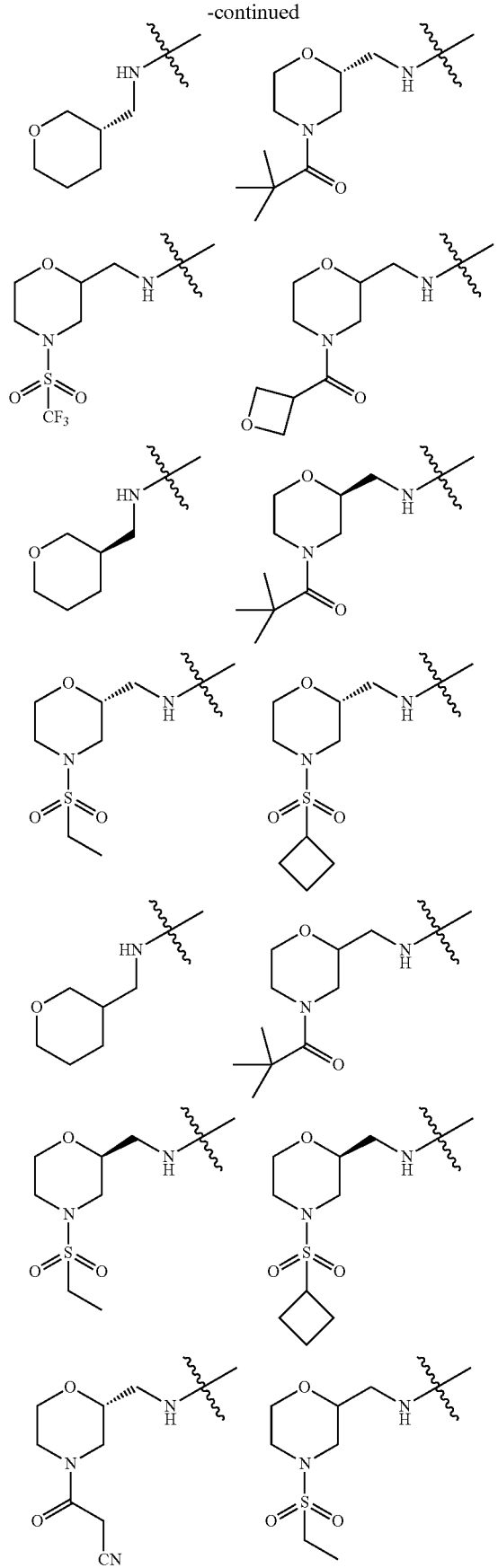
228
-continued
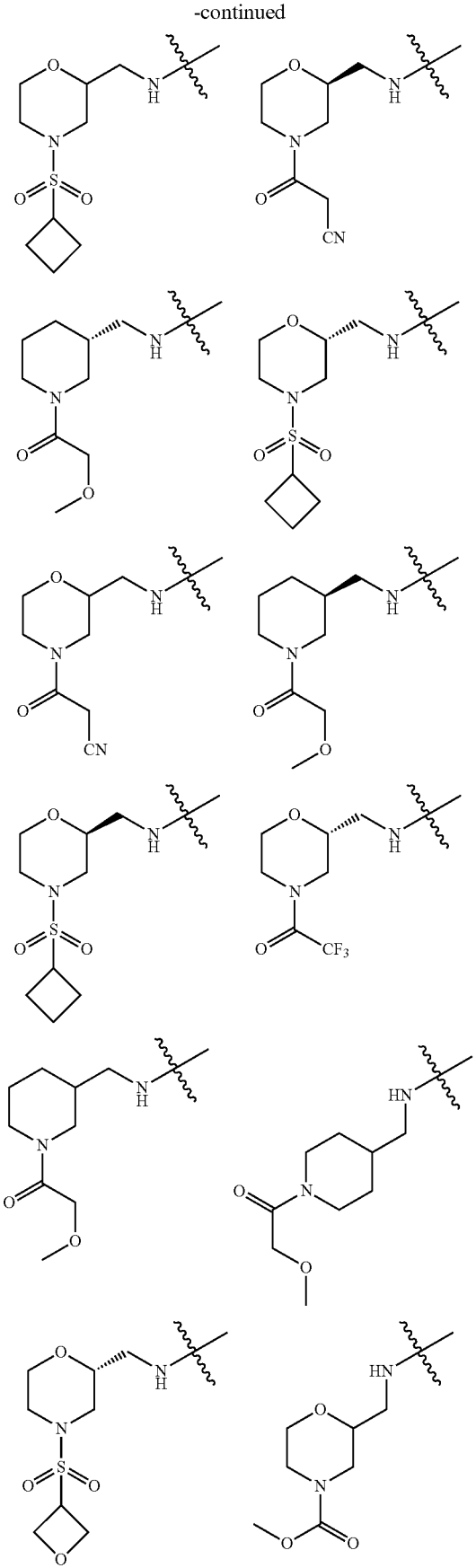

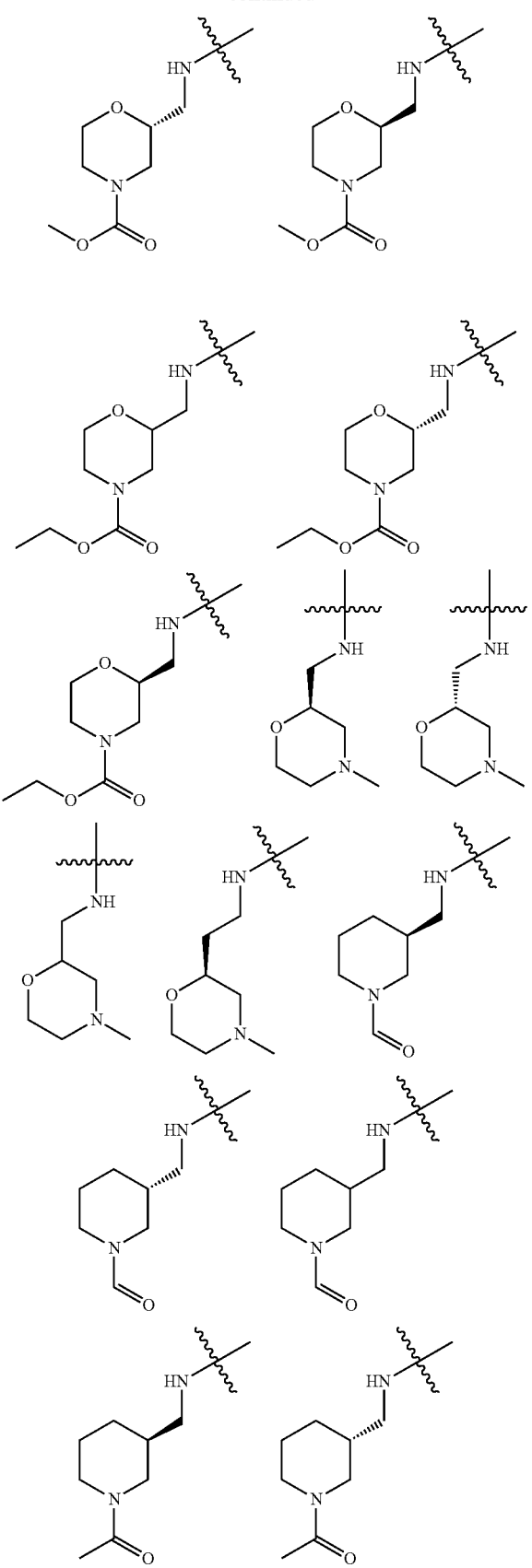
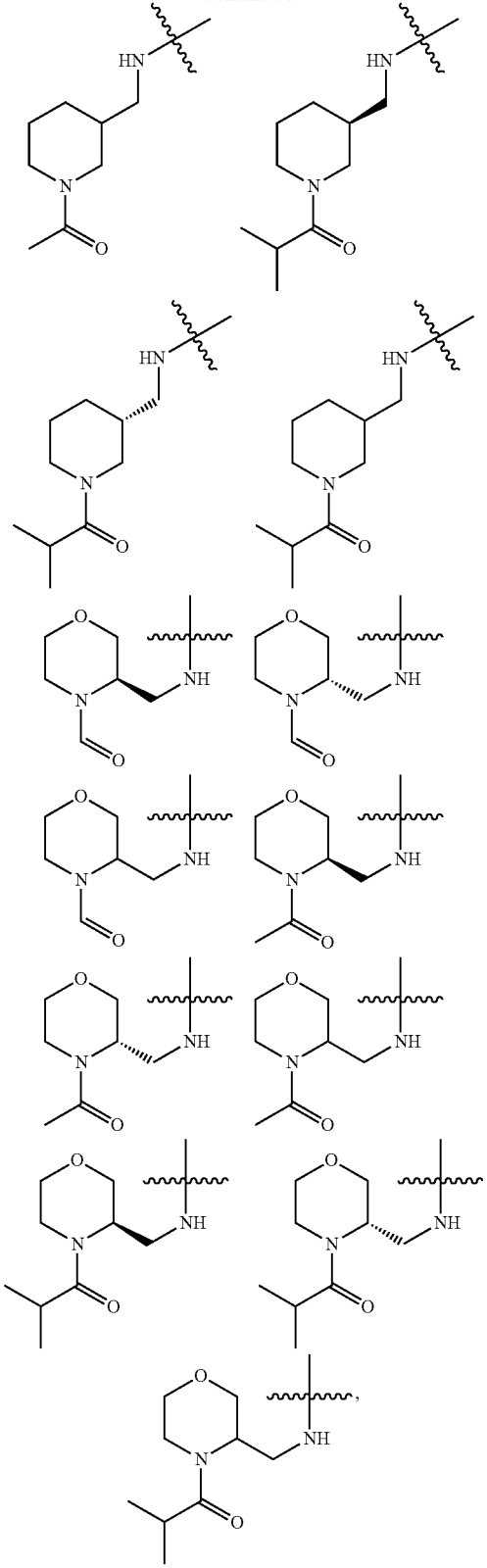
or a pharmaceutically acceptable salt thereof.
17. The compound of formula I, the stereoisomer thereof or the pharmaceutically acceptable salt thereof according to claim 16, wherein the compound of formula I is

18. The compound of formula I, the stereoisomer thereof or the pharmaceutically acceptable salt thereof according to claim 16, wherein the compound of formula I is

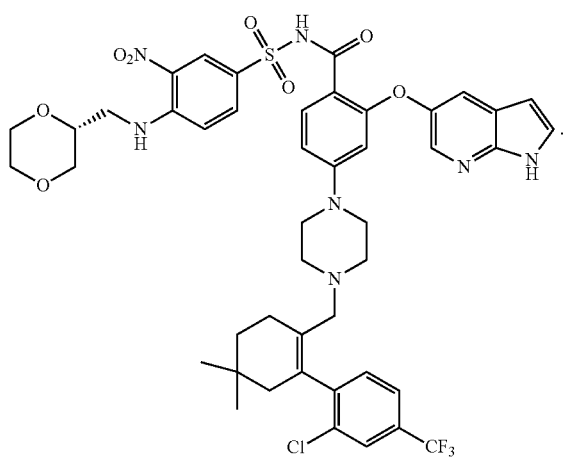 [SMILES: CC1(C)CCC(CN2CCN(c3ccc(C(=O)NS(=O)(=O)c4ccc(NC[C@@H]5COCCO5)c([N+](=O)[O-])c4)c(Oc4cnc5[nH]ccc5c4)c3)CC2)=C(c2ccc(C(F)(F)F)cc2Cl)C1]

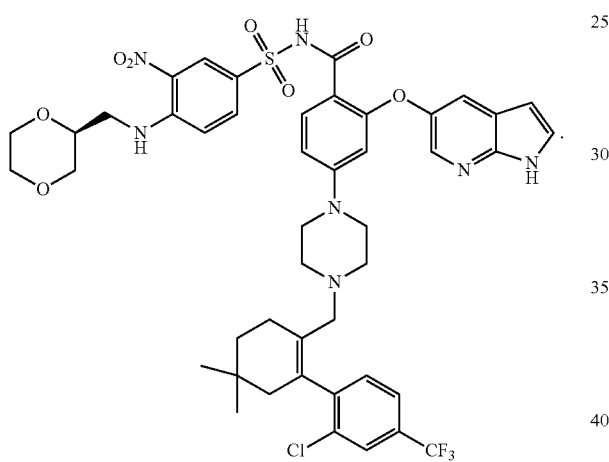

19. The compound of formula I, the stereoisomer thereof or the pharmaceutically acceptable salt thereof according to claim 16, wherein the compound of formula I is

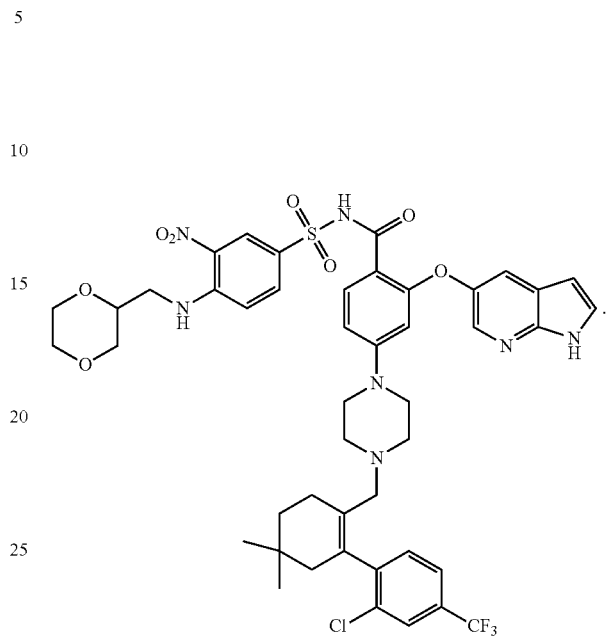

20. A method for treating an anti-apoptotic protein BCL-2-related disease, comprising administering to a patient a therapeutically effective amount of the compound, the stereoisomer thereof or the pharmaceutically acceptable salt thereof according to claim 1, or the pharmaceutical composition thereof.

* * * * *